United States Patent
Calo et al.

(10) Patent No.: US 9,902,704 B2
(45) Date of Patent: Feb. 27, 2018

(54) SUBSTITUTED N-(TETRAZOL-5-YL)- AND N-(TRIAZOL-5-YL)ARYLCARBOXAMIDE COMPOUNDS AND THEIR USE AS HERBICIDES

(71) Applicant: BASF SE, Ludwigshafen (DE)

(72) Inventors: Frederick Calo, Mannheim (DE); Markus Kordes, Frankenthal (DE); Helmut Kraus, Wissembourg (FR); Thomas Seitz, Viernheim (DE); Trevor William Newton, Neustadt (DE); Klaus Kreuz, Denzlingen (DE); Maciej Pasternak, Ludwigshafen (DE); Dario Massa, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/027,891

(22) PCT Filed: Oct. 7, 2014

(86) PCT No.: PCT/EP2014/071384
§ 371 (c)(1),
(2) Date: Apr. 7, 2016

(87) PCT Pub. No.: WO2015/052153
PCT Pub. Date: Apr. 16, 2015

(65) Prior Publication Data
US 2016/0251322 A1     Sep. 1, 2016

(30) Foreign Application Priority Data
Oct. 10, 2013 (EP) .................................... 13188029

(51) Int. Cl.
| | | |
|---|---|---|
| *C07D 401/14* | (2006.01) | |
| *C07D 257/04* | (2006.01) | |
| *C07D 249/08* | (2006.01) | |
| *A01N 43/40* | (2006.01) | |
| *A01N 43/647* | (2006.01) | |
| *A01N 43/653* | (2006.01) | |
| *A01N 43/713* | (2006.01) | |
| *C07D 257/06* | (2006.01) | |
| *C07D 401/12* | (2006.01) | |
| *A01N 43/80* | (2006.01) | |
| *C07D 249/14* | (2006.01) | |

(52) U.S. Cl.
CPC ......... *C07D 257/06* (2013.01); *A01N 43/653* (2013.01); *A01N 43/713* (2013.01); *A01N 43/80* (2013.01); *C07D 249/14* (2013.01); *C07D 401/12* (2013.01)

(58) Field of Classification Search
None
See application file for complete search history.

(56) References Cited

U.S. PATENT DOCUMENTS

| | | |
|---|---|---|
| 5,013,659 A | 5/1991 | Bedbrook et al. |
| 5,559,024 A | 9/1996 | Leroux et al. |
| 5,948,917 A | 9/1999 | Adachi et al. |
| 6,124,469 A | 9/2000 | Rheinheimer et al. |
| 6,222,100 B1 | 4/2001 | Anderson et al. |
| 6,277,847 B1 | 8/2001 | Theodoridis et al. |
| 6,689,356 B1 | 2/2004 | Zlotkin et al. |
| 6,703,348 B2 | 3/2004 | Almsick et al. |
| 6,756,497 B1 | 6/2004 | Nakagawa et al. |
| 8,286,316 B2 | 10/2012 | Koehn et al. |
| 8,481,749 B2 | 7/2013 | Braun et al. |
| 9,204,650 B2 | 12/2015 | Koehn et al. |
| 2007/0191335 A1 | 8/2007 | Lemoine et al. |
| 2012/0058892 A1 | 3/2012 | Braun et al. |
| 2014/0296069 A1 | 10/2014 | Gatzweiler |
| 2015/0264933 A1 | 9/2015 | Menne |

FOREIGN PATENT DOCUMENTS

| | | |
|---|---|---|
| CA | 2858757 | 6/2013 |
| EP | 0242236 | 10/1987 |
| EP | 242246 | 10/1987 |
| EP | 0257993 | 3/1988 |
| EP | 0392225 | 10/1990 |
| EP | 374753 | 5/1991 |
| EP | 427529 | 5/1991 |
| EP | 451878 | 10/1991 |
| WO | WO 1992000377 | 1/1992 |
| WO | WO 1993007278 | 4/1993 |
| WO | WO 1995034656 | 12/1995 |
| WO | WO 1996026202 | 6/1996 |

(Continued)

OTHER PUBLICATIONS

Bowden et al., "Structure-Activity Relations. Part 10. Metal Ion Complexation Studies of a Series of Substituted Benzamidotetrazoles." Journal of Chemical Research, Science Reviews Ltd., (1991), p. 304.

(Continued)

*Primary Examiner* — Alton Pryor
(74) *Attorney, Agent, or Firm* — Brinks Gilson & Lione

(57) ABSTRACT

The present invention relates to a triazole compound of formula I, an N-oxide or an agriculturally suitable salt thereof, wherein the variables are defined as in the specification. The invention further refers to a composition comprising such compound and to the use thereof for controlling unwanted vegetation.

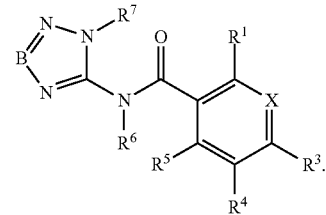

30 Claims, No Drawings

(56) References Cited

FOREIGN PATENT DOCUMENTS

| WO | WO 1997041116 | 11/1997 |
|---|---|---|
| WO | WO 1997041117 | 11/1997 |
| WO | WO 1997041216 | 11/1997 |
| WO | WO 1997046530 | 12/1997 |
| WO | WO 1998002525 | 1/1998 |
| WO | WO 1998002527 | 1/1998 |
| WO | WO 1998031581 | 7/1998 |
| WO | WO 1998031676 | 7/1998 |
| WO | WO 2000003988 | 1/2000 |
| WO | WO 2000026390 | 5/2000 |
| WO | WO 2001082685 | 11/2001 |
| WO | WO 2001083459 | 11/2001 |
| WO | WO 2002015701 | 2/2002 |
| WO | WO 2002018352 | 3/2002 |
| WO | WO 2003013225 | 2/2003 |
| WO | WO 2003014356 | 2/2003 |
| WO | WO 2003014357 | 2/2003 |
| WO | WO 2003018810 | 3/2003 |
| WO | WO 2003052073 | 6/2003 |
| WO | WO 2004016073 | 2/2004 |
| WO | WO 2004106529 | 12/2004 |
| WO | WO 2005020673 | 3/2005 |
| WO | WO 2006074991 | 6/2006 |
| WO | WO 2011035874 | 3/2011 |
| WO | WO 2012028579 | 3/2012 |
| WO | 2013064457 | 5/2013 |
| WO | 2013076316 | 5/2013 |
| WO | 2013083859 | 6/2013 |
| WO | WO 2013087577 | 6/2013 |
| WO | 2013174845 | 11/2013 |
| WO | 2014184016 | 11/2014 |
| WO | 2015/007564 | 1/2015 |

OTHER PUBLICATIONS

Hartmann et al, "Synthese und Charakterisierung von α-(1H-1,2,4-Triazol-5-yl)-aminonitrien." Zeitschaft für Chemie, vol. 30, No. 12, (1990), pp. 436-437.

Henry and Finnegan, 'Mono-alkylation of Sodium 5-Aminoietrazole in Aqueous Medium.' Journal of the American Chemical Society, vol. 76, (1954), pp. 923-926.

Henry et al., "Thermal Isomerization of Substituted 5-Aminoterazoles," Journal of the American Chemical Society, vol. 76, (1954), pp. 88-93.

International Preliminary Report on Patentability, issued in PCT/EP2014/071384, dated Apr. 12, 2016.

International Search Report, issued in PCT/EP2014/071384, dated Nov. 12, 2014.

Kroeger et al, "Die Kondensation Methylsubstituierter Aminoguanidine mit Aliphatischen Carbonsaeuren," Chemische Berichte, vol. 97, No. 2, pp. 396-404, 1964.

Bellamy and Ou, "Selective Reduction of Aromatic Nitro Compounds with Stannous Chloride in Non Acidic and Non Aqueous Medium," Tetrahedron Letters, vol. 25, (1984), pp. 839-842.

Hazlet and Dornfeld, "The Reduction of Aromatic Nitro Compounds with Activated Iron," Journal of the American Chemical Society, vol. 66, (1944), pp. 1781-1782.

Heropoulos et al., "High Intensity Ultrasound-Assisted Reduction of Sterically Demanding Nitroaromatics," Tetrahedron Letters, vol. 46, (2005), pp. 2469-2473.

Liu et al., "A Practical and Chemoselective Reduction of Nitroarenes to Anilines Using Activated Iron," Adv. Synth. Catal., vol. 347, (2005), pp. 217-219.

Nagaraja and Pasha, "Reduction of Aryl Nitro Compounds with Aluminum/NH4Cl: Effect of Ultrasound on the Rate of the Reaction," Tetrahedron Letters, vol. 40, (1999), pp. 7855-7856.

Sukhanov et al., "Reaction of 3-nitro-1,2,4-triazole Derivatives with Alkylating Agents. 2. Alkylation of a Neutral Heterocycle by Dimethyl Sulfate," Chemistry of Heterocyclic Compounds, vol. 41, No. 8, (2005), pp. 994-998.

Wang et al., "Reduction of Nitroarenes to Aromatic Amines with Nanosized Activated Metallic Iron Powder in Water," Synthesis, (2003), pp. 2001-2004.

Office Action, issued in co-pending U.S. Appl. No. 14/905,056, dated Feb. 8, 2017.

Office Action, issued in co-pending U.S. Appl. No. 14/890,713, dated Aug. 21, 2017.

SUBSTITUTED N-(TETRAZOL-5-YL)- AND N-(TRIAZOL-5-YL)ARYLCARBOXAMIDE COMPOUNDS AND THEIR USE AS HERBICIDES

This application is a National Stage application of International Application No. PCT/EP2014/071384, filed Oct. 7, 2014. This application also claims priority under 35 U.S.C. § 119 to European Patent Application No. 13188029.6, filed Oct. 10, 2013.

The present invention relates to substituted N-(tetrazol-5-yl)- and N-(triazol-5-yl)arylcarboxamide compounds and the N-oxides and salts thereof and to compositions comprising the same. The invention also relates to the use of the N-(tetrazol-5-yl)- and N-(triazol-5-yl)arylcarboxamide compounds or of the compositions comprising such compounds for controlling unwanted vegetation. Furthermore, the invention relates to methods of applying such compounds.

For the purposes of controlling unwanted vegetation, especially in crops, there is an ongoing need for new herbicides which have high activities and selectivities together with a substantial lack of toxicity for humans and animals.

WO 2011/035874 describes N-(1,2,5-oxadiazol-3-yl)benzamides carrying 3 substituents in the 2-, 3- and 4-positions of the phenyl ring and their use as herbicides.

WO 2012/028579 describes N-(tetrazol-4-yl)- and N-(triazol-3-yl)arylcarboxylic acid amides carrying 3 substituents in the 2-, 3- and 4-positions of the aryl ring and their use as herbicides.

The compounds of the prior art often suffer form insufficient herbicidal activity in particular at low application rates and/or unsatisfactory selectivity resulting in a low compatibility with crop plants.

Accordingly, it is an object of the present invention to provide further N-(tetrazol-5-yl)- and N-(triazol-5-yl)arylcarboxamide compounds having a strong herbicidal activity, in particular even at low application rates, a sufficiently low toxicity for humans and animals and/or a high compatibility with crop plants. The N-(tetrazol-5-yl)- and N-(triazol-5-yl)arylcarboxamide compounds should also show a broad activity spectrum against a large number of different unwanted plants. These and further objectives are achieved by the compounds of formula I defined below and their N-oxides and also their agriculturally suitable salts.

It has been found that the above objectives can be achieved by substituted N-(tetrazol-5-yl)- and N-(triazol-5-yl)arylcarboxamide compounds of the general formula I, as defined below, including their N-oxides and their salts, in particular their agriculturally suitable salts. Therefore, in a first aspect the present invention relates to compounds of formula I,

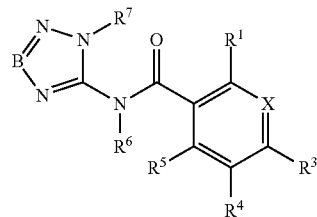

I an N-oxide or an agriculturally suitable salt thereof, wherein $R^1$ is selected from the group consisting of halogen, $C_1$-$C_8$-alkyl, $C_1$-$C_8$-haloalkyl, nitro, $C_1$-$C_4$-alkoxy-$C_1$-$C_4$-alkyl, cyano-$Z^1$, $C_2$-$C_8$-alkenyl, $C_2$-$C_8$-alkynyl, $C_3$-$C_{10}$-cycloalkyl-$Z^1$, $C_2$-$C_8$-haloalkenyl, $C_3$-$C_8$-haloalkynyl, $C_1$-$C_8$-alkoxy, $C_1$-$C_4$-alkoxy-$C_1$-$C_4$-alkoxy-$Z^1$, $C_1$-$C_4$-alkylthio-$C_1$-$C_4$-alkyl, $C_1$-$C_4$-alkylthio-$C_1$-$C_4$-alkylthio-$Z^1$, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkyl, $C_1$-$C_4$-haloalkoxy-$C_1$-$C_4$-alkoxy-$Z^1$, $R^{1b}$—S(O)$_k$—$Z^1$, phe-noxy-$Z^1$ and heterocyclyloxy-$Z^1$, where heterocyclyloxy is an oxygen bound 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenoxy and heterocyclyloxy are unsubstituted or substituted by 1, 2, 3 or 4 groups $R^{11}$, which are identical or different;

X is N or $CR^2$;

$R^2$ is selected from the group consisting of hydrogen, halogen, hydroxy-$Z^2$, nitro, $C_1$-$C_4$-nitroalkyl, cyano, $C_1$-$C_4$-cyanoalkyl, $C_1$-$C_6$-alkyl, $C_2$-$C_8$-alkenyl, $C_2$-$C_8$-alkynyl, $C_3$-$C_{10}$-cycloalkyl-$Z^2$, $C_3$-$C_{10}$-cycloalkoxy-$Z^2$, where the $C_3$-$C_{10}$-cycloalkyl groups in the two aforementioned radicals are unsubstituted or partially or completely halogenated, $C_1$-$C_8$-haloalkyl, $C_2$-$C_8$-haloalkenyl, $C_3$-$C_8$-haloalkynyl, $C_1$-$C_8$-alkoxy-$Z^2$, $C_1$-$C_8$-haloalkoxy-$Z^2$, $C_3$-$C_{10}$-cycloalkyl-$C_1$-$C_2$-alkoxy, $C_1$-$C_4$-alkoxy-$C_1$-$C_4$-alkoxy-$Z^2$, $C_1$-$C_4$-alkylthio-$C_1$-$C_4$-alkylthio-$Z^2$, $C_2$-$C_8$-alkenyloxy-$Z^2$, $C_2$-$C_8$-alkynyloxy-$Z^2$, $C_2$-$C_8$-haloalkenyloxy-$Z^2$, $C_3$-$C_8$-haloalkynyloxy-$Z^2$, $C_1$-$C_4$-haloalkoxy-$C_1$-$C_4$-alkoxy-$Z^2$, (tri-$C_1$-$C_4$-alkyl)silyl-$Z^2$, $R^{2b}$—S(O)$_k$—$Z^2$, $R^{2c}$—C(=O)—$Z^2$, $R^{2d}$O—C(=O)—$Z^2$, $R^{2d}$O—N=CH—$Z^2$, $R^{2d}$O—N=CC$_1$-$C_4$-alkyl-$Z^2$, $R^{2d}$O—N=CC$_1$-$C_4$-haloalkyl-$Z^2$, $R^{2c}R^{2d}$C=N—O—$C_1$-$C_4$-alkyl, $R^{2e}R^{2f}$N—C(=O)—$Z^2$, $R^{2g}R^{2h}$N—$Z^2$, phenyl-$Z^{2a}$, heterocyclyl-$Z^{2a}$, where heterocyclyl is a 3-, 4-, 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenyl-$Z^{2a}$ and heterocyclyl-$Z^{2a}$ are unsubstituted or substituted by 1, 2, 3 or 4 groups $R^{21}$, which are identical or different, rhodano, $C_3$-$C_6$-cycloalkenyl, OC(O)OR$^{22}$, OC(O)N(R$^{22}$)$_2$, ONC(R$^{23}$)$_2$, OSO$_2$R$^{25}$, SO$_2$OR$^{22}$, SO$_2$N(R$^{22}$)$_2$, N(R$^{22}$)C(O)OR$^{22}$, N(R$^{22}$)C(O)N(R$^{22}$)$_2$, C(O)N(R$^{22}$)OR$^{22}$, P(O)(O—$C_1$-$C_4$-alkyl)$_2$, $C_1$-$C_6$-alkyl-OC(O)R$^{22}$, $C_1$-$C_6$-alkyl-OSO$_2$R$^{25}$, $C_1$-$C_6$-alkyl-SO$_2$OR$^{22}$, $C_1$-$C_6$-alkyl-SO$_2$N(R$^{22}$)$_2$, $C_1$-$C_6$-alkyl-P(O)(O—$C_1$-$C_4$-alkyl)$_2$,

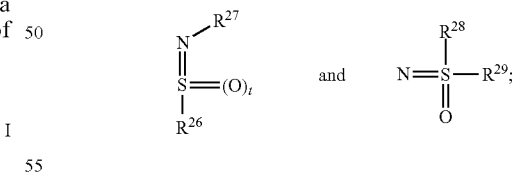

$R^3$ is selected from the group consisting of hydrogen, halogen, hydroxy-$Z^2$, nitro, $C_1$-$C_4$-nitroalkyl, cyano, $C_1$-$C_4$-cyanoalkyl, $C_1$-$C_6$-alkyl, $C_2$-$C_8$-alkenyl, $C_2$-$C_8$-alkynyl, $C_3$-$C_{10}$-cycloalkyl-$Z^2$, $C_3$-$C_{10}$-cycloalkoxy-$Z^2$, where the $C_3$-$C_{10}$-cycloalkyl groups in the two aforementioned radicals are unsubstituted or partially or completely halogenated, $C_1$-$C_8$-haloalkyl, $C_2$-$C_8$-haloalkenyl, $C_3$-$C_8$-haloalkynyl, $C_1$-$C_8$-alkoxy-$Z^2$, $C_1$-$C_8$-haloalkoxy-$Z^2$, $C_3$-$C_{10}$-cycloalkyl-$C_1$-$C_2$-alkoxy, $C_1$-$C_4$-alkoxy-$C_1$-$C_4$-alkoxy-$Z^2$, $C_1$-$C_4$-alkylthio-$C_1$-$C_4$-alkylthio-$Z^2$, $C_2$-$C_8$-alkenyloxy-$Z^2$, $C_2$-$C_8$-alkynyloxy-$Z^2$, $C_2$-$C_8$-haloalkenyloxy-$Z^2$, $C_3$-$C_8$-haloalkynyloxy-$Z^2$, $C_1$-$C_4$-haloalkoxy-$C_1$-$C_4$-alkoxy-$Z^2$, (tri- C$_1$-C$_4$-alkyl)silyl-Z$^2$, R$^{2b}$—S(O)$_k$—Z$^2$, R$^{2c}$—C(=O)—Z$^2$, R$^{2d}$O—C(=O)—Z$^2$, R$^{2d}$O—N=CH—Z$^2$, R$^{2c}$R$^{2d}$C=N—O—C$_1$-C$_4$-alkyl, R$^{2e}$R$^{2f}$N—C(=O)—Z$^2$, R$^{2g}$R$^{2h}$N—Z$^2$, phenyl-Z$^{2a}$, heterocyclyl-Z$^{2a}$, where heterocyclyl is a 3-, 4-, 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenyl-Z$^{2a}$ and heterocyclyl-Z$^{2a}$ are unsubstituted or substituted by 1, 2, 3 or 4 groups R$^{21}$, which are identical or different, rhodano, C$_3$-C$_6$-cycloalkenyl, C$_3$-C$_6$-halocycloalkenyl, C$_3$-C$_6$-cycloalkenyl-C$_1$-C$_6$-alkyl, C$_3$-C$_6$-halocycloalkenyl-C$_1$-C$_6$-alkyl, OC(O)R$^{22}$, OC(O)OR$^{25}$, OC(O)N(R$^{22}$)$_2$, OSO$_2$R$^{25}$, SO$_2$OR$^{22}$, SO$_2$N(R$^{22}$)$_2$, SO$_2$N(R$^{22}$)C(O)R$^{22}$, SO$_2$N(R$^{22}$)C(O)OR$^{25}$, SO$_2$N(R$^{22}$)C(O)N(R$^{22}$)$_2$, N(R$^{22}$)C(O)OR$^{25}$, N(R$^{22}$)C(O)N(R$^{22}$)$_2$, N(R$^{22}$)S(O)$_2$OR$^{22}$, N(R$^{22}$)S(O)$_2$N(R$^{22}$)$_2$, C(O)N(R$^{22}$)OR$^{22}$, C(O)N(R$^{22}$)N(R$^{22}$)$_2$, C(O)N(R$^{22}$)C(O)R$^{22}$, C(O)N(R$^{22}$)C(O)OR$^{25}$, C(O)N(R$^{22}$)C(O)N(R$^{22}$)$_2$, C(O)N(R$^{22}$)SO$_2$R$^{25}$, C(O)N(R$^{22}$)SO$_2$OR$^{22}$, C(O)N(R$^{22}$)SO$_2$N(R$^{22}$)$_2$, P(O)(OH)$_2$, P(O)(O—C$_1$-C$_4$-alkyl)$_2$, C$_1$-C$_6$-alkyl-OC(O)R$^{22}$, C$_1$-C$_6$-alkyl-OC(O)OR$^{25}$, C$_1$-C$_6$-alkyl-OC(O)N(R$^{22}$)$_2$, C$_1$-C$_6$-alkyl-OSO$_2$R$^{25}$, C$_1$-C$_6$-alkyl-SO$_2$OR$^{22}$, C$_1$-C$_6$-alkyl-SO$_2$N(R$^{22}$)$_2$, C$_1$-C$_6$-alkyl-SO$_2$N(R$^{22}$)C(O)R$^{22}$, C$_1$-C$_6$-alkyl-SO$_2$N(R$^{22}$)C(O)OR$^{25}$, C$_1$-C$_6$-alkyl-SO$_2$N(R$^{22}$)C(O)N(R$^{22}$)$_2$, C$_1$-C$_6$-alkyl-N(R$^{22}$)C(O)OR$^{25}$, C$_1$-C$_6$-alkyl-N(R$^{22}$)C(O)N(R$^{22}$)$_2$, C$_1$-C$_6$-alkyl-N(R$^{22}$)S(O)$_2$OR$^{22}$, C$_1$-C$_6$-alkyl-N(R$^{22}$)S(O)$_2$N(R$^{22}$)$_2$, C$_1$-C$_6$-alkyl-C(O)N(R$^{22}$)OR$^{22}$, C$_1$-C$_6$-alkyl-C(O)N(R$^{22}$)N(R$^{22}$)$_2$, C$_1$-C$_6$-alkyl-C(O)N(R$^{22}$)C(O)R$^{22}$, C$_1$-C$_6$-alkyl-C(O)N(R$^{22}$)C(O)OR$^{25}$, C$_1$-C$_6$-alkyl-C(O)N(R$^{22}$)C(O)N(R$^{22}$)$_2$, C$_1$-C$_6$-alkyl-C(O)N(R$^{22}$)SO$_2$R$^{25}$, C$_1$-C$_6$-alkyl-C(O)N(R$^{22}$)SO$_2$OR$^{22}$, C$_1$-C$_6$-alkyl-C(O)N(R$^{22}$)SO$_2$N(R$^{22}$)$_2$, C$_1$-C$_6$-alkyl-P(O)(OH)$_2$ and C$_1$-C$_6$-alkyl-P(O)(O—C$_1$-C$_4$-alkyl)$_2$;

R$^4$ is selected from the group consisting of hydrogen, halogen, C$_1$-C$_8$-alkyl, cyano-Z$^1$, nitro, C$_3$-C$_7$-cycloalkyl, C$_3$-C$_7$-cycloalkyl-C$_1$-C$_4$-alkyl, where the C$_3$-C$_7$-cycloalkyl groups in the two aforementioned radicals are unsubstituted or partially or completely halogenated, C$_2$-C$_8$-alkenyl, C$_2$-C$_8$-alkynyl, C$_1$-C$_8$-haloalkyl, C$_1$-C$_3$-alkylamino, C$_1$-C$_3$-dialkylamino, C$_1$-C$_3$-alkylamino-S(O)$_k$, C$_1$-C$_3$-alkylcarbonyl, C$_1$-C$_8$-alkoxy, C$_1$-C$_4$-alkoxy-C$_1$-C$_4$-alkyl, C$_1$-C$_4$-alkoxy-C$_1$-C$_4$-alkoxy-Z$^1$, C$_1$-C$_4$-alkylthio-C$_1$-C$_4$-alkyl, C$_1$-C$_4$-alkylthio-C$_1$-C$_4$-alkyl-Z$^1$, C$_2$-C$_6$-alkenyloxy, C$_2$-C$_6$-alkynyloxy, C$_1$-C$_6$-haloalkoxy, C$_1$-C$_4$-haloalkoxy-C$_1$-C$_4$-alkyl, C$_1$-C$_4$-haloalkoxy-C$_1$-C$_4$-alkoxy-Z$^1$, R$^{1b}$—S(O)$_k$—Z$^1$, phenoxy-Z$^1$ and heterocyclyloxy-Z$^1$, where heterocyclyloxy is an oxygen bound 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenoxy and heterocyclyloxy are unsubstituted or substituted by 1, 2, 3 or 4 groups R$^{11}$, which are identical or different;

R$^5$ is selected from the group consisting of halogen, cyano-Z$^1$, nitro, C$_1$-C$_8$-alkyl, C$_3$-C$_7$-cycloalkyl, C$_3$-C$_7$-cycloalkyl-C$_1$-C$_4$-alkyl, where the C$_3$-C$_7$-cycloalkyl groups in the two aforementioned radicals are unsubstituted or partially or completely halogenated, C$_2$-C$_8$-alkenyl, C$_2$-C$_8$-alkynyl, C$_1$-C$_8$-haloalkyl, C$_1$-C$_3$-alkylamino, C$_1$-C$_3$-dialkylamino, C$_1$-C$_3$-alkylamino-S(O)$_k$, C$_1$-C$_3$-alkylcarbonyl, C$_1$-C$_8$-alkoxy, C$_1$-C$_4$-alkoxy-C$_1$-C$_4$-alkyl, C$_1$-C$_4$-alkoxy-C$_1$-C$_4$-alkoxy-Z$^1$, C$_1$-C$_4$-alkylthio-C$_1$-C$_4$-alkyl, C$_1$-C$_4$-alkylthio-C$_1$-C$_4$-alkylthio-Z$^1$, C$_2$-C$_6$-alkenyloxy, C$_2$-C$_6$-alkynyloxy, C$_1$-C$_6$-haloalkoxy, C$_1$-C$_4$-haloalkoxy-C$_1$-C$_4$-alkyl, C$_1$-C$_4$-haloalkoxy-C$_1$-C$_4$-alkoxy-Z$^1$, R$^{1b}$—S(O)$_k$—Z$^1$, phenoxy-Z$^1$ and heterocyclyloxy-Z$^1$, where heterocyclyloxy is an oxygen bound 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenoxy and heterocyclyloxy are unsubstituted or substituted by 1, 2, 3 or 4 groups R$^{11}$, which are identical or different;

R$^6$ is selected from the group consisting of cyano, nitro, hydroxy, amino, C$_1$-C$_6$-alkyl, C$_1$-C$_6$-cyano-alkyl, C$_3$-C$_7$-cycloalkyl, C$_3$-C$_7$-cycloalkyl-C$_1$-C$_4$-alkyl, where the C$_3$-C$_7$-cycloalkyl groups in the two aforementioned radicals are unsubstituted or partially or completely halogenated, C$_1$-C$_6$-haloalkyl, C$_1$-C$_6$-alkoxy, C$_1$-C$_6$-alkylcarbonyl, C$_1$-C$_6$-alkyaminocarbonyl, C$_1$-C$_6$-dialkyl-aminocarbonyl, C$_1$-C$_6$-alkyamino, C$_1$-C$_6$-dialkyl-amino, C$_2$-C$_6$-alkenyl, C$_2$-C$_6$-haloalkenyl, C$_2$-C$_6$-alkynyl, C$_2$-C$_6$-haloalkynyl, C$_1$-C$_4$-alkoxy-C$_1$-C$_4$-alkyl, C$_1$-C$_4$-haloalkoxy-C$_1$-C$_4$-alkyl, R$^b$R$^b$N—S(O)$_n$—Z, R$^b$O—S(O)$_n$—Z, R$^b$—S(O)$_n$—Z, R$^c$R$^c$N—C$_1$-C$_3$-alkyl-S(O)$_n$—C$_1$-C$_3$-alkyl, R$^c$—C(=O)—C$_1$-C$_3$-alkyl, R$^d$—C(=O)O—C$_1$-C$_3$-alkyl, R$^d$—O—C(=O)O—C$_1$-C$_3$-alkyl, R$^d$O—C(=O)—C$_1$-C$_3$-alkyl, R$^e$R$^f$N—C(=O)—C$_1$-C$_3$-alkyl, R$^c$—C(=O)R$^e$N—C$_1$-C$_3$-alkyl, R$^b$—S(O)$_n$—R$^e$N—C$_1$-C$_3$-alkyl, R$^c$R$^c$N—C$_1$-C$_3$-alkyl, phenyl-Z and heterocyclyl-Z, where heterocyclyl is a 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups R', which are identical or different;

R$^7$ is selected from the group consisting of hydrogen, C$_1$-C$_6$-alkyl, C$_3$-C$_7$-cycloalkyl, C$_3$-C$_7$-cycloalkyl-C$_1$-C$_4$-alkyl, where the C$_3$-C$_7$-cycloalkyl groups in the two aforementioned radicals are unsubstituted or partially or completely halogenated, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C$_1$-C$_4$-alkoxy-C$_1$-C$_4$-alkyl, C$_1$-C$_4$-haloalkoxy-C$_1$-C$_4$-alkyl, R$^b$—S(O)$_n$—C$_1$-C$_3$-alkyl, R$^c$—C(=O)—C$_1$-C$_3$-alkyl, R$^d$O—C(=O)—C$_1$-C$_3$-alkyl, R$^e$R$^f$N—C(=O)—C$_1$-C$_3$-alkyl, R$^g$R$^h$N—C$_1$-C$_3$-alkyl, phenyl-Z and heterocyclyl-Z, where heterocyclyl is a 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups R', which are identical or different;

B is N or CH;

R', R$^{11}$, R$^{21}$ independently of each other are selected from the group consisting of halogen, NO$_2$, ON, C$_1$-C$_6$-alkyl, C$_3$-C$_7$-cycloalkyl, C$_3$-C$_7$-halocycloalkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C$_1$-C$_6$-alkoxy, C$_1$-C$_4$-alkoxy-C$_1$-C$_4$-alkyl, C$_1$-C$_4$-alkylthio-C$_1$-C$_4$-alkyl, C$_1$-C$_4$-haloalkoxy-C$_1$-C$_4$-alkyl, C$_1$-C$_4$-alkoxy-C$_1$-C$_4$-alkoxy, C$_3$-C$_7$-cycloalkoxy and C$_1$-C$_6$-haloalkyloxy, or two vicinal radicals R', R$^{11}$ or R$^{21}$ together may form a group =O;

Z, Z$^1$, Z$^2$ independently of each other are selected from the group consisting of a covalent bond and C$_1$-C$_4$-alkanediyl;

Z$^{2a}$ is s Z$^{2a}$ elected from the group consisting of a covalent bond, C$_1$-C$_4$-alkanediyl, O—C$_1$-C$_4$-alkanediyl, C$_1$-C$_4$-alkanediyl-O and C$_1$-C$_4$-alkanediyl-O—C$_1$-C$_4$-alkanediyl;

$R^b$, $R^{1b}$, $R^{2b}$ independently of each other are selected from the group consisting of $C_1$-$C_6$-alkyl, $C_3$-$C_7$-cycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, phenyl and heterocyclyl, where heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^c$, $R^{2c}$ independently of each other are selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl, benzyl and heterocyclyl, where heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl, benzyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^d$, $R^{2d}$ independently of each other are selected from the group consisting of $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^e$, $R^f$ independently of each other are selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^e$, $R^f$ together with the nitrogen atom, to which they are bound may form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^{2e}$, $R^{2f}$ independently of each other have the meanings given for $R^e$, $R^f$;

$R^g$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-alkylsulfonyl, $C_1$-$C_4$-alkylcarbonyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^h$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-alkylsulfonyl, $C_1$-$C_4$-alkylcarbonyl, a radical C(=O)—$R^k$, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^g$, $R^h$ together with the nitrogen atom, to which they are bound may form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of =O, halogen, $C_1$-$C_4$-alkyl, $C_1$-$C_4$-haloalkyl, $C_1$-$C_4$-alkoxy and $C_1$-$C_4$-haloalkoxy;

$R^{2g}$, $R^{2h}$ independently of each other have the meanings given for $R^g$, $R^h$;

$R^k$ has the meanings given for $R^c$;

$R^{22}$ is selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, $C_3$-$C_6$-cycloalkenyl, $C_3$-$C_6$-halocycloalkyl, $C_3$-$C_6$-cycloalkyl-$C_1$-$C_6$-alkyl, $C_1$-$C_6$-alkoxy-$C_1$-$C_6$-alkyl, $C_3$-$C_6$-cycloalkyl-$C_1$-$C_6$-alkoxy-$C_1$-$C_6$-alkyl, phenyl, phenyl-$C_1$-$C_6$-alkyl, heteroaryl, heteroaryl-$C_1$-$C_6$-alkyl, heterocyclyl, heterocyclyl-$C_1$-$C_6$-alkyl, phenyl-O—$C_1$-$C_6$-alkyl, heteroaryl-O—$C_1$-$C_6$-alkyl, heterocyclyl-O—$C_1$-$C_6$-alkyl, phenyl-N($R^{23}$)—$C_1$-$C_6$-alkyl, heteroaryl-N($R^{23}$)—$C_1$-$C_6$-alkyl, heterocyclyl-N($R^{23}$)—$C_1$-$C_6$-alkyl, phenyl-S(O)$_n$—$C_1$-$C_6$-alkyl, heteroaryl-S(O)$_n$—$C_1$-$C_6$-alkyl, heterocyclyl-S(O)$_n$—$C_1$-$C_6$-alkyl, where the 15 aforementioned radicals are substituted by s residues selected from the group consisting of nitro, halogen, cyano, rhodano, $C_1$-$C_6$-alkyl, $C_1$-$C_6$-haloalkyl, $C_3$-$C_6$-cycloalkyl, C(O)O$R^{23}$, C(O)N($R^{23}$)$_2$, O$R^{23}$, N($R^{23}$)$_2$, S(O)$_n$$R^{24}$, S(O)$_2$O$R^{23}$, S(O)$_2$N($R^{23}$)$_2$ and $R^{23}$O—$C_1$-$C_6$-alkyl, and where heterocyclyl bears 0, 1 or 2 oxo groups;

$R^{23}$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl and phenyl;

$R^{24}$ is selected from the group consisting of $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl and phenyl;

$R^{25}$ is selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, $C_3$-$C_6$-cycloalkenyl, $C_3$-$C_6$-halocycloalkyl, $C_3$-$C_6$-cycloalkyl-$C_1$-$C_6$-alkyl, $C_1$-$C_6$-alkoxy-$C_1$-$C_6$-alkyl, $C_3$-$C_6$-cycloalkyl-$C_1$-$C_6$-alkoxy-$C_1$-$C_6$-alkyl, phenyl, phenyl-$C_1$-$C_6$-alkyl, heteroaryl, heteroaryl-$C_1$-$C_6$-alkyl, heterocyclyl, heterocyclyl-$C_1$-$C_6$-alkyl, phenyl-O—$C_1$-$C_6$-alkyl, heteroaryl-O—$C_1$-$C_6$-alkyl, heterocyclyl-O—$C_1$-$C_6$-alkyl, phenyl-N($R^{23}$)—$C_1$-$C_6$-alkyl, heteroaryl-N($R^{23}$)—$C_1$-$C_6$-alkyl, heterocyclyl-N($R^{23}$)—$C_1$-$C_6$-alkyl, phenyl-S(O)$_n$—$C_1$-$C_6$-alkyl, heteroaryl-S(O)$_n$—$C_1$-$C_6$-alkyl, heterocyclyl-S(O)$_n$—

$C_1$-$C_6$-alkyl, where the 15 aforementioned radicals are substituted by s residues selected from the group consisting of nitro, halogen, cyano, rhodano, $C_1$-$C_6$-alkyl, $C_1$-$C_6$-haloalkyl, $C_3$-$C_6$-cycloalkyl, $C(O)OR^{23}$, $C(O)N(R^{23})_2$, $OR^{23}$, $N(R^{23})_2$, $S(O)_n R^{24}$, $S(O)_2 OR^{23}$, $S(O)_2 N(R^{23})_2$ and $R^{23}O$—$C_1$-$C_6$-alkyl, and where heterocyclyl bears 0, 1 or 2 oxo groups;

$R^{26}$ is $C_1$-$C_6$-alkyl or $C_1$-$C_4$-alkoxy-$C_1$-$C_4$-alkyl;

$R^{27}$ is selected from the group consisting of hydrogen, cyano and $C_1$-$C_4$-haloalkylcarbonyl;

$R^{28}$, $R^{29}$ independently of each other are $C_1$-$C_6$-alkyl, or $R^{28}$, $R^{29}$ together with the sulfur atom, to which they are bound may form a 5- or 6-membered saturated ring, which may carry as a ring member 1 oxygen atom;

k is 0, 1 or 2;

n is 0, 1 or 2;

s is 0, 1, 2 or 3;

t is 0 or 1.

The compounds of the present invention, i.e. the compounds of formula I, their N-oxides, or their salts are particularly useful for controlling unwanted vegetation. Therefore, the invention also relates to the use of a compound of the present invention, an N-oxide or a salt thereof or of a composition comprising at least one compound of the invention, an N-oxide or an agriculturally suitable salt thereof for combating or controlling unwanted vegetation.

The invention also relates to a composition comprising at least one compound according to the invention, including an N-oxide or a salt thereof, and at least one auxiliary. In particular, the invention relates to an agricultural composition comprising at least one compound according to the invention including an N-oxide or an agriculturally suitable salt thereof, and at least one auxiliary customary for crop protection formulations.

The present invention also relates to a method for combating or controlling unwanted vegetation, which method comprises allowing a herbicidally effective amount of at least one compound according to the invention, including an N-oxide or a salt thereof, to act on unwanted plants, their seed and/or their habitat.

Depending on the substitution pattern, the compounds of formula I may have one or more centers of chirality, in which case they are present as mixtures of enantiomers or diastereomers. The invention provides both the pure enantiomers or pure diastereomers of the compounds of formula I, and their mixtures and the use according to the invention of the pure enantiomers or pure diastereomers of the compound of formula I or its mixtures. Suitable compounds of formula I also include all possible geometrical stereoisomers (cis/trans isomers) and mixtures thereof.

Cis/trans isomers may be present with respect to an alkene, carbon-nitrogen double-bond, nitrogen-sulfur double bond or amide group. The term "stereoisomer(s)" encompasses both optical isomers, such as enantiomers or diastereomers, the latter existing due to more than one center of chirality in the molecule, as well as geometrical isomers (cis/trans isomers).

Depending on the substitution pattern, the compounds of formula I may be present in the form of their tautomers. Hence the invention also relates to the tautomers of the formula I and the stereoisomers, salts and N-oxides of said tautomers.

The term "N-oxide" includes any compound of the present invention which has at least one tertiary nitrogen atom that is oxidized to an N-oxide moiety. N-oxides in compounds of formula I can in particular be prepared by oxidizing the ring nitrogen atom(s) of the N-(1,2,4-triazol-3-yl)arylcarboxamide ring with a suitable oxidizing agent, such as peroxo carboxylic acids or other peroxides, or the ring nitrogen atom(s) of a heterocyclic substituent R, $R^1$, $R^2$ or $R^3$.

The present invention moreover relates to compounds as defined herein, wherein one or more of the atoms depicted in formula I have been replaced by its stable, preferably non-radioactive isotope (e.g., hydrogen by deuterium, $^{12}C$ by $^{13}C$, $^{14}N$ by $^{15}N$, $^{16}O$ by $^{18}O$) and in particular wherein at least one hydrogen atom has been replaced by a deuterium atom. Of course, the compounds according to the invention contain more of the respective isotope than this naturally occurs and thus is anyway present in the compounds of formula I.

The compounds of the present invention may be amorphous or may exist in one ore more different crystalline states (polymorphs) which may have different macroscopic properties such as stability or show different biological properties such as activities. The present invention includes both amorphous and crystalline compounds of formula I, their enantiomers or diastereomers, mixtures of different crystalline states of the respective compound of formula I, its enantiomers or diastereomers, as well as amorphous or crystalline salts thereof.

Salts of the compounds of the present invention are preferably agriculturally suitable salts. They can be formed in a customary method, e.g. by reacting the compound with an acid if the compound of the present invention has a basic functionality or by reacting the compound with a suitable base if the compound of the present invention has an acidic functionality.

Useful agriculturally suitable salts are especially the salts of those cations or the acid addition salts of those acids whose cations and anions, respectively, do not have any adverse effect on the herbicidal action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of the present invention with an acid of the corresponding anion, preferably with hydrochloric acid, hydrobromic acid, sulfuric acid, phosphoric acid or nitric acid.

The term "undesired vegetation" ("weeds") is understood to include any vegetation growing in non-crop-areas or at a crop plant site or locus of seeded and otherwise desired crop, where the vegetation is any plant species, including their germinant seeds, emerging seedlings and established vegetation, other than the seeded or desired crop (if any). Weeds, in the broadest sense, are plants considered undesirable in a particular location.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "partially or completely halogenated" will be taken to mean that 1 or more, e.g. 1, 2, 3, 4 or 5 or all of the hydrogen atoms of a given radical have been replaced by a halogen atom, in particular by fluorine or chlorine. A partially or completely halogenated radical is termed below also "halo-radical". For example, partially or completely halogenated alkyl is also termed haloalkyl.

The term "alkyl" as used herein (and in the alkyl moieties of other groups comprising an alkyl group, e.g. alkoxy, alkylcarbonyl, alkoxycarbonyl, alkylthio, alkylsulfonyl and alkoxyalkyl) denotes in each case a straight-chain or branched alkyl group having usually from 1 to 10 carbon atoms, frequently from 1 to 6 carbon atoms, preferably 1 to 4 carbon atoms and in particular from 1 to 3 carbon atoms. Examples of $C_1$-$C_4$-alkyl are methyl, ethyl, n-propyl, isopropyl, n-butyl, 2-butyl (sec-butyl), isobutyl and tert-butyl. Examples for $C_1$-$C_6$-alkyl are, apart those mentioned for $C_1$-$C_4$-alkyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Examples for $C_1$-$C_{10}$-alkyl are, apart those mentioned for $C_1$-$C_6$-alkyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methyloctyl, 2-methylheptyl, 1-ethylhexyl, 2-ethylhexyl, 1,2-dimethylhexyl, 1-propylpentyl, 2-propylpentyl, nonyl, decyl, 2-propylheptyl and 3-propylheptyl.

The term "alkylene" (or alkanediyl) as used herein in each case denotes an alkyl radical as defined above, wherein one hydrogen atom at any position of the carbon backbone is replaced by one further binding site, thus forming a bivalent moiety.

The term "haloalkyl" as used herein (and in the haloalkyl moieties of other groups comprising a haloalkyl group, e.g. haloalkoxy, haloalkylthio, haloalkylcarbonyl, haloalkylsulfonyl and haloalkylsulfinyl) denotes in each case a straight-chain or branched alkyl group having usually from 1 to 8 carbon atoms ("$C_1$-$C_8$-haloalkyl"), frequently from 1 to 6 carbon atoms ("$C_1$-$C_6$-haloalkyl"), more frequently 1 to 4 carbon atoms ("$C_1$-$C_4$-haloalkyl"), wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, more preferably from halomethyl, in particular from $C_1$-$C_2$-fluoroalkyl. Halomethyl is methyl in which 1, 2 or 3 of the hydrogen atoms are replaced by halogen atoms. Examples are bromomethyl, chloromethyl, dichloromethyl, trichloromethyl, fluoromethyl, difluoromethyl, trifluoromethyl, chlorofluoromethyl, dichlorofluoromethyl, chlorodifluoromethyl and the like. Examples for $C_1$-$C_2$-fluoroalkyl are fluoromethyl, difluoromethyl, trifluoromethyl, 1-fluoroethyl, 2-fluoroethyl, 2,2-difluoroethyl, 2,2,2-trifluoroethyl, pentafluoroethyl, and the like. Examples for $C_1$-$C_2$-haloalkyl are, apart those mentioned for $C_1$-$C_2$-fluoroalkyl, chloromethyl, dichloromethyl, trichloromethyl, bromomethyl, chlorofluoromethyl, dichlorofluoromethyl, chlorodifluoromethyl, 1-chloroethyl, 2-chloroethyl, 2,2,-dichloroethyl, 2,2,2-trichloroethyl, 2-chloro-2-fluoroethyl, 2-chloro-2,2-difluoroethyl, 2,2-dichloro-2-fluoroethyl, 1-bromoethyl, and the like. Examples for $C_1$-$C_4$-haloalkyl are, apart those mentioned for $C_1$-$C_2$-haloalkyl, 1-fluoropropyl, 2-fluoropropyl, 3-fluoropropyl, 3,3-difluoropropyl, 3,3,3-trifluoropropyl, heptafluoropropyl, 1,1,1-trifluoroprop-2-yl, 3-chloropropyl, 4-chlorobutyl and the like.

The term "cycloalkyl" as used herein (and in the cycloalkyl moieties of other groups comprising a cycloalkyl group, e.g. cycloalkoxy and cycloalkylalkyl) denotes in each case a mono- or bicyclic cycloaliphatic radical having usually from 3 to 10 carbon atoms ("$C_3$-$C_{10}$-cycloalkyl"), preferably 3 to 7 carbon atoms ("$C_3$-$C_7$-cycloalkyl") or in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 7 carbon atoms comprise cyclopropyl, cyclobutyl, cyclopentyl, cyclohexyl and cycloheptyl. Examples of bicyclic radicals having 7 or 8 carbon atoms comprise bicyclo[2.1.1]hexyl, bicyclo[2.2.1]heptyl, bicyclo[3.1.1]heptyl, bicyclo[2.2.1]heptyl, bicyclo[2.2.2]octyl and bicyclo[3.2.1]octyl.

The term "halocycloalkyl" as used herein (and in the halocycloalkyl moieties of other groups comprising an halocycloalkyl group, e.g. halocycloalkylmethyl) denotes in each case a mono- or bicyclic cycloaliphatic radical having usually from 3 to 10 carbon atoms, preferably 3 to 7 carbon atoms or in particular 3 to 6 carbon atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-, 2- and 3-fluorocyclopentyl, 1,2-, 2,2-, 2,3-, 3,3-, 3,4-, 2,5-difluorocyclopentyl, 1-, 2- and 3-chlorocyclopentyl, 1,2-, 2,2-, 2,3-, 3,3-, 3,4-, 2,5-dichlorocyclopentyl and the like.

The term "cycloalkyl-alkyl" used herein denotes a cycloalkyl group, as defined above, which is bound to the remainder of the molecule via an alkylene group. The term "$C_3$-$C_7$-cycloalkyl-$C_1$-$C_4$-alkyl" refers to a $C_3$-$C_7$-cycloalkyl group as defined above which is bound to the remainder of the molecule via a $C_1$-$C_4$-alkyl group, as defined above. Examples are cyclo-propylmethyl, cyclopropylethyl, cyclopropylpropyl, cyclobutylmethyl, cyclobutylethyl, cyclobu-tylpropyl, cyclopentylmethyl, cyclopentylethyl, cyclopentylpropyl, cyclohexylmethyl, cyclohexylethyl, cyclohexylpropyl, and the like.

The term "alkenyl" as used herein denotes in each case a monounsaturated straight-chain or branched hydrocarbon radical having usually 2 to 8 ("$C_2$-$C_8$-alkenyl"), preferably 2 to 6 carbon atoms ("$C_2$-$C_6$-alkenyl"), in particular 2 to 4 carbon atoms ("$C_2$-$C_4$-alkenyl"), and a double bond in any position, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_8$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl and the positional isomers thereof.

The term "haloalkenyl" as used herein, which may also be expressed as "alkenyl which is substituted by halogen", and the haloalkenyl moieties in haloalkenyloxy and the like refers to unsaturated straight-chain or branched hydrocarbon radicals having 2 to 8 ("$C_2$-$C_8$-haloalkenyl") or 2 to 6 ("$C_2$-$C_6$-haloalkenyl") or 2 to 4 ("$C_2$-$C_4$-haloalkenyl") carbon atoms and a double bond in any position, where some or all of the hydrogen atoms in these groups are replaced by halogen atoms as mentioned above, in particular fluorine, chlorine and bromine, for example chlorovinyl, chloroallyl and the like.

The term "alkynyl" as used herein denotes unsaturated straight-chain or branched hydrocarbon radicals having usually 2 to 8 ("$C_2$-$C_8$-alkynyl"), frequently 2 to 6 ("$C_2$-$C_6$-alkynyl"), preferably 2 to 4 carbon atoms ("$C_2$-$C_4$-alkynyl") and a triple bond in any position, for example $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like.

The term "haloalkynyl" as used herein, which is also expressed as "alkynyl which is substituted by halogen", refers to unsaturated straight-chain or branched hydrocarbon radicals having usually 2 to 8 carbon atoms ("$C_2$-$C_8$-haloalkynyl"), frequently 2 to 6 ("$C_2$-$C_6$-haloalkynyl"), preferably 2 to 4 carbon atoms ("$C_2$-$C_4$-haloalkynyl"), and a triple bond in any position (as mentioned above), where some or all of the hydrogen atoms in these groups are replaced by halogen atoms as mentioned above, in particular fluorine, chlorine and bromine.

The term "alkoxy" as used herein denotes in each case a straight-chain or branched alkyl group usually having from 1 to 8 carbon atoms ("$C_1$-$C_6$-alkoxy"), frequently from 1 to 6 carbon atoms ("$C_1$-$C_6$-alkoxy"), preferably 1 to 4 carbon atoms ("$C_1$-$C_4$-alkoxy"), which is bound to the remainder of the molecule via an oxygen atom. $C_1$-$C_2$-Alkoxy is methoxy or ethoxy. $C_1$-$C_4$-Alkoxy is additionally, for example, n-propoxy, 1-methylethoxy (isopropoxy), butoxy, 1-methylpropoxy (sec-butoxy), 2-methylpropoxy (isobutoxy) or 1,1-dimethylethoxy (tert-butoxy).

$C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof.

The term "haloalkoxy" as used herein denotes in each case a straight-chain or branched alkoxy group, as defined above, having from 1 to 8 carbon atoms ("$C_1$-$C_8$-haloalkoxy"), frequently from 1 to 6 carbon atoms ("$C_1$-$C_6$-haloalkoxy"), preferably 1 to 4 carbon atoms ("$C_1$-$C_4$-haloalkoxy"), more preferably 1 to 3 carbon atoms ("$C_1$-$C_3$-haloalkoxy"), wherein the hydrogen atoms of this group are partially or totally replaced with halogen atoms, in particular fluorine atoms. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, unde-cafluoropentoxy, 6-fluorohexoxy, 6-chlorohexoxy, 6-bromohexoxy, 6-iodohexoxy or dodecafluo-rohexoxy.

The term "alkoxyalkyl" as used herein denotes in each case alkyl usually comprising 1 to 6 carbon atoms, preferably 1 to 4 carbon atoms, wherein 1 carbon atom carries an alkoxy radical usually comprising 1 to 8, frequently 1 to 6, in particular 1 to 4, carbon atoms as defined above. "$C_1$-$C_6$-alkoxy-$C_1$-$C_6$-alkyl" is a $C_1$-$C_6$-alkyl group, as defined above, in which one hydrogen atom is replaced by a $C_1$-$C_6$-alkoxy group, as defined above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methyl-propoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)-butyl, 3-(2-methyl-propoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "haloalkoxy-alkyl" as used herein denotes in each case alkyl as defined above, usually comprising 1 to 6 carbon atoms, preferably 1 to 4 carbon atoms, wherein 1 carbon atom carries an haloalkoxy radical as defined above, usually comprising 1 to 8, frequently 1 to 6, in particular 1 to 4, carbon atoms as defined above. Examples are fluoromethoxymethyl, difluoro-methoxymethyl, trifluoromethoxymethyl, 1-fluoroethoxymethyl, 2-fluoroethoxymethyl, 1,1-difluoroethoxymethyl, 1,2-difluoroethoxymethyl, 2,2-difluoroethoxymethyl, 1,1,2-trifluoroethoxymethyl, 1,2,2-trifluoroethoxymethyl, 2,2,2-trifluoroethoxymethyl, pentafluoroethox-ymethyl, 1-fluoroethoxy-1-ethyl, 2-fluoroethoxy-1-ethyl, 1,1-difluoroethoxy-1-ethyl, 1,2-difluoroethoxy-1-ethyl, 2,2-difluoroethoxy-1-ethyl, 1,1,2-trifluoroethoxy-1-ethyl, 1,2,2-trifluoroethoxy-1-ethyl, 2,2,2-trifluoroethoxy-1-ethyl, pentafluoroethoxy-1-ethyl, 1-fluoroethoxy-2-ethyl, 2-fluoroethoxy-2-ethyl, 1,1-difluoroethoxy-2-ethyl, 1,2-difluoroethoxy-2-ethyl, 2,2-difluoroethoxy-2-ethyl, 1,1,2-trifluoroethoxy-2-ethyl, 1,2,2-trifluoroethoxy-2-ethyl, 2,2,2-trifluoroethoxy-2-ethyl, pentafluoroethoxy-2-ethyl, and the like.

The term "alkylthio" (also alkylsulfanyl, "alkyl-S" or "alkyl-S(O)$_k$" (wherein k is 0)) as used herein denotes in each case a straight-chain or branched saturated alkyl group as defined above, usually comprising 1 to 8 carbon atoms ("$C_1$-$C_8$-alkylthio"), frequently comprising 1 to 6 carbon atoms ("$C_1$-$C_6$-alkylthio"), preferably 1 to 4 carbon atoms ("$C_1$-$C_4$-alkylthio"), which is attached via a sulfur atom at any position in the alkyl group. $C_1$-$C_2$-Alkylthio is methylthio or ethylthio. $C_1$-$C_4$-Alkylthio is additionally, for example, n-propylthio, 1-methylethylthio (iso-propylthio), butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof.

The term "haloalkylthio" as used herein refers to an alkylthio group as defined above wherein the hydrogen atoms are partially or completely substituted by fluorine, chlorine, bromine and/or iodine. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The terms "alkylsulfinyl" and "alkyl-S(O)$_k$" (wherein k is 1) are equivalent and, as used herein, denote an alkyl group, as defined above, attached via a sulfinyl [S(O)] group. For example, the term "$C_1$-$C_2$-alkylsulfinyl" refers to a $C_1$-$C_2$-alkyl group, as defined above, attached via a sulfinyl [S(O)] group. The term "$C_1$-$C_4$-alkylsulfinyl" refers to a $C_1$-$C_4$-alkyl group, as defined above, attached via a sulfinyl [S(O)] group. The term "$C_1$-$C_6$-alkylsulfinyl" refers to a $C_1$-$C_6$-alkyl group, as defined above, attached via a sulfinyl [S(O)] group. $C_1$-$C_2$-alkylsulfinyl is methylsulfinyl or ethylsulfinyl. $C_1$-$C_4$-alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The terms "alkylsulfonyl" and "alkyl-S(O)$_k$" (wherein k is 2) are equivalent and, as used herein, denote an alkyl group, as defined above, attached via a sulfonyl [S(O)$_2$] group. The term "$C_1$-$C_2$-alkylsulfonyl" refers to a $C_1$-$C_2$-alkyl group, as defined above, attached via a sulfonyl [S(O)$_2$] group. The term "$C_1$-$C_4$-alkylsulfonyl" refers to a $C_1$-$C_4$-alkyl group, as defined above, attached via a sulfonyl [S(O)$_2$] group. The term "$C_1$-$C_6$-alkylsulfonyl" refers to a $C_1$-$C_6$-alkyl group, as defined above, attached via a sulfonyl [S(O)$_2$] group. $C_1$-$C_2$-alkylsulfonyl is methylsulfonyl or ethylsulfonyl. $C_1$-$C_4$-alkylsulfonyl is additionally, for example, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

The term "alkylamino" as used herein denotes in each case a group R*HN—, wherein R* is a straight-chain or branched alkyl group usually having from 1 to 6 carbon atoms ("$C_1$-$C_6$-alkylamino"), preferably 1 to 4 carbon atoms ("$C_1$-$C_4$-alkylamino"). Examples of $C_1$-$C_6$-alkylamino are methylamino, ethylamino, n-propylamino, isopropylamino, n-butylamino, 2-butylamino, iso-butylamino, tert-butylamino, and the like.

The term "dialkylamino" as used herein denotes in each case a group R*R°N—, wherein R* and R°, independently of each other, are a straight-chain or branched alkyl group each usually having from 1 to 6 carbon atoms ("di-($C_1$-$C_6$-alkyl)-amino"), preferably 1 to 4 carbon atoms ("di-($C_1$-$C_4$-alkyl)-amino"). Examples of a di-($C_1$-$C_6$-alkyl)-amino group are dimethylamino, diethyla-mino, dipropylamino, dibutylamino, methyl-ethyl-amino, methyl-propyl-amino, methyl-isopropylamino, methyl-butyl-amino, methyl-isobutyl-amino, ethyl-propyl-amino, ethyl-isopropylamino, ethyl-butyl-amino, ethyl-isobutyl-amino, and the like.

The suffix "-carbonyl" in a group denotes in each case that the group is bound to the remainder of the molecule via a carbonyl C=O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl.

The term "het(ero)aryl" as used herein refers to a mono-, bi- or tricyclic heteroaromatic hydrocarbon radical, preferably to a monocyclic heteroaromatic radical, such as pyridyl, pyrimidyl and the like.

The term "3-, 4-, 5- or 6-membered monocyclic or 8-, 9- or 10-membered bicyclic saturated, unsaturated or aromatic heterocycle containing 1, 2, 3 or 4 heteroatoms as ring members selected from the groups consisting of N, O and S" as used herein denotes monocyclic or bicyclic radicals, the monocyclic or bicyclic radicals being saturated, unsaturated or aromatic where N can optionally be oxidized, i.e. in the form of an N-oxide, and S can also optionally be oxidized to various oxidation states, i.e. as SO or $SO_2$. An unsaturated heterocycle contains at least one C—C and/or C—N and/or N—N double bond(s). A fully unsaturated heterocycle contains as many conjugated C—C and/or C—N and/or N—N double bonds as allowed by the size(s) of the ring(s). An aromatic monocyclic heterocycle is a fully unsaturated 5- or 6-membered monocyclic heterocycle. An aromatic bicyclic heterocycle is an 8-, 9- or 10-membered bicyclic heterocycle consisting of a 5- or 6-membered heteroaromatic ring which is fused to a phenyl ring or to another 5- or 6-membered heteroaromatic ring. The heterocycle may be attached to the remainder of the molecule via a carbon ring member or via a nitrogen ring member. As a matter of course, the heterocyclic ring contains at least one carbon ring atom. If the ring contains more than one O ring atom, these are not adjacent.

Examples of a 3-, 4-, 5- or 6-membered monocyclic saturated heterocycle include: oxirane-2-yl, aziridine-1-yl, aziridine-2-yl, oxetan-2-yl, azetidine-1-yl, azetidine-2-yl, azetidine-3-yl, thietane-1-yl, thietan-2-yl, thietane-3-yl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl and the like.

Examples of a 5- or 6-membered monocyclic partially unsaturated heterocycle include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl and 1,2,4-di- or tetrahydrotriazin-3-yl.

A 5- or 6-membered monocyclic fully unsaturated (including aromatic) heterocyclic ring is e.g. a 5- or 6-membered monocyclic fully unsaturated (including aromatic) heterocyclic ring. Examples are: 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl.

Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like.

If two radicals bound on the same nitrogen atom (for example $R^e$ and $R^f$ or $R^{2e}$ and $R^{2f}$ or $R^g$ and $R^h$ or $R^{2g}$ and $R^{2h}$) together with the nitrogen atom, to which they are bound, form a 5-, 6 or 7-membered, saturated or unsaturated N-bound heterocyclic radical, which may carry as a ring member a further heteroatom selected from O, S and N, this is for example pyrrolidine-1-yl, pyrazolidin-1-yl, imidazolidin-1-yl, oxazolidin-3-yl, thiazolidin-3-yl, isoxazolidin-2-yl, isothiazolin-2-yl, [1,2,3]-triazolidin-1-yl, [1,2,3]-triazolidin-2-yl, [1,2,4]-triazolidin-1-yl, [1,2,4]-triazolidin-4-yl, [1,2,3]-oxadiazolidin-2-yl, [1,2,3]-oxadiazolidin-3-yl, [1,2,5]-oxadiazolidin-2-yl, [1,2,4]-oxadiazolidin-2-yl, [1,2,4]-oxadiazolidin-4-yl, [1,3,4]-oxadiazolidin-3-yl, [1,2,3]-thiadiazolidin-2-yl, [1,2,3]-thiadiazolidin-3-yl, [1,2,5]-thiadiazolidin-2-yl, [1,2,4]-thiadiazolidin-2-yl, [1,2,4]-thiadiazolidin-4-yl, [1,3,4]-thiadiazolidin-3-yl, piperdin-1-yl, piperazine-1-yl, morpholin-1-yl, thiomorpholin-1-yl, 1-oxothiomorpholin-1-yl, 1,1-dioxothiomorpholin-1-yl, azepan-1-yl, 1,4-diazepan-1-yl, pyrrolin-1-yl, pyrazolin-1-yl, imidazolin-1-yl, oxazolin-3-yl, isoxazolin-2-yl, thiazolin-3-yl, isothiazolin-1-yl, 1,2-dihydropyridin-1-yl, 1,2,3,4-tetrahydropyridin-1-yl, 1,2,5,6-tetrahydropyridin-1-yl, 1,2-dihydropyridazin, 1,6-dihydropyridazin, 1,2,3,4-tetrahydropyridazin-1-yl, 1,2,5,6-tetrahydropyridazin-1-yl, 1,2-dihydropyrimidin, 1,6-dihydropyrimidin, 1,2,3,4-tetrahydropyrimidin-1-yl, 1,2,5,6-tetrahydropyrimidin-1-yl, 1,2-dihydropyrazin-1-yl, 1,2,3,4-tetrahydropyrazin-1-yl, 1,2,5,6-tetrahydropyrazin-1-yl, pyrrol-1-yl, pyrazol-1-yl, imidazol-1-yl, [1,2,3]-1H-triazol-1-yl, [1,2,3]-2H-triazol-2-yl, [1,2,4]-1H-triazol-1-yl and [1,2,4]-4H-triazol-4-yl.

The remarks made below as to preferred embodiments of the variables (substituents) of the compounds of formula I are valid on their own as well as preferably in combination with each other, as well as in combination with the stereoisomers, salts, tautomers or N-oxides thereof.

The remarks made below concerning preferred embodiments of the variables further are valid on their own as well as preferably in combination with each other concerning the compounds of formulae I, where applicable, as well as concerning the uses and methods according to the invention and the composition according to the invention.

Preferred compounds according to the invention are compounds of formula I or a stereoisomer, salt or N-oxide thereof, wherein the salt is an agriculturally suitable salt. Further preferred compounds according to the invention are compounds of formula I or an N-oxide or salt thereof, especially an agriculturally suitable salt. Particularly preferred compounds according to the invention are compounds of formula I or a salt thereof, especially an agriculturally suitable salt thereof.

According to one embodiment of the invention the variable X in the compounds of formula I is N.

According to another embodiment of the invention the variable X in the compounds of formula I is $CR^2$.

In a preferred embodiment, B is N.

In another preferred embodiment, B is CH.

Preferred compounds according to the invention are compounds of formula I, wherein $R^1$ is selected from the group consisting of cyano, halogen, nitro, $C_1$-$C_6$-alkyl, $C_3$-$C_6$-cycloalkyl, $C_2$-$C_6$-alkenyl, $C_2$-$C_6$-alkynyl, $C_1$-$C_6$-haloalkyl, $C_1$-$C_6$-alkoxy, $C_1$-$C_4$-alkoxy-$C_1$-$C_4$-alkyl, $C_1$-$C_4$-haloalkoxy-$C_1$-$C_4$-alkyl, $C_1$-$C_4$-alkoxy-$C_1$-$C_4$-alkoxy-$Z^1$, $C_1$-$C_4$-alkylthio-$C_1$-$C_4$-alkyl, $C_1$-$C_4$-alkylthio-$C_1$-$C_4$-alkylthio-$Z^1$, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy and $R^{1b}$—$S(O)_k$, where $Z^1$ is as defined in claim 1, where k is 0, 1 or 2 and where $R^{1b}$ is selected from $C_1$-$C_4$-alkyl and $C_1$-$C_4$-haloalkyl.

In a more preferred embodiment, in the compound of formula I, $R^1$ is selected from the group consisting of halogen, CN, nitro, $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkyl, $C_1$-$C_4$-alkylthio-$C_1$-$C_4$-alkylthio-$C_1$-$C_4$-alkyl, $C_1$-$C_4$-alkoxy, $C_1$-$C_4$-haloalkoxy, $C_3$-$C_4$-alkenyloxy, $C_3$-$C_4$-alkynyloxy, $C_1$-$C_4$-alkoxy-$C_1$-$C_4$-alkoxy, $C_1$-$C_4$-haloalkoxy-$C_1$-$C_4$-alkoxy, $C_1$-$C_4$-alkyl-$S(O)_k$ and $C_1$-$C_4$-haloalkyl-$S(O)_k$, where k is 0 or 2.

In a highly preferred embodiment, in the compound of formula I, $R^1$ is selected from the group consisting of halogen, nitro, $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio and $C_1$-$C_4$-alkylsulfonyl.

In one preferred embodiment of the present invention, X as used in the context of formula I is N (nitrogen).

In an alternative group of embodiments of the present invention, where X is $CR^2$, the variable $R^2$ is hydrogen.

In another group of embodiments of the invention, where X is $CR^2$, the variable $R^2$ of the compounds of formula I has any one of the meanings given above for $R^2$ with the exception of hydrogen.

According to a preferred embodiment of the invention the variable $R^2$ is 5- or 6-membered heterocyclyl, where heterocyclyl is a saturated, partially unsaturated or aromatic heterocyclic radical, which contains as a ring member 1 heteroatom selected from the group consisting of O, N and S and 0, 1, 2 or 3 further nitrogen atoms, where heterocyclyl is unsubstituted or carries 1, 2 or 3 radicals $R^{21}$ which are identical or different.

According to an even more preferred embodiment of the invention, the variable $R^2$ is 5- or 6-membered heterocyclyl selected from the group consisting of isoxazolinyl, 1,2-dihydrotetrazolonyl, 1,4-dihydrotetrazolonyl, tetrahydrofuryl, dioxolanyl, piperidinyl, morpholinyl, piperazinyl, isoxazolyl, pyrazolyl, thiazolyl, oxazolyl, furyl, pyridinyl, pyrimidinyl and pyrazinyl, where heterocyclyl is unsubstituted or carries 1, 2 or 3 radicals $R^{21}$ which are identical or different and selected from the group consisting of $C_1$-$C_4$-alkyl, $C_1$-$C_4$-haloalkyl, $C_1$-$C_4$-alkoxy, $C_1$-$C_4$-alkoxy-$C_1$-$C_4$-alkyl and $C_1$-$C_4$-alkylthio-$C_1$-$C_4$-alkyl.

According to a particular embodiment of the invention the variable $R^2$ is selected from the group consisting of hydrogen, halogen, $C_1$-$C_6$-alkyl, $C_3$-$C_6$-cycloalkyl-$C_1$-$C_4$-alkoxy, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxy-$C_1$-$C_4$-alkoxy, $C_1$-$C_4$-alkoxycarbonyl, $C_1$-$C_4$-alkyl-$S(O)_k$ and $C_1$-$C_4$-haloalkyl-$S(O)_k$, where k is 0, 1 or 2, $N(C_1$-$C_4$-alkyl) $SO_2(C_1$-$C_4$-alkyl), isoxazolyl and isoxazolinyl, where the last two mentioned radicals may be unsubstituted or carry 1 or 2 radicals selected from halogen and $C_1$-$C_4$-alkyl.

In another particular embodiment of the invention, the variable $R^2$ in formula I is

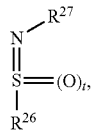

where
$R^{26}$ is selected from the group consisting of methyl, ethyl and methoxyethyl,
$R^{27}$ is selected from the group consisting of hydrogen, cyano and trifluoroacetyl,
t is 0 or 1;
or

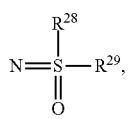

where
$R^{28}$ is ethyl and $R^{29}$ is ethyl, or
$R^{28}$ and $R^{29}$ together are —(CH$_2$)$_5$— or —(CH$_2$)$_2$—O—(CH$_2$)$_2$—.

According to a more preferred embodiment of the invention the variable $R^2$ in the compounds of formula I is a radical of the following formula:

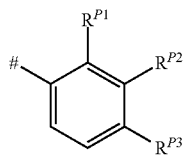

in which # denotes the bond through which the group $R^2$ is attached and:
$R^{P1}$ is hydrogen or halogen, preferably hydrogen, Cl, Br or F, and in particular H or F;
$R^{P2}$ is hydrogen, halogen or $C_1$-$C_2$-alkoxy, preferably hydrogen, Cl, Br, F, OCH$_3$ or OCH$_2$CH$_3$, and in particular H, F, Cl or OCH$_3$; and
$R^{P3}$ is hydrogen, halogen, $C_1$-$C_2$-alkyl, $C_1$-$C_2$-haloalkyl, $C_1$-$C_2$-alkoxy, $C_1$-$C_2$-alkoxy-$C_1$-$C_2$-alkoxy, preferably hydrogen, Cl, Br, F, CH$_3$, C$_2$H$_5$, CF$_3$, CHF$_2$, CH$_2$F, CCl$_2$F, CF$_2$Cl, CH$_2$CF$_3$, CH$_2$CHF$_2$, CF$_2$CF$_3$, OCH$_3$, OCH$_2$CH$_3$, OCH$_2$OCH$_3$, OCH$_2$CH$_2$OCH$_2$CH$_3$, OCH$_2$OCH$_2$CH$_3$ or OCH$_2$CH$_2$OCH$_3$, and in particular is H, F, Cl, CH$_3$, CF$_3$, OCH$_3$, OCH$_2$CH$_3$, OCH$_2$OCH$_3$ or OCH$_2$CH$_2$OCH$_3$.

According to a particular embodiment of the invention the variable $R^2$ in the compounds of formula I is phenyl which is unsubstituted or carries one radical $R^{21}$, where $R^{21}$ is preferably attached to position 4 of the phenyl group and is as defined above and in particular selected from $C_1$-$C_2$-alkyl, $C_1$-$C_2$-alkoxy, $C_1$-$C_2$-haloalkyl and $C_1$-$C_2$-alkoxy-$C_1$-$C_2$-alkoxy, preferably form CH$_3$, C$_2$H$_5$, OCH$_3$, OC$_2$H$_5$, CHF$_2$, CF$_3$, OCH$_2$OCH$_3$ and OCH$_2$CH$_2$OCH$_3$, and specifically from OCH$_3$ and OC$_2$H$_5$.

According to a preferred embodiment of the invention the variable $R^2$ in the compounds of formula I is selected from the group consisting of hydrogen, halogen, $C_1$-$C_6$-alkyl, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $C_1$-$C_4$-alkyl-S(O)$_k$ and $C_1$-$C_4$-haloalkyl-S(O)$_k$, where k is 0, 1 or 2, isoxazolyl and isoxazolinyl, where the last two mentioned radicals may be unsubstituted or carry 1 or 2 radicals selected from halogen and $C_1$-$C_4$-alkyl.

According to another preferred embodiment of the invention the variable $R^2$ in the compounds of formula I is selected from the group consisting of halogen, $C_1$-$C_6$-alkyl, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $C_1$-$C_4$-alkyl-S(O)$_k$ and $C_1$-$C_4$-haloalkyl-S(O)$_k$, where k is 0, 1 or 2, isoxazolyl and isoxazolinyl, where the last two mentioned radicals may be unsubstituted or carry 1 or 2 radicals selected from halogen and $C_1$-$C_4$-alkyl.

According to a more preferred embodiment of the invention the variable $R^2$ in the compounds of formula I is selected from $C_2$-$C_4$-alkenyl, $C_2$-$C_4$-alkynyl, $C_1$-$C_4$-alkoxy, $C_1$-$C_2$-haloalkoxy-$C_1$-$C_2$-alkyl, $C_3$-$C_4$-alkenyloxy, $C_3$-$C_4$-alkynyloxy, $C_1$-$C_4$-alkoxycarbonyl and $C_1$-$C_4$-alkyl-S(O$_2$), and in particular from CH=CH$_2$, CH=CHCH$_3$, CH$_2$OCH$_2$CF$_3$, OC$_2$H$_5$, OCH$_2$CH=CH$_2$, OCH$_2$C≡CH, C(O)OCH$_3$, C(O)OC$_2$H$_5$, SO$_2$CH$_3$, SO$_2$C$_2$H$_5$ and SO$_2$CH(CH$_3$)$_2$.

According to a specifically preferred embodiment of the invention the variable $R^2$ in the compounds of formula I is selected from the group consisting of hydrogen, 4,5-dihydroisoxazol-3-yl, which is unsubstituted or substituted in position 5 with CH$_3$, CH$_2$F or CHF$_2$, 4,5-dihydroisoxazol-5-yl, which is unsubstituted or substituted in position 3 with CH$_3$, OCH$_3$, CH$_2$OCH$_3$, CH$_2$SCH$_3$, 1-methyl-5-oxo-1,5-dihydrotetrazol-2-yl, 4-methyl-5-oxo-4,5-dihydrotetrazol-1-yl, morpholin-4-yl, isoxazol-3-yl, 5-methyl-isoxazol-3-yl, isoxazol-5-yl, 3-methyl-isoxazol-5-yl, 1-methyl-1H-pyrazol-3-yl, 2-methyl-2H-pyrazol-3-yl, thiazol-2-yl, 4-CH$_3$-phenyl, 4-C$_2$H$_5$-phenyl, 4-OCH$_3$-phenyl, 4-OC$_2$H$_5$-phenyl, 4-CHF$_2$-phenyl, 4-CF$_3$-phenyl, 4-OCH$_2$OCH$_3$-phenyl, 4-OCH$_2$CH$_2$OCH$_3$-phenyl, CH=CH$_2$, CH=CHCH$_3$, CH$_2$OCH$_2$CF$_3$, OC$_2$H$_5$, OCH$_2$CH=CH$_2$, OCH$_2$C≡CH, C(O)OCH$_3$, C(O)OC$_2$H$_5$, SO$_2$CH$_3$, SO$_2$C$_2$H$_5$ and SO$_2$CH(CH$_3$)$_2$, in particular selected from hydrogen, halogen, methyl, CH$_2$OCH$_2$CF$_3$, methylsulfonyl, ethylsulfonyl, methylsulfanyl, ethylsulfanyl, 3-isoxazolinyl, 5-methyl-3-isoxazolinyl, 5-isoxazolinyl, 3-methyl-5-isoxazolinyl, 3-isoxazolyl, 5-methyl-3-isoxazolyl, 5-isoxazolyl and 3-methyl-5-isoxazolyl, and specifically selected from hydrogen, chlorine, methylsulfonyl, methylsulfanyl, CH$_2$OCH$_2$CF$_3$, 3-isoxazolinyl, 5-methyl-3-isoxazolinyl, 3-methyl-5-isoxazolinyl, 3-isoxazolyl, 5-methyl-3-isoxazolyl and 3-methyl-5-isoxazolyl.

In a highly preferred embodiment, $R^2$ is selected from the group consisting of hydrogen, halogen, $C_1$-$C_4$-alkyl, $C_1$-$C_4$-alkoxy, $C_1$-$C_4$-haloalkoxy, $C_3$-$C_6$-cycloalkyl-$C_1$-$C_2$-alkoxy, $C_1$-$C_2$-alkoxy-$C_1$-$C_2$-alkyl, $C_1$-$C_2$-haloalkoxy-$C_1$-$C_2$-alkyl, $C_1$-$C_2$-alkoxy-$C_1$-$C_2$-alkoxy, $C_1$-$C_4$-alkyl-S(O)$_k$, where k is 0, 1 or 2, N(C$_1$-$C_4$-alkyl)SO$_2$(C$_1$-$C_4$-alkyl), isoxazolyl and isoxazolinyl, where the last two mentioned radicals may be unsubstituted or carry 1 or 2 radicals selected from halogen and $C_1$-$C_4$-alkyl.

In a particularly preferred embodiment, $R^2$ in formula I is selected from the group consisting of hydrogen, chlorine, fluorine, methyl, methoxy, ethoxy, $OCH_2(cyclo-C_3H_5)$, $OCHF_2$, $OCH_2CF_3$, $OCH_2CH_2OCH_3$, methoxymethyl, $CH_2OCH_2CF_3$, methylsulfonyl, ethylsulfonyl, methylsulfinyl, ethylsulfinyl, methylsulfanyl, ethylsulfanyl, $NCH_3SO_2CH_3$, 3-isoxazolinyl, 5-methyl-3-isoxazolinyl, 5-isoxazolinyl, 3-methyl-5-isoxazolinyl, 3-isoxazolyl, 5-methyl-3-isoxazolyl, 5-isoxazolyl and 3-methyl-5-isoxazolyl, in particular selected from the group consisting of hydrogen, chlorine, fluorine, methyl, $CH_2OCH_2CF_3$, methylsulfonyl, ethylsulfonyl, methylsulfanyl, ethylsulfanyl, 3-isoxazolinyl, 5-methyl-3-isoxazolinyl, 5-isoxazolinyl, 3-methyl-5-isoxazolinyl, 3-isoxazolyl, 5-methyl-3-isoxazolyl, 5-isoxazolyl and 3-methyl-5-isoxazolyl.

Preferred compounds according to the invention are compounds of formula I, wherein $R^3$ is selected from the group consisting of hydrogen, halogen, cyano, nitro, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_3$-$C_4$-alkenyloxy, $C_3$-$C_4$-alkynyloxy or $R^{2b}$—$S(O)_k$, where k is 0, 1 or 2 and where $R^{2b}$ is selected from $C_1$-$C_4$-alkyl and $C_1$-$C_4$-haloalkyl.

More preferably, $R^3$ is selected from $R^3$ is selected from the group consisting of hydrogen, halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkyl-$S(O)_2$ and $C_1$-$C_4$-haloalkyl-$S(O)_2$.

In particular $R^3$ selected from the group consisting of chlorine, fluorine, $CF_3$, $SO_2CH_3$, cyano, nitro, hydrogen and $CH_3$.

Preferred compounds according to the invention are compounds of formula I, wherein $R^4$ is selected from the group consisting of hydrogen, cyano, halogen, nitro, $C_1$-$C_2$-alkyl and $C_1$-$C_2$-haloalkyl, in particular from the group consisting of hydrogen, $CHF_2$, $CF_3$, CN, $NO_2$, $CH_3$ and halogen, and specifically from hydrogen, $CHF_2$, $CF_3$, CN, $NO_2$, $CH_3$, Cl, Br and F.

In particular, $R^4$ is selected from the group consisting of hydrogen, $CHF_2$, $CF_3$, CN, $NO_2$, $CH_3$ and halogen.

Preferred compounds according to the invention are compounds of formula I, wherein $R^5$ is selected from the group consisting of halogen, $C_1$-$C_2$-alkyl and $C_1$-$C_2$-haloalkyl, and in particular from the group consisting of $CHF_2$, $CF_3$ and halogen.

According to a particular embodiment of the invention, $R^5$ is selected from the group consisting of $CHF_2$, $CF_3$ and halogen.

According to a particular embodiment of the invention, $R^4$ is hydrogen and $R^5$ is chlorine or fluorine.

According to a preferred embodiment of the invention, $R^6$ in the compounds formula I is selected from the group consisting of cyano, $C_1$-$C_6$-alkyl, $C_1$-$C_6$-cyano-alkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-haloalkoxy-$C_1$-$C_4$-alkyl, $R^bR^bN$—$S(O)_n$—Z, $R^bO$—$S(O)_n$—Z, $R^b$—$S(O)_n$—Z, $R^d$—$C(=O)O$—$C_1$-$C_3$-alkyl, $R^d$—O—$C(=O)O$—$C_1$-$C_3$-alkyl, $R^dO$—$C(=O)$—$C_1$-$C_3$-alkyl, $R^eR^fN$—$C(=O)$—$C_1$-$C_3$-alkyl, phenyl-Z and where phenyl is unsubstituted or substituted by 1, 2, 3 or 4 groups R', which are identical or different.

Preferred compounds according to the invention are compounds of formula I, wherein $R^6$ is selected from the group consisting of $C_1$-$C_4$-alkyl, $C_2$-$C_6$-alkenyl, $C_2$-$C_6$-alkynyl, $C_1$-$C_4$-alkoxy-$C_1$-$C_4$-alkyl, $C_3$-$C_7$-cycloalkyl, $C_1$-$C_4$-haloalkyl, $R^c$—$C(=O)$—$C_1$-$C_2$-alkyl, $R^dO$—$C(=O)$—$C_1$-$C_2$-alkyl, $R^eR^fN$—$C(=O)$—$C_1$-$C_2$-alkyl, $R^k$—$C(=O)NH$—$C_1$-$C_2$-alkyl and benzyl, where $R^c$ is $C_1$-$C_4$-alkyl or $C_1$-$C_4$-haloalkyl,
$R^d$ is $C_1$-$C_4$-alkyl,
$R^e$ is hydrogen or $C_1$-$C_4$-alkyl,
$R^f$ is hydrogen or $C_1$-$C_4$-alkyl, or
$R^e$, $R^f$ together with the nitrogen atom, to which they are bound may form a 5-, 6 or 7-membered, saturated N-bound heterocyclic radical, which may carry as a ring member a further heteroatom selected from O, S and N and which is unsubstituted or may carry 1, 2, 3 or 4 methyl groups,
$R^k$ is $C_1$-$C_4$-alkyl.

Further preferred compounds according to the invention are compounds of formula I, wherein $R^6$ is selected from the group consisting of $C_1$-$C_6$-alkyl, $C_2$-$C_6$-alkenyl, $C_2$-$C_6$-alkynyl, $C_1$-$C_4$-alkoxy-$C_1$-$C_4$-alkyl, $R^dO$—$C(=O)$—$C_1$-$C_3$-alkyl, phenyl-Z and where phenyl is unsubstituted or substituted by 1, 2, 3 or 4 groups R', which are identical or different.

More preferred compounds according to the invention are compounds of formula I, wherein $R^6$ is selected from the group consisting of cyano, $C_1$-$C_6$-alkyl, $C_1$-$C_6$-cyano-alkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-haloalkoxy-$C_1$-$C_4$-alkyl, $R^bR^bN$—$S(O)_n$—Z, $R^bO$—$S(O)_n$—Z, $R^b$—$S(O)_n$—Z, $R^d$—$C(=O)O$—$C_1$-$C_3$-alkyl, $R^dO$—$C(=O)$—$C_1$-$C_3$-alkyl, $R^eR^fN$—$C(=O)$—$C_1$-$C_3$-alkyl, phenyl-Z and where phenyl is unsubstituted or substituted by 1, 2, 3 or 4 groups R', which are identical or different.

Highly preferably, $R^6$ is selected from the group consisting of $C_1$-$C_6$-alkyl, $C_2$-$C_6$-alkenyl, $C_2$-$C_6$-alkynyl, $C_1$-$C_4$-alkoxy-$C_1$-$C_4$-alkyl, $R^dO$—$C(=O)$—$C_1$-$C_3$-alkyl, phenyl-Z and where phenyl is unsubstituted or substituted by 1, 2, 3 or 4 groups R', which are identical or different.

Particularly, R6 is selected from the group consisting of methyl, ethyl, methoxymethyl, ethoxymethyl, prop-2-ynyl and methoxycarbonylmethyl;

According to one embodiment, preferred compounds according to the invention are compounds of formula I, wherein $R^7$ is selected from the group consisting of hydrogen, $C_1$-$C_4$-alkyl, $C_2$-$C_6$-alkenyl, $C_2$-$C_6$-alkynyl, $C_1$-$C_4$-alkoxy-$C_1$-$C_4$-alkyl, $C_3$-$C_7$-cycloalkyl, $C_1$-$C_4$-haloalkyl, $R^c$—$C(=O)$—$C_1$-$C_2$-alkyl, $R^dO$—$C(=O)$—$C_1$-$C_2$-alkyl, $R^eR^fN$—$C(=O)$—$C_1$-$C_2$-alkyl, $R^k$—$C(=O)NH$—$C_1$-$C_2$-alkyl and benzyl, where $R^c$ is $C_1$-$C_4$-alkyl or $C_1$-$C_4$-haloalkyl,
$R^d$ is $C_1$-$C_4$-alkyl,
$R^e$ is hydrogen or $C_1$-$C_4$-alkyl,
$R^f$ is hydrogen or $C_1$-$C_4$-alkyl, or
$R^e$, $R^f$ together with the nitrogen atom, to which they are bound may form a 5-, 6 or 7-membered, saturated N-bound heterocyclic radical, which may carry as a ring member a further heteroatom selected from O, S and N and which is unsubstituted or may carry 1, 2, 3 or 4 methyl groups,
$R^k$ is $C_1$-$C_4$-alkyl.

According to a highly preferred embodiment, $R^7$ is selected from the group consisting of $C_1$-$C_4$-alkyl, $C_3$-$C_7$-cycloalkyl, $C_1$-$C_4$-haloalkyl, $C_2$-$C_6$-alkenyl, $C_2$-$C_6$-alkynyl and $C_1$-$C_4$-alkoxy-$C_1$-$C_4$-alkyl.

Even more preferably, $R^7$ is selected from the group consisting of methyl, ethyl, propyl, methoxymethyl, methoxyethyl and ethoxymethyl, in particular selected from the group consisting of methyl, ethyl and methoxyethyl.

In this context, the variables R', $R^{11}$, $R^{21}$, $R^{22}$, $R^{23}$, $R^{24}$, $R^{25}$, $R^{26}$, $R^{27}$, $R^{28}$, Z, $Z^1$, $Z^2$, $Z^{2a}$, $R^a$, $R^b$, $R^{1b}$, $R^{2b}$, $R^{2c}$, $R^d$, $R^{2d}$, $R^e$, $R^{2e}$, $R^f$, $R^{2f}$, $R^g$, $R^{2g}$, $R^h$, $R^{2h}$, $R^k$, n and k, independently of each other, preferably have one of the following meanings:

R', $R^{11}$, $R^{21}$ independently of each other are selected from halogen, $C_1$-$C_4$-alkyl, $C_3$-$C_6$-cycloalkyl, $C_3$-$C_6$-halocycloalkyl, $C_1$-$C_4$-haloalkyl, $C_1$-$C_4$-alkoxy, $C_1$-$C_4$-alkoxy-$C_1$-$C_4$-alkyl, $C_1$-$C_4$-alkylthio-$C_1$-$C_4$-alkyl, $C_1$-$C_4$-alkoxy-$C_1$-$C_4$-alkoxy and $C_1$-$C_6$-haloalkyloxy, more preferably from halogen, $C_1$-$C_4$-alkyl, $C_3$-$C_6$-cycloalkyl, $C_1$-$C_4$-haloalkyl and $C_1$-$C_4$-alkoxy.

More preferably R', $R^{11}$, $R^{21}$ independently of each other are selected from the group consisting of halogen, $C_1$-$C_4$-alkyl, $C_3$-$C_6$-cycloalkyl, $C_1$-$C_4$-haloalkyl, $C_1$-$C_4$-alkoxy, $C_1$-$C_4$-alkoxy-$C_1$-$C_4$-alkyl, $C_1$-$C_4$-alkylthio-$C_1$-$C_4$-alkyl and $C_1$-$C_4$-alkoxy-$C_1$-$C_4$-alkoxy; in particular selected from halogen, $C_1$-$C_4$-alkyl, $C_1$-$C_4$-alkoxy, $C_1$-$C_4$-haloalkyl, $C_1$-$C_4$-alkoxy-$C_1$-$C_4$-alkyl and $C_1$-$C_4$-alkoxy-$C_1$-$C_4$-alkoxy; and specifically from Cl, F, Br, methyl, ethyl, methoxy and trifluoromethyl.

$R^{22}$ is selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, $C_3$-$C_6$-cycloalkenyl, $C_3$-$C_6$-halocycloalkyl, $C_3$-$C_6$-cycloalkyl-$C_1$-$C_6$-alkyl, $C_1$-$C_6$-alkoxy-$C_1$-$C_6$-alkyl, $C_3$-$C_6$-cycloalkyl-$C_1$-$C_6$-alkoxy-$C_1$-$C_6$-alkyl, phenyl, phenyl-$C_1$-$C_6$-alkyl, heteroaryl, heteroaryl-$C_1$-$C_6$-alkyl, heterocyclyl, heterocyclyl-$C_1$-$C_6$-alkyl, phenyl-O—$C_1$-$C_6$-alkyl, heteroaryl-O—$C_1$-$C_6$-alkyl, heterocyclyl-O—$C_1$-$C_6$-alkyl, phenyl-N($R^{23}$)—$C_1$-$C_6$-alkyl, heteroaryl-N($R^{23}$)—$C_1$-$C_6$-alkyl, heterocyclyl-N($R^{23}$)—$C_1$-$C_6$-alkyl, phenyl-S(O)$_n$—$C_1$-$C_6$-alkyl, heteroaryl-S(O)$_n$—$C_1$-$C_6$-alkyl, heterocyclyl-S(O)$_n$—$C_1$-$C_6$-alkyl, where the 15 aforementioned radicals are substituted by s residues selected from the group consisting of nitro, halogen, cyano, rhodano, $C_1$-$C_6$-alkyl, $C_1$-$C_6$-haloalkyl, $C_3$-$C_6$-cycloalkyl, C(O)O$R^{23}$, C(O)N($R^{23}$)$_2$, O$R^{23}$, N($R^{23}$)$_2$, S(O)$_n$$R^{24}$, S(O)$_2$O$R^{23}$, S(O)$_2$N($R^{23}$)$_2$ and $R^{23}$O—$C_1$-$C_6$-alkyl, and where heterocyclyl bears 0, 1 or 2 oxo groups;

$R^{23}$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl and phenyl;

$R^{24}$ is selected from the group consisting of $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl and phenyl;

$R^{25}$ is selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, $C_3$-$C_6$-cycloalkenyl, $C_3$-$C_6$-halocycloalkyl, $C_3$-$C_6$-cycloalkyl-$C_1$-$C_6$-alkyl, $C_1$-$C_6$-alkoxy-$C_1$-$C_6$-alkyl, $C_3$-$C_6$-cycloalkyl-$C_1$-$C_6$-alkoxy-$C_1$-$C_6$-alkyl, phenyl, phenyl-$C_1$-$C_6$-alkyl, heteroaryl, heteroaryl-$C_1$-$C_6$-alkyl, heterocyclyl, heterocyclyl-$C_1$-$C_6$-alkyl, phenyl-O—$C_1$-$C_6$-alkyl, heteroaryl-O—$C_1$-$C_6$-alkyl, heterocyclyl-O—$C_1$-$C_6$-alkyl, phenyl-N($R^{23}$)—$C_1$-$C_6$-alkyl, heteroaryl-N($R^{23}$)—$C_1$-$C_6$-alkyl, heterocyclyl-N($R^{23}$)—$C_1$-$C_6$-alkyl, phenyl-S(O)$_n$—$C_1$-$C_6$-alkyl, heteroaryl-S(O)$_n$—$C_1$-$C_6$-alkyl, heterocyclyl-S(O)$_n$—$C_1$-$C_6$-alkyl, where the 15 aforementioned radicals are substituted by s residues selected from the group consisting of nitro, halogen, cyano, rhodano, $C_1$-$C_6$-alkyl, $C_1$-$C_6$-haloalkyl, $C_3$-$C_6$-cycloalkyl, C(O)O$R^{23}$, C(O)N($R^{23}$)$_2$, O$R^{23}$, N($R^{23}$)$_2$, S(O)$_n$$R^{24}$, S(O)$_2$O$R^{23}$, S(O)$_2$N($R^{23}$)$_2$ and $R^{23}$O—$C_1$-$C_6$-alkyl, and where heterocyclyl bears 0, 1 or 2 oxo groups;

$R^{26}$ is $C_1$-$C_6$-alkyl or $C_1$-$C_4$-alkoxy-$C_1$-$C_4$-alkyl;

$R^{27}$ is selected from the group consisting of hydrogen, cyano and $C_1$-$C_4$-haloalkylcarbonyl;

$R^{28}$, $R^{29}$ independently of each other are $C_1$-$C_6$-alkyl, or $R^{28}$, $R^{29}$ together with the sulfur atom, to which they are bound may form a 5- or 6-membered saturated ring, which may carry as a ring member 1 oxygen atom;

Z, $Z^1$, $Z^2$ independently of each other are selected from a covalent bond, methanediyl and ethanediyl, and in particular are a covalent bond.

$Z^{2a}$ is selected from a covalent bond, $C_1$-$C_2$-alkanediyl, O—$C_1$-$C_2$-alkanediyl, $C_1$-$C_2$-alkanediyl-O and $C_1$-$C_2$-alkanediyl-O—$C_1$-$C_2$-alkanediyl; more preferably from a covalent bond, methanediyl, ethanediyl, O-methanediyl, O-ethanediyl, methanediyl-O, and ethanediyl-O; and in particular from a covalent bond, methanediyl and ethanediyl.

$R^b$, $R^{1b}$, $R^{2b}$ independently of each other are selected from $C_1$-$C_6$-alkyl, $C_3$-$C_7$-cycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, phenyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S, where phenyl and heterocyclyl are unsubstituted or substituted by 1, 2 or 3 groups, which are identical or different and selected from the group consisting of halogen, $C_1$-$C_4$-alkyl, $C_1$-$C_2$-haloalkyl and $C_1$-$C_2$-alkoxy.

More preferably $R^b$, $R^{1b}$, $R^{2b}$ independently of each other are selected from the group consisting of $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl, phenyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S.

In particular, $R^b$, $R^{1b}$, $R^{2b}$ independently of each other are selected from $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_3$-$C_6$-cycloalkyl, phenyl and heterocyclyl, where heterocyclyl is a 5- or 6-membered aromatic heterocyclic radical having 1 or 2 nitrogen atoms as ring members.

$R^c$, $R^{2c}$, $R^k$ independently of each other are selected from hydrogen, $C_1$-$C_6$-alkyl, $C_3$-$C_7$-cycloalkyl, which is unsubstituted or partly or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl, benzyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S, where phenyl, benzyl and heterocyclyl are unsubstituted or substituted by 1, 2 or 3 groups, which are identical or different and selected from the group consisting of halogen, $C_1$-$C_4$-alkyl, $C_1$-$C_4$-haloalkyl and $C_1$-$C_4$-alkoxy.

More preferably $R^c$, $R^{2c}$, $R^k$ independently of each other are selected from hydrogen, $C_1$-$C_4$-alkyl, $C_1$-$C_4$-haloalkyl, $C_2$—C-alkenyl, $C_2$—C-haloalkenyl, $C_2$—C-alkynyl, $C_3$-$C_6$-cycloalkyl, phenyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S.

In particular, $R^c$, $R^{2c}$, $R^k$ independently of each other are selected from hydrogen, $C_1$-$C_4$-alkyl, $C_1$-$C_4$-haloalkyl, $C_2$-$C_4$-alkenyl, $C_2$-$C_4$-haloalkenyl, $C_3$-$C_6$-cycloalkyl, phenyl and heterocyclyl, where heterocyclyl is a 5- or 6-membered aromatic heterocyclic radical having 1 or 2 nitrogen atoms as ring members.

$R^d$, $R^{2d}$ independently of each other are selected from $C_1$-$C_6$-alkyl, $C_3$-$C_7$-cycloalkyl, which is unsubstituted or partly or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl.

More preferably $R^d$, $R^{2d}$ independently of each other are selected from $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_1$-$C_4$-alkoxy-$C_1$-$C_4$-alkyl and $C_3$-$C_7$-cycloalkyl, which is unsubstituted or partly or completely halogenated, and in particular selected from $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl and $C_3$-$C_6$-cycloalkyl.

$R^e$, $R^f$, $R^{2e}$, $R^{2f}$ independently of each other are selected from the group consisting of hydrogen, $C_1$-$C_6$-alkyl, $C_3$-$C_7$-cycloalkyl, which is unsubstituted or partially or completely halogenated, $C_1$-$C_6$-haloalkyl, $C_2$-$C_6$-alkenyl, $C_2$-$C_6$-haloalkenyl, $C_1$-$C_4$-alkoxy-$C_1$-$C_4$-alkyl, phenyl and benzyl, where phenyl and benzyl are unsubstituted or substituted by 1, 2 or 3 groups, which are identical or different and selected from the group consisting of halogen, $C_1$-$C_4$-alkyl, $C_1$-$C_4$-haloalkyl and $C_1$-$C_4$-alkoxy, or $R^e$ and $R^f$ or $R^{2e}$ and $R^{2f}$ together with the nitrogen atom, to which they are bound may form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of halogen, $C_1$-$C_4$-alkyl, $C_1$-$C_4$-haloalkyl and $C_1$-$C_4$-alkoxy.

More preferably $R^e$, $R^f$, $R^{2e}$, $R^{2f}$ independently of each other are selected from hydrogen, $C_1$-$C_6$-alkyl, $C_1$-$C_6$-haloalkyl and benzyl, or $R^e$ and $R^f$ or $R^{2e}$ and $R^{2f}$ together with the nitrogen atom, to which they are bound may form a 5- or 6-membered, saturated or unsaturated N-bound heterocyclic radical, which may carry as a ring member a further heteroatom selected from O, S and N and which is unsubstituted or may carry 1, 2 or 3 groups, which are identical or different and selected from the group consisting of halogen, $C_1$-$C_4$-alkyl and $C_1$-$C_4$-haloalkyl.

In particular, $R^e$, $R^f$, $R^{2e}$, $R^{2f}$ independently of each other are selected from hydrogen and $C_1$-$C_4$-alkyl, or $R^e$ and $R^f$ or $R^{2e}$ and $R^{2f}$ together with the nitrogen atom, to which they are bound may form a 5- or 6-membered, saturated N-bound heterocyclic radical, which may carry as a ring member a further heteroatom selected from O, S and N and which is unsubstituted or may carry 1, 2 or 3 methyl groups.

$R^g$, $R^{2g}$ independently of each other are selected from hydrogen, $C_1$-$C_6$-alkyl, $C_3$-$C_7$-cycloalkyl, which is unsubstituted or partly or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-alkylsulfonyl, $C_1$-$C_4$-alkylcarbonyl, phenyl and benzyl.

More preferably $R^g$, $R^{2g}$ independently of each other are selected from hydrogen, $C_1$-$C_6$-alkyl, $C_1$-$C_6$-haloalkyl, $C_2$-$C_6$-alkenyl, $C_2$-$C_6$-haloalkenyl, benzyl, $C_1$-$C_4$-alkoxy-$C_1$-$C_4$-alkyl and $C_3$-$C_7$-cycloalkyl, which is unsubstituted or partly or completely halogenated, and in particular selected from $C_1$-$C_4$-alkyl, $C_1$-$C_4$-haloalkyl, $C_2$-$C_4$-alkenyl, $C_2$-$C_4$-haloalkenyl, benzyl and $C_3$-$C_6$-cycloalkyl.

$R^h$, $R^{2h}$ independently of each other are selected from hydrogen, $C_1$-$C_6$-alkyl, $C_3$-$C_7$-cycloalkyl, which is unsubstituted or partly or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-alkylsulfonyl, $C_1$-$C_4$-alkylcarbonyl, phenyl, benzyl and a radical C(=O)—$R^k$, where $R^k$ is H, $C_1$-$C_4$-alkyl, $C_1$-$C_4$-haloalkyl or phenyl.

More preferably $R^h$, $R^{2h}$ independently of each other are selected from hydrogen, $C_1$-$C_6$-alkyl, $C_1$-$C_6$-haloalkyl, $C_2$-$C_6$-alkenyl, $C_2$-$C_6$-haloalkenyl, benzyl, $C_1$-$C_4$-alkoxy-$C_1$-$C_4$-alkyl and $C_3$-$C_7$-cycloalkyl, which is unsubstituted or partly or completely halogenated, and in particular selected from hydrogen, $C_1$-$C_4$-alkyl, $C_1$-$C_4$-haloalkyl, $C_2$-$C_4$-alkenyl, $C_2$-$C_4$-haloalkenyl, benzyl and $C_3$-$C_6$-cycloalkyl; or $R^g$ and $R^h$ or $R^{2g}$ and $R^{2h}$ together with the nitrogen atom, to which they are bound may form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of =O, halogen, $C_1$-$C_4$-alkyl and $C_1$-$C_4$-haloalkyl and $C_1$-$C_4$-alkoxy;

more preferably $R^g$ and $R^h$ or $R^{2g}$ and $R^{2h}$ together with the nitrogen atom, to which they are bound may form a 5- or 6-membered, saturated or unsaturated N-bound heterocyclic radical, which may carry as a ring member a further heteroatom selected from O, S and N and which is unsubstituted or may carry 1, 2 or 3 groups, which are identical or different and selected from the group consisting of halogen, $C_1$-$C_4$-alkyl and $C_1$-$C_4$-haloalkyl;

and in particular, $R^g$ and $R^h$ or $R^{2g}$ and $R^{2h}$ together with the nitrogen atom, to which they are bound may form a 5- or 6-membered, saturated N-bound heterocyclic radical, which may carry as a ring member a further heteroatom selected from O, S and N and which is unsubstituted or may carry 1, 2 or 3 methyl groups.

n and k independently of each other are 0 or 2, and in particular 2.

s is 0, 1, 2 or 3.

t is 0 or 1.

Particularly preferably, the variables have the following meaning:

$R^{22}$ is selected from hydrogen, $C_1$-$C_6$-alkyl, $C_1$-$C_6$-haloalkyl, $C_3$-$C_6$-cycloalkyl, $C_3$-$C_6$-halocycloalkyl, $C_3$-$C_6$-cycloalkyl-$C_1$-$C_6$-alkyl, $C_1$-$C_6$-alkoxy-$C_1$-$C_6$-alkyl, $C_3$-$C_6$-cycloalkyl-$C_1$-$C_6$-alkoxy-$C_1$-$C_6$-alkyl, phenyl, phenyl-$C_1$-$C_6$-alkyl, heteroaryl, heteroaryl-$C_1$-$C_6$-alkyl, heterocyclyl, heterocyclyl-$C_1$-$C_6$-alkyl, phenyl-O—$C_1$-$C_6$-alkyl, heteroaryl-O—$C_1$-$C_6$-alkyl, heterocyclyl-O—$C_1$-$C_6$-alkyl, where the 9 aforementioned radicals are substituted by s residues selected from the group consisting of nitro, halogen, $C_1$-$C_6$-alkyl, $C_1$-$C_6$-haloalkyl, C(O)O$R^{23}$, C(O)N($R^{23}$)$_2$, O$R^{23}$, N($R^{23}$)$_2$, S(O)$_n$$R^{24}$ and $R^{23}$O—$C_1$-$C_6$-alkyl, and where heterocyclyl bears 0, 1 or 2 oxo groups.

More preferably $R^{22}$ is selected from hydrogen, $C_1$-$C_4$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkyl-$C_1$-$C_2$-alkyl, phenyl and phenyl-$C_1$-$C_2$-alkyl. In particular, $R^{22}$ is hydrogen or $C_1$-$C_4$-alkyl.

$R^{23}$ is selected from hydrogen, $C_1$-$C_4$-alkyl, $C_1$-$C_4$-haloalkyl and $C_3$-$C_6$-cycloalkyl. In particular, $R^{23}$ is hydrogen or $C_1$-$C_4$-alkyl.

$R^{24}$ is selected from $C_1$-$C_4$-alkyl, $C_1$-$C_4$-haloalkyl and $C_3$-$C_6$-cycloalkyl. In particular, $R^{24}$ is $C_1$-$C_4$-alkyl.

$R^{25}$ is selected from $C_1$-$C_6$-alkyl, $C_1$-$C_6$-haloalkyl, $C_3$-$C_6$-cycloalkyl, $C_3$-$C_6$-halocycloalkyl, $C_3$-$C_6$-cycloalkyl-$C_1$-$C_6$-alkyl, $C_1$-$C_6$-alkoxy-$C_1$-$C_6$-alkyl, $C_3$-$C_6$-cycloalkyl-$C_1$-$C_6$-alkoxy-$C_1$-$C_6$-alkyl, phenyl, phenyl-$C_1$-$C_6$-alkyl, heteroaryl, heteroaryl-$C_1$-$C_6$-alkyl, heterocyclyl, heterocyclyl-$C_1$-$C_6$-alkyl, phenyl-O—$C_1$-$C_6$-alkyl, heteroaryl-O—$C_1$-$C_6$-alkyl, heterocyclyl-O—$C_1$-$C_6$-alkyl, where the 9 aforementioned radicals are substituted by s residues selected from the group consisting of nitro, halogen, $C_1$-$C_6$-alkyl, $C_1$-$C_6$-haloalkyl, C(O)O$R^{23}$, C(O)N($R^{23}$)$_2$, O$R^{23}$, $N(R^{23})_2$, $S(O)_nR^{24}$ and $R^{23}O$—$C_1$-$C_6$-alkyl, and where heterocyclyl bears 0, 1 or 2 oxo groups.

More preferably $R^{25}$ is selected from $C_1$-$C_4$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkyl-$C_1$-$C_2$-alkyl, phenyl and phenyl-$C_1$-$C_2$-alkyl. In particular, $R^{25}$ is $C_1$-$C_4$-alkyl.

$R^{26}$ is selected from the group consisting of methyl, ethyl and methoxyethyl.

$R^{27}$ is selected from the group consisting of hydrogen, cyano and trifluoroacetyl.

$R^{28}$ is ethyl and $R^{29}$ is ethyl, or $R^{28}$ and $R^{29}$ together are —$(CH_2)_5$— or —$(CH_2)_2$—O—$(CH_2)_2$—.

s is 0, 1, 2 or 3. In one particular embodiment of the invention, s is 0. In another particular embodiment of the invention, s is 1, 2 or 3.

t is 0 or 1. In one particular embodiment of the invention, t is 0. In another particular embodiment of the invention, t is 1.

According to one embodiment, preferred compounds according to the invention are compounds of formula I, where $R^1$ is selected from the group consisting of halogen, nitro, $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio and $C_1$-$C_4$-alkylsulfonyl; and $R^3$ is selected from the group consisting of hydrogen, halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio and $C_1$-$C_4$-alkylsulfonyl.

According to an even more preferred embodiment, compounds according to the invention are compounds of formula I, where X is $CR^2$ and the variables $R^1$, $R^2$, $R^3$, $R^4$, $R^5$, $R^6$ and $R^7$ have the following meanings:

$R^1$ is selected from the group consisting of halogen, nitro, cyclopropyl, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl and $C_1$-$C_4$-alkyl-$S(O)_2$;

$R^2$ is selected from the group consisting of hydrogen, halogen, $C_1$-$C_4$-alkyl, $C_1$-$C_4$-alkoxy, $C_1$-$C_4$-haloalkoxy, $C_3$-$C_6$-cycloalkyl-$C_1$-$C_2$-alkoxy, $C_1$-$C_2$-alkoxy-$C_1$-$C_2$-alkyl, $C_1$-$C_2$-haloalkoxy-$C_1$-$C_2$-alkyl, $C_1$-$C_2$-alkoxy-$C_1$-$C_2$-alkoxy, $C_1$-$C_4$-alkyl-$S(O)_k$, where k is 0, 1 or 2, $N(C_1$-$C_4$-alkyl)$SO_2(C_1$-$C_4$-alkyl), isoxazolyl and isoxazolinyl, where the last two mentioned radicals may be unsubstituted or carry 1 or 2 radicals selected from halogen and $C_1$-$C_4$-alkyl;

$R^3$ is selected from the group consisting of hydrogen, halogen, cyano, nitro, $C_1$-$C_4$-alkyl, $C_1$-$C_4$-haloalkyl and $C_1$-$C_4$-alkyl-$S(O)_2$;

$R^4$ is selected from the group consisting of hydrogen, cyano, methyl and halogen;

$R^5$ is selected from the group consisting of halogen, $CHF_2$ and $CF_3$;

$R^6$ is selected from the group consisting of $C_1$-$C_4$-alkyl, $C_1$-$C_2$-alkoxy-$C_1$-$C_2$-alkyl, $C_2$-$C_4$-alkenyl, $C_2$-$C_4$-alkynyl, $C_1$-$C_4$-alkoxycarbonyl-$C_1$-$C_4$-alkyl and phenyl-$C_1$-$C_2$-alkyl;

$R^7$ is selected from the group consisting of $C_1$-$C_4$-alkyl and $C_1$-$C_2$-alkoxy-$C_1$-$C_2$-alkyl.

In a preferred embodiment, X is $CR^2$ and the variables $R^1$, $R^2$, $R^3$, $R^4$, $R^5$, $R^6$ and $R^7$ have the following meanings:

$R^1$ is selected from the group consisting of chlorine, nitro, methyl, cyclopropyl, trifluoromethyl, methoxymethyl, $CH_2OCH_2CH_2OCH_3$ and methylsulfonyl;

$R^2$ is selected from the group consisting of hydrogen, chlorine, fluorine, methyl, methoxy, ethoxy, $OCH_2(cyclo$-$C_3H_5)$, $OCHF_2$, $OCH_2CF_3$, $OCH_2CH_2OCH_3$, methoxymethyl, $CH_2OCH_2CF_3$, methylsulfonyl, ethylsulfonyl, methylsulfinyl, ethylsulfinyl, methylsulfanyl, ethylsulfanyl, $NCH_3SO_2CH_3$, 3-isoxazolinyl, 5-methyl-3-isoxazolinyl, 5-isoxazolinyl, 3-methyl-5-isoxazolinyl, 3-isoxazolyl, 5-methyl-3-isoxazolyl, 5-isoxazolyl and 3-methyl-5-isoxazolyl;

$R^3$ is selected from the group consisting of hydrogen, fluorine, chlorine, bromine, cyano, nitro, methyl, trifluoromethyl and methylsulfonyl;

$R^4$ is selected from the group consisting of hydrogen, cyano, methyl, chlorine and fluorine;

$R^5$ is selected from the group consisting of chlorine and fluorine;

$R^6$ is selected from the group consisting of methyl, ethyl, methoxymethyl, ethoxymethyl, prop-2-enyl, prop-2-ynyl, methoxycarbonylmethyl and benzyl;

$R^7$ is selected from the group consisting of methyl, ethyl, propyl, methoxymethyl, methoxyethyl and ethoxymethyl.

In another preferred embodiment of the present invention, X is N and the variables $R^1$, $R^3$, $R^4$, $R^5$, $R^6$ and $R^7$ have the following meanings:

$R^1$ is selected from the group consisting of halogen, nitro, cyclopropyl, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl and $C_1$-$C_4$-alkyl-$S(O)_2$;

$R^3$ is selected from the group consisting of hydrogen, halogen, cyano, nitro, $C_1$-$C_4$-alkyl, $C_1$-$C_4$-haloalkyl and $C_1$-$C_4$-alkyl-$S(O)_2$;

$R^4$ is selected from the group consisting of hydrogen, cyano, methyl and halogen;

$R^5$ is selected from the group consisting of halogen, $CHF_2$ and $CF_3$;

$R^6$ is selected from the group consisting of $C_1$-$C_4$-alkyl, $C_1$-$C_2$-alkoxy-$C_1$-$C_2$-alkyl, $C_2$-$C_4$-alkenyl, $C_2$-$C_4$-alkynyl, $C_1$-$C_4$-alkoxycarbonyl-$C_1$-$C_4$-alkyl and phenyl-$C_1$-$C_2$-alkyl;

$R^7$ is selected from the group consisting of $C_1$-$C_4$-alkyl and $C_1$-$C_2$-alkoxy-$C_1$-$C_2$-alkyl.

In a more preferred embodiment of the present invention, X is N and the variables $R^1$, $R^3$, $R^4$, $R^5$, $R^6$ and $R^7$ have the following meanings:

$R^1$ is selected from the group consisting of chlorine, nitro, methyl, cyclopropyl, trifluoromethyl, methoxymethyl, $CH_2OCH_2CH_2OCH_3$ and methylsulfonyl;

$R^3$ is selected from the group consisting of hydrogen, fluorine, chlorine, bromine, cyano, nitro, methyl, trifluoromethyl and methylsulfonyl;

$R^4$ is selected from the group consisting of hydrogen, cyano, methyl, chlorine and fluorine;

$R^5$ is selected from the group consisting of chlorine and fluorine;

$R^6$ is selected from the group consisting of methyl, ethyl, methoxymethyl, ethoxymethyl, prop-2-enyl, prop-2-ynyl, methoxycarbonylmethyl and benzyl;

$R^7$ is selected from the group consisting of methyl, ethyl, propyl, methoxymethyl, methoxyethyl and ethoxymethyl.

In another preferred embodiment of the present invention, X is $CR^2$ and the variables $R^1$, $R^2$, $R^3$, $R^4$, $R^5$, $R^6$ and $R^7$ have the following meanings:

$R^1$ is selected from the group consisting of chlorine, nitro, methyl, cyclopropyl, trifluoromethyl, methoxymethyl, $CH_2OCH_2CH_2OCH_3$ and methylsulfonyl;

$R^2$ is selected from the group consisting of hydrogen, chlorine, fluorine, methyl, $CH_2OCH_2CF_3$, methylsulfonyl, ethylsulfonyl, methylsulfanyl, ethylsulfanyl, 3-isoxazolinyl, 5-methyl-3-isoxazolinyl, 5-isoxazolinyl, 3-methyl-5-isoxazolinyl, 3-isoxazolyl, 5-methyl-3-isoxazolyl, 5-isoxazolyl and 3-methyl-5-isoxazolyl;

$R^3$ is selected from the group consisting of hydrogen, fluorine, chlorine, cyano, nitro, methyl, trifluoromethyl and methylsulfonyl;

$R^4$ is selected from the group consisting of hydrogen, cyano, methyl, chlorine and fluorine;

$R^5$ is selected from the group consisting of chlorine and fluorine;

$R^6$ is selected from the group consisting of methyl, ethyl, methoxymethyl, ethoxymethyl, prop-2-ynyl and methoxycarbonylmethyl;

$R^7$ is selected from the group consisting of methyl, ethyl and methoxyethyl.

In a still further embodiment of the present invention, X is $CR^2$ and the variable $R^3$ is not hydrogen, in particular X is $CR^2$ and the variables $R^2$ and $R^3$ are not hydrogen.

A second aspect of the present invention relates to a composition comprising at least one compound, an N-oxide or an agriculturally suitable salt thereof, according to the present invention and at least one auxiliary, which is customary for formulating crop protection compounds.

A further aspect of the present invention refers to the use of a compound, an N-oxide or an agriculturally suitable salt thereof, or a composition according to the present invention for controlling unwanted vegetation.

A still further aspect of the present invention relates to a method for controlling unwanted vegetation which comprises allowing a herbicidally effective amount of at least one compound, an N-oxide or an agriculturally suitable salt thereof, or a composition according to the present invention to act on plants, their seed and/or their habitat.

According to another preferred embodiment of the invention, where X is $CR^2$, the variables $R^1$, $R^2$, $R^3$, $R^4$ and $R^5$ together form one of the following substitution patterns on the phenyl ring of compounds of formula I, provided that position 1 is the attachment point of the phenyl ring to the remainder of the molecule:

2-Br-4,6-Cl$_2$, 2,6-Cl$_2$-4-CN, 2,4,6-Cl$_3$, 2,6-Cl$_2$-4-F, 2,6-Cl$_2$-4-CF$_3$, 2,6-Cl$_2$-4-S(O)$_2$CH$_3$, 2-CF$_3$-4-CN-6-Cl, 2-CF$_3$-4,6-Cl$_2$, 2-CF$_3$-4-CF$_3$-6-Cl, 2-CF$_3$-4-S(O)$_2$CH$_3$-6-Cl, 2-CF$_3$-4-F-6-Cl, 2-CH$_3$—CN-6-Cl, 2-CH$_3$-4,6-Cl$_2$, 2-CH$_3$-4-CF$_3$-6-Cl, 2-CH$_3$-4-S(O)$_2$CH$_3$-6-Cl, 2-CH$_3$-4-F-6-Cl, 2-S(O)$_2$CH$_3$-4-CN-6-Cl, 2-S(O)$_2$CH$_3$-4,6-Cl$_2$, 2-S(O)$_2$CH$_3$-4-CF$_3$-6-Cl, 2-S(O)$_2$CH$_3$-4-S(O)$_2$CH$_3$- 6-Cl, 2-S(O)$_2$CH$_3$-4-F-6-Cl, 2-Cl-4-CN-6-F, 2-Cl-4-CF$_3$-6-F, 2-Cl-4-S(O)$_2$CH$_3$-6-F, 2,4-Cl$_2$-6-F, 2-Cl-4,6-F$_2$, 2-CF$_3$-4-CN-6-F, 2-CF$_3$-4-CF$_3$-6-F, 2-CF$_3$-4-S(O)$_2$CH$_3$-6-F, 2-CF$_3$-4-Cl-6-F, 2-CF$_3$-4,6-F$_2$, 2-CH$_3$-4-CN-6-F, 2-CH$_3$-4-CF$_3$-6-F, 2-CH$_3$-4-S(O)$_2$CH$_3$-6-F, 2-CH$_3$-4-Cl-6-F, 2-CH$_3$-4,6- F$_2$, 2-S(O)$_2$CH$_3$-4-CN-6-F, 2-S(O)$_2$CH$_3$-4-CF$_3$-6-F, 2-S(O)$_2$CH$_3$-4-S(O)$_2$CH$_3$-6-F, 2-S(O)$_2$CH$_3$-4- Cl-6-F or 2-S(O)$_2$CH$_3$-4,6-F$_2$.

According to another preferred embodiment of the invention the variables $R^1$, $R^2$, $R^3$, $R^4$ and $R^5$ together form one of the following substitution patterns on the phenyl ring of compounds of formula I, provided that position 1 is the attachment point of the phenyl ring to the remainder of the molecule:

2,6-Cl$_2$-3-(3-isoxazolinyl)-4-CN, 2,4,6-Cl$_3$-3-(3-isoxazolinyl), 2,6-Cl$_2$-3-(3-isoxazolinyl)-4-F, 2,6-Cl$_2$-3-(3-isoxazolinyl)-4-CF$_3$, 2,6-Cl$_2$-3-(3-isoxazolinyl)-4-S(O)$_2$CH$_3$, 2-CF$_3$-3-(3-isoxazolinyl)-4-CN-6-Cl, 2-CF$_3$-3-(3-isoxazolinyl)-4,6-Cl$_2$, 2-CF$_3$-3-(3-isoxazolinyl)-4-CF$_3$-6-Cl, 2-CF$_3$-3-(3-isoxazolinyl)-4-S(O)$_2$CH$_3$-6-Cl, 2-CF$_3$-3-(3-isoxazolinyl)-4-F-6-Cl, 2-CH$_3$-3-(3-isoxazolinyl)-4-CN-6-Cl, 2-CH$_3$-3-(3-isoxazolinyl)-4,6-Cl$_2$, 2-CH$_3$-3-(3-isoxazolinyl)-4-CF$_3$-6-Cl, 2-CH$_3$-3-(3-isoxazolinyl)-4-S(O)$_2$CH$_3$-6-Cl, 2-CH$_3$-3-(3-isoxazolinyl)-4-F-6-Cl, 2-S(O)$_2$CH$_3$-3-(3-isoxazolinyl)-4-CN-6-Cl, 2-S(O)$_2$CH$_3$-3-(3-isoxazolinyl)-4,6-Cl$_2$, 2-S(O)$_2$CH$_3$-3-(3-isoxazolinyl)-4-CF$_3$-6-Cl, 2-S(O)$_2$CH$_3$-3-(3-isoxazolinyl)-4-S(O)$_2$CH$_3$-6-Cl, 2-S(O)$_2$CH$_3$-3-(3-isoxazolinyl)-4-F-6-Cl, 2-Cl-3-(3-isoxazolinyl)-4-CN-6-F, 2-Cl-3-(3-isoxazolinyl)-4-CF$_3$-6-F, 2-Cl-3-(3-isoxazolinyl)-4-S(O)$_2$CH$_3$-6-F, 2,4-Cl$_2$-3-(3-isoxazolinyl)-6-F, 2-Cl-3-(3-isoxazolinyl)-4,6-F$_2$, 2-CF$_3$-3-(3-isoxazolinyl)-4-CN-6-F, 2-CF$_3$-3-(3-isoxazolinyl)-4-CF$_3$-6-F, 2-CF$_3$-3-(3-isoxazolinyl)-4-S(O)$_2$CH$_3$-6-F, 2-CF$_3$-3-(3-isoxazolinyl)-4-Cl-6-F, 2-CF$_3$-3-(3-isoxazolinyl)-4,6-F$_2$, 2-CH$_3$-3-(3-isoxazolinyl)-4-CN-6-F, 2-CH$_3$-3-(3-isoxazolinyl)-4-CF$_3$-6-F, 2-CH$_3$-3-(3-isoxazolinyl)-4-S(O)$_2$CH$_3$-6-F, 2-CH$_3$-3-(3-isoxazolinyl)-4-Cl-6-F, 2-CH$_3$-3-(3-isoxazolinyl)-4,6-F$_2$, 2-S(O)$_2$CH$_3$-3-(3-isoxazolinyl)-4-CN-6-F, 2-S(O)$_2$CH$_3$-3-(3-isoxazolinyl)-4-CF$_3$-6-F, 2-S(O)$_2$CH$_3$-3-(3-isoxazolinyl)-4-S(O)$_2$CH$_3$-6-F, 2-S(O)$_2$CH$_3$-3-(3-isoxazolinyl)-4-Cl-6-F, 2-S(O)$_2$CH$_3$-3-(3-isoxazolinyl)-4,6-F$_2$, 2,6-Cl$_2$-3-(CH$_2$—O—CH$_2$CF$_3$)-4-CN, 2,4,6-Cl$_3$-3-(3-isoxazolinyl), 2,6-Cl$_2$-3-(CH$_2$—O—CH$_2$CF$_3$)-4-F, 2,6-Cl$_2$-3-(CH$_2$—O—CH$_2$CF$_3$)-4-CF$_3$, 2,6-Cl$_2$-3-(CH$_2$—O—CH$_2$CF$_3$)-4-S(O)$_2$CH$_3$, 2-CF$_3$-3-(CH$_2$—O—CH$_2$CF$_3$)-4-CN-6-Cl, 2-CF$_3$-3-(CH$_2$—O—CH$_2$CF$_3$)-4,6-Cl$_2$, 2-CF$_3$-3-(CH$_2$—O—CH$_2$CF$_3$)-4-CF$_3$-6-Cl, 2-CF$_3$-3-(CH$_2$—O—CH$_2$CF$_3$)-4-S(O)$_2$CH$_3$-6-Cl, 2-CF$_3$-3-(CH$_2$—O—CH$_2$CF$_3$)-4-F-6-Cl, 2-CH$_3$-3-(CH$_2$—O—CH$_2$CF$_3$)-4-CN-6-Cl, 2-CH$_3$-3-(CH$_2$—O—CH$_2$CF$_3$)-4,6-Cl$_2$, 2-CH$_3$-3-(CH$_2$—O—CH$_2$CF$_3$)-4-CF$_3$-6-Cl, 2-CH$_3$-3-(CH$_2$—O—CH$_2$CF$_3$)-4-S(O)$_2$CH$_3$-6-Cl, 2-CH$_3$-3-(CH$_2$—O—CH$_2$CF$_3$)-4-F-6-Cl, 2-S(O)$_2$CH$_3$-3-(CH$_2$—O—CH$_2$CF$_3$)-4-CN-6-Cl, 2-S(O)$_2$CH$_3$-3-(CH$_2$—O—CH$_2$CF$_3$)-4,6-Cl$_2$, 2-S(O)$_2$CH$_3$-3-(CH$_2$—O—CH$_2$CF$_3$)-4-CF$_3$- 6- Cl, 2-S(O)$_2$CH$_3$-3-(CH$_2$—O—CH$_2$CF$_3$)-4-S(O)$_2$CH$_3$-6-Cl, 2-S(O)$_2$CH$_3$-3-(CH$_2$—O—CH$_2$CF$_3$)-4-F-6-Cl, 2-Cl-3-(CH$_2$—O—CH$_2$CF$_3$)-4-CN-6-F, 2-Cl-3-(CH$_2$—O—CH$_2$CF$_3$)-4-CF$_3$-6-F, 2-Cl-3-(CH$_2$—O—CH$_2$CF$_3$)- 4-S(O)$_2$CH$_3$-6-F, 2,4-Cl$_2$-3-(CH$_2$—O—CH$_2$CF$_3$)-6-F, 2-Cl-3-(CH$_2$—O—CH$_2$CF$_3$)-4,6-F$_2$, 2-CF$_3$-3-(CH$_2$—O—CH$_2$CF$_3$)-4-CN-6-F, 2-CF$_3$-3-(CH$_2$—O—CH$_2$CF$_3$)-4-CF$_3$-6-F, 2-CF$_3$-3-(CH$_2$—O—CH$_2$CF$_3$)-4-S(O)$_2$CH$_3$-6-F, 2-CF$_3$-3-(CH$_2$—O—CH$_2$CF$_3$)-4,6-F$_2$, 2-CH$_3$-3-(CH$_2$—O—CH$_2$CF$_3$)-4-CN-6-F, 2-CH$_3$-3-(CH$_2$—O—CH$_2$CF$_3$)-4-CF$_3$-6-F, 2-CH$_3$-3-(CH$_2$—O—CH$_2$CF$_3$)-4-S(O)$_2$CH$_3$-6-F, 2-CH$_3$-3-(CH$_2$—O—CH$_2$CF$_3$)-4-Cl-6-F, 2-CH$_3$-3-(CH$_2$—O—CH$_2$CF$_3$)-4,6-F$_2$, 2-S(O)$_2$CH$_3$-3-(CH$_2$—O—CH$_2$CF$_3$)-4-CN-6-F, 2-S(O)$_2$CH$_3$-3-(CH$_2$—O—CH$_2$CF$_3$)-4-CF$_3$-6-F, 2- S(O)$_2$CH$_3$-3-(CH$_2$—O—CH$_2$CF$_3$)-4-S(O)$_2$CH$_3$-6-F, 2-S(O)$_2$CH$_3$-3-(CH$_2$—O—CH$_2$CF$_3$)-4-Cl-6-F or 2-S(O)$_2$CH$_3$-3-(CH$_2$—O—CH$_2$CF$_3$)-4,6-F$_2$.

Examples of preferred compounds I.A, where X is N, are the individual compounds compiled in Tables 1 to 20 below. Moreover, the meanings mentioned below for the individual variables in the Tables are per se, independently of the combination in which they are mentioned, a particularly preferred embodiment of the substituents in question.

I.A

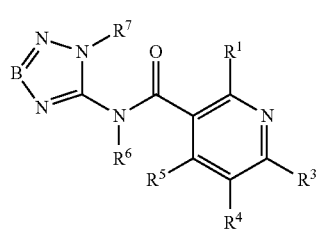

Table 1 Compounds of formula I.A (I.A-1.1-I.A-1.2304) in which B is CH, $R^4$ is H and $R^5$ is F and the combination of $R^1$, $R^3$, $R^6$ and $R^7$ for a compound corresponds in each case to one row of Table A;

Table 2 Compounds of formula I.A (I.A-2.1-I.A-2.2304) in which B is CH, $R^4$ is H and $R^5$ is Cl and the combination of $R^1$, $R^3$, $R^6$ and $R^7$ for a compound corresponds in each case to one row of Table A;

Table 3 Compounds of formula I.A (I.A-3.1-I.A-3.2304) in which B is CH, $R^4$ is F and $R^5$ is F and the combination of $R^1$, $R^3$, $R^6$ and $R^7$ for a compound corresponds in each case to one row of Table A;

Table 4 Compounds of formula I.A (I.A-4.1-I.A-4.2304) in which B is CH, $R^4$ is F and $R^5$ is Cl and the combination of $R^1$, $R^3$, $R^6$ and $R^7$ for a compound corresponds in each case to one row of Table A;

Table 5 Compounds of formula I.A (I.A-5.1-I.A-5.2304) in which B is CH, $R^4$ is Cl and $R^5$ is F and the combination of $R^1$, $R^3$, $R^6$ and $R^7$ for a compound corresponds in each case to one row of Table A;

Table 6 Compounds of formula I.A (I.A-6.1-I.A-6.2304) in which B is CH, $R^4$ is Cl and $R^5$ is Cl and the combination of $R^1$, $R^3$, $R^6$ and $R^7$ for a compound corresponds in each case to one row of Table A;

Table 7 Compounds of formula I.A (I.A-7.1-I.A-7.2304) in which B is CH, $R^4$ is CN and $R^5$ is F and the combination of $R^1$, $R^3$, $R^6$ and $R^7$ for a compound corresponds in each case to one row of Table A;

Table 8 Compounds of formula I.A (I.A-8.1-I.A-8.2304) in which B is CH, $R^4$ is CN and $R^5$ is Cl and the combination of $R^1$, $R^3$, $R^6$ and $R^7$ for a compound corresponds in each case to one row of Table A;

Table 9 Compounds of formula I.A (I.A-9.1-I.A-9.2304) in which B is CH, $R^4$ is $CH_3$ and $R^5$ is F and the combination of $R^1$, $R^3$, $R^6$ and $R^7$ for a compound corresponds in each case to one row of Table A;

Table 10 Compounds of formula I.A (I.A-10.1-I.A-10.2304) in which B is CH, $R^4$ is $CH_3$ and $R^5$ is Cl and the combination of $R^1$, $R^3$, $R^6$ and $R^7$ for a compound corresponds in each case to one row of Table A;

Table 11 Compounds of formula I.A (I.A-11.1-I.A-11.2304) in which B is N, $R^4$ is H and $R^5$ is F and the combination of $R^1$, $R^3$, $R^6$ and $R^7$ for a compound corresponds in each case to one row of Table A;

Table 12 Compounds of formula I.A (I.A-12.1-I.A-12.2304) in which B is N, $R^4$ is H and $R^5$ is Cl and the combination of $R^1$, $R^3$, $R^6$ and $R^7$ for a compound corresponds in each case to one row of Table A;

Table 13 Compounds of formula I.A (I.A-13.1-I.A-13.2304) in which B is N, $R^4$ is F and $R^5$ is F and the combination of $R^1$, $R^3$, $R^6$ and $R^7$ for a compound corresponds in each case to one row of Table A;

Table 14 Compounds of formula I.A (I.A-14.1-I.A-14.2304) in which B is N, $R^4$ is F and $R^5$ is Cl and the combination of $R^1$, $R^3$, $R^6$ and $R^7$ for a compound corresponds in each case to one row of Table A;

Table 15 Compounds of formula I.A (I.A-15.1-I.A-15.2304) in which B is N, $R^4$ is Cl and $R^5$ is F and the combination of $R^1$, $R^3$, $R^6$ and $R^7$ for a compound corresponds in each case to one row of Table A;

Table 16 Compounds of formula I.A (I.A-16.1-I.A-16.2304) in which B is N, $R^4$ is Cl and $R^5$ is Cl and the combination of $R^1$, $R^3$, $R^6$ and $R^7$ for a compound corresponds in each case to one row of Table A;

Table 17 Compounds of formula I.A (I.A-17.1-I.A-17.2304) in which B is N, $R^4$ is CN and $R^5$ is F and the combination of $R^1$, $R^3$, $R^6$ and $R^7$ for a compound corresponds in each case to one row of Table A;

Table 18 Compounds of formula I.A (I.A-18.1-I.A-18.2304) in which B is N, $R^4$ is CN and $R^5$ is Cl and the combination of $R^1$, $R^3$, $R^6$ and $R^7$ for a compound corresponds in each case to one row of Table A;

Table 19 Compounds of formula I.A (I.A-19.1-I.A-19.2304) in which B is N, $R^4$ is $CH_3$ and $R^5$ is F and the combination of $R^1$, $R^3$, $R^6$ and $R^7$ for a compound corresponds in each case to one row of Table A;

Table 20 Compounds of formula I.A (I.A-20.1-I.A-20.2304) in which B is N, $R^4$ is $CH_3$ and $R^5$ is Cl and the combination of $R^1$, $R^3$, $R^6$ and $R^7$ for a compound corresponds in each case to one row of Table A;

TABLE A

|  | $R^1$ | $R^3$ | $R^6$ | $R^7$ |
|---|---|---|---|---|
| A-1 | Cl | H | $CH_3$ | $CH_3$ |
| A-2 | Cl | H | $CH_3$ | $CH_2CH_3$ |
| A-3 | Cl | H | $CH_3$ | $CH_2CH_2CH_3$ |
| A-4 | Cl | H | $CH_3$ | $CH_2CH_2OCH_3$ |
| A-5 | Cl | H | $CH_2CH_3$ | $CH_3$ |
| A-6 | Cl | H | $CH_2CH_3$ | $CH_2CH_3$ |
| A-7 | Cl | H | $CH_2CH_3$ | $CH_2CH_2CH_3$ |
| A-8 | Cl | H | $CH_2CH_3$ | $CH_2CH_2OCH_3$ |
| A-9 | Cl | H | $CH_2OCH_3$ | $CH_3$ |
| A-10 | Cl | H | $CH_2OCH_3$ | $CH_2CH_3$ |
| A-11 | Cl | H | $CH_2OCH_3$ | $CH_2CH_2CH_3$ |
| A-12 | Cl | H | $CH_2OCH_3$ | $CH_2CH_2OCH_3$ |
| A-13 | Cl | H | $CH_2OCH_2CH_3$ | $CH_3$ |
| A-14 | Cl | H | $CH_2OCH_2CH_3$ | $CH_2CH_3$ |
| A-15 | Cl | H | $CH_2OCH_2CH_3$ | $CH_2CH_2CH_3$ |
| A-16 | Cl | H | $CH_2OCH_2CH_3$ | $CH_2CH_2OCH_3$ |
| A-17 | Cl | H | $CH_2(CO)OCH_3$ | $CH_3$ |
| A-18 | Cl | H | $CH_2(CO)OCH_3$ | $CH_2CH_3$ |
| A-19 | Cl | H | $CH_2(CO)OCH_3$ | $CH_2CH_2CH_3$ |
| A-20 | Cl | H | $CH_2(CO)OCH_3$ | $CH_2CH_2OCH_3$ |
| A-21 | Cl | H | $CH_2CHCH_2$ | $CH_3$ |
| A-22 | Cl | H | $CH_2CHCH_2$ | $CH_2CH_3$ |
| A-23 | Cl | H | $CH_2CHCH_2$ | $CH_2CH_2CH_3$ |
| A-24 | Cl | H | $CH_2CHCH_2$ | $CH_2CH_2OCH_3$ |
| A-25 | Cl | H | $CH_2CCH$ | $CH_3$ |
| A-26 | Cl | H | $CH_2CCH$ | $CH_2CH_3$ |
| A-27 | Cl | H | $CH_2CCH$ | $CH_2CH_2CH_3$ |
| A-28 | Cl | H | $CH_2CCH$ | $CH_2CH_2OCH_3$ |
| A-29 | Cl | H | $CH_2C_6H_5$ | $CH_3$ |

TABLE A-continued

| | $R^1$ | $R^3$ | $R^6$ | $R^7$ |
|---|---|---|---|---|
| A-30 | Cl | H | $CH_2C_6H_5$ | $CH_2CH_3$ |
| A-31 | Cl | H | $CH_2C_6H_5$ | $CH_2CH_2CH_3$ |
| A-32 | Cl | H | $CH_2C_6H_5$ | $CH_2CH_2OCH_3$ |
| A-33 | Cl | F | $CH_3$ | $CH_3$ |
| A-34 | Cl | F | $CH_3$ | $CH_2CH_3$ |
| A-35 | Cl | F | $CH_3$ | $CH_2CH_2CH_3$ |
| A-36 | Cl | F | $CH_3$ | $CH_2CH_2OCH_3$ |
| A-37 | Cl | F | $CH_2CH_3$ | $CH_3$ |
| A-38 | Cl | F | $CH_2CH_3$ | $CH_2CH_3$ |
| A-39 | Cl | F | $CH_2CH_3$ | $CH_2CH_2CH_3$ |
| A-40 | Cl | F | $CH_2CH_3$ | $CH_2CH_2OCH_3$ |
| A-41 | Cl | F | $CH_2OCH_3$ | $CH_3$ |
| A-42 | Cl | F | $CH_2OCH_3$ | $CH_2CH_3$ |
| A-43 | Cl | F | $CH_2OCH_3$ | $CH_2CH_2CH_3$ |
| A-44 | Cl | F | $CH_2OCH_3$ | $CH_2CH_2OCH_3$ |
| A-45 | Cl | F | $CH_2OCH_2CH_3$ | $CH_3$ |
| A-46 | Cl | F | $CH_2OCH_2CH_3$ | $CH_2CH_3$ |
| A-47 | Cl | F | $CH_2OCH_2CH_3$ | $CH_2CH_2CH_3$ |
| A-48 | Cl | F | $CH_2OCH_2CH_3$ | $CH_2CH_2OCH_3$ |
| A-49 | Cl | F | $CH_2(CO)OCH_3$ | $CH_3$ |
| A-50 | Cl | F | $CH_2(CO)OCH_3$ | $CH_2CH_3$ |
| A-51 | Cl | F | $CH_2(CO)OCH_3$ | $CH_2CH_2CH_3$ |
| A-52 | Cl | F | $CH_2(CO)OCH_3$ | $CH_2CH_2OCH_3$ |
| A-53 | Cl | F | $CH_2CHCH_2$ | $CH_3$ |
| A-54 | Cl | F | $CH_2CHCH_2$ | $CH_2CH_3$ |
| A-55 | Cl | F | $CH_2CHCH_2$ | $CH_2CH_2CH_3$ |
| A-56 | Cl | F | $CH_2CHCH_2$ | $CH_2CH_2OCH_3$ |
| A-57 | Cl | F | $CH_2CCH$ | $CH_3$ |
| A-58 | Cl | F | $CH_2CCH$ | $CH_2CH_3$ |
| A-59 | Cl | F | $CH_2CCH$ | $CH_2CH_2CH_3$ |
| A-60 | Cl | F | $CH_2CCH$ | $CH_2CH_2OCH_3$ |
| A-61 | Cl | F | $CH_2C_6H_5$ | $CH_3$ |
| A-62 | Cl | F | $CH_2C_6H_5$ | $CH_2CH_3$ |
| A-63 | Cl | F | $CH_2C_6H_5$ | $CH_2CH_2CH_3$ |
| A-64 | Cl | F | $CH_2C_6H_5$ | $CH_2CH_2OCH_3$ |
| A-65 | Cl | Cl | $CH_3$ | $CH_3$ |
| A-66 | Cl | Cl | $CH_3$ | $CH_2CH_3$ |
| A-67 | Cl | Cl | $CH_3$ | $CH_2CH_2CH_3$ |
| A-68 | Cl | Cl | $CH_3$ | $CH_2CH_2OCH_3$ |
| A-69 | Cl | Cl | $CH_2CH_3$ | $CH_3$ |
| A-70 | Cl | Cl | $CH_2CH_3$ | $CH_2CH_3$ |
| A-71 | Cl | Cl | $CH_2CH_3$ | $CH_2CH_2CH_3$ |
| A-72 | Cl | Cl | $CH_2CH_3$ | $CH_2CH_2OCH_3$ |
| A-73 | Cl | Cl | $CH_2OCH_3$ | $CH_3$ |
| A-74 | Cl | Cl | $CH_2OCH_3$ | $CH_2CH_3$ |
| A-75 | Cl | Cl | $CH_2OCH_3$ | $CH_2CH_2CH_3$ |
| A-76 | Cl | Cl | $CH_2OCH_3$ | $CH_2CH_2OCH_3$ |
| A-77 | Cl | Cl | $CH_2OCH_2CH_3$ | $CH_3$ |
| A-78 | Cl | Cl | $CH_2OCH_2CH_3$ | $CH_2CH_3$ |
| A-79 | Cl | Cl | $CH_2OCH_2CH_3$ | $CH_2CH_2CH_3$ |
| A-80 | Cl | Cl | $CH_2OCH_2CH_3$ | $CH_2CH_2OCH_3$ |
| A-81 | Cl | Cl | $CH_2(CO)OCH_3$ | $CH_3$ |
| A-82 | Cl | Cl | $CH_2(CO)OCH_3$ | $CH_2CH_3$ |
| A-83 | Cl | Cl | $CH_2(CO)OCH_3$ | $CH_2CH_2CH_3$ |
| A-84 | Cl | Cl | $CH_2(CO)OCH_3$ | $CH_2CH_2OCH_3$ |
| A-85 | Cl | Cl | $CH_2CHCH_2$ | $CH_3$ |
| A-86 | Cl | Cl | $CH_2CHCH_2$ | $CH_2CH_3$ |
| A-87 | Cl | Cl | $CH_2CHCH_2$ | $CH_2CH_2CH_3$ |
| A-88 | Cl | Cl | $CH_2CHCH_2$ | $CH_2CH_2OCH_3$ |
| A-89 | Cl | Cl | $CH_2CCH$ | $CH_3$ |
| A-90 | Cl | Cl | $CH_2CCH$ | $CH_2CH_3$ |
| A-91 | Cl | Cl | $CH_2CCH$ | $CH_2CH_2CH_3$ |
| A-92 | Cl | Cl | $CH_2CCH$ | $CH_2CH_2OCH_3$ |
| A-93 | Cl | Cl | $CH_2C_6H_5$ | $CH_3$ |
| A-94 | Cl | Cl | $CH_2C_6H_5$ | $CH_2CH_3$ |
| A-95 | Cl | Cl | $CH_2C_6H_5$ | $CH_2CH_2CH_3$ |
| A-96 | Cl | Cl | $CH_2C_6H_5$ | $CH_2CH_2OCH_3$ |
| A-97 | Cl | Br | $CH_3$ | $CH_3$ |
| A-98 | Cl | Br | $CH_3$ | $CH_2CH_3$ |
| A-99 | Cl | Br | $CH_3$ | $CH_2CH_2CH_3$ |
| A-100 | Cl | Br | $CH_3$ | $CH_2CH_2OCH_3$ |
| A-101 | Cl | Br | $CH_2CH_3$ | $CH_3$ |
| A-102 | Cl | Br | $CH_2CH_3$ | $CH_2CH_3$ |
| A-103 | Cl | Br | $CH_2CH_3$ | $CH_2CH_2CH_3$ |
| A-104 | Cl | Br | $CH_2CH_3$ | $CH_2CH_2OCH_3$ |
| A-105 | Cl | Br | $CH_2OCH_3$ | $CH_3$ |
| A-106 | Cl | Br | $CH_2OCH_3$ | $CH_2CH_3$ |
| A-107 | Cl | Br | $CH_2OCH_3$ | $CH_2CH_2CH_3$ |

TABLE A-continued

|  | R¹ | R³ | R⁶ | R⁷ |
|---|---|---|---|---|
| A-108 | Cl | Br | CH₂OCH₃ | CH₂CH₂OCH₃ |
| A-109 | Cl | Br | CH₂OCH₂CH₃ | CH₃ |
| A-110 | Cl | Br | CH₂OCH₂CH₃ | CH₂CH₃ |
| A-111 | Cl | Br | CH₂OCH₂CH₃ | CH₂CH₂CH₃ |
| A-112 | Cl | Br | CH₂OCH₂CH₃ | CH₂CH₂OCH₃ |
| A-113 | Cl | Br | CH₂(CO)OCH₃ | CH₃ |
| A-114 | Cl | Br | CH₂(CO)OCH₃ | CH₂CH₃ |
| A-115 | Cl | Br | CH₂(CO)OCH₃ | CH₂CH₂CH₃ |
| A-116 | Cl | Br | CH₂(CO)OCH₃ | CH₂CH₂OCH₃ |
| A-117 | Cl | Br | CH₂CHCH₂ | CH₃ |
| A-118 | Cl | Br | CH₂CHCH₂ | CH₂CH₃ |
| A-119 | Cl | Br | CH₂CHCH₂ | CH₂CH₂CH₃ |
| A-120 | Cl | Br | CH₂CHCH₂ | CH₂CH₂OCH₃ |
| A-121 | Cl | Br | CH₂CCH | CH₃ |
| A-122 | Cl | Br | CH₂CCH | CH₂CH₃ |
| A-123 | Cl | Br | CH₂CCH | CH₂CH₂CH₃ |
| A-124 | Cl | Br | CH₂CCH | CH₂CH₂OCH₃ |
| A-125 | Cl | Br | CH₂C₆H₅ | CH₃ |
| A-126 | Cl | Br | CH₂C₆H₅ | CH₂CH₃ |
| A-127 | Cl | Br | CH₂C₆H₅ | CH₂CH₂CH₃ |
| A-128 | Cl | Br | CH₂C₆H₅ | CH₂CH₂OCH₃ |
| A-129 | Cl | CN | CH₃ | CH₃ |
| A-130 | Cl | CN | CH₃ | CH₂CH₃ |
| A-131 | Cl | CN | CH₃ | CH₂CH₂CH₃ |
| A-132 | Cl | CN | CH₃ | CH₂CH₂OCH₃ |
| A-133 | Cl | CN | CH₂CH₃ | CH₃ |
| A-134 | Cl | CN | CH₂CH₃ | CH₂CH₃ |
| A-135 | Cl | CN | CH₂CH₃ | CH₂CH₂CH₃ |
| A-136 | Cl | CN | CH₂CH₃ | CH₂CH₂OCH₃ |
| A-137 | Cl | CN | CH₂OCH₃ | CH₃ |
| A-138 | Cl | CN | CH₂OCH₃ | CH₂CH₃ |
| A-139 | Cl | CN | CH₂OCH₃ | CH₂CH₂CH₃ |
| A-140 | Cl | CN | CH₂OCH₃ | CH₂CH₂OCH₃ |
| A-141 | Cl | CN | CH₂OCH₂CH₃ | CH₃ |
| A-142 | Cl | CN | CH₂OCH₂CH₃ | CH₂CH₃ |
| A-143 | Cl | CN | CH₂OCH₂CH₃ | CH₂CH₂CH₃ |
| A-144 | Cl | CN | CH₂OCH₂CH₃ | CH₂CH₂OCH₃ |
| A-145 | Cl | CN | CH₂(CO)OCH₃ | CH₃ |
| A-146 | Cl | CN | CH₂(CO)OCH₃ | CH₂CH₃ |
| A-147 | Cl | CN | CH₂(CO)OCH₃ | CH₂CH₂CH₃ |
| A-148 | Cl | CN | CH₂(CO)OCH₃ | CH₂CH₂OCH₃ |
| A-149 | Cl | CN | CH₂CHCH₂ | CH₃ |
| A-150 | Cl | CN | CH₂CHCH₂ | CH₂CH₃ |
| A-151 | Cl | CN | CH₂CHCH₂ | CH₂CH₂CH₃ |
| A-152 | Cl | CN | CH₂CHCH₂ | CH₂CH₂OCH₃ |
| A-153 | Cl | CN | CH₂CCH | CH₃ |
| A-154 | Cl | CN | CH₂CCH | CH₂CH₃ |
| A-155 | Cl | CN | CH₂CCH | CH₂CH₂CH₃ |
| A-156 | Cl | CN | CH₂CCH | CH₂CH₂OCH₃ |
| A-157 | Cl | CN | CH₂C₆H₅ | CH₃ |
| A-158 | Cl | CN | CH₂C₆H₅ | CH₂CH₃ |
| A-159 | Cl | CN | CH₂C₆H₅ | CH₂CH₂CH₃ |
| A-160 | Cl | CN | CH₂C₆H₅ | CH₂CH₂OCH₃ |
| A-161 | Cl | CH₃ | CH₃ | CH₃ |
| A-162 | Cl | CH₃ | CH₃ | CH₂CH₃ |
| A-163 | Cl | CH₃ | CH₃ | CH₂CH₂CH₃ |
| A-164 | Cl | CH₃ | CH₃ | CH₂CH₂OCH₃ |
| A-165 | Cl | CH₃ | CH₂CH₃ | CH₃ |
| A-166 | Cl | CH₃ | CH₂CH₃ | CH₂CH₃ |
| A-167 | Cl | CH₃ | CH₂CH₃ | CH₂CH₂CH₃ |
| A-168 | Cl | CH₃ | CH₂CH₃ | CH₂CH₂OCH₃ |
| A-169 | Cl | CH₃ | CH₂OCH₃ | CH₃ |
| A-170 | Cl | CH₃ | CH₂OCH₃ | CH₂CH₃ |
| A-171 | Cl | CH₃ | CH₂OCH₃ | CH₂CH₂CH₃ |
| A-172 | Cl | CH₃ | CH₂OCH₃ | CH₂CH₂OCH₃ |
| A-173 | Cl | CH₃ | CH₂OCH₂CH₃ | CH₃ |
| A-174 | Cl | CH₃ | CH₂OCH₂CH₃ | CH₂CH₃ |
| A-175 | Cl | CH₃ | CH₂OCH₂CH₃ | CH₂CH₂CH₃ |
| A-176 | Cl | CH₃ | CH₂OCH₂CH₃ | CH₂CH₂OCH₃ |
| A-177 | Cl | CH₃ | CH₂(CO)OCH₃ | CH₃ |
| A-178 | Cl | CH₃ | CH₂(CO)OCH₃ | CH₂CH₃ |
| A-179 | Cl | CH₃ | CH₂(CO)OCH₃ | CH₂CH₂CH₃ |
| A-180 | Cl | CH₃ | CH₂(CO)OCH₃ | CH₂CH₂OCH₃ |
| A-181 | Cl | CH₃ | CH₂CHCH₂ | CH₃ |
| A-182 | Cl | CH₃ | CH₂CHCH₂ | CH₂CH₃ |
| A-183 | Cl | CH₃ | CH₂CHCH₂ | CH₂CH₂CH₃ |
| A-184 | Cl | CH₃ | CH₂CHCH₂ | CH₂CH₂OCH₃ |
| A-185 | Cl | CH₃ | CH₂CCH | CH₃ |

TABLE A-continued

|  | R¹ | R³ | R⁶ | R⁷ |
|---|---|---|---|---|
| A-186 | Cl | CH₃ | CH₂CCH | CH₂CH₃ |
| A-187 | Cl | CH₃ | CH₂CCH | CH₂CH₂CH₃ |
| A-188 | Cl | CH₃ | CH₂CCH | CH₂CH₂OCH₃ |
| A-189 | Cl | CH₃ | CH₂C₆H₅ | CH₃ |
| A-190 | Cl | CH₃ | CH₂C₆H₅ | CH₂CH₃ |
| A-191 | Cl | CH₃ | CH₂C₆H₅ | CH₂CH₂CH₃ |
| A-192 | Cl | CH₃ | CH₂C₆H₅ | CH₂CH₂OCH₃ |
| A-193 | Cl | CF₃ | CH₃ | CH₃ |
| A-194 | Cl | CF₃ | CH₃ | CH₂CH₃ |
| A-195 | Cl | CF₃ | CH₃ | CH₂CH₂CH₃ |
| A-196 | Cl | CF₃ | CH₃ | CH₂CH₂OCH₃ |
| A-197 | Cl | CF₃ | CH₂CH₃ | CH₃ |
| A-198 | Cl | CF₃ | CH₂CH₃ | CH₂CH₃ |
| A-199 | Cl | CF₃ | CH₂CH₃ | CH₂CH₂CH₃ |
| A-200 | Cl | CF₃ | CH₂CH₃ | CH₂CH₂OCH₃ |
| A-201 | Cl | CF₃ | CH₂OCH₃ | CH₃ |
| A-202 | Cl | CF₃ | CH₂OCH₃ | CH₂CH₃ |
| A-203 | Cl | CF₃ | CH₂OCH₃ | CH₂CH₂CH₃ |
| A-204 | Cl | CF₃ | CH₂OCH₃ | CH₂CH₂OCH₃ |
| A-205 | Cl | CF₃ | CH₂OCH₂CH₃ | CH₃ |
| A-206 | Cl | CF₃ | CH₂OCH₂CH₃ | CH₂CH₃ |
| A-207 | Cl | CF₃ | CH₂OCH₂CH₃ | CH₂CH₂CH₃ |
| A-208 | Cl | CF₃ | CH₂OCH₂CH₃ | CH₂CH₂OCH₃ |
| A-209 | Cl | CF₃ | CH₂(CO)OCH₃ | CH₃ |
| A-210 | Cl | CF₃ | CH₂(CO)OCH₃ | CH₂CH₃ |
| A-211 | Cl | CF₃ | CH₂(CO)OCH₃ | CH₂CH₂CH₃ |
| A-212 | Cl | CF₃ | CH₂(CO)OCH₃ | CH₂CH₂OCH₃ |
| A-213 | Cl | CF₃ | CH₂CHCH₂ | CH₃ |
| A-214 | Cl | CF₃ | CH₂CHCH₂ | CH₂CH₃ |
| A-215 | Cl | CF₃ | CH₂CHCH₂ | CH₂CH₂CH₃ |
| A-216 | Cl | CF₃ | CH₂CHCH₂ | CH₂CH₂OCH₃ |
| A-217 | Cl | CF₃ | CH₂CCH | CH₃ |
| A-218 | Cl | CF₃ | CH₂CCH | CH₂CH₃ |
| A-219 | Cl | CF₃ | CH₂CCH | CH₂CH₂CH₃ |
| A-220 | Cl | CF₃ | CH₂CCH | CH₂CH₂OCH₃ |
| A-221 | Cl | CF₃ | CH₂C₆H₅ | CH₃ |
| A-222 | Cl | CF₃ | CH₂C₆H₅ | CH₂CH₃ |
| A-223 | Cl | CF₃ | CH₂C₆H₅ | CH₂CH₂CH₃ |
| A-224 | Cl | CF₃ | CH₂C₆H₅ | CH₂CH₂OCH₃ |
| A-225 | Cl | SO₂CH₃ | CH₃ | CH₃ |
| A-226 | Cl | SO₂CH₃ | CH₃ | CH₂CH₃ |
| A-227 | Cl | SO₂CH₃ | CH₃ | CH₂CH₂CH₃ |
| A-228 | Cl | SO₂CH₃ | CH₃ | CH₂CH₂OCH₃ |
| A-229 | Cl | SO₂CH₃ | CH₂CH₃ | CH₃ |
| A-230 | Cl | SO₂CH₃ | CH₂CH₃ | CH₂CH₃ |
| A-231 | Cl | SO₂CH₃ | CH₂CH₃ | CH₂CH₂CH₃ |
| A-232 | Cl | SO₂CH₃ | CH₂CH₃ | CH₂CH₂OCH₃ |
| A-233 | Cl | SO₂CH₃ | CH₂OCH₃ | CH₃ |
| A-234 | Cl | SO₂CH₃ | CH₂OCH₃ | CH₂CH₃ |
| A-235 | Cl | SO₂CH₃ | CH₂OCH₃ | CH₂CH₂CH₃ |
| A-236 | Cl | SO₂CH₃ | CH₂OCH₃ | CH₂CH₂OCH₃ |
| A-237 | Cl | SO₂CH₃ | CH₂OCH₂CH₃ | CH₃ |
| A-238 | Cl | SO₂CH₃ | CH₂OCH₂CH₃ | CH₂CH₃ |
| A-239 | Cl | SO₂CH₃ | CH₂OCH₂CH₃ | CH₂CH₂CH₃ |
| A-240 | Cl | SO₂CH₃ | CH₂OCH₂CH₃ | CH₂CH₂OCH₃ |
| A-241 | Cl | SO₂CH₃ | CH₂(CO)OCH₃ | CH₃ |
| A-242 | Cl | SO₂CH₃ | CH₂(CO)OCH₃ | CH₂CH₃ |
| A-243 | Cl | SO₂CH₃ | CH₂(CO)OCH₃ | CH₂CH₂CH₃ |
| A-244 | Cl | SO₂CH₃ | CH₂(CO)OCH₃ | CH₂CH₂OCH₃ |
| A-245 | Cl | SO₂CH₃ | CH₂CHCH₂ | CH₃ |
| A-246 | Cl | SO₂CH₃ | CH₂CHCH₂ | CH₂CH₃ |
| A-247 | Cl | SO₂CH₃ | CH₂CHCH₂ | CH₂CH₂CH₃ |
| A-248 | Cl | SO₂CH₃ | CH₂CHCH₂ | CH₂CH₂OCH₃ |
| A-249 | Cl | SO₂CH₃ | CH₂CCH | CH₃ |
| A-250 | Cl | SO₂CH₃ | CH₂CCH | CH₂CH₃ |
| A-251 | Cl | SO₂CH₃ | CH₂CCH | CH₂CH₂CH₃ |
| A-252 | Cl | SO₂CH₃ | CH₂CCH | CH₂CH₂OCH₃ |
| A-253 | Cl | SO₂CH₃ | CH₂C₆H₅ | CH₃ |
| A-254 | Cl | SO₂CH₃ | CH₂C₆H₅ | CH₂CH₃ |
| A-255 | Cl | SO₂CH₃ | CH₂C₆H₅ | CH₂CH₂CH₃ |
| A-256 | Cl | SO₂CH₃ | CH₂C₆H₅ | CH₂CH₂OCH₃ |
| A-257 | Cl | NO₂ | CH₃ | CH₃ |
| A-258 | Cl | NO₂ | CH₃ | CH₂CH₃ |
| A-259 | Cl | NO₂ | CH₃ | CH₂CH₂CH₃ |
| A-260 | Cl | NO₂ | CH₃ | CH₂CH₂OCH₃ |
| A-261 | Cl | NO₂ | CH₂CH₃ | CH₃ |
| A-262 | Cl | NO₂ | CH₂CH₃ | CH₂CH₃ |
| A-263 | Cl | NO₂ | CH₂CH₃ | CH₂CH₂CH₃ |

TABLE A-continued

|  | R¹ | R³ | R⁶ | R⁷ |
|---|---|---|---|---|
| A-264 | Cl | NO₂ | CH₂CH₃ | CH₂CH₂OCH₃ |
| A-265 | Cl | NO₂ | CH₂OCH₃ | CH₃ |
| A-266 | Cl | NO₂ | CH₂OCH₃ | CH₂CH₃ |
| A-267 | Cl | NO₂ | CH₂OCH₃ | CH₂CH₂CH₃ |
| A-268 | Cl | NO₂ | CH₂OCH₃ | CH₂CH₂OCH₃ |
| A-269 | Cl | NO₂ | CH₂OCH₂CH₃ | CH₃ |
| A-270 | Cl | NO₂ | CH₂OCH₂CH₃ | CH₂CH₃ |
| A-271 | Cl | NO₂ | CH₂OCH₂CH₃ | CH₂CH₂CH₃ |
| A-272 | Cl | NO₂ | CH₂OCH₂CH₃ | CH₂CH₂OCH₃ |
| A-273 | Cl | NO₂ | CH₂(CO)OCH₃ | CH₃ |
| A-274 | Cl | NO₂ | CH₂(CO)OCH₃ | CH₂CH₃ |
| A-275 | Cl | NO₂ | CH₂(CO)OCH₃ | CH₂CH₂CH₃ |
| A-276 | Cl | NO₂ | CH₂(CO)OCH₃ | CH₂CH₂OCH₃ |
| A-277 | Cl | NO₂ | CH₂CHCH₂ | CH₃ |
| A-278 | Cl | NO₂ | CH₂CHCH₂ | CH₂CH₃ |
| A-279 | Cl | NO₂ | CH₂CHCH₂ | CH₂CH₂CH₃ |
| A-280 | Cl | NO₂ | CH₂CHCH₂ | CH₂CH₂OCH₃ |
| A-281 | Cl | NO₂ | CH₂CCH | CH₃ |
| A-282 | Cl | NO₂ | CH₂CCH | CH₂CH₃ |
| A-283 | Cl | NO₂ | CH₂CCH | CH₂CH₂CH₃ |
| A-284 | Cl | NO₂ | CH₂CCH | CH₂CH₂OCH₃ |
| A-285 | Cl | NO₂ | CH₂C₆H₅ | CH₃ |
| A-286 | Cl | NO₂ | CH₂C₆H₅ | CH₂CH₃ |
| A-287 | Cl | NO₂ | CH₂C₆H₅ | CH₂CH₂CH₃ |
| A-288 | Cl | NO₂ | CH₂C₆H₅ | CH₂CH₂OCH₃ |
| A-289 | NO₂ | H | CH₃ | CH₃ |
| A-290 | NO₂ | H | CH₃ | CH₂CH₃ |
| A-291 | NO₂ | H | CH₃ | CH₂CH₂CH₃ |
| A-292 | NO₂ | H | CH₃ | CH₂CH₂OCH₃ |
| A-293 | NO₂ | H | CH₂CH₃ | CH₃ |
| A-294 | NO₂ | H | CH₂CH₃ | CH₂CH₃ |
| A-295 | NO₂ | H | CH₂CH₃ | CH₂CH₂CH₃ |
| A-296 | NO₂ | H | CH₂CH₃ | CH₂CH₂OCH₃ |
| A-297 | NO₂ | H | CH₂OCH₃ | CH₃ |
| A-298 | NO₂ | H | CH₂OCH₃ | CH₂CH₃ |
| A-299 | NO₂ | H | CH₂OCH₃ | CH₂CH₂CH₃ |
| A-300 | NO₂ | H | CH₂OCH₃ | CH₂CH₂OCH₃ |
| A-301 | NO₂ | H | CH₂OCH₂CH₃ | CH₃ |
| A-302 | NO₂ | H | CH₂OCH₂CH₃ | CH₂CH₃ |
| A-303 | NO₂ | H | CH₂OCH₂CH₃ | CH₂CH₂CH₃ |
| A-304 | NO₂ | H | CH₂OCH₂CH₃ | CH₂CH₂OCH₃ |
| A-305 | NO₂ | H | CH₂(CO)OCH₃ | CH₃ |
| A-306 | NO₂ | H | CH₂(CO)OCH₃ | CH₂CH₃ |
| A-307 | NO₂ | H | CH₂(CO)OCH₃ | CH₂CH₂CH₃ |
| A-308 | NO₂ | H | CH₂(CO)OCH₃ | CH₂CH₂OCH₃ |
| A-309 | NO₂ | H | CH₂CHCH₂ | CH₃ |
| A-310 | NO₂ | H | CH₂CHCH₂ | CH₂CH₃ |
| A-311 | NO₂ | H | CH₂CHCH₂ | CH₂CH₂CH₃ |
| A-312 | NO₂ | H | CH₂CHCH₂ | CH₂CH₂OCH₃ |
| A-313 | NO₂ | H | CH₂CCH | CH₃ |
| A-314 | NO₂ | H | CH₂CCH | CH₂CH₃ |
| A-315 | NO₂ | H | CH₂CCH | CH₂CH₂CH₃ |
| A-316 | NO₂ | H | CH₂CCH | CH₂CH₂OCH₃ |
| A-317 | NO₂ | H | CH₂C₆H₅ | CH₃ |
| A-318 | NO₂ | H | CH₂C₆H₅ | CH₂CH₃ |
| A-319 | NO₂ | H | CH₂C₆H₅ | CH₂CH₂CH₃ |
| A-320 | NO₂ | H | CH₂C₆H₅ | CH₂CH₂OCH₃ |
| A-321 | NO₂ | F | CH₃ | CH₃ |
| A-322 | NO₂ | F | CH₃ | CH₂CH₃ |
| A-323 | NO₂ | F | CH₃ | CH₂CH₂CH₃ |
| A-324 | NO₂ | F | CH₃ | CH₂CH₂OCH₃ |
| A-325 | NO₂ | F | CH₂CH₃ | CH₃ |
| A-326 | NO₂ | F | CH₂CH₃ | CH₂CH₃ |
| A-327 | NO₂ | F | CH₂CH₃ | CH₂CH₂CH₃ |
| A-328 | NO₂ | F | CH₂CH₃ | CH₂CH₂OCH₃ |
| A-329 | NO₂ | F | CH₂OCH₃ | CH₃ |
| A-330 | NO₂ | F | CH₂OCH₃ | CH₂CH₃ |
| A-331 | NO₂ | F | CH₂OCH₃ | CH₂CH₂CH₃ |
| A-332 | NO₂ | F | CH₂OCH₃ | CH₂CH₂OCH₃ |
| A-333 | NO₂ | F | CH₂OCH₂CH₃ | CH₃ |
| A-334 | NO₂ | F | CH₂OCH₂CH₃ | CH₂CH₃ |
| A-335 | NO₂ | F | CH₂OCH₂CH₃ | CH₂CH₂CH₃ |
| A-336 | NO₂ | F | CH₂OCH₂CH₃ | CH₂CH₂OCH₃ |
| A-337 | NO₂ | F | CH₂(CO)OCH₃ | CH₃ |
| A-338 | NO₂ | F | CH₂(CO)OCH₃ | CH₂CH₃ |
| A-339 | NO₂ | F | CH₂(CO)OCH₃ | CH₂CH₂CH₃ |
| A-340 | NO₂ | F | CH₂(CO)OCH₃ | CH₂CH₂OCH₃ |
| A-341 | NO₂ | F | CH₂CHCH₂ | CH₃ |

TABLE A-continued

| | R¹ | R³ | R⁶ | R⁷ |
|---|---|---|---|---|
| A-342 | $NO_2$ | F | $CH_2CHCH_2$ | $CH_2CH_3$ |
| A-343 | $NO_2$ | F | $CH_2CHCH_2$ | $CH_2CH_2CH_3$ |
| A-344 | $NO_2$ | F | $CH_2CHCH_2$ | $CH_2CH_2OCH_3$ |
| A-345 | $NO_2$ | F | $CH_2CCH$ | $CH_3$ |
| A-346 | $NO_2$ | F | $CH_2CCH$ | $CH_2CH_3$ |
| A-347 | $NO_2$ | F | $CH_2CCH$ | $CH_2CH_2CH_3$ |
| A-348 | $NO_2$ | F | $CH_2CCH$ | $CH_2CH_2OCH_3$ |
| A-349 | $NO_2$ | F | $CH_2C_6H_5$ | $CH_3$ |
| A-350 | $NO_2$ | F | $CH_2C_6H_5$ | $CH_2CH_3$ |
| A-351 | $NO_2$ | F | $CH_2C_6H_5$ | $CH_2CH_2CH_3$ |
| A-352 | $NO_2$ | F | $CH_2C_6H_5$ | $CH_2CH_2OCH_3$ |
| A-353 | $NO_2$ | Cl | $CH_3$ | $CH_3$ |
| A-354 | $NO_2$ | Cl | $CH_3$ | $CH_2CH_3$ |
| A-355 | $NO_2$ | Cl | $CH_3$ | $CH_2CH_2CH_3$ |
| A-356 | $NO_2$ | Cl | $CH_3$ | $CH_2CH_2OCH_3$ |
| A-357 | $NO_2$ | Cl | $CH_2CH_3$ | $CH_3$ |
| A-358 | $NO_2$ | Cl | $CH_2CH_3$ | $CH_2CH_3$ |
| A-359 | $NO_2$ | Cl | $CH_2CH_3$ | $CH_2CH_2CH_3$ |
| A-360 | $NO_2$ | Cl | $CH_2CH_3$ | $CH_2CH_2OCH_3$ |
| A-361 | $NO_2$ | Cl | $CH_2OCH_3$ | $CH_3$ |
| A-362 | $NO_2$ | Cl | $CH_2OCH_3$ | $CH_2CH_3$ |
| A-363 | $NO_2$ | Cl | $CH_2OCH_3$ | $CH_2CH_2CH_3$ |
| A-364 | $NO_2$ | Cl | $CH_2OCH_3$ | $CH_2CH_2OCH_3$ |
| A-365 | $NO_2$ | Cl | $CH_2OCH_2CH_3$ | $CH_3$ |
| A-366 | $NO_2$ | Cl | $CH_2OCH_2CH_3$ | $CH_2CH_3$ |
| A-367 | $NO_2$ | Cl | $CH_2OCH_2CH_3$ | $CH_2CH_2CH_3$ |
| A-368 | $NO_2$ | Cl | $CH_2OCH_2CH_3$ | $CH_2CH_2OCH_3$ |
| A-369 | $NO_2$ | Cl | $CH_2(CO)OCH_3$ | $CH_3$ |
| A-370 | $NO_2$ | Cl | $CH_2(CO)OCH_3$ | $CH_2CH_3$ |
| A-371 | $NO_2$ | Cl | $CH_2(CO)OCH_3$ | $CH_2CH_2CH_3$ |
| A-372 | $NO_2$ | Cl | $CH_2(CO)OCH_3$ | $CH_2CH_2OCH_3$ |
| A-373 | $NO_2$ | Cl | $CH_2CHCH_2$ | $CH_3$ |
| A-374 | $NO_2$ | Cl | $CH_2CHCH_2$ | $CH_2CH_3$ |
| A-375 | $NO_2$ | Cl | $CH_2CHCH_2$ | $CH_2CH_2CH_3$ |
| A-376 | $NO_2$ | Cl | $CH_2CHCH_2$ | $CH_2CH_2OCH_3$ |
| A-377 | $NO_2$ | Cl | $CH_2CCH$ | $CH_3$ |
| A-378 | $NO_2$ | Cl | $CH_2CCH$ | $CH_2CH_3$ |
| A-379 | $NO_2$ | Cl | $CH_2CCH$ | $CH_2CH_2CH_3$ |
| A-380 | $NO_2$ | Cl | $CH_2CCH$ | $CH_2CH_2OCH_3$ |
| A-381 | $NO_2$ | Cl | $CH_2C_6H_5$ | $CH_3$ |
| A-382 | $NO_2$ | Cl | $CH_2C_6H_5$ | $CH_2CH_3$ |
| A-383 | $NO_2$ | Cl | $CH_2C_6H_5$ | $CH_2CH_2CH_3$ |
| A-384 | $NO_2$ | Cl | $CH_2C_6H_5$ | $CH_2CH_2OCH_3$ |
| A-385 | $NO_2$ | Br | $CH_3$ | $CH_3$ |
| A-386 | $NO_2$ | Br | $CH_3$ | $CH_2CH_3$ |
| A-387 | $NO_2$ | Br | $CH_3$ | $CH_2CH_2CH_3$ |
| A-388 | $NO_2$ | Br | $CH_3$ | $CH_2CH_2OCH_3$ |
| A-389 | $NO_2$ | Br | $CH_2CH_3$ | $CH_3$ |
| A-390 | $NO_2$ | Br | $CH_2CH_3$ | $CH_2CH_3$ |
| A-391 | $NO_2$ | Br | $CH_2CH_3$ | $CH_2CH_2CH_3$ |
| A-392 | $NO_2$ | Br | $CH_2CH_3$ | $CH_2CH_2OCH_3$ |
| A-393 | $NO_2$ | Br | $CH_2OCH_3$ | $CH_3$ |
| A-394 | $NO_2$ | Br | $CH_2OCH_3$ | $CH_2CH_3$ |
| A-395 | $NO_2$ | Br | $CH_2OCH_3$ | $CH_2CH_2CH_3$ |
| A-396 | $NO_2$ | Br | $CH_2OCH_3$ | $CH_2CH_2OCH_3$ |
| A-397 | $NO_2$ | Br | $CH_2OCH_2CH_3$ | $CH_3$ |
| A-398 | $NO_2$ | Br | $CH_2OCH_2CH_3$ | $CH_2CH_3$ |
| A-399 | $NO_2$ | Br | $CH_2OCH_2CH_3$ | $CH_2CH_2CH_3$ |
| A-400 | $NO_2$ | Br | $CH_2OCH_2CH_3$ | $CH_2CH_2OCH_3$ |
| A-401 | $NO_2$ | Br | $CH_2(CO)OCH_3$ | $CH_3$ |
| A-402 | $NO_2$ | Br | $CH_2(CO)OCH_3$ | $CH_2CH_3$ |
| A-403 | $NO_2$ | Br | $CH_2(CO)OCH_3$ | $CH_2CH_2CH_3$ |
| A-404 | $NO_2$ | Br | $CH_2(CO)OCH_3$ | $CH_2CH_2OCH_3$ |
| A-405 | $NO_2$ | Br | $CH_2CHCH_2$ | $CH_3$ |
| A-406 | $NO_2$ | Br | $CH_2CHCH_2$ | $CH_2CH_3$ |
| A-407 | $NO_2$ | Br | $CH_2CHCH_2$ | $CH_2CH_2CH_3$ |
| A-408 | $NO_2$ | Br | $CH_2CHCH_2$ | $CH_2CH_2OCH_3$ |
| A-409 | $NO_2$ | Br | $CH_2CCH$ | $CH_3$ |
| A-410 | $NO_2$ | Br | $CH_2CCH$ | $CH_2CH_3$ |
| A-411 | $NO_2$ | Br | $CH_2CCH$ | $CH_2CH_2CH_3$ |
| A-412 | $NO_2$ | Br | $CH_2CCH$ | $CH_2CH_2OCH_3$ |
| A-413 | $NO_2$ | Br | $CH_2C_6H_5$ | $CH_3$ |
| A-414 | $NO_2$ | Br | $CH_2C_6H_5$ | $CH_2CH_3$ |
| A-415 | $NO_2$ | Br | $CH_2C_6H_5$ | $CH_2CH_2CH_3$ |
| A-416 | $NO_2$ | Br | $CH_2C_6H_5$ | $CH_2CH_2OCH_3$ |
| A-417 | $NO_2$ | CN | $CH_3$ | $CH_3$ |
| A-418 | $NO_2$ | CN | $CH_3$ | $CH_2CH_3$ |
| A-419 | $NO_2$ | CN | $CH_3$ | $CH_2CH_2CH_3$ |

TABLE A-continued

| | R¹ | R³ | R⁶ | R⁷ |
|---|---|---|---|---|
| A-420 | NO₂ | CN | CH₃ | CH₂CH₂OCH₃ |
| A-421 | NO₂ | CN | CH₂CH₃ | CH₃ |
| A-422 | NO₂ | CN | CH₂CH₃ | CH₂CH₃ |
| A-423 | NO₂ | CN | CH₂CH₃ | CH₂CH₂CH₃ |
| A-424 | NO₂ | CN | CH₂CH₃ | CH₂CH₂OCH₃ |
| A-425 | NO₂ | CN | CH₂OCH₃ | CH₃ |
| A-426 | NO₂ | CN | CH₂OCH₃ | CH₂CH₃ |
| A-427 | NO₂ | CN | CH₂OCH₃ | CH₂CH₂CH₃ |
| A-428 | NO₂ | CN | CH₂OCH₃ | CH₂CH₂OCH₃ |
| A-429 | NO₂ | CN | CH₂OCH₂CH₃ | CH₃ |
| A-430 | NO₂ | CN | CH₂OCH₂CH₃ | CH₂CH₃ |
| A-431 | NO₂ | CN | CH₂OCH₂CH₃ | CH₂CH₂CH₃ |
| A-432 | NO₂ | CN | CH₂OCH₂CH₃ | CH₂CH₂OCH₃ |
| A-433 | NO₂ | CN | CH₂(CO)OCH₃ | CH₃ |
| A-434 | NO₂ | CN | CH₂(CO)OCH₃ | CH₂CH₃ |
| A-435 | NO₂ | CN | CH₂(CO)OCH₃ | CH₂CH₂CH₃ |
| A-436 | NO₂ | CN | CH₂(CO)OCH₃ | CH₂CH₂OCH₃ |
| A-437 | NO₂ | CN | CH₂CHCH₂ | CH₃ |
| A-438 | NO₂ | CN | CH₂CHCH₂ | CH₂CH₃ |
| A-439 | NO₂ | CN | CH₂CHCH₂ | CH₂CH₂CH₃ |
| A-440 | NO₂ | CN | CH₂CHCH₂ | CH₂CH₂OCH₃ |
| A-441 | NO₂ | CN | CH₂CCH | CH₃ |
| A-442 | NO₂ | CN | CH₂CCH | CH₂CH₃ |
| A-443 | NO₂ | CN | CH₂CCH | CH₂CH₂CH₃ |
| A-444 | NO₂ | CN | CH₂CCH | CH₂CH₂OCH₃ |
| A-445 | NO₂ | CN | CH₂C₆H₅ | CH₃ |
| A-446 | NO₂ | CN | CH₂C₆H₅ | CH₂CH₃ |
| A-447 | NO₂ | CN | CH₂C₆H₅ | CH₂CH₂CH₃ |
| A-448 | NO₂ | CN | CH₂C₆H₅ | CH₂CH₂OCH₃ |
| A-449 | NO₂ | CH₃ | CH₃ | CH₃ |
| A-450 | NO₂ | CH₃ | CH₃ | CH₂CH₃ |
| A-451 | NO₂ | CH₃ | CH₃ | CH₂CH₂CH₃ |
| A-452 | NO₂ | CH₃ | CH₃ | CH₂CH₂OCH₃ |
| A-453 | NO₂ | CH₃ | CH₂CH₃ | CH₃ |
| A-454 | NO₂ | CH₃ | CH₂CH₃ | CH₂CH₃ |
| A-455 | NO₂ | CH₃ | CH₂CH₃ | CH₂CH₂CH₃ |
| A-456 | NO₂ | CH₃ | CH₂CH₃ | CH₂CH₂OCH₃ |
| A-457 | NO₂ | CH₃ | CH₂OCH₃ | CH₃ |
| A-458 | NO₂ | CH₃ | CH₂OCH₃ | CH₂CH₃ |
| A-459 | NO₂ | CH₃ | CH₂OCH₃ | CH₂CH₂CH₃ |
| A-460 | NO₂ | CH₃ | CH₂OCH₃ | CH₂CH₂OCH₃ |
| A-461 | NO₂ | CH₃ | CH₂OCH₂CH₃ | CH₃ |
| A-462 | NO₂ | CH₃ | CH₂OCH₂CH₃ | CH₂CH₃ |
| A-463 | NO₂ | CH₃ | CH₂OCH₂CH₃ | CH₂CH₂CH₃ |
| A-464 | NO₂ | CH₃ | CH₂OCH₂CH₃ | CH₂CH₂OCH₃ |
| A-465 | NO₂ | CH₃ | CH₂(CO)OCH₃ | CH₃ |
| A-466 | NO₂ | CH₃ | CH₂(CO)OCH₃ | CH₂CH₃ |
| A-467 | NO₂ | CH₃ | CH₂(CO)OCH₃ | CH₂CH₂CH₃ |
| A-468 | NO₂ | CH₃ | CH₂(CO)OCH₃ | CH₂CH₂OCH₃ |
| A-469 | NO₂ | CH₃ | CH₂CHCH₂ | CH₃ |
| A-470 | NO₂ | CH₃ | CH₂CHCH₂ | CH₂CH₃ |
| A-471 | NO₂ | CH₃ | CH₂CHCH₂ | CH₂CH₂CH₃ |
| A-472 | NO₂ | CH₃ | CH₂CHCH₂ | CH₂CH₂OCH₃ |
| A-473 | NO₂ | CH₃ | CH₂CCH | CH₃ |
| A-474 | NO₂ | CH₃ | CH₂CCH | CH₂CH₃ |
| A-475 | NO₂ | CH₃ | CH₂CCH | CH₂CH₂CH₃ |
| A-476 | NO₂ | CH₃ | CH₂CCH | CH₂CH₂OCH₃ |
| A-477 | NO₂ | CH₃ | CH₂C₆H₅ | CH₃ |
| A-478 | NO₂ | CH₃ | CH₂C₆H₅ | CH₂CH₃ |
| A-479 | NO₂ | CH₃ | CH₂C₆H₅ | CH₂CH₂CH₃ |
| A-480 | NO₂ | CH₃ | CH₂C₆H₅ | CH₂CH₂OCH₃ |
| A-481 | NO₂ | CF₃ | CH₃ | CH₃ |
| A-482 | NO₂ | CF₃ | CH₃ | CH₂CH₃ |
| A-483 | NO₂ | CF₃ | CH₃ | CH₂CH₂CH₃ |
| A-484 | NO₂ | CF₃ | CH₃ | CH₂CH₂OCH₃ |
| A-485 | NO₂ | CF₃ | CH₂CH₃ | CH₃ |
| A-486 | NO₂ | CF₃ | CH₂CH₃ | CH₂CH₃ |
| A-487 | NO₂ | CF₃ | CH₂CH₃ | CH₂CH₂CH₃ |
| A-488 | NO₂ | CF₃ | CH₂CH₃ | CH₂CH₂OCH₃ |
| A-489 | NO₂ | CF₃ | CH₂OCH₃ | CH₃ |
| A-490 | NO₂ | CF₃ | CH₂OCH₃ | CH₂CH₃ |
| A-491 | NO₂ | CF₃ | CH₂OCH₃ | CH₂CH₂CH₃ |
| A-492 | NO₂ | CF₃ | CH₂OCH₃ | CH₂CH₂OCH₃ |
| A-493 | NO₂ | CF₃ | CH₂OCH₂CH₃ | CH₃ |
| A-494 | NO₂ | CF₃ | CH₂OCH₂CH₃ | CH₂CH₃ |
| A-495 | NO₂ | CF₃ | CH₂OCH₂CH₃ | CH₂CH₂CH₃ |
| A-496 | NO₂ | CF₃ | CH₂OCH₂CH₃ | CH₂CH₂OCH₃ |
| A-497 | NO₂ | CF₃ | CH₂(CO)OCH₃ | CH₃ |

TABLE A-continued

| | $R^1$ | $R^3$ | $R^6$ | $R^7$ |
|---|---|---|---|---|
| A-498 | $NO_2$ | $CF_3$ | $CH_2(CO)OCH_3$ | $CH_2CH_3$ |
| A-499 | $NO_2$ | $CF_3$ | $CH_2(CO)OCH_3$ | $CH_2CH_2CH_3$ |
| A-500 | $NO_2$ | $CF_3$ | $CH_2(CO)OCH_3$ | $CH_2CH_2OCH_3$ |
| A-501 | $NO_2$ | $CF_3$ | $CH_2CHCH_2$ | $CH_3$ |
| A-502 | $NO_2$ | $CF_3$ | $CH_2CHCH_2$ | $CH_2CH_3$ |
| A-503 | $NO_2$ | $CF_3$ | $CH_2CHCH_2$ | $CH_2CH_2CH_3$ |
| A-504 | $NO_2$ | $CF_3$ | $CH_2CHCH_2$ | $CH_2CH_2OCH_3$ |
| A-505 | $NO_2$ | $CF_3$ | $CH_2CCH$ | $CH_3$ |
| A-506 | $NO_2$ | $CF_3$ | $CH_2CCH$ | $CH_2CH_3$ |
| A-507 | $NO_2$ | $CF_3$ | $CH_2CCH$ | $CH_2CH_2CH_3$ |
| A-508 | $NO_2$ | $CF_3$ | $CH_2CCH$ | $CH_2CH_2OCH_3$ |
| A-509 | $NO_2$ | $CF_3$ | $CH_2C_6H_5$ | $CH_3$ |
| A-510 | $NO_2$ | $CF_3$ | $CH_2C_6H_5$ | $CH_2CH_3$ |
| A-511 | $NO_2$ | $CF_3$ | $CH_2C_6H_5$ | $CH_2CH_2CH_3$ |
| A-512 | $NO_2$ | $CF_3$ | $CH_2C_6H_5$ | $CH_2CH_2OCH_3$ |
| A-513 | $NO_2$ | $SO_2CH_3$ | $CH_3$ | $CH_3$ |
| A-514 | $NO_2$ | $SO_2CH_3$ | $CH_3$ | $CH_2CH_3$ |
| A-515 | $NO_2$ | $SO_2CH_3$ | $CH_3$ | $CH_2CH_2CH_3$ |
| A-516 | $NO_2$ | $SO_2CH_3$ | $CH_3$ | $CH_2CH_2OCH_3$ |
| A-517 | $NO_2$ | $SO_2CH_3$ | $CH_2CH_3$ | $CH_3$ |
| A-518 | $NO_2$ | $SO_2CH_3$ | $CH_2CH_3$ | $CH_2CH_3$ |
| A-519 | $NO_2$ | $SO_2CH_3$ | $CH_2CH_3$ | $CH_2CH_2CH_3$ |
| A-520 | $NO_2$ | $SO_2CH_3$ | $CH_2CH_3$ | $CH_2CH_2OCH_3$ |
| A-521 | $NO_2$ | $SO_2CH_3$ | $CH_2OCH_3$ | $CH_3$ |
| A-522 | $NO_2$ | $SO_2CH_3$ | $CH_2OCH_3$ | $CH_2CH_3$ |
| A-523 | $NO_2$ | $SO_2CH_3$ | $CH_2OCH_3$ | $CH_2CH_2CH_3$ |
| A-524 | $NO_2$ | $SO_2CH_3$ | $CH_2OCH_3$ | $CH_2CH_2OCH_3$ |
| A-525 | $NO_2$ | $SO_2CH_3$ | $CH_2OCH_2CH_3$ | $CH_3$ |
| A-526 | $NO_2$ | $SO_2CH_3$ | $CH_2OCH_2CH_3$ | $CH_2CH_3$ |
| A-527 | $NO_2$ | $SO_2CH_3$ | $CH_2OCH_2CH_3$ | $CH_2CH_2CH_3$ |
| A-528 | $NO_2$ | $SO_2CH_3$ | $CH_2OCH_2CH_3$ | $CH_2CH_2OCH_3$ |
| A-529 | $NO_2$ | $SO_2CH_3$ | $CH_2(CO)OCH_3$ | $CH_3$ |
| A-530 | $NO_2$ | $SO_2CH_3$ | $CH_2(CO)OCH_3$ | $CH_2CH_3$ |
| A-531 | $NO_2$ | $SO_2CH_3$ | $CH_2(CO)OCH_3$ | $CH_2CH_2CH_3$ |
| A-532 | $NO_2$ | $SO_2CH_3$ | $CH_2(CO)OCH_3$ | $CH_2CH_2OCH_3$ |
| A-533 | $NO_2$ | $SO_2CH_3$ | $CH_2CHCH_2$ | $CH_3$ |
| A-534 | $NO_2$ | $SO_2CH_3$ | $CH_2CHCH_2$ | $CH_2CH_3$ |
| A-535 | $NO_2$ | $SO_2CH_3$ | $CH_2CHCH_2$ | $CH_2CH_2CH_3$ |
| A-536 | $NO_2$ | $SO_2CH_3$ | $CH_2CHCH_2$ | $CH_2CH_2OCH_3$ |
| A-537 | $NO_2$ | $SO_2CH_3$ | $CH_2CCH$ | $CH_3$ |
| A-538 | $NO_2$ | $SO_2CH_3$ | $CH_2CCH$ | $CH_2CH_3$ |
| A-539 | $NO_2$ | $SO_2CH_3$ | $CH_2CCH$ | $CH_2CH_2CH_3$ |
| A-540 | $NO_2$ | $SO_2CH_3$ | $CH_2CCH$ | $CH_2CH_2OCH_3$ |
| A-541 | $NO_2$ | $SO_2CH_3$ | $CH_2C_6H_5$ | $CH_3$ |
| A-542 | $NO_2$ | $SO_2CH_3$ | $CH_2C_6H_5$ | $CH_2CH_3$ |
| A-543 | $NO_2$ | $SO_2CH_3$ | $CH_2C_6H_5$ | $CH_2CH_2CH_3$ |
| A-544 | $NO_2$ | $SO_2CH_3$ | $CH_2C_6H_5$ | $CH_2CH_2OCH_3$ |
| A-545 | $NO_2$ | $NO_2$ | $CH_3$ | $CH_3$ |
| A-546 | $NO_2$ | $NO_2$ | $CH_3$ | $CH_2CH_3$ |
| A-547 | $NO_2$ | $NO_2$ | $CH_3$ | $CH_2CH_2CH_3$ |
| A-548 | $NO_2$ | $NO_2$ | $CH_3$ | $CH_2CH_2OCH_3$ |
| A-549 | $NO_2$ | $NO_2$ | $CH_2CH_3$ | $CH_3$ |
| A-550 | $NO_2$ | $NO_2$ | $CH_2CH_3$ | $CH_2CH_3$ |
| A-551 | $NO_2$ | $NO_2$ | $CH_2CH_3$ | $CH_2CH_2CH_3$ |
| A-552 | $NO_2$ | $NO_2$ | $CH_2CH_3$ | $CH_2CH_2OCH_3$ |
| A-553 | $NO_2$ | $NO_2$ | $CH_2OCH_3$ | $CH_3$ |
| A-554 | $NO_2$ | $NO_2$ | $CH_2OCH_3$ | $CH_2CH_3$ |
| A-555 | $NO_2$ | $NO_2$ | $CH_2OCH_3$ | $CH_2CH_2CH_3$ |
| A-556 | $NO_2$ | $NO_2$ | $CH_2OCH_3$ | $CH_2CH_2OCH_3$ |
| A-557 | $NO_2$ | $NO_2$ | $CH_2OCH_2CH_3$ | $CH_3$ |
| A-558 | $NO_2$ | $NO_2$ | $CH_2OCH_2CH_3$ | $CH_2CH_3$ |
| A-559 | $NO_2$ | $NO_2$ | $CH_2OCH_2CH_3$ | $CH_2CH_2CH_3$ |
| A-560 | $NO_2$ | $NO_2$ | $CH_2OCH_2CH_3$ | $CH_2CH_2OCH_3$ |
| A-561 | $NO_2$ | $NO_2$ | $CH_2(CO)OCH_3$ | $CH_3$ |
| A-562 | $NO_2$ | $NO_2$ | $CH_2(CO)OCH_3$ | $CH_2CH_3$ |
| A-563 | $NO_2$ | $NO_2$ | $CH_2(CO)OCH_3$ | $CH_2CH_2CH_3$ |
| A-564 | $NO_2$ | $NO_2$ | $CH_2(CO)OCH_3$ | $CH_2CH_2OCH_3$ |
| A-565 | $NO_2$ | $NO_2$ | $CH_2CHCH_2$ | $CH_3$ |
| A-566 | $NO_2$ | $NO_2$ | $CH_2CHCH_2$ | $CH_2CH_3$ |
| A-567 | $NO_2$ | $NO_2$ | $CH_2CHCH_2$ | $CH_2CH_2CH_3$ |
| A-568 | $NO_2$ | $NO_2$ | $CH_2CHCH_2$ | $CH_2CH_2OCH_3$ |
| A-569 | $NO_2$ | $NO_2$ | $CH_2CCH$ | $CH_3$ |
| A-570 | $NO_2$ | $NO_2$ | $CH_2CCH$ | $CH_2CH_3$ |
| A-571 | $NO_2$ | $NO_2$ | $CH_2CCH$ | $CH_2CH_2CH_3$ |
| A-572 | $NO_2$ | $NO_2$ | $CH_2CCH$ | $CH_2CH_2OCH_3$ |
| A-573 | $NO_2$ | $NO_2$ | $CH_2C_6H_5$ | $CH_3$ |
| A-574 | $NO_2$ | $NO_2$ | $CH_2C_6H_5$ | $CH_2CH_3$ |
| A-575 | $NO_2$ | $NO_2$ | $CH_2C_6H_5$ | $CH_2CH_2CH_3$ |

TABLE A-continued

| | R$^1$ | R$^3$ | R$^6$ | R$^7$ |
|---|---|---|---|---|
| A-576 | NO$_2$ | NO$_2$ | CH$_2$C$_6$H$_5$ | CH$_2$CH$_2$OCH$_3$ |
| A-577 | CH$_3$ | H | CH$_3$ | CH$_3$ |
| A-578 | CH$_3$ | H | CH$_3$ | CH$_2$CH$_3$ |
| A-579 | CH$_3$ | H | CH$_3$ | CH$_2$CH$_2$CH$_3$ |
| A-580 | CH$_3$ | H | CH$_3$ | CH$_2$CH$_2$OCH$_3$ |
| A-581 | CH$_3$ | H | CH$_2$CH$_3$ | CH$_3$ |
| A-582 | CH$_3$ | H | CH$_2$CH$_3$ | CH$_2$CH$_3$ |
| A-583 | CH$_3$ | H | CH$_2$CH$_3$ | CH$_2$CH$_2$CH$_3$ |
| A-584 | CH$_3$ | H | CH$_2$CH$_3$ | CH$_2$CH$_2$OCH$_3$ |
| A-585 | CH$_3$ | H | CH$_2$OCH$_3$ | CH$_3$ |
| A-586 | CH$_3$ | H | CH$_2$OCH$_3$ | CH$_2$CH$_3$ |
| A-587 | CH$_3$ | H | CH$_2$OCH$_3$ | CH$_2$CH$_2$CH$_3$ |
| A-588 | CH$_3$ | H | CH$_2$OCH$_3$ | CH$_2$CH$_2$OCH$_3$ |
| A-589 | CH$_3$ | H | CH$_2$OCH$_2$CH$_3$ | CH$_3$ |
| A-590 | CH$_3$ | H | CH$_2$OCH$_2$CH$_3$ | CH$_2$CH$_3$ |
| A-591 | CH$_3$ | H | CH$_2$OCH$_2$CH$_3$ | CH$_2$CH$_2$CH$_3$ |
| A-592 | CH$_3$ | H | CH$_2$OCH$_2$CH$_3$ | CH$_2$CH$_2$OCH$_3$ |
| A-593 | CH$_3$ | H | CH$_2$(CO)OCH$_3$ | CH$_3$ |
| A-594 | CH$_3$ | H | CH$_2$(CO)OCH$_3$ | CH$_2$CH$_3$ |
| A-595 | CH$_3$ | H | CH$_2$(CO)OCH$_3$ | CH$_2$CH$_2$CH$_3$ |
| A-596 | CH$_3$ | H | CH$_2$(CO)OCH$_3$ | CH$_2$CH$_2$OCH$_3$ |
| A-597 | CH$_3$ | H | CH$_2$CHCH$_2$ | CH$_3$ |
| A-598 | CH$_3$ | H | CH$_2$CHCH$_2$ | CH$_2$CH$_3$ |
| A-599 | CH$_3$ | H | CH$_2$CHCH$_2$ | CH$_2$CH$_2$CH$_3$ |
| A-600 | CH$_3$ | H | CH$_2$CHCH$_2$ | CH$_2$CH$_2$OCH$_3$ |
| A-601 | CH$_3$ | H | CH$_2$CCH | CH$_3$ |
| A-602 | CH$_3$ | H | CH$_2$CCH | CH$_2$CH$_3$ |
| A-603 | CH$_3$ | H | CH$_2$CCH | CH$_2$CH$_2$CH$_3$ |
| A-604 | CH$_3$ | H | CH$_2$CCH | CH$_2$CH$_2$OCH$_3$ |
| A-605 | CH$_3$ | H | CH$_2$C$_6$H$_5$ | CH$_3$ |
| A-606 | CH$_3$ | H | CH$_2$C$_6$H$_5$ | CH$_2$CH$_3$ |
| A-607 | CH$_3$ | H | CH$_2$C$_6$H$_5$ | CH$_2$CH$_2$CH$_3$ |
| A-608 | CH$_3$ | H | CH$_2$C$_6$H$_5$ | CH$_2$CH$_2$OCH$_3$ |
| A-609 | CH$_3$ | F | CH$_3$ | CH$_3$ |
| A-610 | CH$_3$ | F | CH$_3$ | CH$_2$CH$_3$ |
| A-611 | CH$_3$ | F | CH$_3$ | CH$_2$CH$_2$CH$_3$ |
| A-612 | CH$_3$ | F | CH$_3$ | CH$_2$CH$_2$OCH$_3$ |
| A-613 | CH$_3$ | F | CH$_2$CH$_3$ | CH$_3$ |
| A-614 | CH$_3$ | F | CH$_2$CH$_3$ | CH$_2$CH$_3$ |
| A-615 | CH$_3$ | F | CH$_2$CH$_3$ | CH$_2$CH$_2$CH$_3$ |
| A-616 | CH$_3$ | F | CH$_2$CH$_3$ | CH$_2$CH$_2$OCH$_3$ |
| A-617 | CH$_3$ | F | CH$_2$OCH$_3$ | CH$_3$ |
| A-618 | CH$_3$ | F | CH$_2$OCH$_3$ | CH$_2$CH$_3$ |
| A-619 | CH$_3$ | F | CH$_2$OCH$_3$ | CH$_2$CH$_2$CH$_3$ |
| A-620 | CH$_3$ | F | CH$_2$OCH$_3$ | CH$_2$CH$_2$OCH$_3$ |
| A-621 | CH$_3$ | F | CH$_2$OCH$_2$CH$_3$ | CH$_3$ |
| A-622 | CH$_3$ | F | CH$_2$OCH$_2$CH$_3$ | CH$_2$CH$_3$ |
| A-623 | CH$_3$ | F | CH$_2$OCH$_2$CH$_3$ | CH$_2$CH$_2$CH$_3$ |
| A-624 | CH$_3$ | F | CH$_2$OCH$_2$CH$_3$ | CH$_2$CH$_2$OCH$_3$ |
| A-625 | CH$_3$ | F | CH$_2$(CO)OCH$_3$ | CH$_3$ |
| A-626 | CH$_3$ | F | CH$_2$(CO)OCH$_3$ | CH$_2$CH$_3$ |
| A-627 | CH$_3$ | F | CH$_2$(CO)OCH$_3$ | CH$_2$CH$_2$CH$_3$ |
| A-628 | CH$_3$ | F | CH$_2$(CO)OCH$_3$ | CH$_2$CH$_2$OCH$_3$ |
| A-629 | CH$_3$ | F | CH$_2$CHCH$_2$ | CH$_3$ |
| A-630 | CH$_3$ | F | CH$_2$CHCH$_2$ | CH$_2$CH$_3$ |
| A-631 | CH$_3$ | F | CH$_2$CHCH$_2$ | CH$_2$CH$_2$CH$_3$ |
| A-632 | CH$_3$ | F | CH$_2$CHCH$_2$ | CH$_2$CH$_2$OCH$_3$ |
| A-633 | CH$_3$ | F | CH$_2$CCH | CH$_3$ |
| A-634 | CH$_3$ | F | CH$_2$CCH | CH$_2$CH$_3$ |
| A-635 | CH$_3$ | F | CH$_2$CCH | CH$_2$CH$_2$CH$_3$ |
| A-636 | CH$_3$ | F | CH$_2$CCH | CH$_2$CH$_2$OCH$_3$ |
| A-637 | CH$_3$ | F | CH$_2$C$_6$H$_5$ | CH$_3$ |
| A-638 | CH$_3$ | F | CH$_2$C$_6$H$_5$ | CH$_2$CH$_3$ |
| A-639 | CH$_3$ | F | CH$_2$C$_6$H$_5$ | CH$_2$CH$_2$CH$_3$ |
| A-640 | CH$_3$ | F | CH$_2$C$_6$H$_5$ | CH$_2$CH$_2$OCH$_3$ |
| A-641 | CH$_3$ | Cl | CH$_3$ | CH$_3$ |
| A-642 | CH$_3$ | Cl | CH$_3$ | CH$_2$CH$_3$ |
| A-643 | CH$_3$ | Cl | CH$_3$ | CH$_2$CH$_2$CH$_3$ |
| A-644 | CH$_3$ | Cl | CH$_3$ | CH$_2$CH$_2$OCH$_3$ |
| A-645 | CH$_3$ | Cl | CH$_2$CH$_3$ | CH$_3$ |
| A-646 | CH$_3$ | Cl | CH$_2$CH$_3$ | CH$_2$CH$_3$ |
| A-647 | CH$_3$ | Cl | CH$_2$CH$_3$ | CH$_2$CH$_2$CH$_3$ |
| A-648 | CH$_3$ | Cl | CH$_2$CH$_3$ | CH$_2$CH$_2$OCH$_3$ |
| A-649 | CH$_3$ | Cl | CH$_2$OCH$_3$ | CH$_3$ |
| A-650 | CH$_3$ | Cl | CH$_2$OCH$_3$ | CH$_2$CH$_3$ |
| A-651 | CH$_3$ | Cl | CH$_2$OCH$_3$ | CH$_2$CH$_2$CH$_3$ |
| A-652 | CH$_3$ | Cl | CH$_2$OCH$_3$ | CH$_2$CH$_2$OCH$_3$ |
| A-653 | CH$_3$ | Cl | CH$_2$OCH$_2$CH$_3$ | CH$_3$ |

TABLE A-continued

|   | R¹ | R³ | R⁶ | R⁷ |
|---|---|---|---|---|
| A-654 | CH₃ | Cl | CH₂OCH₂CH₃ | CH₃ |
| A-655 | CH₃ | Cl | CH₂OCH₂CH₃ | CH₂CH₃ |
| A-656 | CH₃ | Cl | CH₂OCH₂CH₃ | CH₂CH₂OCH₃ |
| A-657 | CH₃ | Cl | CH₂(CO)OCH₃ | CH₃ |
| A-658 | CH₃ | Cl | CH₂(CO)OCH₃ | CH₂CH₃ |
| A-659 | CH₃ | Cl | CH₂(CO)OCH₃ | CH₂CH₂CH₃ |
| A-660 | CH₃ | Cl | CH₂(CO)OCH₃ | CH₂CH₂OCH₃ |
| A-661 | CH₃ | Cl | CH₂CHCH₂ | CH₃ |
| A-662 | CH₃ | Cl | CH₂CHCH₂ | CH₂CH₃ |
| A-663 | CH₃ | Cl | CH₂CHCH₂ | CH₂CH₂CH₃ |
| A-664 | CH₃ | Cl | CH₂CHCH₂ | CH₂CH₂OCH₃ |
| A-665 | CH₃ | Cl | CH₂CCH | CH₃ |
| A-666 | CH₃ | Cl | CH₂CCH | CH₂CH₃ |
| A-667 | CH₃ | Cl | CH₂CCH | CH₂CH₂CH₃ |
| A-668 | CH₃ | Cl | CH₂CCH | CH₂CH₂OCH₃ |
| A-669 | CH₃ | Cl | CH₂C₆H₅ | CH₃ |
| A-670 | CH₃ | Cl | CH₂C₆H₅ | CH₂CH₃ |
| A-671 | CH₃ | Cl | CH₂C₆H₅ | CH₂CH₂CH₃ |
| A-672 | CH₃ | Cl | CH₂C₆H₅ | CH₂CH₂OCH₃ |
| A-673 | CH₃ | Br | CH₃ | CH₃ |
| A-674 | CH₃ | Br | CH₃ | CH₂CH₃ |
| A-675 | CH₃ | Br | CH₃ | CH₂CH₂CH₃ |
| A-676 | CH₃ | Br | CH₃ | CH₂CH₂OCH₃ |
| A-677 | CH₃ | Br | CH₂CH₃ | CH₃ |
| A-678 | CH₃ | Br | CH₂CH₃ | CH₂CH₃ |
| A-679 | CH₃ | Br | CH₂CH₃ | CH₂CH₂CH₃ |
| A-680 | CH₃ | Br | CH₂CH₃ | CH₂CH₂OCH₃ |
| A-681 | CH₃ | Br | CH₂OCH₃ | CH₃ |
| A-682 | CH₃ | Br | CH₂OCH₃ | CH₂CH₃ |
| A-683 | CH₃ | Br | CH₂OCH₃ | CH₂CH₂CH₃ |
| A-684 | CH₃ | Br | CH₂OCH₃ | CH₂CH₂OCH₃ |
| A-685 | CH₃ | Br | CH₂OCH₂CH₃ | CH₃ |
| A-686 | CH₃ | Br | CH₂OCH₂CH₃ | CH₂CH₃ |
| A-687 | CH₃ | Br | CH₂OCH₂CH₃ | CH₂CH₂CH₃ |
| A-688 | CH₃ | Br | CH₂OCH₂CH₃ | CH₂CH₂OCH₃ |
| A-689 | CH₃ | Br | CH₂(CO)OCH₃ | CH₃ |
| A-690 | CH₃ | Br | CH₂(CO)OCH₃ | CH₂CH₃ |
| A-691 | CH₃ | Br | CH₂(CO)OCH₃ | CH₂CH₂CH₃ |
| A-692 | CH₃ | Br | CH₂(CO)OCH₃ | CH₂CH₂OCH₃ |
| A-693 | CH₃ | Br | CH₂CHCH₂ | CH₃ |
| A-694 | CH₃ | Br | CH₂CHCH₂ | CH₂CH₃ |
| A-695 | CH₃ | Br | CH₂CHCH₂ | CH₂CH₂CH₃ |
| A-696 | CH₃ | Br | CH₂CHCH₂ | CH₂CH₂OCH₃ |
| A-697 | CH₃ | Br | CH₂CCH | CH₃ |
| A-698 | CH₃ | Br | CH₂CCH | CH₂CH₃ |
| A-699 | CH₃ | Br | CH₂CCH | CH₂CH₂CH₃ |
| A-700 | CH₃ | Br | CH₂CCH | CH₂CH₂OCH₃ |
| A-701 | CH₃ | Br | CH₂C₆H₅ | CH₃ |
| A-702 | CH₃ | Br | CH₂C₆H₅ | CH₂CH₃ |
| A-703 | CH₃ | Br | CH₂C₆H₅ | CH₂CH₂CH₃ |
| A-704 | CH₃ | Br | CH₂C₆H₅ | CH₂CH₂OCH₃ |
| A-705 | CH₃ | CN | CH₃ | CH₃ |
| A-706 | CH₃ | CN | CH₃ | CH₂CH₃ |
| A-707 | CH₃ | CN | CH₃ | CH₂CH₂CH₃ |
| A-708 | CH₃ | CN | CH₃ | CH₂CH₂OCH₃ |
| A-709 | CH₃ | CN | CH₂CH₃ | CH₃ |
| A-710 | CH₃ | CN | CH₂CH₃ | CH₂CH₃ |
| A-711 | CH₃ | CN | CH₂CH₃ | CH₂CH₂CH₃ |
| A-712 | CH₃ | CN | CH₂CH₃ | CH₂CH₂OCH₃ |
| A-713 | CH₃ | CN | CH₂OCH₃ | CH₃ |
| A-714 | CH₃ | CN | CH₂OCH₃ | CH₂CH₃ |
| A-715 | CH₃ | CN | CH₂OCH₃ | CH₂CH₂CH₃ |
| A-716 | CH₃ | CN | CH₂OCH₃ | CH₂CH₂OCH₃ |
| A-717 | CH₃ | CN | CH₂OCH₂CH₃ | CH₃ |
| A-718 | CH₃ | CN | CH₂OCH₂CH₃ | CH₂CH₃ |
| A-719 | CH₃ | CN | CH₂OCH₂CH₃ | CH₂CH₂CH₃ |
| A-720 | CH₃ | CN | CH₂OCH₂CH₃ | CH₂CH₂OCH₃ |
| A-721 | CH₃ | CN | CH₂(CO)OCH₃ | CH₃ |
| A-722 | CH₃ | CN | CH₂(CO)OCH₃ | CH₂CH₃ |
| A-723 | CH₃ | CN | CH₂(CO)OCH₃ | CH₂CH₂CH₃ |
| A-724 | CH₃ | CN | CH₂(CO)OCH₃ | CH₂CH₂OCH₃ |
| A-725 | CH₃ | CN | CH₂CHCH₂ | CH₃ |
| A-726 | CH₃ | CN | CH₂CHCH₂ | CH₂CH₃ |
| A-727 | CH₃ | CN | CH₂CHCH₂ | CH₂CH₂CH₃ |
| A-728 | CH₃ | CN | CH₂CHCH₂ | CH₂CH₂OCH₃ |
| A-729 | CH₃ | CN | CH₂CCH | CH₃ |
| A-730 | CH₃ | CN | CH₂CCH | CH₂CH₃ |
| A-731 | CH₃ | CN | CH₂CCH | CH₂CH₂CH₃ |

TABLE A-continued

|  | R¹ | R³ | R⁶ | R⁷ |
|---|---|---|---|---|
| A-732 | CH₃ | CN | CH₂CCH | CH₂CH₂OCH₃ |
| A-733 | CH₃ | CN | CH₂C₆H₅ | CH₃ |
| A-734 | CH₃ | CN | CH₂C₆H₅ | CH₂CH₃ |
| A-735 | CH₃ | CN | CH₂C₆H₅ | CH₂CH₂CH₃ |
| A-736 | CH₃ | CN | CH₂C₆H₅ | CH₂CH₂OCH₃ |
| A-737 | CH₃ | CH₃ | CH₃ | CH₃ |
| A-738 | CH₃ | CH₃ | CH₃ | CH₂CH₃ |
| A-739 | CH₃ | CH₃ | CH₃ | CH₂CH₂CH₃ |
| A-740 | CH₃ | CH₃ | CH₃ | CH₂CH₂OCH₃ |
| A-741 | CH₃ | CH₃ | CH₂CH₃ | CH₃ |
| A-742 | CH₃ | CH₃ | CH₂CH₃ | CH₂CH₃ |
| A-743 | CH₃ | CH₃ | CH₂CH₃ | CH₂CH₂CH₃ |
| A-744 | CH₃ | CH₃ | CH₂CH₃ | CH₂CH₂OCH₃ |
| A-745 | CH₃ | CH₃ | CH₂OCH₃ | CH₃ |
| A-746 | CH₃ | CH₃ | CH₂OCH₃ | CH₂CH₃ |
| A-747 | CH₃ | CH₃ | CH₂OCH₃ | CH₂CH₂CH₃ |
| A-748 | CH₃ | CH₃ | CH₂OCH₃ | CH₂CH₂OCH₃ |
| A-749 | CH₃ | CH₃ | CH₂OCH₂CH₃ | CH₃ |
| A-750 | CH₃ | CH₃ | CH₂OCH₂CH₃ | CH₂CH₃ |
| A-751 | CH₃ | CH₃ | CH₂OCH₂CH₃ | CH₂CH₂CH₃ |
| A-752 | CH₃ | CH₃ | CH₂OCH₂CH₃ | CH₂CH₂OCH₃ |
| A-753 | CH₃ | CH₃ | CH₂(CO)OCH₃ | CH₃ |
| A-754 | CH₃ | CH₃ | CH₂(CO)OCH₃ | CH₂CH₃ |
| A-755 | CH₃ | CH₃ | CH₂(CO)OCH₃ | CH₂CH₂CH₃ |
| A-756 | CH₃ | CH₃ | CH₂(CO)OCH₃ | CH₂CH₂OCH₃ |
| A-757 | CH₃ | CH₃ | CH₂CHCH₂ | CH₃ |
| A-758 | CH₃ | CH₃ | CH₂CHCH₂ | CH₂CH₃ |
| A-759 | CH₃ | CH₃ | CH₂CHCH₂ | CH₂CH₂CH₃ |
| A-760 | CH₃ | CH₃ | CH₂CHCH₂ | CH₂CH₂OCH₃ |
| A-761 | CH₃ | CH₃ | CH₂CCH | CH₃ |
| A-762 | CH₃ | CH₃ | CH₂CCH | CH₂CH₃ |
| A-763 | CH₃ | CH₃ | CH₂CCH | CH₂CH₂CH₃ |
| A-764 | CH₃ | CH₃ | CH₂CCH | CH₂CH₂OCH₃ |
| A-765 | CH₃ | CH₃ | CH₂C₆H₅ | CH₃ |
| A-766 | CH₃ | CH₃ | CH₂C₆H₅ | CH₂CH₃ |
| A-767 | CH₃ | CH₃ | CH₂C₆H₅ | CH₂CH₂CH₃ |
| A-768 | CH₃ | CH₃ | CH₂C₆H₅ | CH₂CH₂OCH₃ |
| A-769 | CH₃ | CF₃ | CH₃ | CH₃ |
| A-770 | CH₃ | CF₃ | CH₃ | CH₂CH₃ |
| A-771 | CH₃ | CF₃ | CH₃ | CH₂CH₂CH₃ |
| A-772 | CH₃ | CF₃ | CH₃ | CH₂CH₂OCH₃ |
| A-773 | CH₃ | CF₃ | CH₂CH₃ | CH₃ |
| A-774 | CH₃ | CF₃ | CH₂CH₃ | CH₂CH₃ |
| A-775 | CH₃ | CF₃ | CH₂CH₃ | CH₂CH₂CH₃ |
| A-776 | CH₃ | CF₃ | CH₂CH₃ | CH₂CH₂OCH₃ |
| A-777 | CH₃ | CF₃ | CH₂OCH₃ | CH₃ |
| A-778 | CH₃ | CF₃ | CH₂OCH₃ | CH₂CH₃ |
| A-779 | CH₃ | CF₃ | CH₂OCH₃ | CH₂CH₂CH₃ |
| A-780 | CH₃ | CF₃ | CH₂OCH₃ | CH₂CH₂OCH₃ |
| A-781 | CH₃ | CF₃ | CH₂OCH₂CH₃ | CH₃ |
| A-782 | CH₃ | CF₃ | CH₂OCH₂CH₃ | CH₂CH₃ |
| A-783 | CH₃ | CF₃ | CH₂OCH₂CH₃ | CH₂CH₂CH₃ |
| A-784 | CH₃ | CF₃ | CH₂OCH₂CH₃ | CH₂CH₂OCH₃ |
| A-785 | CH₃ | CF₃ | CH₂(CO)OCH₃ | CH₃ |
| A-786 | CH₃ | CF₃ | CH₂(CO)OCH₃ | CH₂CH₃ |
| A-787 | CH₃ | CF₃ | CH₂(CO)OCH₃ | CH₂CH₂CH₃ |
| A-788 | CH₃ | CF₃ | CH₂(CO)OCH₃ | CH₂CH₂OCH₃ |
| A-789 | CH₃ | CF₃ | CH₂CHCH₂ | CH₃ |
| A-790 | CH₃ | CF₃ | CH₂CHCH₂ | CH₂CH₃ |
| A-791 | CH₃ | CF₃ | CH₂CHCH₂ | CH₂CH₂CH₃ |
| A-792 | CH₃ | CF₃ | CH₂CHCH₂ | CH₂CH₂OCH₃ |
| A-793 | CH₃ | CF₃ | CH₂CCH | CH₃ |
| A-794 | CH₃ | CF₃ | CH₂CCH | CH₂CH₃ |
| A-795 | CH₃ | CF₃ | CH₂CCH | CH₂CH₂CH₃ |
| A-796 | CH₃ | CF₃ | CH₂CCH | CH₂CH₂OCH₃ |
| A-797 | CH₃ | CF₃ | CH₂C₆H₅ | CH₃ |
| A-798 | CH₃ | CF₃ | CH₂C₆H₅ | CH₂CH₃ |
| A-799 | CH₃ | CF₃ | CH₂C₆H₅ | CH₂CH₂CH₃ |
| A-800 | CH₃ | CF₃ | CH₂C₆H₅ | CH₂CH₂OCH₃ |
| A-801 | CH₃ | SO₂CH₃ | CH₃ | CH₃ |
| A-802 | CH₃ | SO₂CH₃ | CH₃ | CH₂CH₃ |
| A-803 | CH₃ | SO₂CH₃ | CH₃ | CH₂CH₂CH₃ |
| A-804 | CH₃ | SO₂CH₃ | CH₃ | CH₂CH₂OCH₃ |
| A-805 | CH₃ | SO₂CH₃ | CH₂CH₃ | CH₃ |
| A-806 | CH₃ | SO₂CH₃ | CH₂CH₃ | CH₂CH₃ |
| A-807 | CH₃ | SO₂CH₃ | CH₂CH₃ | CH₂CH₂CH₃ |
| A-808 | CH₃ | SO₂CH₃ | CH₂CH₃ | CH₂CH₂OCH₃ |
| A-809 | CH₃ | SO₂CH₃ | CH₂OCH₃ | CH₃ |

TABLE A-continued

| | R¹ | R³ | R⁶ | R⁷ |
|---|---|---|---|---|
| A-810 | CH₃ | SO₂CH₃ | CH₂OCH₃ | CH₂CH₃ |
| A-811 | CH₃ | SO₂CH₃ | CH₂OCH₃ | CH₂CH₂CH₃ |
| A-812 | CH₃ | SO₂CH₃ | CH₂OCH₃ | CH₂CH₂OCH₃ |
| A-813 | CH₃ | SO₂CH₃ | CH₂OCH₂CH₃ | CH₃ |
| A-814 | CH₃ | SO₂CH₃ | CH₂OCH₂CH₃ | CH₂CH₃ |
| A-815 | CH₃ | SO₂CH₃ | CH₂OCH₂CH₃ | CH₂CH₂CH₃ |
| A-816 | CH₃ | SO₂CH₃ | CH₂OCH₂CH₃ | CH₂CH₂OCH₃ |
| A-817 | CH₃ | SO₂CH₃ | CH₂(CO)OCH₃ | CH₃ |
| A-818 | CH₃ | SO₂CH₃ | CH₂(CO)OCH₃ | CH₂CH₃ |
| A-819 | CH₃ | SO₂CH₃ | CH₂(CO)OCH₃ | CH₂CH₂CH₃ |
| A-820 | CH₃ | SO₂CH₃ | CH₂(CO)OCH₃ | CH₂CH₂OCH₃ |
| A-821 | CH₃ | SO₂CH₃ | CH₂CHCH₂ | CH₃ |
| A-822 | CH₃ | SO₂CH₃ | CH₂CHCH₂ | CH₂CH₃ |
| A-823 | CH₃ | SO₂CH₃ | CH₂CHCH₂ | CH₂CH₂CH₃ |
| A-824 | CH₃ | SO₂CH₃ | CH₂CHCH₂ | CH₂CH₂OCH₃ |
| A-825 | CH₃ | SO₂CH₃ | CH₂CCH | CH₃ |
| A-826 | CH₃ | SO₂CH₃ | CH₂CCH | CH₂CH₃ |
| A-827 | CH₃ | SO₂CH₃ | CH₂CCH | CH₂CH₂CH₃ |
| A-828 | CH₃ | SO₂CH₃ | CH₂CCH | CH₂CH₂OCH₃ |
| A-829 | CH₃ | SO₂CH₃ | CH₂C₆H₅ | CH₃ |
| A-830 | CH₃ | SO₂CH₃ | CH₂C₆H₅ | CH₂CH₃ |
| A-831 | CH₃ | SO₂CH₃ | CH₂C₆H₅ | CH₂CH₂CH₃ |
| A-832 | CH₃ | SO₂CH₃ | CH₂C₆H₅ | CH₂CH₂OCH₃ |
| A-833 | CH₃ | NO₂ | CH₃ | CH₃ |
| A-834 | CH₃ | NO₂ | CH₃ | CH₂CH₃ |
| A-835 | CH₃ | NO₂ | CH₃ | CH₂CH₂CH₃ |
| A-836 | CH₃ | NO₂ | CH₃ | CH₂CH₂OCH₃ |
| A-837 | CH₃ | NO₂ | CH₂CH₃ | CH₃ |
| A-838 | CH₃ | NO₂ | CH₂CH₃ | CH₂CH₃ |
| A-839 | CH₃ | NO₂ | CH₂CH₃ | CH₂CH₂CH₃ |
| A-840 | CH₃ | NO₂ | CH₂CH₃ | CH₂CH₂OCH₃ |
| A-841 | CH₃ | NO₂ | CH₂OCH₃ | CH₃ |
| A-842 | CH₃ | NO₂ | CH₂OCH₃ | CH₂CH₃ |
| A-843 | CH₃ | NO₂ | CH₂OCH₃ | CH₂CH₂CH₃ |
| A-844 | CH₃ | NO₂ | CH₂OCH₃ | CH₂CH₂OCH₃ |
| A-845 | CH₃ | NO₂ | CH₂OCH₂CH₃ | CH₃ |
| A-846 | CH₃ | NO₂ | CH₂OCH₂CH₃ | CH₂CH₃ |
| A-847 | CH₃ | NO₂ | CH₂OCH₂CH₃ | CH₂CH₂CH₃ |
| A-848 | CH₃ | NO₂ | CH₂OCH₂CH₃ | CH₂CH₂OCH₃ |
| A-849 | CH₃ | NO₂ | CH₂(CO)OCH₃ | CH₃ |
| A-850 | CH₃ | NO₂ | CH₂(CO)OCH₃ | CH₂CH₃ |
| A-851 | CH₃ | NO₂ | CH₂(CO)OCH₃ | CH₂CH₂CH₃ |
| A-852 | CH₃ | NO₂ | CH₂(CO)OCH₃ | CH₂CH₂OCH₃ |
| A-853 | CH₃ | NO₂ | CH₂CHCH₂ | CH₃ |
| A-854 | CH₃ | NO₂ | CH₂CHCH₂ | CH₂CH₃ |
| A-855 | CH₃ | NO₂ | CH₂CHCH₂ | CH₂CH₂CH₃ |
| A-856 | CH₃ | NO₂ | CH₂CHCH₂ | CH₂CH₂OCH₃ |
| A-857 | CH₃ | NO₂ | CH₂CCH | CH₃ |
| A-858 | CH₃ | NO₂ | CH₂CCH | CH₂CH₃ |
| A-859 | CH₃ | NO₂ | CH₂CCH | CH₂CH₂CH₃ |
| A-860 | CH₃ | NO₂ | CH₂CCH | CH₂CH₂OCH₃ |
| A-861 | CH₃ | NO₂ | CH₂C₆H₅ | CH₃ |
| A-862 | CH₃ | NO₂ | CH₂C₆H₅ | CH₂CH₃ |
| A-863 | CH₃ | NO₂ | CH₂C₆H₅ | CH₂CH₂CH₃ |
| A-864 | CH₃ | NO₂ | CH₂C₆H₅ | CH₂CH₂OCH₃ |
| A-865 | cyclopropyl | H | CH₃ | CH₃ |
| A-866 | cyclopropyl | H | CH₃ | CH₂CH₃ |
| A-867 | cyclopropyl | H | CH₃ | CH₂CH₂CH₃ |
| A-868 | cyclopropyl | H | CH₃ | CH₂CH₂OCH₃ |
| A-869 | cyclopropyl | H | CH₂CH₃ | CH₃ |
| A-870 | cyclopropyl | H | CH₂CH₃ | CH₂CH₃ |
| A-871 | cyclopropyl | H | CH₂CH₃ | CH₂CH₂CH₃ |
| A-872 | cyclopropyl | H | CH₂CH₃ | CH₂CH₂OCH₃ |
| A-873 | cyclopropyl | H | CH₂OCH₃ | CH₃ |
| A-874 | cyclopropyl | H | CH₂OCH₃ | CH₂CH₃ |
| A-875 | cyclopropyl | H | CH₂OCH₃ | CH₂CH₂CH₃ |
| A-876 | cyclopropyl | H | CH₂OCH₃ | CH₂CH₂OCH₃ |
| A-877 | cyclopropyl | H | CH₂OCH₂CH₃ | CH₃ |
| A-878 | cyclopropyl | H | CH₂OCH₂CH₃ | CH₂CH₃ |
| A-879 | cyclopropyl | H | CH₂OCH₂CH₃ | CH₂CH₂CH₃ |
| A-880 | cyclopropyl | H | CH₂OCH₂CH₃ | CH₂CH₂OCH₃ |
| A-881 | cyclopropyl | H | CH₂(CO)OCH₃ | CH₃ |
| A-882 | cyclopropyl | H | CH₂(CO)OCH₃ | CH₂CH₃ |
| A-883 | cyclopropyl | H | CH₂(CO)OCH₃ | CH₂CH₂CH₃ |
| A-884 | cyclopropyl | H | CH₂(CO)OCH₃ | CH₂CH₂OCH₃ |
| A-885 | cyclopropyl | H | CH₂CHCH₂ | CH₃ |
| A-886 | cyclopropyl | H | CH₂CHCH₂ | CH₂CH₃ |
| A-887 | cyclopropyl | H | CH₂CHCH₂ | CH₂CH₂CH₃ |

TABLE A-continued

|  | $R^1$ | $R^3$ | $R^6$ | $R^7$ |
|---|---|---|---|---|
| A-888 | cyclopropyl | H | $CH_2CHCH_2$ | $CH_2CH_2OCH_3$ |
| A-889 | cyclopropyl | H | $CH_2CCH$ | $CH_3$ |
| A-890 | cyclopropyl | H | $CH_2CCH$ | $CH_2CH_3$ |
| A-891 | cyclopropyl | H | $CH_2CCH$ | $CH_2CH_2CH_3$ |
| A-892 | cyclopropyl | H | $CH_2CCH$ | $CH_2CH_2OCH_3$ |
| A-893 | cyclopropyl | H | $CH_2C_6H_5$ | $CH_3$ |
| A-894 | cyclopropyl | H | $CH_2C_6H_5$ | $CH_2CH_3$ |
| A-895 | cyclopropyl | H | $CH_2C_6H_5$ | $CH_2CH_2CH_3$ |
| A-896 | cyclopropyl | H | $CH_2C_6H_5$ | $CH_2CH_2OCH_3$ |
| A-897 | cyclopropyl | F | $CH_3$ | $CH_3$ |
| A-898 | cyclopropyl | F | $CH_3$ | $CH_2CH_3$ |
| A-899 | cyclopropyl | F | $CH_3$ | $CH_2CH_2CH_3$ |
| A-900 | cyclopropyl | F | $CH_3$ | $CH_2CH_2OCH_3$ |
| A-901 | cyclopropyl | F | $CH_2CH_3$ | $CH_3$ |
| A-902 | cyclopropyl | F | $CH_2CH_3$ | $CH_2CH_3$ |
| A-903 | cyclopropyl | F | $CH_2CH_3$ | $CH_2CH_2CH_3$ |
| A-904 | cyclopropyl | F | $CH_2CH_3$ | $CH_2CH_2OCH_3$ |
| A-905 | cyclopropyl | F | $CH_2OCH_3$ | $CH_3$ |
| A-906 | cyclopropyl | F | $CH_2OCH_3$ | $CH_2CH_3$ |
| A-907 | cyclopropyl | F | $CH_2OCH_3$ | $CH_2CH_2CH_3$ |
| A-908 | cyclopropyl | F | $CH_2OCH_3$ | $CH_2CH_2OCH_3$ |
| A-909 | cyclopropyl | F | $CH_2OCH_2CH_3$ | $CH_3$ |
| A-910 | cyclopropyl | F | $CH_2OCH_2CH_3$ | $CH_2CH_3$ |
| A-911 | cyclopropyl | F | $CH_2OCH_2CH_3$ | $CH_2CH_2CH_3$ |
| A-912 | cyclopropyl | F | $CH_2OCH_2CH_3$ | $CH_2CH_2OCH_3$ |
| A-913 | cyclopropyl | F | $CH_2(CO)OCH_3$ | $CH_3$ |
| A-914 | cyclopropyl | F | $CH_2(CO)OCH_3$ | $CH_2CH_3$ |
| A-915 | cyclopropyl | F | $CH_2(CO)OCH_3$ | $CH_2CH_2CH_3$ |
| A-916 | cyclopropyl | F | $CH_2(CO)OCH_3$ | $CH_2CH_2OCH_3$ |
| A-917 | cyclopropyl | F | $CH_2CHCH_2$ | $CH_3$ |
| A-918 | cyclopropyl | F | $CH_2CHCH_2$ | $CH_2CH_3$ |
| A-919 | cyclopropyl | F | $CH_2CHCH_2$ | $CH_2CH_2CH_3$ |
| A-920 | cyclopropyl | F | $CH_2CHCH_2$ | $CH_2CH_2OCH_3$ |
| A-921 | cyclopropyl | F | $CH_2CCH$ | $CH_3$ |
| A-922 | cyclopropyl | F | $CH_2CCH$ | $CH_2CH_3$ |
| A-923 | cyclopropyl | F | $CH_2CCH$ | $CH_2CH_2CH_3$ |
| A-924 | cyclopropyl | F | $CH_2CCH$ | $CH_2CH_2OCH_3$ |
| A-925 | cyclopropyl | F | $CH_2C_6H_5$ | $CH_3$ |
| A-926 | cyclopropyl | F | $CH_2C_6H_5$ | $CH_2CH_3$ |
| A-927 | cyclopropyl | F | $CH_2C_6H_5$ | $CH_2CH_2CH_3$ |
| A-928 | cyclopropyl | F | $CH_2C_6H_5$ | $CH_2CH_2OCH_3$ |
| A-929 | cyclopropyl | Cl | $CH_3$ | $CH_3$ |
| A-930 | cyclopropyl | Cl | $CH_3$ | $CH_2CH_3$ |
| A-931 | cyclopropyl | Cl | $CH_3$ | $CH_2CH_2CH_3$ |
| A-932 | cyclopropyl | Cl | $CH_3$ | $CH_2CH_2OCH_3$ |
| A-933 | cyclopropyl | Cl | $CH_2CH_3$ | $CH_3$ |
| A-934 | cyclopropyl | Cl | $CH_2CH_3$ | $CH_2CH_3$ |
| A-935 | cyclopropyl | Cl | $CH_2CH_3$ | $CH_2CH_2CH_3$ |
| A-936 | cyclopropyl | Cl | $CH_2CH_3$ | $CH_2CH_2OCH_3$ |
| A-937 | cyclopropyl | Cl | $CH_2OCH_3$ | $CH_3$ |
| A-938 | cyclopropyl | Cl | $CH_2OCH_3$ | $CH_2CH_3$ |
| A-939 | cyclopropyl | Cl | $CH_2OCH_3$ | $CH_2CH_2CH_3$ |
| A-940 | cyclopropyl | Cl | $CH_2OCH_3$ | $CH_2CH_2OCH_3$ |
| A-941 | cyclopropyl | Cl | $CH_2OCH_2CH_3$ | $CH_3$ |
| A-942 | cyclopropyl | Cl | $CH_2OCH_2CH_3$ | $CH_2CH_3$ |
| A-943 | cyclopropyl | Cl | $CH_2OCH_2CH_3$ | $CH_2CH_2CH_3$ |
| A-944 | cyclopropyl | Cl | $CH_2OCH_2CH_3$ | $CH_2CH_2OCH_3$ |
| A-945 | cyclopropyl | Cl | $CH_2(CO)OCH_3$ | $CH_3$ |
| A-946 | cyclopropyl | Cl | $CH_2(CO)OCH_3$ | $CH_2CH_3$ |
| A-947 | cyclopropyl | Cl | $CH_2(CO)OCH_3$ | $CH_2CH_2CH_3$ |
| A-948 | cyclopropyl | Cl | $CH_2(CO)OCH_3$ | $CH_2CH_2OCH_3$ |
| A-949 | cyclopropyl | Cl | $CH_2CHCH_2$ | $CH_3$ |
| A-950 | cyclopropyl | Cl | $CH_2CHCH_2$ | $CH_2CH_3$ |
| A-951 | cyclopropyl | Cl | $CH_2CHCH_2$ | $CH_2CH_2CH_3$ |
| A-952 | cyclopropyl | Cl | $CH_2CHCH_2$ | $CH_2CH_2OCH_3$ |
| A-953 | cyclopropyl | Cl | $CH_2CCH$ | $CH_3$ |
| A-954 | cyclopropyl | Cl | $CH_2CCH$ | $CH_2CH_3$ |
| A-955 | cyclopropyl | Cl | $CH_2CCH$ | $CH_2CH_2CH_3$ |
| A-956 | cyclopropyl | Cl | $CH_2CCH$ | $CH_2CH_2OCH_3$ |
| A-957 | cyclopropyl | Cl | $CH_2C_6H_5$ | $CH_3$ |
| A-958 | cyclopropyl | Cl | $CH_2C_6H_5$ | $CH_2CH_3$ |
| A-959 | cyclopropyl | Cl | $CH_2C_6H_5$ | $CH_2CH_2CH_3$ |
| A-960 | cyclopropyl | Cl | $CH_2C_6H_5$ | $CH_2CH_2OCH_3$ |
| A-961 | cyclopropyl | Br | $CH_3$ | $CH_3$ |
| A-962 | cyclopropyl | Br | $CH_3$ | $CH_2CH_3$ |
| A-963 | cyclopropyl | Br | $CH_3$ | $CH_2CH_2CH_3$ |
| A-964 | cyclopropyl | Br | $CH_3$ | $CH_2CH_2OCH_3$ |
| A-965 | cyclopropyl | Br | $CH_2CH_3$ | $CH_3$ |

TABLE A-continued

|  | R¹ | R³ | R⁶ | R⁷ |
|---|---|---|---|---|
| A-966 | cyclopropyl | Br | $CH_2CH_3$ | $CH_2CH_3$ |
| A-967 | cyclopropyl | Br | $CH_2CH_3$ | $CH_2CH_2CH_3$ |
| A-968 | cyclopropyl | Br | $CH_2CH_3$ | $CH_2CH_2OCH_3$ |
| A-969 | cyclopropyl | Br | $CH_2OCH_3$ | $CH_3$ |
| A-970 | cyclopropyl | Br | $CH_2OCH_3$ | $CH_2CH_3$ |
| A-971 | cyclopropyl | Br | $CH_2OCH_3$ | $CH_2CH_2CH_3$ |
| A-972 | cyclopropyl | Br | $CH_2OCH_3$ | $CH_2CH_2OCH_3$ |
| A-973 | cyclopropyl | Br | $CH_2OCH_2CH_3$ | $CH_3$ |
| A-974 | cyclopropyl | Br | $CH_2OCH_2CH_3$ | $CH_2CH_3$ |
| A-975 | cyclopropyl | Br | $CH_2OCH_2CH_3$ | $CH_2CH_2CH_3$ |
| A-976 | cyclopropyl | Br | $CH_2OCH_2CH_3$ | $CH_2CH_2OCH_3$ |
| A-977 | cyclopropyl | Br | $CH_2(CO)OCH_3$ | $CH_3$ |
| A-978 | cyclopropyl | Br | $CH_2(CO)OCH_3$ | $CH_2CH_3$ |
| A-979 | cyclopropyl | Br | $CH_2(CO)OCH_3$ | $CH_2CH_2CH_3$ |
| A-980 | cyclopropyl | Br | $CH_2(CO)OCH_3$ | $CH_2CH_2OCH_3$ |
| A-981 | cyclopropyl | Br | $CH_2CHCH_2$ | $CH_3$ |
| A-982 | cyclopropyl | Br | $CH_2CHCH_2$ | $CH_2CH_3$ |
| A-983 | cyclopropyl | Br | $CH_2CHCH_2$ | $CH_2CH_2CH_3$ |
| A-984 | cyclopropyl | Br | $CH_2CHCH_2$ | $CH_2CH_2OCH_3$ |
| A-985 | cyclopropyl | Br | $CH_2CCH$ | $CH_3$ |
| A-986 | cyclopropyl | Br | $CH_2CCH$ | $CH_2CH_3$ |
| A-987 | cyclopropyl | Br | $CH_2CCH$ | $CH_2CH_2CH_3$ |
| A-988 | cyclopropyl | Br | $CH_2CCH$ | $CH_2CH_2OCH_3$ |
| A-989 | cyclopropyl | Br | $CH_2C_6H_5$ | $CH_3$ |
| A-990 | cyclopropyl | Br | $CH_2C_6H_5$ | $CH_2CH_3$ |
| A-991 | cyclopropyl | Br | $CH_2C_6H_5$ | $CH_2CH_2CH_3$ |
| A-992 | cyclopropyl | Br | $CH_2C_6H_5$ | $CH_2CH_2OCH_3$ |
| A-993 | cyclopropyl | CN | $CH_3$ | $CH_3$ |
| A-994 | cyclopropyl | CN | $CH_3$ | $CH_2CH_3$ |
| A-995 | cyclopropyl | CN | $CH_3$ | $CH_2CH_2CH_3$ |
| A-996 | cyclopropyl | CN | $CH_3$ | $CH_2CH_2OCH_3$ |
| A-997 | cyclopropyl | CN | $CH_2CH_3$ | $CH_3$ |
| A-998 | cyclopropyl | CN | $CH_2CH_3$ | $CH_2CH_3$ |
| A-999 | cyclopropyl | CN | $CH_2CH_3$ | $CH_2CH_2CH_3$ |
| A-1000 | cyclopropyl | CN | $CH_2CH_3$ | $CH_2CH_2OCH_3$ |
| A-1001 | cyclopropyl | CN | $CH_2OCH_3$ | $CH_3$ |
| A-1002 | cyclopropyl | CN | $CH_2OCH_3$ | $CH_2CH_3$ |
| A-1003 | cyclopropyl | CN | $CH_2OCH_3$ | $CH_2CH_2CH_3$ |
| A-1004 | cyclopropyl | CN | $CH_2OCH_3$ | $CH_2CH_2OCH_3$ |
| A-1005 | cyclopropyl | CN | $CH_2OCH_2CH_3$ | $CH_3$ |
| A-1006 | cyclopropyl | CN | $CH_2OCH_2CH_3$ | $CH_2CH_3$ |
| A-1007 | cyclopropyl | CN | $CH_2OCH_2CH_3$ | $CH_2CH_2CH_3$ |
| A-1008 | cyclopropyl | CN | $CH_2OCH_2CH_3$ | $CH_2CH_2OCH_3$ |
| A-1009 | cyclopropyl | CN | $CH_2(CO)OCH_3$ | $CH_3$ |
| A-1010 | cyclopropyl | CN | $CH_2(CO)OCH_3$ | $CH_2CH_3$ |
| A-1011 | cyclopropyl | CN | $CH_2(CO)OCH_3$ | $CH_2CH_2CH_3$ |
| A-1012 | cyclopropyl | CN | $CH_2(CO)OCH_3$ | $CH_2CH_2OCH_3$ |
| A-1013 | cyclopropyl | CN | $CH_2CHCH_2$ | $CH_3$ |
| A-1014 | cyclopropyl | CN | $CH_2CHCH_2$ | $CH_2CH_3$ |
| A-1015 | cyclopropyl | CN | $CH_2CHCH_2$ | $CH_2CH_2CH_3$ |
| A-1016 | cyclopropyl | CN | $CH_2CHCH_2$ | $CH_2CH_2OCH_3$ |
| A-1017 | cyclopropyl | CN | $CH_2CCH$ | $CH_3$ |
| A-1018 | cyclopropyl | CN | $CH_2CCH$ | $CH_2CH_3$ |
| A-1019 | cyclopropyl | CN | $CH_2CCH$ | $CH_2CH_2CH_3$ |
| A-1020 | cyclopropyl | CN | $CH_2CCH$ | $CH_2CH_2OCH_3$ |
| A-1021 | cyclopropyl | CN | $CH_2C_6H_5$ | $CH_3$ |
| A-1022 | cyclopropyl | CN | $CH_2C_6H_5$ | $CH_2CH_3$ |
| A-1023 | cyclopropyl | CN | $CH_2C_6H_5$ | $CH_2CH_2CH_3$ |
| A-1024 | cyclopropyl | CN | $CH_2C_6H_5$ | $CH_2CH_2OCH_3$ |
| A-1025 | cyclopropyl | $CH_3$ | $CH_3$ | $CH_3$ |
| A-1026 | cyclopropyl | $CH_3$ | $CH_3$ | $CH_2CH_3$ |
| A-1027 | cyclopropyl | $CH_3$ | $CH_3$ | $CH_2CH_2CH_3$ |
| A-1028 | cyclopropyl | $CH_3$ | $CH_3$ | $CH_2CH_2OCH_3$ |
| A-1029 | cyclopropyl | $CH_3$ | $CH_2CH_3$ | $CH_3$ |
| A-1030 | cyclopropyl | $CH_3$ | $CH_2CH_3$ | $CH_2CH_3$ |
| A-1031 | cyclopropyl | $CH_3$ | $CH_2CH_3$ | $CH_2CH_2CH_3$ |
| A-1032 | cyclopropyl | $CH_3$ | $CH_2CH_3$ | $CH_2CH_2OCH_3$ |
| A-1033 | cyclopropyl | $CH_3$ | $CH_2OCH_3$ | $CH_3$ |
| A-1034 | cyclopropyl | $CH_3$ | $CH_2OCH_3$ | $CH_2CH_3$ |
| A-1035 | cyclopropyl | $CH_3$ | $CH_2OCH_3$ | $CH_2CH_2CH_3$ |
| A-1036 | cyclopropyl | $CH_3$ | $CH_2OCH_3$ | $CH_2CH_2OCH_3$ |
| A-1037 | cyclopropyl | $CH_3$ | $CH_2OCH_2CH_3$ | $CH_3$ |
| A-1038 | cyclopropyl | $CH_3$ | $CH_2OCH_2CH_3$ | $CH_2CH_3$ |
| A-1039 | cyclopropyl | $CH_3$ | $CH_2OCH_2CH_3$ | $CH_2CH_2CH_3$ |
| A-1040 | cyclopropyl | $CH_3$ | $CH_2OCH_2CH_3$ | $CH_2CH_2OCH_3$ |
| A-1041 | cyclopropyl | $CH_3$ | $CH_2(CO)OCH_3$ | $CH_3$ |
| A-1042 | cyclopropyl | $CH_3$ | $CH_2(CO)OCH_3$ | $CH_2CH_3$ |
| A-1043 | cyclopropyl | $CH_3$ | $CH_2(CO)OCH_3$ | $CH_2CH_2CH_3$ |

TABLE A-continued

|   | R¹ | R³ | R⁶ | R⁷ |
|---|---|---|---|---|
| A-1044 | cyclopropyl | CH₃ | CH₂(CO)OCH₃ | CH₂CH₂OCH₃ |
| A-1045 | cyclopropyl | CH₃ | CH₂CHCH₂ | CH₃ |
| A-1046 | cyclopropyl | CH₃ | CH₂CHCH₂ | CH₂CH₃ |
| A-1047 | cyclopropyl | CH₃ | CH₂CHCH₂ | CH₂CH₂CH₃ |
| A-1048 | cyclopropyl | CH₃ | CH₂CHCH₂ | CH₂CH₂OCH₃ |
| A-1049 | cyclopropyl | CH₃ | CH₂CCH | CH₃ |
| A-1050 | cyclopropyl | CH₃ | CH₂CCH | CH₂CH₃ |
| A-1051 | cyclopropyl | CH₃ | CH₂CCH | CH₂CH₂CH₃ |
| A-1052 | cyclopropyl | CH₃ | CH₂CCH | CH₂CH₂OCH₃ |
| A-1053 | cyclopropyl | CH₃ | CH₂C₆H₅ | CH₃ |
| A-1054 | cyclopropyl | CH₃ | CH₂C₆H₅ | CH₂CH₃ |
| A-1055 | cyclopropyl | CH₃ | CH₂C₆H₅ | CH₂CH₂CH₃ |
| A-1056 | cyclopropyl | CH₃ | CH₂C₆H₅ | CH₂CH₂OCH₃ |
| A-1057 | cyclopropyl | CF₃ | CH₃ | CH₃ |
| A-1058 | cyclopropyl | CF₃ | CH₃ | CH₂CH₃ |
| A-1059 | cyclopropyl | CF₃ | CH₃ | CH₂CH₂CH₃ |
| A-1060 | cyclopropyl | CF₃ | CH₃ | CH₂CH₂OCH₃ |
| A-1061 | cyclopropyl | CF₃ | CH₂CH₃ | CH₃ |
| A-1062 | cyclopropyl | CF₃ | CH₂CH₃ | CH₂CH₃ |
| A-1063 | cyclopropyl | CF₃ | CH₂CH₃ | CH₂CH₂CH₃ |
| A-1064 | cyclopropyl | CF₃ | CH₂CH₃ | CH₂CH₂OCH₃ |
| A-1065 | cyclopropyl | CF₃ | CH₂OCH₃ | CH₃ |
| A-1066 | cyclopropyl | CF₃ | CH₂OCH₃ | CH₂CH₃ |
| A-1067 | cyclopropyl | CF₃ | CH₂OCH₃ | CH₂CH₂CH₃ |
| A-1068 | cyclopropyl | CF₃ | CH₂OCH₃ | CH₂CH₂OCH₃ |
| A-1069 | cyclopropyl | CF₃ | CH₂OCH₂CH₃ | CH₃ |
| A-1070 | cyclopropyl | CF₃ | CH₂OCH₂CH₃ | CH₂CH₃ |
| A-1071 | cyclopropyl | CF₃ | CH₂OCH₂CH₃ | CH₂CH₂CH₃ |
| A-1072 | cyclopropyl | CF₃ | CH₂OCH₂CH₃ | CH₂CH₂OCH₃ |
| A-1073 | cyclopropyl | CF₃ | CH₂(CO)OCH₃ | CH₃ |
| A-1074 | cyclopropyl | CF₃ | CH₂(CO)OCH₃ | CH₂CH₃ |
| A-1075 | cyclopropyl | CF₃ | CH₂(CO)OCH₃ | CH₂CH₂CH₃ |
| A-1076 | cyclopropyl | CF₃ | CH₂(CO)OCH₃ | CH₂CH₂OCH₃ |
| A-1077 | cyclopropyl | CF₃ | CH₂CHCH₂ | CH₃ |
| A-1078 | cyclopropyl | CF₃ | CH₂CHCH₂ | CH₂CH₃ |
| A-1079 | cyclopropyl | CF₃ | CH₂CHCH₂ | CH₂CH₂CH₃ |
| A-1080 | cyclopropyl | CF₃ | CH₂CHCH₂ | CH₂CH₂OCH₃ |
| A-1081 | cyclopropyl | CF₃ | CH₂CCH | CH₃ |
| A-1082 | cyclopropyl | CF₃ | CH₂CCH | CH₂CH₃ |
| A-1083 | cyclopropyl | CF₃ | CH₂CCH | CH₂CH₂CH₃ |
| A-1084 | cyclopropyl | CF₃ | CH₂CCH | CH₂CH₂OCH₃ |
| A-1085 | cyclopropyl | CF₃ | CH₂C₆H₅ | CH₃ |
| A-1086 | cyclopropyl | CF₃ | CH₂C₆H₅ | CH₂CH₃ |
| A-1087 | cyclopropyl | CF₃ | CH₂C₆H₅ | CH₂CH₂CH₃ |
| A-1088 | cyclopropyl | CF₃ | CH₂C₆H₅ | CH₂CH₂OCH₃ |
| A-1089 | cyclopropyl | SO₂CH₃ | CH₃ | CH₃ |
| A-1090 | cyclopropyl | SO₂CH₃ | CH₃ | CH₂CH₃ |
| A-1091 | cyclopropyl | SO₂CH₃ | CH₃ | CH₂CH₂CH₃ |
| A-1092 | cyclopropyl | SO₂CH₃ | CH₃ | CH₂CH₂OCH₃ |
| A-1093 | cyclopropyl | SO₂CH₃ | CH₂CH₃ | CH₃ |
| A-1094 | cyclopropyl | SO₂CH₃ | CH₂CH₃ | CH₂CH₃ |
| A-1095 | cyclopropyl | SO₂CH₃ | CH₂CH₃ | CH₂CH₂CH₃ |
| A-1096 | cyclopropyl | SO₂CH₃ | CH₂CH₃ | CH₂CH₂OCH₃ |
| A-1097 | cyclopropyl | SO₂CH₃ | CH₂OCH₃ | CH₃ |
| A-1098 | cyclopropyl | SO₂CH₃ | CH₂OCH₃ | CH₂CH₃ |
| A-1099 | cyclopropyl | SO₂CH₃ | CH₂OCH₃ | CH₂CH₂CH₃ |
| A-1100 | cyclopropyl | SO₂CH₃ | CH₂OCH₃ | CH₂CH₂OCH₃ |
| A-1101 | cyclopropyl | SO₂CH₃ | CH₂OCH₂CH₃ | CH₃ |
| A-1102 | cyclopropyl | SO₂CH₃ | CH₂OCH₂CH₃ | CH₂CH₃ |
| A-1103 | cyclopropyl | SO₂CH₃ | CH₂OCH₂CH₃ | CH₂CH₂CH₃ |
| A-1104 | cyclopropyl | SO₂CH₃ | CH₂OCH₂CH₃ | CH₂CH₂OCH₃ |
| A-1105 | cyclopropyl | SO₂CH₃ | CH₂(CO)OCH₃ | CH₃ |
| A-1106 | cyclopropyl | SO₂CH₃ | CH₂(CO)OCH₃ | CH₂CH₃ |
| A-1107 | cyclopropyl | SO₂CH₃ | CH₂(CO)OCH₃ | CH₂CH₂CH₃ |
| A-1108 | cyclopropyl | SO₂CH₃ | CH₂(CO)OCH₃ | CH₂CH₂OCH₃ |
| A-1109 | cyclopropyl | SO₂CH₃ | CH₂CHCH₂ | CH₃ |
| A-1110 | cyclopropyl | SO₂CH₃ | CH₂CHCH₂ | CH₂CH₃ |
| A-1111 | cyclopropyl | SO₂CH₃ | CH₂CHCH₂ | CH₂CH₂CH₃ |
| A-1112 | cyclopropyl | SO₂CH₃ | CH₂CHCH₂ | CH₂CH₂OCH₃ |
| A-1113 | cyclopropyl | SO₂CH₃ | CH₂CCH | CH₃ |
| A-1114 | cyclopropyl | SO₂CH₃ | CH₂CCH | CH₂CH₃ |
| A-1115 | cyclopropyl | SO₂CH₃ | CH₂CCH | CH₂CH₂CH₃ |
| A-1116 | cyclopropyl | SO₂CH₃ | CH₂CCH | CH₂CH₂OCH₃ |
| A-1117 | cyclopropyl | SO₂CH₃ | CH₂C₆H₅ | CH₃ |
| A-1118 | cyclopropyl | SO₂CH₃ | CH₂C₆H₅ | CH₂CH₃ |
| A-1119 | cyclopropyl | SO₂CH₃ | CH₂C₆H₅ | CH₂CH₂CH₃ |
| A-1120 | cyclopropyl | SO₂CH₃ | CH₂C₆H₅ | CH₂CH₂OCH₃ |
| A-1121 | cyclopropyl | NO₂ | CH₃ | CH₃ |

TABLE A-continued

| | R¹ | R³ | R⁶ | R⁷ |
|---|---|---|---|---|
| A-1122 | cyclopropyl | NO$_2$ | CH$_3$ | CH$_2$CH$_3$ |
| A-1123 | cyclopropyl | NO$_2$ | CH$_3$ | CH$_2$CH$_2$CH$_3$ |
| A-1124 | cyclopropyl | NO$_2$ | CH$_3$ | CH$_2$CH$_2$OCH$_3$ |
| A-1125 | cyclopropyl | NO$_2$ | CH$_2$CH$_3$ | CH$_3$ |
| A-1126 | cyclopropyl | NO$_2$ | CH$_2$CH$_3$ | CH$_2$CH$_3$ |
| A-1127 | cyclopropyl | NO$_2$ | CH$_2$CH$_3$ | CH$_2$CH$_2$CH$_3$ |
| A-1128 | cyclopropyl | NO$_2$ | CH$_2$CH$_3$ | CH$_2$CH$_2$OCH$_3$ |
| A-1129 | cyclopropyl | NO$_2$ | CH$_2$OCH$_3$ | CH$_3$ |
| A-1130 | cyclopropyl | NO$_2$ | CH$_2$OCH$_3$ | CH$_2$CH$_3$ |
| A-1131 | cyclopropyl | NO$_2$ | CH$_2$OCH$_3$ | CH$_2$CH$_2$CH$_3$ |
| A-1132 | cyclopropyl | NO$_2$ | CH$_2$OCH$_3$ | CH$_2$CH$_2$OCH$_3$ |
| A-1133 | cyclopropyl | NO$_2$ | CH$_2$OCH$_2$CH$_3$ | CH$_3$ |
| A-1134 | cyclopropyl | NO$_2$ | CH$_2$OCH$_2$CH$_3$ | CH$_2$CH$_3$ |
| A-1135 | cyclopropyl | NO$_2$ | CH$_2$OCH$_2$CH$_3$ | CH$_2$CH$_2$CH$_3$ |
| A-1136 | cyclopropyl | NO$_2$ | CH$_2$OCH$_2$CH$_3$ | CH$_2$CH$_2$OCH$_3$ |
| A-1137 | cyclopropyl | NO$_2$ | CH$_2$(CO)OCH$_3$ | CH$_3$ |
| A-1138 | cyclopropyl | NO$_2$ | CH$_2$(CO)OCH$_3$ | CH$_2$CH$_3$ |
| A-1139 | cyclopropyl | NO$_2$ | CH$_2$(CO)OCH$_3$ | CH$_2$CH$_2$CH$_3$ |
| A-1140 | cyclopropyl | NO$_2$ | CH$_2$(CO)OCH$_3$ | CH$_2$CH$_2$OCH$_3$ |
| A-1141 | cyclopropyl | NO$_2$ | CH$_2$CHCH$_2$ | CH$_3$ |
| A-1142 | cyclopropyl | NO$_2$ | CH$_2$CHCH$_2$ | CH$_2$CH$_3$ |
| A-1143 | cyclopropyl | NO$_2$ | CH$_2$CHCH$_2$ | CH$_2$CH$_2$CH$_3$ |
| A-1144 | cyclopropyl | NO$_2$ | CH$_2$CHCH$_2$ | CH$_2$CH$_2$OCH$_3$ |
| A-1145 | cyclopropyl | NO$_2$ | CH$_2$CCH | CH$_3$ |
| A-1146 | cyclopropyl | NO$_2$ | CH$_2$CCH | CH$_2$CH$_3$ |
| A-1147 | cyclopropyl | NO$_2$ | CH$_2$CCH | CH$_2$CH$_2$CH$_3$ |
| A-1148 | cyclopropyl | NO$_2$ | CH$_2$CCH | CH$_2$CH$_2$OCH$_3$ |
| A-1149 | cyclopropyl | NO$_2$ | CH$_2$C$_6$H$_5$ | CH$_3$ |
| A-1150 | cyclopropyl | NO$_2$ | CH$_2$C$_6$H$_5$ | CH$_2$CH$_3$ |
| A-1151 | cyclopropyl | NO$_2$ | CH$_2$C$_6$H$_5$ | CH$_2$CH$_2$CH$_3$ |
| A-1152 | cyclopropyl | NO$_2$ | CH$_2$C$_6$H$_5$ | CH$_2$CH$_2$OCH$_3$ |
| A-1153 | CH$_2$OCH$_3$ | H | CH$_3$ | CH$_3$ |
| A-1154 | CH$_2$OCH$_3$ | H | CH$_3$ | CH$_2$CH$_3$ |
| A-1155 | CH$_2$OCH$_3$ | H | CH$_3$ | CH$_2$CH$_2$CH$_3$ |
| A-1156 | CH$_2$OCH$_3$ | H | CH$_3$ | CH$_2$CH$_2$OCH$_3$ |
| A-1157 | CH$_2$OCH$_3$ | H | CH$_2$CH$_3$ | CH$_3$ |
| A-1158 | CH$_2$OCH$_3$ | H | CH$_2$CH$_3$ | CH$_2$CH$_3$ |
| A-1159 | CH$_2$OCH$_3$ | H | CH$_2$CH$_3$ | CH$_2$CH$_2$CH$_3$ |
| A-1160 | CH$_2$OCH$_3$ | H | CH$_2$CH$_3$ | CH$_2$CH$_2$OCH$_3$ |
| A-1161 | CH$_2$OCH$_3$ | H | CH$_2$OCH$_3$ | CH$_3$ |
| A-1162 | CH$_2$OCH$_3$ | H | CH$_2$OCH$_3$ | CH$_2$CH$_3$ |
| A-1163 | CH$_2$OCH$_3$ | H | CH$_2$OCH$_3$ | CH$_2$CH$_2$CH$_3$ |
| A-1164 | CH$_2$OCH$_3$ | H | CH$_2$OCH$_3$ | CH$_2$CH$_2$OCH$_3$ |
| A-1165 | CH$_2$OCH$_3$ | H | CH$_2$OCH$_2$CH$_3$ | CH$_3$ |
| A-1166 | CH$_2$OCH$_3$ | H | CH$_2$OCH$_2$CH$_3$ | CH$_2$CH$_3$ |
| A-1167 | CH$_2$OCH$_3$ | H | CH$_2$OCH$_2$CH$_3$ | CH$_2$CH$_2$CH$_3$ |
| A-1168 | CH$_2$OCH$_3$ | H | CH$_2$OCH$_2$CH$_3$ | CH$_2$CH$_2$OCH$_3$ |
| A-1169 | CH$_2$OCH$_3$ | H | CH$_2$(CO)OCH$_3$ | CH$_3$ |
| A-1170 | CH$_2$OCH$_3$ | H | CH$_2$(CO)OCH$_3$ | CH$_2$CH$_3$ |
| A-1171 | CH$_2$OCH$_3$ | H | CH$_2$(CO)OCH$_3$ | CH$_2$CH$_2$CH$_3$ |
| A-1172 | CH$_2$OCH$_3$ | H | CH$_2$(CO)OCH$_3$ | CH$_2$CH$_2$OCH$_3$ |
| A-1173 | CH$_2$OCH$_3$ | H | CH$_2$CHCH$_2$ | CH$_3$ |
| A-1174 | CH$_2$OCH$_3$ | H | CH$_2$CHCH$_2$ | CH$_2$CH$_3$ |
| A-1175 | CH$_2$OCH$_3$ | H | CH$_2$CHCH$_2$ | CH$_2$CH$_2$CH$_3$ |
| A-1176 | CH$_2$OCH$_3$ | H | CH$_2$CHCH$_2$ | CH$_2$CH$_2$OCH$_3$ |
| A-1177 | CH$_2$OCH$_3$ | H | CH$_2$CCH | CH$_3$ |
| A-1178 | CH$_2$OCH$_3$ | H | CH$_2$CCH | CH$_2$CH$_3$ |
| A-1179 | CH$_2$OCH$_3$ | H | CH$_2$CCH | CH$_2$CH$_2$CH$_3$ |
| A-1180 | CH$_2$OCH$_3$ | H | CH$_2$CCH | CH$_2$CH$_2$OCH$_3$ |
| A-1181 | CH$_2$OCH$_3$ | H | CH$_2$C$_6$H$_5$ | CH$_3$ |
| A-1182 | CH$_2$OCH$_3$ | H | CH$_2$C$_6$H$_5$ | CH$_2$CH$_3$ |
| A-1183 | CH$_2$OCH$_3$ | H | CH$_2$C$_6$H$_5$ | CH$_2$CH$_2$CH$_3$ |
| A-1184 | CH$_2$OCH$_3$ | H | CH$_2$C$_6$H$_5$ | CH$_2$CH$_2$OCH$_3$ |
| A-1185 | CH$_2$OCH$_3$ | F | CH$_3$ | CH$_3$ |
| A-1186 | CH$_2$OCH$_3$ | F | CH$_3$ | CH$_2$CH$_3$ |
| A-1187 | CH$_2$OCH$_3$ | F | CH$_3$ | CH$_2$CH$_2$CH$_3$ |
| A-1188 | CH$_2$OCH$_3$ | F | CH$_3$ | CH$_2$CH$_2$OCH$_3$ |
| A-1189 | CH$_2$OCH$_3$ | F | CH$_2$CH$_3$ | CH$_3$ |
| A-1190 | CH$_2$OCH$_3$ | F | CH$_2$CH$_3$ | CH$_2$CH$_3$ |
| A-1191 | CH$_2$OCH$_3$ | F | CH$_2$CH$_3$ | CH$_2$CH$_2$CH$_3$ |
| A-1192 | CH$_2$OCH$_3$ | F | CH$_2$CH$_3$ | CH$_2$CH$_2$OCH$_3$ |
| A-1193 | CH$_2$OCH$_3$ | F | CH$_2$OCH$_3$ | CH$_3$ |
| A-1194 | CH$_2$OCH$_3$ | F | CH$_2$OCH$_3$ | CH$_2$CH$_3$ |
| A-1195 | CH$_2$OCH$_3$ | F | CH$_2$OCH$_3$ | CH$_2$CH$_2$CH$_3$ |
| A-1196 | CH$_2$OCH$_3$ | F | CH$_2$OCH$_3$ | CH$_2$CH$_2$OCH$_3$ |
| A-1197 | CH$_2$OCH$_3$ | F | CH$_2$OCH$_2$CH$_3$ | CH$_3$ |
| A-1198 | CH$_2$OCH$_3$ | F | CH$_2$OCH$_2$CH$_3$ | CH$_2$CH$_3$ |
| A-1199 | CH$_2$OCH$_3$ | F | CH$_2$OCH$_2$CH$_3$ | CH$_2$CH$_2$CH$_3$ |

TABLE A-continued

|   | R¹ | R³ | R⁶ | R⁷ |
| --- | --- | --- | --- | --- |
| A-1200 | CH₂OCH₃ | F | CH₂OCH₂CH₃ | CH₂CH₂OCH₃ |
| A-1201 | CH₂OCH₃ | F | CH₂(CO)OCH₃ | CH₃ |
| A-1202 | CH₂OCH₃ | F | CH₂(CO)OCH₃ | CH₂CH₃ |
| A-1203 | CH₂OCH₃ | F | CH₂(CO)OCH₃ | CH₂CH₂CH₃ |
| A-1204 | CH₂OCH₃ | F | CH₂(CO)OCH₃ | CH₂CH₂OCH₃ |
| A-1205 | CH₂OCH₃ | F | CH₂CHCH₂ | CH₃ |
| A-1206 | CH₂OCH₃ | F | CH₂CHCH₂ | CH₂CH₃ |
| A-1207 | CH₂OCH₃ | F | CH₂CHCH₂ | CH₂CH₂CH₃ |
| A-1208 | CH₂OCH₃ | F | CH₂CHCH₂ | CH₂CH₂OCH₃ |
| A-1209 | CH₂OCH₃ | F | CH₂CCH | CH₃ |
| A-1210 | CH₂OCH₃ | F | CH₂CCH | CH₂CH₃ |
| A-1211 | CH₂OCH₃ | F | CH₂CCH | CH₂CH₂CH₃ |
| A-1212 | CH₂OCH₃ | F | CH₂CCH | CH₂CH₂OCH₃ |
| A-1213 | CH₂OCH₃ | F | CH₂C₆H₅ | CH₃ |
| A-1214 | CH₂OCH₃ | F | CH₂C₆H₅ | CH₂CH₃ |
| A-1215 | CH₂OCH₃ | F | CH₂C₆H₅ | CH₂CH₂CH₃ |
| A-1216 | CH₂OCH₃ | F | CH₂C₆H₅ | CH₂CH₂OCH₃ |
| A-1217 | CH₂OCH₃ | Cl | CH₃ | CH₃ |
| A-1218 | CH₂OCH₃ | Cl | CH₃ | CH₂CH₃ |
| A-1219 | CH₂OCH₃ | Cl | CH₃ | CH₂CH₂CH₃ |
| A-1220 | CH₂OCH₃ | Cl | CH₃ | CH₂CH₂OCH₃ |
| A-1221 | CH₂OCH₃ | Cl | CH₂CH₃ | CH₃ |
| A-1222 | CH₂OCH₃ | Cl | CH₂CH₃ | CH₂CH₃ |
| A-1223 | CH₂OCH₃ | Cl | CH₂CH₃ | CH₂CH₂CH₃ |
| A-1224 | CH₂OCH₃ | Cl | CH₂CH₃ | CH₂CH₂OCH₃ |
| A-1225 | CH₂OCH₃ | Cl | CH₂OCH₃ | CH₃ |
| A-1226 | CH₂OCH₃ | Cl | CH₂OCH₃ | CH₂CH₃ |
| A-1227 | CH₂OCH₃ | Cl | CH₂OCH₃ | CH₂CH₂CH₃ |
| A-1228 | CH₂OCH₃ | Cl | CH₂OCH₃ | CH₂CH₂OCH₃ |
| A-1229 | CH₂OCH₃ | Cl | CH₂OCH₂CH₃ | CH₃ |
| A-1230 | CH₂OCH₃ | Cl | CH₂OCH₂CH₃ | CH₂CH₃ |
| A-1231 | CH₂OCH₃ | Cl | CH₂OCH₂CH₃ | CH₂CH₂CH₃ |
| A-1232 | CH₂OCH₃ | Cl | CH₂OCH₂CH₃ | CH₂CH₂OCH₃ |
| A-1233 | CH₂OCH₃ | Cl | CH₂(CO)OCH₃ | CH₃ |
| A-1234 | CH₂OCH₃ | Cl | CH₂(CO)OCH₃ | CH₂CH₃ |
| A-1235 | CH₂OCH₃ | Cl | CH₂(CO)OCH₃ | CH₂CH₂CH₃ |
| A-1236 | CH₂OCH₃ | Cl | CH₂(CO)OCH₃ | CH₂CH₂OCH₃ |
| A-1237 | CH₂OCH₃ | Cl | CH₂CHCH₂ | CH₃ |
| A-1238 | CH₂OCH₃ | Cl | CH₂CHCH₂ | CH₂CH₃ |
| A-1239 | CH₂OCH₃ | Cl | CH₂CHCH₂ | CH₂CH₂CH₃ |
| A-1240 | CH₂OCH₃ | Cl | CH₂CHCH₂ | CH₂CH₂OCH₃ |
| A-1241 | CH₂OCH₃ | Cl | CH₂CCH | CH₃ |
| A-1242 | CH₂OCH₃ | Cl | CH₂CCH | CH₂CH₃ |
| A-1243 | CH₂OCH₃ | Cl | CH₂CCH | CH₂CH₂CH₃ |
| A-1244 | CH₂OCH₃ | Cl | CH₂CCH | CH₂CH₂OCH₃ |
| A-1245 | CH₂OCH₃ | Cl | CH₂C₆H₅ | CH₃ |
| A-1246 | CH₂OCH₃ | Cl | CH₂C₆H₅ | CH₂CH₃ |
| A-1247 | CH₂OCH₃ | Cl | CH₂C₆H₅ | CH₂CH₂CH₃ |
| A-1248 | CH₂OCH₃ | Cl | CH₂C₆H₅ | CH₂CH₂OCH₃ |
| A-1249 | CH₂OCH₃ | Br | CH₃ | CH₃ |
| A-1250 | CH₂OCH₃ | Br | CH₃ | CH₂CH₃ |
| A-1251 | CH₂OCH₃ | Br | CH₃ | CH₂CH₂CH₃ |
| A-1252 | CH₂OCH₃ | Br | CH₃ | CH₂CH₂OCH₃ |
| A-1253 | CH₂OCH₃ | Br | CH₂CH₃ | CH₃ |
| A-1254 | CH₂OCH₃ | Br | CH₂CH₃ | CH₂CH₃ |
| A-1255 | CH₂OCH₃ | Br | CH₂CH₃ | CH₂CH₂CH₃ |
| A-1256 | CH₂OCH₃ | Br | CH₂CH₃ | CH₂CH₂OCH₃ |
| A-1257 | CH₂OCH₃ | Br | CH₂OCH₃ | CH₃ |
| A-1258 | CH₂OCH₃ | Br | CH₂OCH₃ | CH₂CH₃ |
| A-1259 | CH₂OCH₃ | Br | CH₂OCH₃ | CH₂CH₂CH₃ |
| A-1260 | CH₂OCH₃ | Br | CH₂OCH₃ | CH₂CH₂OCH₃ |
| A-1261 | CH₂OCH₃ | Br | CH₂OCH₂CH₃ | CH₃ |
| A-1262 | CH₂OCH₃ | Br | CH₂OCH₂CH₃ | CH₂CH₃ |
| A-1263 | CH₂OCH₃ | Br | CH₂OCH₂CH₃ | CH₂CH₂CH₃ |
| A-1264 | CH₂OCH₃ | Br | CH₂OCH₂CH₃ | CH₂CH₂OCH₃ |
| A-1265 | CH₂OCH₃ | Br | CH₂(CO)OCH₃ | CH₃ |
| A-1266 | CH₂OCH₃ | Br | CH₂(CO)OCH₃ | CH₂CH₃ |
| A-1267 | CH₂OCH₃ | Br | CH₂(CO)OCH₃ | CH₂CH₂CH₃ |
| A-1268 | CH₂OCH₃ | Br | CH₂(CO)OCH₃ | CH₂CH₂OCH₃ |
| A-1269 | CH₂OCH₃ | Br | CH₂CHCH₂ | CH₃ |
| A-1270 | CH₂OCH₃ | Br | CH₂CHCH₂ | CH₂CH₃ |
| A-1271 | CH₂OCH₃ | Br | CH₂CHCH₂ | CH₂CH₂CH₃ |
| A-1272 | CH₂OCH₃ | Br | CH₂CHCH₂ | CH₂CH₂OCH₃ |
| A-1273 | CH₂OCH₃ | Br | CH₂CCH | CH₃ |
| A-1274 | CH₂OCH₃ | Br | CH₂CCH | CH₂CH₃ |
| A-1275 | CH₂OCH₃ | Br | CH₂CCH | CH₂CH₂CH₃ |
| A-1276 | CH₂OCH₃ | Br | CH₂CCH | CH₂CH₂OCH₃ |
| A-1277 | CH₂OCH₃ | Br | CH₂C₆H₅ | CH₃ |

TABLE A-continued

| | R¹ | R³ | R⁶ | R⁷ |
|---|---|---|---|---|
| A-1278 | CH₂OCH₃ | Br | CH₂C₆H₅ | CH₂CH₃ |
| A-1279 | CH₂OCH₃ | Br | CH₂C₆H₅ | CH₂CH₂CH₃ |
| A-1280 | CH₂OCH₃ | Br | CH₂C₆H₅ | CH₂CH₂OCH₃ |
| A-1281 | CH₂OCH₃ | CN | CH₃ | CH₃ |
| A-1282 | CH₂OCH₃ | CN | CH₃ | CH₂CH₃ |
| A-1283 | CH₂OCH₃ | CN | CH₃ | CH₂CH₂CH₃ |
| A-1284 | CH₂OCH₃ | CN | CH₃ | CH₂CH₂OCH₃ |
| A-1285 | CH₂OCH₃ | CN | CH₂CH₃ | CH₃ |
| A-1286 | CH₂OCH₃ | CN | CH₂CH₃ | CH₂CH₃ |
| A-1287 | CH₂OCH₃ | CN | CH₂CH₃ | CH₂CH₂CH₃ |
| A-1288 | CH₂OCH₃ | CN | CH₂CH₃ | CH₂CH₂OCH₃ |
| A-1289 | CH₂OCH₃ | CN | CH₂OCH₃ | CH₃ |
| A-1290 | CH₂OCH₃ | CN | CH₂OCH₃ | CH₂CH₃ |
| A-1291 | CH₂OCH₃ | CN | CH₂OCH₃ | CH₂CH₂CH₃ |
| A-1292 | CH₂OCH₃ | CN | CH₂OCH₃ | CH₂CH₂OCH₃ |
| A-1293 | CH₂OCH₃ | CN | CH₂OCH₂CH₃ | CH₃ |
| A-1294 | CH₂OCH₃ | CN | CH₂OCH₂CH₃ | CH₂CH₃ |
| A-1295 | CH₂OCH₃ | CN | CH₂OCH₂CH₃ | CH₂CH₂CH₃ |
| A-1296 | CH₂OCH₃ | CN | CH₂OCH₂CH₃ | CH₂CH₂OCH₃ |
| A-1297 | CH₂OCH₃ | CN | CH₂(CO)OCH₃ | CH₃ |
| A-1298 | CH₂OCH₃ | CN | CH₂(CO)OCH₃ | CH₂CH₃ |
| A-1299 | CH₂OCH₃ | CN | CH₂(CO)OCH₃ | CH₂CH₂CH₃ |
| A-1300 | CH₂OCH₃ | CN | CH₂(CO)OCH₃ | CH₂CH₂OCH₃ |
| A-1301 | CH₂OCH₃ | CN | CH₂CHCH₂ | CH₃ |
| A-1302 | CH₂OCH₃ | CN | CH₂CHCH₂ | CH₂CH₃ |
| A-1303 | CH₂OCH₃ | CN | CH₂CHCH₂ | CH₂CH₂CH₃ |
| A-1304 | CH₂OCH₃ | CN | CH₂CHCH₂ | CH₂CH₂OCH₃ |
| A-1305 | CH₂OCH₃ | CN | CH₂CCH | CH₃ |
| A-1306 | CH₂OCH₃ | CN | CH₂CCH | CH₂CH₃ |
| A-1307 | CH₂OCH₃ | CN | CH₂CCH | CH₂CH₂CH₃ |
| A-1308 | CH₂OCH₃ | CN | CH₂CCH | CH₂CH₂OCH₃ |
| A-1309 | CH₂OCH₃ | CN | CH₂C₆H₅ | CH₃ |
| A-1310 | CH₂OCH₃ | CN | CH₂C₆H₅ | CH₂CH₃ |
| A-1311 | CH₂OCH₃ | CN | CH₂C₆H₅ | CH₂CH₂CH₃ |
| A-1312 | CH₂OCH₃ | CN | CH₂C₆H₅ | CH₂CH₂OCH₃ |
| A-1313 | CH₂OCH₃ | CH₃ | CH₃ | CH₃ |
| A-1314 | CH₂OCH₃ | CH₃ | CH₃ | CH₂CH₃ |
| A-1315 | CH₂OCH₃ | CH₃ | CH₃ | CH₂CH₂CH₃ |
| A-1316 | CH₂OCH₃ | CH₃ | CH₃ | CH₂CH₂OCH₃ |
| A-1317 | CH₂OCH₃ | CH₃ | CH₂CH₃ | CH₃ |
| A-1318 | CH₂OCH₃ | CH₃ | CH₂CH₃ | CH₂CH₃ |
| A-1319 | CH₂OCH₃ | CH₃ | CH₂CH₃ | CH₂CH₂CH₃ |
| A-1320 | CH₂OCH₃ | CH₃ | CH₂CH₃ | CH₂CH₂OCH₃ |
| A-1321 | CH₂OCH₃ | CH₃ | CH₂OCH₃ | CH₃ |
| A-1322 | CH₂OCH₃ | CH₃ | CH₂OCH₃ | CH₂CH₃ |
| A-1323 | CH₂OCH₃ | CH₃ | CH₂OCH₃ | CH₂CH₂CH₃ |
| A-1324 | CH₂OCH₃ | CH₃ | CH₂OCH₃ | CH₂CH₂OCH₃ |
| A-1325 | CH₂OCH₃ | CH₃ | CH₂OCH₂CH₃ | CH₃ |
| A-1326 | CH₂OCH₃ | CH₃ | CH₂OCH₂CH₃ | CH₂CH₃ |
| A-1327 | CH₂OCH₃ | CH₃ | CH₂OCH₂CH₃ | CH₂CH₂CH₃ |
| A-1328 | CH₂OCH₃ | CH₃ | CH₂OCH₂CH₃ | CH₂CH₂OCH₃ |
| A-1329 | CH₂OCH₃ | CH₃ | CH₂(CO)OCH₃ | CH₃ |
| A-1330 | CH₂OCH₃ | CH₃ | CH₂(CO)OCH₃ | CH₂CH₃ |
| A-1331 | CH₂OCH₃ | CH₃ | CH₂(CO)OCH₃ | CH₂CH₂CH₃ |
| A-1332 | CH₂OCH₃ | CH₃ | CH₂(CO)OCH₃ | CH₂CH₂OCH₃ |
| A-1333 | CH₂OCH₃ | CH₃ | CH₂CHCH₂ | CH₃ |
| A-1334 | CH₂OCH₃ | CH₃ | CH₂CHCH₂ | CH₂CH₃ |
| A-1335 | CH₂OCH₃ | CH₃ | CH₂CHCH₂ | CH₂CH₂CH₃ |
| A-1336 | CH₂OCH₃ | CH₃ | CH₂CHCH₂ | CH₂CH₂OCH₃ |
| A-1337 | CH₂OCH₃ | CH₃ | CH₂CCH | CH₃ |
| A-1338 | CH₂OCH₃ | CH₃ | CH₂CCH | CH₂CH₃ |
| A-1339 | CH₂OCH₃ | CH₃ | CH₂CCH | CH₂CH₂CH₃ |
| A-1340 | CH₂OCH₃ | CH₃ | CH₂CCH | CH₂CH₂OCH₃ |
| A-1341 | CH₂OCH₃ | CH₃ | CH₂C₆H₅ | CH₃ |
| A-1342 | CH₂OCH₃ | CH₃ | CH₂C₆H₅ | CH₂CH₃ |
| A-1343 | CH₂OCH₃ | CH₃ | CH₂C₆H₅ | CH₂CH₂CH₃ |
| A-1344 | CH₂OCH₃ | CH₃ | CH₂C₆H₅ | CH₂CH₂OCH₃ |
| A-1345 | CH₂OCH₃ | CF₃ | CH₃ | CH₃ |
| A-1346 | CH₂OCH₃ | CF₃ | CH₃ | CH₂CH₃ |
| A-1347 | CH₂OCH₃ | CF₃ | CH₃ | CH₂CH₂CH₃ |
| A-1348 | CH₂OCH₃ | CF₃ | CH₃ | CH₂CH₂OCH₃ |
| A-1349 | CH₂OCH₃ | CF₃ | CH₂CH₃ | CH₃ |
| A-1350 | CH₂OCH₃ | CF₃ | CH₂CH₃ | CH₂CH₃ |
| A-1351 | CH₂OCH₃ | CF₃ | CH₂CH₃ | CH₂CH₂CH₃ |
| A-1352 | CH₂OCH₃ | CF₃ | CH₂CH₃ | CH₂CH₂OCH₃ |
| A-1353 | CH₂OCH₃ | CF₃ | CH₂OCH₃ | CH₃ |
| A-1354 | CH₂OCH₃ | CF₃ | CH₂OCH₃ | CH₂CH₃ |
| A-1355 | CH₂OCH₃ | CF₃ | CH₂OCH₃ | CH₂CH₂CH₃ |

TABLE A-continued

| | $R^1$ | $R^3$ | $R^6$ | $R^7$ |
|---|---|---|---|---|
| A-1356 | CH$_2$OCH$_3$ | CF$_3$ | CH$_2$OCH$_3$ | CH$_2$CH$_2$OCH$_3$ |
| A-1357 | CH$_2$OCH$_3$ | CF$_3$ | CH$_2$OCH$_2$CH$_3$ | CH$_3$ |
| A-1358 | CH$_2$OCH$_3$ | CF$_3$ | CH$_2$OCH$_2$CH$_3$ | CH$_2$CH$_3$ |
| A-1359 | CH$_2$OCH$_3$ | CF$_3$ | CH$_2$OCH$_2$CH$_3$ | CH$_2$CH$_2$CH$_3$ |
| A-1360 | CH$_2$OCH$_3$ | CF$_3$ | CH$_2$OCH$_2$CH$_3$ | CH$_2$CH$_2$OCH$_3$ |
| A-1361 | CH$_2$OCH$_3$ | CF$_3$ | CH$_2$(CO)OCH$_3$ | CH$_3$ |
| A-1362 | CH$_2$OCH$_3$ | CF$_3$ | CH$_2$(CO)OCH$_3$ | CH$_2$CH$_3$ |
| A-1363 | CH$_2$OCH$_3$ | CF$_3$ | CH$_2$(CO)OCH$_3$ | CH$_2$CH$_2$CH$_3$ |
| A-1364 | CH$_2$OCH$_3$ | CF$_3$ | CH$_2$(CO)OCH$_3$ | CH$_2$CH$_2$OCH$_3$ |
| A-1365 | CH$_2$OCH$_3$ | CF$_3$ | CH$_2$CHCH$_2$ | CH$_3$ |
| A-1366 | CH$_2$OCH$_3$ | CF$_3$ | CH$_2$CHCH$_2$ | CH$_2$CH$_3$ |
| A-1367 | CH$_2$OCH$_3$ | CF$_3$ | CH$_2$CHCH$_2$ | CH$_2$CH$_2$CH$_3$ |
| A-1368 | CH$_2$OCH$_3$ | CF$_3$ | CH$_2$CHCH$_2$ | CH$_2$CH$_2$OCH$_3$ |
| A-1369 | CH$_2$OCH$_3$ | CF$_3$ | CH$_2$CCH | CH$_3$ |
| A-1370 | CH$_2$OCH$_3$ | CF$_3$ | CH$_2$CCH | CH$_2$CH$_3$ |
| A-1371 | CH$_2$OCH$_3$ | CF$_3$ | CH$_2$CCH | CH$_2$CH$_2$CH$_3$ |
| A-1372 | CH$_2$OCH$_3$ | CF$_3$ | CH$_2$CCH | CH$_2$CH$_2$OCH$_3$ |
| A-1373 | CH$_2$OCH$_3$ | CF$_3$ | CH$_2$C$_6$H$_5$ | CH$_3$ |
| A-1374 | CH$_2$OCH$_3$ | CF$_3$ | CH$_2$C$_6$H$_5$ | CH$_2$CH$_3$ |
| A-1375 | CH$_2$OCH$_3$ | CF$_3$ | CH$_2$C$_6$H$_5$ | CH$_2$CH$_2$CH$_3$ |
| A-1376 | CH$_2$OCH$_3$ | CF$_3$ | CH$_2$C$_6$H$_5$ | CH$_2$CH$_2$OCH$_3$ |
| A-1377 | CH$_2$OCH$_3$ | SO$_2$CH$_3$ | CH$_3$ | CH$_3$ |
| A-1378 | CH$_2$OCH$_3$ | SO$_2$CH$_3$ | CH$_3$ | CH$_2$CH$_3$ |
| A-1379 | CH$_2$OCH$_3$ | SO$_2$CH$_3$ | CH$_3$ | CH$_2$CH$_2$CH$_3$ |
| A-1380 | CH$_2$OCH$_3$ | SO$_2$CH$_3$ | CH$_3$ | CH$_2$CH$_2$OCH$_3$ |
| A-1381 | CH$_2$OCH$_3$ | SO$_2$CH$_3$ | CH$_2$CH$_3$ | CH$_3$ |
| A-1382 | CH$_2$OCH$_3$ | SO$_2$CH$_3$ | CH$_2$CH$_3$ | CH$_2$CH$_3$ |
| A-1383 | CH$_2$OCH$_3$ | SO$_2$CH$_3$ | CH$_2$CH$_3$ | CH$_2$CH$_2$CH$_3$ |
| A-1384 | CH$_2$OCH$_3$ | SO$_2$CH$_3$ | CH$_2$CH$_3$ | CH$_2$CH$_2$OCH$_3$ |
| A-1385 | CH$_2$OCH$_3$ | SO$_2$CH$_3$ | CH$_2$OCH$_3$ | CH$_3$ |
| A-1386 | CH$_2$OCH$_3$ | SO$_2$CH$_3$ | CH$_2$OCH$_3$ | CH$_2$CH$_3$ |
| A-1387 | CH$_2$OCH$_3$ | SO$_2$CH$_3$ | CH$_2$OCH$_3$ | CH$_2$CH$_2$CH$_3$ |
| A-1388 | CH$_2$OCH$_3$ | SO$_2$CH$_3$ | CH$_2$OCH$_3$ | CH$_2$CH$_2$OCH$_3$ |
| A-1389 | CH$_2$OCH$_3$ | SO$_2$CH$_3$ | CH$_2$OCH$_2$CH$_3$ | CH$_3$ |
| A-1390 | CH$_2$OCH$_3$ | SO$_2$CH$_3$ | CH$_2$OCH$_2$CH$_3$ | CH$_2$CH$_3$ |
| A-1391 | CH$_2$OCH$_3$ | SO$_2$CH$_3$ | CH$_2$OCH$_2$CH$_3$ | CH$_2$CH$_2$CH$_3$ |
| A-1392 | CH$_2$OCH$_3$ | SO$_2$CH$_3$ | CH$_2$OCH$_2$CH$_3$ | CH$_2$CH$_2$OCH$_3$ |
| A-1393 | CH$_2$OCH$_3$ | SO$_2$CH$_3$ | CH$_2$(CO)OCH$_3$ | CH$_3$ |
| A-1394 | CH$_2$OCH$_3$ | SO$_2$CH$_3$ | CH$_2$(CO)OCH$_3$ | CH$_2$CH$_3$ |
| A-1395 | CH$_2$OCH$_3$ | SO$_2$CH$_3$ | CH$_2$(CO)OCH$_3$ | CH$_2$CH$_2$CH$_3$ |
| A-1396 | CH$_2$OCH$_3$ | SO$_2$CH$_3$ | CH$_2$(CO)OCH$_3$ | CH$_2$CH$_2$OCH$_3$ |
| A-1397 | CH$_2$OCH$_3$ | SO$_2$CH$_3$ | CH$_2$CHCH$_2$ | CH$_3$ |
| A-1398 | CH$_2$OCH$_3$ | SO$_2$CH$_3$ | CH$_2$CHCH$_2$ | CH$_2$CH$_3$ |
| A-1399 | CH$_2$OCH$_3$ | SO$_2$CH$_3$ | CH$_2$CHCH$_2$ | CH$_2$CH$_2$CH$_3$ |
| A-1400 | CH$_2$OCH$_3$ | SO$_2$CH$_3$ | CH$_2$CHCH$_2$ | CH$_2$CH$_2$OCH$_3$ |
| A-1401 | CH$_2$OCH$_3$ | SO$_2$CH$_3$ | CH$_2$CCH | CH$_3$ |
| A-1402 | CH$_2$OCH$_3$ | SO$_2$CH$_3$ | CH$_2$CCH | CH$_2$CH$_3$ |
| A-1403 | CH$_2$OCH$_3$ | SO$_2$CH$_3$ | CH$_2$CCH | CH$_2$CH$_2$CH$_3$ |
| A-1404 | CH$_2$OCH$_3$ | SO$_2$CH$_3$ | CH$_2$CCH | CH$_2$CH$_2$OCH$_3$ |
| A-1405 | CH$_2$OCH$_3$ | SO$_2$CH$_3$ | CH$_2$C$_6$H$_5$ | CH$_3$ |
| A-1406 | CH$_2$OCH$_3$ | SO$_2$CH$_3$ | CH$_2$C$_6$H$_5$ | CH$_2$CH$_3$ |
| A-1407 | CH$_2$OCH$_3$ | SO$_2$CH$_3$ | CH$_2$C$_6$H$_5$ | CH$_2$CH$_2$CH$_3$ |
| A-1408 | CH$_2$OCH$_3$ | SO$_2$CH$_3$ | CH$_2$C$_6$H$_5$ | CH$_2$CH$_2$OCH$_3$ |
| A-1409 | CH$_2$OCH$_3$ | NO$_2$ | CH$_3$ | CH$_3$ |
| A-1410 | CH$_2$OCH$_3$ | NO$_2$ | CH$_3$ | CH$_2$CH$_3$ |
| A-1411 | CH$_2$OCH$_3$ | NO$_2$ | CH$_3$ | CH$_2$CH$_2$CH$_3$ |
| A-1412 | CH$_2$OCH$_3$ | NO$_2$ | CH$_3$ | CH$_2$CH$_2$OCH$_3$ |
| A-1413 | CH$_2$OCH$_3$ | NO$_2$ | CH$_2$CH$_3$ | CH$_3$ |
| A-1414 | CH$_2$OCH$_3$ | NO$_2$ | CH$_2$CH$_3$ | CH$_2$CH$_3$ |
| A-1415 | CH$_2$OCH$_3$ | NO$_2$ | CH$_2$CH$_3$ | CH$_2$CH$_2$CH$_3$ |
| A-1416 | CH$_2$OCH$_3$ | NO$_2$ | CH$_2$CH$_3$ | CH$_2$CH$_2$OCH$_3$ |
| A-1417 | CH$_2$OCH$_3$ | NO$_2$ | CH$_2$OCH$_3$ | CH$_3$ |
| A-1418 | CH$_2$OCH$_3$ | NO$_2$ | CH$_2$OCH$_3$ | CH$_2$CH$_3$ |
| A-1419 | CH$_2$OCH$_3$ | NO$_2$ | CH$_2$OCH$_3$ | CH$_2$CH$_2$CH$_3$ |
| A-1420 | CH$_2$OCH$_3$ | NO$_2$ | CH$_2$OCH$_3$ | CH$_2$CH$_2$OCH$_3$ |
| A-1421 | CH$_2$OCH$_3$ | NO$_2$ | CH$_2$OCH$_2$CH$_3$ | CH$_3$ |
| A-1422 | CH$_2$OCH$_3$ | NO$_2$ | CH$_2$OCH$_2$CH$_3$ | CH$_2$CH$_3$ |
| A-1423 | CH$_2$OCH$_3$ | NO$_2$ | CH$_2$OCH$_2$CH$_3$ | CH$_2$CH$_2$CH$_3$ |
| A-1424 | CH$_2$OCH$_3$ | NO$_2$ | CH$_2$OCH$_2$CH$_3$ | CH$_2$CH$_2$OCH$_3$ |
| A-1425 | CH$_2$OCH$_3$ | NO$_2$ | CH$_2$(CO)OCH$_3$ | CH$_3$ |
| A-1426 | CH$_2$OCH$_3$ | NO$_2$ | CH$_2$(CO)OCH$_3$ | CH$_2$CH$_3$ |
| A-1427 | CH$_2$OCH$_3$ | NO$_2$ | CH$_2$(CO)OCH$_3$ | CH$_2$CH$_2$CH$_3$ |
| A-1428 | CH$_2$OCH$_3$ | NO$_2$ | CH$_2$(CO)OCH$_3$ | CH$_2$CH$_2$OCH$_3$ |
| A-1429 | CH$_2$OCH$_3$ | NO$_2$ | CH$_2$CHCH$_2$ | CH$_3$ |
| A-1430 | CH$_2$OCH$_3$ | NO$_2$ | CH$_2$CHCH$_2$ | CH$_2$CH$_3$ |
| A-1431 | CH$_2$OCH$_3$ | NO$_2$ | CH$_2$CHCH$_2$ | CH$_2$CH$_2$CH$_3$ |
| A-1432 | CH$_2$OCH$_3$ | NO$_2$ | CH$_2$CHCH$_2$ | CH$_2$CH$_2$OCH$_3$ |
| A-1433 | CH$_2$OCH$_3$ | NO$_2$ | CH$_2$CCH | CH$_3$ |

TABLE A-continued

|  | R¹ | R³ | R⁶ | R⁷ |
|---|---|---|---|---|
| A-1434 | CH₂OCH₃ | NO₂ | CH₂CCH | CH₂CH₃ |
| A-1435 | CH₂OCH₃ | NO₂ | CH₂CCH | CH₂CH₂CH₃ |
| A-1436 | CH₂OCH₃ | NO₂ | CH₂CCH | CH₂CH₂OCH₃ |
| A-1437 | CH₂OCH₃ | NO₂ | CH₂C₆H₅ | CH₃ |
| A-1438 | CH₂OCH₃ | NO₂ | CH₂C₆H₅ | CH₂CH₃ |
| A-1439 | CH₂OCH₃ | NO₂ | CH₂C₆H₅ | CH₂CH₂CH₃ |
| A-1440 | CH₂OCH₃ | NO₂ | CH₂C₆H₅ | CH₂CH₂OCH₃ |
| A-1441 | CH₂OCH₂CH₂OCH₃ | H | CH₃ | CH₃ |
| A-1442 | CH₂OCH₂CH₂OCH₃ | H | CH₃ | CH₂CH₃ |
| A-1443 | CH₂OCH₂CH₂OCH₃ | H | CH₃ | CH₂CH₂CH₃ |
| A-1444 | CH₂OCH₂CH₂OCH₃ | H | CH₃ | CH₂CH₂OCH₃ |
| A-1445 | CH₂OCH₂CH₂OCH₃ | H | CH₂CH₃ | CH₃ |
| A-1446 | CH₂OCH₂CH₂OCH₃ | H | CH₂CH₃ | CH₂CH₃ |
| A-1447 | CH₂OCH₂CH₂OCH₃ | H | CH₂CH₃ | CH₂CH₂CH₃ |
| A-1448 | CH₂OCH₂CH₂OCH₃ | H | CH₂CH₃ | CH₂CH₂OCH₃ |
| A-1449 | CH₂OCH₂CH₂OCH₃ | H | CH₂OCH₃ | CH₃ |
| A-1450 | CH₂OCH₂CH₂OCH₃ | H | CH₂OCH₃ | CH₂CH₃ |
| A-1451 | CH₂OCH₂CH₂OCH₃ | H | CH₂OCH₃ | CH₂CH₂CH₃ |
| A-1452 | CH₂OCH₂CH₂OCH₃ | H | CH₂OCH₃ | CH₂CH₂OCH₃ |
| A-1453 | CH₂OCH₂CH₂OCH₃ | H | CH₂OCH₂CH₃ | CH₃ |
| A-1454 | CH₂OCH₂CH₂OCH₃ | H | CH₂OCH₂CH₃ | CH₂CH₃ |
| A-1455 | CH₂OCH₂CH₂OCH₃ | H | CH₂OCH₂CH₃ | CH₂CH₂CH₃ |
| A-1456 | CH₂OCH₂CH₂OCH₃ | H | CH₂OCH₂CH₃ | CH₂CH₂OCH₃ |
| A-1457 | CH₂OCH₂CH₂OCH₃ | H | CH₂(CO)OCH₃ | CH₃ |
| A-1458 | CH₂OCH₂CH₂OCH₃ | H | CH₂(CO)OCH₃ | CH₂CH₃ |
| A-1459 | CH₂OCH₂CH₂OCH₃ | H | CH₂(CO)OCH₃ | CH₂CH₂CH₃ |
| A-1460 | CH₂OCH₂CH₂OCH₃ | H | CH₂(CO)OCH₃ | CH₂CH₂OCH₃ |
| A-1461 | CH₂OCH₂CH₂OCH₃ | H | CH₂CHCH₂ | CH₃ |
| A-1462 | CH₂OCH₂CH₂OCH₃ | H | CH₂CHCH₂ | CH₂CH₃ |
| A-1463 | CH₂OCH₂CH₂OCH₃ | H | CH₂CHCH₂ | CH₂CH₂CH₃ |
| A-1464 | CH₂OCH₂CH₂OCH₃ | H | CH₂CHCH₂ | CH₂CH₂OCH₃ |
| A-1465 | CH₂OCH₂CH₂OCH₃ | H | CH₂CCH | CH₃ |
| A-1466 | CH₂OCH₂CH₂OCH₃ | H | CH₂CCH | CH₂CH₃ |
| A-1467 | CH₂OCH₂CH₂OCH₃ | H | CH₂CCH | CH₂CH₂CH₃ |
| A-1468 | CH₂OCH₂CH₂OCH₃ | H | CH₂CCH | CH₂CH₂OCH₃ |
| A-1469 | CH₂OCH₂CH₂OCH₃ | H | CH₂C₆H₅ | CH₃ |
| A-1470 | CH₂OCH₂CH₂OCH₃ | H | CH₂C₆H₅ | CH₂CH₃ |
| A-1471 | CH₂OCH₂CH₂OCH₃ | H | CH₂C₆H₅ | CH₂CH₂CH₃ |
| A-1472 | CH₂OCH₂CH₂OCH₃ | H | CH₂C₆H₅ | CH₂CH₂OCH₃ |
| A-1473 | CH₂OCH₂CH₂OCH₃ | F | CH₃ | CH₃ |
| A-1474 | CH₂OCH₂CH₂OCH₃ | F | CH₃ | CH₂CH₃ |
| A-1475 | CH₂OCH₂CH₂OCH₃ | F | CH₃ | CH₂CH₂CH₃ |
| A-1476 | CH₂OCH₂CH₂OCH₃ | F | CH₃ | CH₂CH₂OCH₃ |
| A-1477 | CH₂OCH₂CH₂OCH₃ | F | CH₂CH₃ | CH₃ |
| A-1478 | CH₂OCH₂CH₂OCH₃ | F | CH₂CH₃ | CH₂CH₃ |
| A-1479 | CH₂OCH₂CH₂OCH₃ | F | CH₂CH₃ | CH₂CH₂CH₃ |
| A-1480 | CH₂OCH₂CH₂OCH₃ | F | CH₂CH₃ | CH₂CH₂OCH₃ |
| A-1481 | CH₂OCH₂CH₂OCH₃ | F | CH₂OCH₃ | CH₃ |
| A-1482 | CH₂OCH₂CH₂OCH₃ | F | CH₂OCH₃ | CH₂CH₃ |
| A-1483 | CH₂OCH₂CH₂OCH₃ | F | CH₂OCH₃ | CH₂CH₂CH₃ |
| A-1484 | CH₂OCH₂CH₂OCH₃ | F | CH₂OCH₃ | CH₂CH₂OCH₃ |
| A-1485 | CH₂OCH₂CH₂OCH₃ | F | CH₂OCH₂CH₃ | CH₃ |
| A-1486 | CH₂OCH₂CH₂OCH₃ | F | CH₂OCH₂CH₃ | CH₂CH₃ |
| A-1487 | CH₂OCH₂CH₂OCH₃ | F | CH₂OCH₂CH₃ | CH₂CH₂CH₃ |
| A-1488 | CH₂OCH₂CH₂OCH₃ | F | CH₂OCH₂CH₃ | CH₂CH₂OCH₃ |
| A-1489 | CH₂OCH₂CH₂OCH₃ | F | CH₂(CO)OCH₃ | CH₃ |
| A-1490 | CH₂OCH₂CH₂OCH₃ | F | CH₂(CO)OCH₃ | CH₂CH₃ |
| A-1491 | CH₂OCH₂CH₂OCH₃ | F | CH₂(CO)OCH₃ | CH₂CH₂CH₃ |
| A-1492 | CH₂OCH₂CH₂OCH₃ | F | CH₂(CO)OCH₃ | CH₂CH₂OCH₃ |
| A-1493 | CH₂OCH₂CH₂OCH₃ | F | CH₂CHCH₂ | CH₃ |
| A-1494 | CH₂OCH₂CH₂OCH₃ | F | CH₂CHCH₂ | CH₂CH₃ |
| A-1495 | CH₂OCH₂CH₂OCH₃ | F | CH₂CHCH₂ | CH₂CH₂CH₃ |
| A-1496 | CH₂OCH₂CH₂OCH₃ | F | CH₂CHCH₂ | CH₂CH₂OCH₃ |
| A-1497 | CH₂OCH₂CH₂OCH₃ | F | CH₂CCH | CH₃ |
| A-1498 | CH₂OCH₂CH₂OCH₃ | F | CH₂CCH | CH₂CH₃ |
| A-1499 | CH₂OCH₂CH₂OCH₃ | F | CH₂CCH | CH₂CH₂CH₃ |
| A-1500 | CH₂OCH₂CH₂OCH₃ | F | CH₂CCH | CH₂CH₂OCH₃ |
| A-1501 | CH₂OCH₂CH₂OCH₃ | F | CH₂C₆H₅ | CH₃ |
| A-1502 | CH₂OCH₂CH₂OCH₃ | F | CH₂C₆H₅ | CH₂CH₃ |
| A-1503 | CH₂OCH₂CH₂OCH₃ | F | CH₂C₆H₅ | CH₂CH₂CH₃ |
| A-1504 | CH₂OCH₂CH₂OCH₃ | F | CH₂C₆H₅ | CH₂CH₂OCH₃ |
| A-1505 | CH₂OCH₂CH₂OCH₃ | Cl | CH₃ | CH₃ |
| A-1506 | CH₂OCH₂CH₂OCH₃ | Cl | CH₃ | CH₂CH₃ |
| A-1507 | CH₂OCH₂CH₂OCH₃ | Cl | CH₃ | CH₂CH₂CH₃ |
| A-1508 | CH₂OCH₂CH₂OCH₃ | Cl | CH₃ | CH₂CH₂OCH₃ |
| A-1509 | CH₂OCH₂CH₂OCH₃ | Cl | CH₂CH₃ | CH₃ |
| A-1510 | CH₂OCH₂CH₂OCH₃ | Cl | CH₂CH₃ | CH₂CH₃ |
| A-1511 | CH₂OCH₂CH₂OCH₃ | Cl | CH₂CH₃ | CH₂CH₂CH₃ |

TABLE A-continued

| | R¹ | R³ | R⁶ | R⁷ |
|---|---|---|---|---|
| A-1512 | CH₂OCH₂CH₂OCH₃ | Cl | CH₂CH₃ | CH₂CH₂OCH₃ |
| A-1513 | CH₂OCH₂CH₂OCH₃ | Cl | CH₂OCH₃ | CH₃ |
| A-1514 | CH₂OCH₂CH₂OCH₃ | Cl | CH₂OCH₃ | CH₂CH₃ |
| A-1515 | CH₂OCH₂CH₂OCH₃ | Cl | CH₂OCH₃ | CH₂CH₂CH₃ |
| A-1516 | CH₂OCH₂CH₂OCH₃ | Cl | CH₂OCH₃ | CH₂CH₂OCH₃ |
| A-1517 | CH₂OCH₂CH₂OCH₃ | Cl | CH₂OCH₂CH₃ | CH₃ |
| A-1518 | CH₂OCH₂CH₂OCH₃ | Cl | CH₂OCH₂CH₃ | CH₂CH₃ |
| A-1519 | CH₂OCH₂CH₂OCH₃ | Cl | CH₂OCH₂CH₃ | CH₂CH₂CH₃ |
| A-1520 | CH₂OCH₂CH₂OCH₃ | Cl | CH₂OCH₂CH₃ | CH₂CH₂OCH₃ |
| A-1521 | CH₂OCH₂CH₂OCH₃ | Cl | CH₂(CO)OCH₃ | CH₃ |
| A-1522 | CH₂OCH₂CH₂OCH₃ | Cl | CH₂(CO)OCH₃ | CH₂CH₃ |
| A-1523 | CH₂OCH₂CH₂OCH₃ | Cl | CH₂(CO)OCH₃ | CH₂CH₂CH₃ |
| A-1524 | CH₂OCH₂CH₂OCH₃ | Cl | CH₂(CO)OCH₃ | CH₂CH₂OCH₃ |
| A-1525 | CH₂OCH₂CH₂OCH₃ | Cl | CH₂CHCH₂ | CH₃ |
| A-1526 | CH₂OCH₂CH₂OCH₃ | Cl | CH₂CHCH₂ | CH₂CH₃ |
| A-1527 | CH₂OCH₂CH₂OCH₃ | Cl | CH₂CHCH₂ | CH₂CH₂CH₃ |
| A-1528 | CH₂OCH₂CH₂OCH₃ | Cl | CH₂CHCH₂ | CH₂CH₂OCH₃ |
| A-1529 | CH₂OCH₂CH₂OCH₃ | Cl | CH₂CCH | CH₃ |
| A-1530 | CH₂OCH₂CH₂OCH₃ | Cl | CH₂CCH | CH₂CH₃ |
| A-1531 | CH₂OCH₂CH₂OCH₃ | Cl | CH₂CCH | CH₂CH₂CH₃ |
| A-1532 | CH₂OCH₂CH₂OCH₃ | Cl | CH₂CCH | CH₂CH₂OCH₃ |
| A-1533 | CH₂OCH₂CH₂OCH₃ | Cl | CH₂C₆H₅ | CH₃ |
| A-1534 | CH₂OCH₂CH₂OCH₃ | Cl | CH₂C₆H₅ | CH₂CH₃ |
| A-1535 | CH₂OCH₂CH₂OCH₃ | Cl | CH₂C₆H₅ | CH₂CH₂CH₃ |
| A-1536 | CH₂OCH₂CH₂OCH₃ | Cl | CH₂C₆H₅ | CH₂CH₂OCH₃ |
| A-1537 | CH₂OCH₂CH₂OCH₃ | Br | CH₃ | CH₃ |
| A-1538 | CH₂OCH₂CH₂OCH₃ | Br | CH₃ | CH₂CH₃ |
| A-1539 | CH₂OCH₂CH₂OCH₃ | Br | CH₃ | CH₂CH₂CH₃ |
| A-1540 | CH₂OCH₂CH₂OCH₃ | Br | CH₃ | CH₂CH₂OCH₃ |
| A-1541 | CH₂OCH₂CH₂OCH₃ | Br | CH₂CH₃ | CH₃ |
| A-1542 | CH₂OCH₂CH₂OCH₃ | Br | CH₂CH₃ | CH₂CH₃ |
| A-1543 | CH₂OCH₂CH₂OCH₃ | Br | CH₂CH₃ | CH₂CH₂CH₃ |
| A-1544 | CH₂OCH₂CH₂OCH₃ | Br | CH₂CH₃ | CH₂CH₂OCH₃ |
| A-1545 | CH₂OCH₂CH₂OCH₃ | Br | CH₂OCH₃ | CH₃ |
| A-1546 | CH₂OCH₂CH₂OCH₃ | Br | CH₂OCH₃ | CH₂CH₃ |
| A-1547 | CH₂OCH₂CH₂OCH₃ | Br | CH₂OCH₃ | CH₂CH₂CH₃ |
| A-1548 | CH₂OCH₂CH₂OCH₃ | Br | CH₂OCH₃ | CH₂CH₂OCH₃ |
| A-1549 | CH₂OCH₂CH₂OCH₃ | Br | CH₂OCH₂CH₃ | CH₃ |
| A-1550 | CH₂OCH₂CH₂OCH₃ | Br | CH₂OCH₂CH₃ | CH₂CH₃ |
| A-1551 | CH₂OCH₂CH₂OCH₃ | Br | CH₂OCH₂CH₃ | CH₂CH₂CH₃ |
| A-1552 | CH₂OCH₂CH₂OCH₃ | Br | CH₂OCH₂CH₃ | CH₂CH₂OCH₃ |
| A-1553 | CH₂OCH₂CH₂OCH₃ | Br | CH₂(CO)OCH₃ | CH₃ |
| A-1554 | CH₂OCH₂CH₂OCH₃ | Br | CH₂(CO)OCH₃ | CH₂CH₃ |
| A-1555 | CH₂OCH₂CH₂OCH₃ | Br | CH₂(CO)OCH₃ | CH₂CH₂CH₃ |
| A-1556 | CH₂OCH₂CH₂OCH₃ | Br | CH₂(CO)OCH₃ | CH₂CH₂OCH₃ |
| A-1557 | CH₂OCH₂CH₂OCH₃ | Br | CH₂CHCH₂ | CH₃ |
| A-1558 | CH₂OCH₂CH₂OCH₃ | Br | CH₂CHCH₂ | CH₂CH₃ |
| A-1559 | CH₂OCH₂CH₂OCH₃ | Br | CH₂CHCH₂ | CH₂CH₂CH₃ |
| A-1560 | CH₂OCH₂CH₂OCH₃ | Br | CH₂CHCH₂ | CH₂CH₂OCH₃ |
| A-1561 | CH₂OCH₂CH₂OCH₃ | Br | CH₂CCH | CH₃ |
| A-1562 | CH₂OCH₂CH₂OCH₃ | Br | CH₂CCH | CH₂CH₃ |
| A-1563 | CH₂OCH₂CH₂OCH₃ | Br | CH₂CCH | CH₂CH₂CH₃ |
| A-1564 | CH₂OCH₂CH₂OCH₃ | Br | CH₂CCH | CH₂CH₂OCH₃ |
| A-1565 | CH₂OCH₂CH₂OCH₃ | Br | CH₂C₆H₅ | CH₃ |
| A-1566 | CH₂OCH₂CH₂OCH₃ | Br | CH₂C₆H₅ | CH₂CH₃ |
| A-1567 | CH₂OCH₂CH₂OCH₃ | Br | CH₂C₆H₅ | CH₂CH₂CH₃ |
| A-1568 | CH₂OCH₂CH₂OCH₃ | Br | CH₂C₆H₅ | CH₂CH₂OCH₃ |
| A-1569 | CH₂OCH₂CH₂OCH₃ | CN | CH₃ | CH₃ |
| A-1570 | CH₂OCH₂CH₂OCH₃ | CN | CH₃ | CH₂CH₃ |
| A-1571 | CH₂OCH₂CH₂OCH₃ | CN | CH₃ | CH₂CH₂CH₃ |
| A-1572 | CH₂OCH₂CH₂OCH₃ | CN | CH₃ | CH₂CH₂OCH₃ |
| A-1573 | CH₂OCH₂CH₂OCH₃ | CN | CH₂CH₃ | CH₃ |
| A-1574 | CH₂OCH₂CH₂OCH₃ | CN | CH₂CH₃ | CH₂CH₃ |
| A-1575 | CH₂OCH₂CH₂OCH₃ | CN | CH₂CH₃ | CH₂CH₂CH₃ |
| A-1576 | CH₂OCH₂CH₂OCH₃ | CN | CH₂CH₃ | CH₂CH₂OCH₃ |
| A-1577 | CH₂OCH₂CH₂OCH₃ | CN | CH₂OCH₃ | CH₃ |
| A-1578 | CH₂OCH₂CH₂OCH₃ | CN | CH₂OCH₃ | CH₂CH₃ |
| A-1579 | CH₂OCH₂CH₂OCH₃ | CN | CH₂OCH₃ | CH₂CH₂CH₃ |
| A-1580 | CH₂OCH₂CH₂OCH₃ | CN | CH₂OCH₃ | CH₂CH₂OCH₃ |
| A-1581 | CH₂OCH₂CH₂OCH₃ | CN | CH₂OCH₂CH₃ | CH₃ |
| A-1582 | CH₂OCH₂CH₂OCH₃ | CN | CH₂OCH₂CH₃ | CH₂CH₃ |
| A-1583 | CH₂OCH₂CH₂OCH₃ | CN | CH₂OCH₂CH₃ | CH₂CH₂CH₃ |
| A-1584 | CH₂OCH₂CH₂OCH₃ | CN | CH₂OCH₂CH₃ | CH₂CH₂OCH₃ |
| A-1585 | CH₂OCH₂CH₂OCH₃ | CN | CH₂(CO)OCH₃ | CH₃ |
| A-1586 | CH₂OCH₂CH₂OCH₃ | CN | CH₂(CO)OCH₃ | CH₂CH₃ |
| A-1587 | CH₂OCH₂CH₂OCH₃ | CN | CH₂(CO)OCH₃ | CH₂CH₂CH₃ |
| A-1588 | CH₂OCH₂CH₂OCH₃ | CN | CH₂(CO)OCH₃ | CH₂CH₂OCH₃ |
| A-1589 | CH₂OCH₂CH₂OCH₃ | CN | CH₂CHCH₂ | CH₃ |

TABLE A-continued

|  | R¹ | R³ | R⁶ | R⁷ |
|---|---|---|---|---|
| A-1590 | CH₂OCH₂CH₂OCH₃ | CN | CH₂CHCH₂ | CH₂CH₃ |
| A-1591 | CH₂OCH₂CH₂OCH₃ | CN | CH₂CHCH₂ | CH₂CH₂CH₃ |
| A-1592 | CH₂OCH₂CH₂OCH₃ | CN | CH₂CHCH₂ | CH₂CH₂OCH₃ |
| A-1593 | CH₂OCH₂CH₂OCH₃ | CN | CH₂CCH | CH₃ |
| A-1594 | CH₂OCH₂CH₂OCH₃ | CN | CH₂CCH | CH₂CH₃ |
| A-1595 | CH₂OCH₂CH₂OCH₃ | CN | CH₂CCH | CH₂CH₂CH₃ |
| A-1596 | CH₂OCH₂CH₂OCH₃ | CN | CH₂CCH | CH₂CH₂OCH₃ |
| A-1597 | CH₂OCH₂CH₂OCH₃ | CN | CH₂C₆H₅ | CH₃ |
| A-1598 | CH₂OCH₂CH₂OCH₃ | CN | CH₂C₆H₅ | CH₂CH₃ |
| A-1599 | CH₂OCH₂CH₂OCH₃ | CN | CH₂C₆H₅ | CH₂CH₂CH₃ |
| A-1600 | CH₂OCH₂CH₂OCH₃ | CN | CH₂C₆H₅ | CH₂CH₂OCH₃ |
| A-1601 | CH₂OCH₂CH₂OCH₃ | CH₃ | CH₃ | CH₃ |
| A-1602 | CH₂OCH₂CH₂OCH₃ | CH₃ | CH₃ | CH₂CH₃ |
| A-1603 | CH₂OCH₂CH₂OCH₃ | CH₃ | CH₃ | CH₂CH₂CH₃ |
| A-1604 | CH₂OCH₂CH₂OCH₃ | CH₃ | CH₃ | CH₂CH₂OCH₃ |
| A-1605 | CH₂OCH₂CH₂OCH₃ | CH₃ | CH₂CH₃ | CH₃ |
| A-1606 | CH₂OCH₂CH₂OCH₃ | CH₃ | CH₂CH₃ | CH₂CH₃ |
| A-1607 | CH₂OCH₂CH₂OCH₃ | CH₃ | CH₂CH₃ | CH₂CH₂CH₃ |
| A-1608 | CH₂OCH₂CH₂OCH₃ | CH₃ | CH₂CH₃ | CH₂CH₂OCH₃ |
| A-1609 | CH₂OCH₂CH₂OCH₃ | CH₃ | CH₂OCH₃ | CH₃ |
| A-1610 | CH₂OCH₂CH₂OCH₃ | CH₃ | CH₂OCH₃ | CH₂CH₃ |
| A-1611 | CH₂OCH₂CH₂OCH₃ | CH₃ | CH₂OCH₃ | CH₂CH₂CH₃ |
| A-1612 | CH₂OCH₂CH₂OCH₃ | CH₃ | CH₂OCH₃ | CH₂CH₂OCH₃ |
| A-1613 | CH₂OCH₂CH₂OCH₃ | CH₃ | CH₂OCH₂CH₃ | CH₃ |
| A-1614 | CH₂OCH₂CH₂OCH₃ | CH₃ | CH₂OCH₂CH₃ | CH₂CH₃ |
| A-1615 | CH₂OCH₂CH₂OCH₃ | CH₃ | CH₂OCH₂CH₃ | CH₂CH₂CH₃ |
| A-1616 | CH₂OCH₂CH₂OCH₃ | CH₃ | CH₂OCH₂CH₃ | CH₂CH₂OCH₃ |
| A-1617 | CH₂OCH₂CH₂OCH₃ | CH₃ | CH₂(CO)OCH₃ | CH₃ |
| A-1618 | CH₂OCH₂CH₂OCH₃ | CH₃ | CH₂(CO)OCH₃ | CH₂CH₃ |
| A-1619 | CH₂OCH₂CH₂OCH₃ | CH₃ | CH₂(CO)OCH₃ | CH₂CH₂CH₃ |
| A-1620 | CH₂OCH₂CH₂OCH₃ | CH₃ | CH₂(CO)OCH₃ | CH₂CH₂OCH₃ |
| A-1621 | CH₂OCH₂CH₂OCH₃ | CH₃ | CH₂CHCH₂ | CH₃ |
| A-1622 | CH₂OCH₂CH₂OCH₃ | CH₃ | CH₂CHCH₂ | CH₂CH₃ |
| A-1623 | CH₂OCH₂CH₂OCH₃ | CH₃ | CH₂CHCH₂ | CH₂CH₂CH₃ |
| A-1624 | CH₂OCH₂CH₂OCH₃ | CH₃ | CH₂CHCH₂ | CH₂CH₂OCH₃ |
| A-1625 | CH₂OCH₂CH₂OCH₃ | CH₃ | CH₂CCH | CH₃ |
| A-1626 | CH₂OCH₂CH₂OCH₃ | CH₃ | CH₂CCH | CH₂CH₃ |
| A-1627 | CH₂OCH₂CH₂OCH₃ | CH₃ | CH₂CCH | CH₂CH₂CH₃ |
| A-1628 | CH₂OCH₂CH₂OCH₃ | CH₃ | CH₂CCH | CH₂CH₂OCH₃ |
| A-1629 | CH₂OCH₂CH₂OCH₃ | CH₃ | CH₂C₆H₅ | CH₃ |
| A-1630 | CH₂OCH₂CH₂OCH₃ | CH₃ | CH₂C₆H₅ | CH₂CH₃ |
| A-1631 | CH₂OCH₂CH₂OCH₃ | CH₃ | CH₂C₆H₅ | CH₂CH₂CH₃ |
| A-1632 | CH₂OCH₂CH₂OCH₃ | CH₃ | CH₂C₆H₅ | CH₂CH₂OCH₃ |
| A-1633 | CH₂OCH₂CH₂OCH₃ | CF₃ | CH₃ | CH₃ |
| A-1634 | CH₂OCH₂CH₂OCH₃ | CF₃ | CH₃ | CH₂CH₃ |
| A-1635 | CH₂OCH₂CH₂OCH₃ | CF₃ | CH₃ | CH₂CH₂CH₃ |
| A-1636 | CH₂OCH₂CH₂OCH₃ | CF₃ | CH₃ | CH₂CH₂OCH₃ |
| A-1637 | CH₂OCH₂CH₂OCH₃ | CF₃ | CH₂CH₃ | CH₃ |
| A-1638 | CH₂OCH₂CH₂OCH₃ | CF₃ | CH₂CH₃ | CH₂CH₃ |
| A-1639 | CH₂OCH₂CH₂OCH₃ | CF₃ | CH₂CH₃ | CH₂CH₂CH₃ |
| A-1640 | CH₂OCH₂CH₂OCH₃ | CF₃ | CH₂CH₃ | CH₂CH₂OCH₃ |
| A-1641 | CH₂OCH₂CH₂OCH₃ | CF₃ | CH₂OCH₃ | CH₃ |
| A-1642 | CH₂OCH₂CH₂OCH₃ | CF₃ | CH₂OCH₃ | CH₂CH₃ |
| A-1643 | CH₂OCH₂CH₂OCH₃ | CF₃ | CH₂OCH₃ | CH₂CH₂CH₃ |
| A-1644 | CH₂OCH₂CH₂OCH₃ | CF₃ | CH₂OCH₃ | CH₂CH₂OCH₃ |
| A-1645 | CH₂OCH₂CH₂OCH₃ | CF₃ | CH₂OCH₂CH₃ | CH₃ |
| A-1646 | CH₂OCH₂CH₂OCH₃ | CF₃ | CH₂OCH₂CH₃ | CH₂CH₃ |
| A-1647 | CH₂OCH₂CH₂OCH₃ | CF₃ | CH₂OCH₂CH₃ | CH₂CH₂CH₃ |
| A-1648 | CH₂OCH₂CH₂OCH₃ | CF₃ | CH₂OCH₂CH₃ | CH₂CH₂OCH₃ |
| A-1649 | CH₂OCH₂CH₂OCH₃ | CF₃ | CH₂(CO)OCH₃ | CH₃ |
| A-1650 | CH₂OCH₂CH₂OCH₃ | CF₃ | CH₂(CO)OCH₃ | CH₂CH₃ |
| A-1651 | CH₂OCH₂CH₂OCH₃ | CF₃ | CH₂(CO)OCH₃ | CH₂CH₂CH₃ |
| A-1652 | CH₂OCH₂CH₂OCH₃ | CF₃ | CH₂(CO)OCH₃ | CH₂CH₂OCH₃ |
| A-1653 | CH₂OCH₂CH₂OCH₃ | CF₃ | CH₂CHCH₂ | CH₃ |
| A-1654 | CH₂OCH₂CH₂OCH₃ | CF₃ | CH₂CHCH₂ | CH₂CH₃ |
| A-1655 | CH₂OCH₂CH₂OCH₃ | CF₃ | CH₂CHCH₂ | CH₂CH₂CH₃ |
| A-1656 | CH₂OCH₂CH₂OCH₃ | CF₃ | CH₂CHCH₂ | CH₂CH₂OCH₃ |
| A-1657 | CH₂OCH₂CH₂OCH₃ | CF₃ | CH₂CCH | CH₃ |
| A-1658 | CH₂OCH₂CH₂OCH₃ | CF₃ | CH₂CCH | CH₂CH₃ |
| A-1659 | CH₂OCH₂CH₂OCH₃ | CF₃ | CH₂CCH | CH₂CH₂CH₃ |
| A-1660 | CH₂OCH₂CH₂OCH₃ | CF₃ | CH₂CCH | CH₂CH₂OCH₃ |
| A-1661 | CH₂OCH₂CH₂OCH₃ | CF₃ | CH₂C₆H₅ | CH₃ |
| A-1662 | CH₂OCH₂CH₂OCH₃ | CF₃ | CH₂C₆H₅ | CH₂CH₃ |
| A-1663 | CH₂OCH₂CH₂OCH₃ | CF₃ | CH₂C₆H₅ | CH₂CH₂CH₃ |
| A-1664 | CH₂OCH₂CH₂OCH₃ | CF₃ | CH₂C₆H₅ | CH₂CH₂OCH₃ |
| A-1665 | CH₂OCH₂CH₂OCH₃ | SO₂CH₃ | CH₃ | CH₃ |
| A-1666 | CH₂OCH₂CH₂OCH₃ | SO₂CH₃ | CH₃ | CH₂CH₃ |
| A-1667 | CH₂OCH₂CH₂OCH₃ | SO₂CH₃ | CH₃ | CH₂CH₂CH₃ |

TABLE A-continued

| | R¹ | R³ | R⁶ | R⁷ |
|---|---|---|---|---|
| A-1668 | CH$_2$OCH$_2$CH$_2$OCH$_3$ | SO$_2$CH$_3$ | CH$_3$ | CH$_2$CH$_2$OCH$_3$ |
| A-1669 | CH$_2$OCH$_2$CH$_2$OCH$_3$ | SO$_2$CH$_3$ | CH$_2$CH$_3$ | CH$_3$ |
| A-1670 | CH$_2$OCH$_2$CH$_2$OCH$_3$ | SO$_2$CH$_3$ | CH$_2$CH$_3$ | CH$_2$CH$_3$ |
| A-1671 | CH$_2$OCH$_2$CH$_2$OCH$_3$ | SO$_2$CH$_3$ | CH$_2$CH$_3$ | CH$_2$CH$_2$CH$_3$ |
| A-1672 | CH$_2$OCH$_2$CH$_2$OCH$_3$ | SO$_2$CH$_3$ | CH$_2$CH$_3$ | CH$_2$CH$_2$OCH$_3$ |
| A-1673 | CH$_2$OCH$_2$CH$_2$OCH$_3$ | SO$_2$CH$_3$ | CH$_2$OCH$_3$ | CH$_3$ |
| A-1674 | CH$_2$OCH$_2$CH$_2$OCH$_3$ | SO$_2$CH$_3$ | CH$_2$OCH$_3$ | CH$_2$CH$_3$ |
| A-1675 | CH$_2$OCH$_2$CH$_2$OCH$_3$ | SO$_2$CH$_3$ | CH$_2$OCH$_3$ | CH$_2$CH$_2$CH$_3$ |
| A-1676 | CH$_2$OCH$_2$CH$_2$OCH$_3$ | SO$_2$CH$_3$ | CH$_2$OCH$_3$ | CH$_2$CH$_2$OCH$_3$ |
| A-1677 | CH$_2$OCH$_2$CH$_2$OCH$_3$ | SO$_2$CH$_3$ | CH$_2$OCH$_2$CH$_3$ | CH$_3$ |
| A-1678 | CH$_2$OCH$_2$CH$_2$OCH$_3$ | SO$_2$CH$_3$ | CH$_2$OCH$_2$CH$_3$ | CH$_2$CH$_3$ |
| A-1679 | CH$_2$OCH$_2$CH$_2$OCH$_3$ | SO$_2$CH$_3$ | CH$_2$OCH$_2$CH$_3$ | CH$_2$CH$_2$CH$_3$ |
| A-1680 | CH$_2$OCH$_2$CH$_2$OCH$_3$ | SO$_2$CH$_3$ | CH$_2$OCH$_2$CH$_3$ | CH$_2$CH$_2$OCH$_3$ |
| A-1681 | CH$_2$OCH$_2$CH$_2$OCH$_3$ | SO$_2$CH$_3$ | CH$_2$(CO)OCH$_3$ | CH$_3$ |
| A-1682 | CH$_2$OCH$_2$CH$_2$OCH$_3$ | SO$_2$CH$_3$ | CH$_2$(CO)OCH$_3$ | CH$_2$CH$_3$ |
| A-1683 | CH$_2$OCH$_2$CH$_2$OCH$_3$ | SO$_2$CH$_3$ | CH$_2$(CO)OCH$_3$ | CH$_2$CH$_2$CH$_3$ |
| A-1684 | CH$_2$OCH$_2$CH$_2$OCH$_3$ | SO$_2$CH$_3$ | CH$_2$(CO)OCH$_3$ | CH$_2$CH$_2$OCH$_3$ |
| A-1685 | CH$_2$OCH$_2$CH$_2$OCH$_3$ | SO$_2$CH$_3$ | CH$_2$CHCH$_2$ | CH$_3$ |
| A-1686 | CH$_2$OCH$_2$CH$_2$OCH$_3$ | SO$_2$CH$_3$ | CH$_2$CHCH$_2$ | CH$_2$CH$_3$ |
| A-1687 | CH$_2$OCH$_2$CH$_2$OCH$_3$ | SO$_2$CH$_3$ | CH$_2$CHCH$_2$ | CH$_2$CH$_2$CH$_3$ |
| A-1688 | CH$_2$OCH$_2$CH$_2$OCH$_3$ | SO$_2$CH$_3$ | CH$_2$CHCH$_2$ | CH$_2$CH$_2$OCH$_3$ |
| A-1689 | CH$_2$OCH$_2$CH$_2$OCH$_3$ | SO$_2$CH$_3$ | CH$_2$CCH | CH$_3$ |
| A-1690 | CH$_2$OCH$_2$CH$_2$OCH$_3$ | SO$_2$CH$_3$ | CH$_2$CCH | CH$_2$CH$_3$ |
| A-1691 | CH$_2$OCH$_2$CH$_2$OCH$_3$ | SO$_2$CH$_3$ | CH$_2$CCH | CH$_2$CH$_2$CH$_3$ |
| A-1692 | CH$_2$OCH$_2$CH$_2$OCH$_3$ | SO$_2$CH$_3$ | CH$_2$CCH | CH$_2$CH$_2$OCH$_3$ |
| A-1693 | CH$_2$OCH$_2$CH$_2$OCH$_3$ | SO$_2$CH$_3$ | CH$_2$C$_6$H$_5$ | CH$_3$ |
| A-1694 | CH$_2$OCH$_2$CH$_2$OCH$_3$ | SO$_2$CH$_3$ | CH$_2$C$_6$H$_5$ | CH$_2$CH$_3$ |
| A-1695 | CH$_2$OCH$_2$CH$_2$OCH$_3$ | SO$_2$CH$_3$ | CH$_2$C$_6$H$_5$ | CH$_2$CH$_2$CH$_3$ |
| A-1696 | CH$_2$OCH$_2$CH$_2$OCH$_3$ | SO$_2$CH$_3$ | CH$_2$C$_6$H$_5$ | CH$_2$CH$_2$OCH$_3$ |
| A-1697 | CH$_2$OCH$_2$CH$_2$OCH$_3$ | NO$_2$ | CH$_3$ | CH$_3$ |
| A-1698 | CH$_2$OCH$_2$CH$_2$OCH$_3$ | NO$_2$ | CH$_3$ | CH$_2$CH$_3$ |
| A-1699 | CH$_2$OCH$_2$CH$_2$OCH$_3$ | NO$_2$ | CH$_3$ | CH$_2$CH$_2$CH$_3$ |
| A-1700 | CH$_2$OCH$_2$CH$_2$OCH$_3$ | NO$_2$ | CH$_3$ | CH$_2$CH$_2$OCH$_3$ |
| A-1701 | CH$_2$OCH$_2$CH$_2$OCH$_3$ | NO$_2$ | CH$_2$CH$_3$ | CH$_3$ |
| A-1702 | CH$_2$OCH$_2$CH$_2$OCH$_3$ | NO$_2$ | CH$_2$CH$_3$ | CH$_2$CH$_3$ |
| A-1703 | CH$_2$OCH$_2$CH$_2$OCH$_3$ | NO$_2$ | CH$_2$CH$_3$ | CH$_2$CH$_2$CH$_3$ |
| A-1704 | CH$_2$OCH$_2$CH$_2$OCH$_3$ | NO$_2$ | CH$_2$CH$_3$ | CH$_2$CH$_2$OCH$_3$ |
| A-1705 | CH$_2$OCH$_2$CH$_2$OCH$_3$ | NO$_2$ | CH$_2$OCH$_3$ | CH$_3$ |
| A-1706 | CH$_2$OCH$_2$CH$_2$OCH$_3$ | NO$_2$ | CH$_2$OCH$_3$ | CH$_2$CH$_3$ |
| A-1707 | CH$_2$OCH$_2$CH$_2$OCH$_3$ | NO$_2$ | CH$_2$OCH$_3$ | CH$_2$CH$_2$CH$_3$ |
| A-1708 | CH$_2$OCH$_2$CH$_2$OCH$_3$ | NO$_2$ | CH$_2$OCH$_3$ | CH$_2$CH$_2$OCH$_3$ |
| A-1709 | CH$_2$OCH$_2$CH$_2$OCH$_3$ | NO$_2$ | CH$_2$OCH$_2$CH$_3$ | CH$_3$ |
| A-1710 | CH$_2$OCH$_2$CH$_2$OCH$_3$ | NO$_2$ | CH$_2$OCH$_2$CH$_3$ | CH$_2$CH$_3$ |
| A-1711 | CH$_2$OCH$_2$CH$_2$OCH$_3$ | NO$_2$ | CH$_2$OCH$_2$CH$_3$ | CH$_2$CH$_2$CH$_3$ |
| A-1712 | CH$_2$OCH$_2$CH$_2$OCH$_3$ | NO$_2$ | CH$_2$OCH$_2$CH$_3$ | CH$_2$CH$_2$OCH$_3$ |
| A-1713 | CH$_2$OCH$_2$CH$_2$OCH$_3$ | NO$_2$ | CH$_2$(CO)OCH$_3$ | CH$_3$ |
| A-1714 | CH$_2$OCH$_2$CH$_2$OCH$_3$ | NO$_2$ | CH$_2$(CO)OCH$_3$ | CH$_2$CH$_3$ |
| A-1715 | CH$_2$OCH$_2$CH$_2$OCH$_3$ | NO$_2$ | CH$_2$(CO)OCH$_3$ | CH$_2$CH$_2$CH$_3$ |
| A-1716 | CH$_2$OCH$_2$CH$_2$OCH$_3$ | NO$_2$ | CH$_2$(CO)OCH$_3$ | CH$_2$CH$_2$OCH$_3$ |
| A-1717 | CH$_2$OCH$_2$CH$_2$OCH$_3$ | NO$_2$ | CH$_2$CHCH$_2$ | CH$_3$ |
| A-1718 | CH$_2$OCH$_2$CH$_2$OCH$_3$ | NO$_2$ | CH$_2$CHCH$_2$ | CH$_2$CH$_3$ |
| A-1719 | CH$_2$OCH$_2$CH$_2$OCH$_3$ | NO$_2$ | CH$_2$CHCH$_2$ | CH$_2$CH$_2$CH$_3$ |
| A-1720 | CH$_2$OCH$_2$CH$_2$OCH$_3$ | NO$_2$ | CH$_2$CHCH$_2$ | CH$_2$CH$_2$OCH$_3$ |
| A-1721 | CH$_2$OCH$_2$CH$_2$OCH$_3$ | NO$_2$ | CH$_2$CCH | CH$_3$ |
| A-1722 | CH$_2$OCH$_2$CH$_2$OCH$_3$ | NO$_2$ | CH$_2$CCH | CH$_2$CH$_3$ |
| A-1723 | CH$_2$OCH$_2$CH$_2$OCH$_3$ | NO$_2$ | CH$_2$CCH | CH$_2$CH$_2$CH$_3$ |
| A-1724 | CH$_2$OCH$_2$CH$_2$OCH$_3$ | NO$_2$ | CH$_2$CCH | CH$_2$CH$_2$OCH$_3$ |
| A-1725 | CH$_2$OCH$_2$CH$_2$OCH$_3$ | NO$_2$ | CH$_2$C$_6$H$_5$ | CH$_3$ |
| A-1726 | CH$_2$OCH$_2$CH$_2$OCH$_3$ | NO$_2$ | CH$_2$C$_6$H$_5$ | CH$_2$CH$_3$ |
| A-1727 | CH$_2$OCH$_2$CH$_2$OCH$_3$ | NO$_2$ | CH$_2$C$_6$H$_5$ | CH$_2$CH$_2$CH$_3$ |
| A-1728 | CH$_2$OCH$_2$CH$_2$OCH$_3$ | NO$_2$ | CH$_2$C$_6$H$_5$ | CH$_2$CH$_2$OCH$_3$ |
| A-1729 | SO$_2$CH$_3$ | H | CH$_3$ | CH$_3$ |
| A-1730 | SO$_2$CH$_3$ | H | CH$_3$ | CH$_2$CH$_3$ |
| A-1731 | SO$_2$CH$_3$ | H | CH$_3$ | CH$_2$CH$_2$CH$_3$ |
| A-1732 | SO$_2$CH$_3$ | H | CH$_3$ | CH$_2$CH$_2$OCH$_3$ |
| A-1733 | SO$_2$CH$_3$ | H | CH$_2$CH$_3$ | CH$_3$ |
| A-1734 | SO$_2$CH$_3$ | H | CH$_2$CH$_3$ | CH$_2$CH$_3$ |
| A-1735 | SO$_2$CH$_3$ | H | CH$_2$CH$_3$ | CH$_2$CH$_2$CH$_3$ |
| A-1736 | SO$_2$CH$_3$ | H | CH$_2$CH$_3$ | CH$_2$CH$_2$OCH$_3$ |
| A-1737 | SO$_2$CH$_3$ | H | CH$_2$OCH$_3$ | CH$_3$ |
| A-1738 | SO$_2$CH$_3$ | H | CH$_2$OCH$_3$ | CH$_2$CH$_3$ |
| A-1739 | SO$_2$CH$_3$ | H | CH$_2$OCH$_3$ | CH$_2$CH$_2$CH$_3$ |
| A-1740 | SO$_2$CH$_3$ | H | CH$_2$OCH$_3$ | CH$_2$CH$_2$OCH$_3$ |
| A-1741 | SO$_2$CH$_3$ | H | CH$_2$OCH$_2$CH$_3$ | CH$_3$ |
| A-1742 | SO$_2$CH$_3$ | H | CH$_2$OCH$_2$CH$_3$ | CH$_2$CH$_3$ |
| A-1743 | SO$_2$CH$_3$ | H | CH$_2$OCH$_2$CH$_3$ | CH$_2$CH$_2$CH$_3$ |
| A-1744 | SO$_2$CH$_3$ | H | CH$_2$OCH$_2$CH$_3$ | CH$_2$CH$_2$OCH$_3$ |
| A-1745 | SO$_2$CH$_3$ | H | CH$_2$(CO)OCH$_3$ | CH$_3$ |

TABLE A-continued

|  | R¹ | R³ | R⁶ | R⁷ |
| --- | --- | --- | --- | --- |
| A-1746 | SO$_2$CH$_3$ | H | CH$_2$(CO)OCH$_3$ | CH$_2$CH$_3$ |
| A-1747 | SO$_2$CH$_3$ | H | CH$_2$(CO)OCH$_3$ | CH$_2$CH$_2$CH$_3$ |
| A-1748 | SO$_2$CH$_3$ | H | CH$_2$(CO)OCH$_3$ | CH$_2$CH$_2$OCH$_3$ |
| A-1749 | SO$_2$CH$_3$ | H | CH$_2$CHCH$_2$ | CH$_3$ |
| A-1750 | SO$_2$CH$_3$ | H | CH$_2$CHCH$_2$ | CH$_2$CH$_3$ |
| A-1751 | SO$_2$CH$_3$ | H | CH$_2$CHCH$_2$ | CH$_2$CH$_2$CH$_3$ |
| A-1752 | SO$_2$CH$_3$ | H | CH$_2$CHCH$_2$ | CH$_2$CH$_2$OCH$_3$ |
| A-1753 | SO$_2$CH$_3$ | H | CH$_2$CCH | CH$_3$ |
| A-1754 | SO$_2$CH$_3$ | H | CH$_2$CCH | CH$_2$CH$_3$ |
| A-1755 | SO$_2$CH$_3$ | H | CH$_2$CCH | CH$_2$CH$_2$CH$_3$ |
| A-1756 | SO$_2$CH$_3$ | H | CH$_2$CCH | CH$_2$CH$_2$OCH$_3$ |
| A-1757 | SO$_2$CH$_3$ | H | CH$_2$C$_6$H$_5$ | CH$_3$ |
| A-1758 | SO$_2$CH$_3$ | H | CH$_2$C$_6$H$_5$ | CH$_2$CH$_3$ |
| A-1759 | SO$_2$CH$_3$ | H | CH$_2$C$_6$H$_5$ | CH$_2$CH$_2$CH$_3$ |
| A-1760 | SO$_2$CH$_3$ | H | CH$_2$C$_6$H$_5$ | CH$_2$CH$_2$OCH$_3$ |
| A-1761 | SO$_2$CH$_3$ | F | CH$_3$ | CH$_3$ |
| A-1762 | SO$_2$CH$_3$ | F | CH$_3$ | CH$_2$CH$_3$ |
| A-1763 | SO$_2$CH$_3$ | F | CH$_3$ | CH$_2$CH$_2$CH$_3$ |
| A-1764 | SO$_2$CH$_3$ | F | CH$_3$ | CH$_2$CH$_2$OCH$_3$ |
| A-1765 | SO$_2$CH$_3$ | F | CH$_2$CH$_3$ | CH$_3$ |
| A-1766 | SO$_2$CH$_3$ | F | CH$_2$CH$_3$ | CH$_2$CH$_3$ |
| A-1767 | SO$_2$CH$_3$ | F | CH$_2$CH$_3$ | CH$_2$CH$_2$CH$_3$ |
| A-1768 | SO$_2$CH$_3$ | F | CH$_2$CH$_3$ | CH$_2$CH$_2$OCH$_3$ |
| A-1769 | SO$_2$CH$_3$ | F | CH$_2$OCH$_3$ | CH$_3$ |
| A-1770 | SO$_2$CH$_3$ | F | CH$_2$OCH$_3$ | CH$_2$CH$_3$ |
| A-1771 | SO$_2$CH$_3$ | F | CH$_2$OCH$_3$ | CH$_2$CH$_2$CH$_3$ |
| A-1772 | SO$_2$CH$_3$ | F | CH$_2$OCH$_3$ | CH$_2$CH$_2$OCH$_3$ |
| A-1773 | SO$_2$CH$_3$ | F | CH$_2$OCH$_2$CH$_3$ | CH$_3$ |
| A-1774 | SO$_2$CH$_3$ | F | CH$_2$OCH$_2$CH$_3$ | CH$_2$CH$_3$ |
| A-1775 | SO$_2$CH$_3$ | F | CH$_2$OCH$_2$CH$_3$ | CH$_2$CH$_2$CH$_3$ |
| A-1776 | SO$_2$CH$_3$ | F | CH$_2$OCH$_2$CH$_3$ | CH$_2$CH$_2$OCH$_3$ |
| A-1777 | SO$_2$CH$_3$ | F | CH$_2$(CO)OCH$_3$ | CH$_3$ |
| A-1778 | SO$_2$CH$_3$ | F | CH$_2$(CO)OCH$_3$ | CH$_2$CH$_3$ |
| A-1779 | SO$_2$CH$_3$ | F | CH$_2$(CO)OCH$_3$ | CH$_2$CH$_2$CH$_3$ |
| A-1780 | SO$_2$CH$_3$ | F | CH$_2$(CO)OCH$_3$ | CH$_2$CH$_2$OCH$_3$ |
| A-1781 | SO$_2$CH$_3$ | F | CH$_2$CHCH$_2$ | CH$_3$ |
| A-1782 | SO$_2$CH$_3$ | F | CH$_2$CHCH$_2$ | CH$_2$CH$_3$ |
| A-1783 | SO$_2$CH$_3$ | F | CH$_2$CHCH$_2$ | CH$_2$CH$_2$CH$_3$ |
| A-1784 | SO$_2$CH$_3$ | F | CH$_2$CHCH$_2$ | CH$_2$CH$_2$OCH$_3$ |
| A-1785 | SO$_2$CH$_3$ | F | CH$_2$CCH | CH$_3$ |
| A-1786 | SO$_2$CH$_3$ | F | CH$_2$CCH | CH$_2$CH$_3$ |
| A-1787 | SO$_2$CH$_3$ | F | CH$_2$CCH | CH$_2$CH$_2$CH$_3$ |
| A-1788 | SO$_2$CH$_3$ | F | CH$_2$CCH | CH$_2$CH$_2$OCH$_3$ |
| A-1789 | SO$_2$CH$_3$ | F | CH$_2$C$_6$H$_5$ | CH$_3$ |
| A-1790 | SO$_2$CH$_3$ | F | CH$_2$C$_6$H$_5$ | CH$_2$CH$_3$ |
| A-1791 | SO$_2$CH$_3$ | F | CH$_2$C$_6$H$_5$ | CH$_2$CH$_2$CH$_3$ |
| A-1792 | SO$_2$CH$_3$ | F | CH$_2$C$_6$H$_5$ | CH$_2$CH$_2$OCH$_3$ |
| A-1793 | SO$_2$CH$_3$ | Cl | CH$_3$ | CH$_3$ |
| A-1794 | SO$_2$CH$_3$ | Cl | CH$_3$ | CH$_2$CH$_3$ |
| A-1795 | SO$_2$CH$_3$ | Cl | CH$_3$ | CH$_2$CH$_2$CH$_3$ |
| A-1796 | SO$_2$CH$_3$ | Cl | CH$_3$ | CH$_2$CH$_2$OCH$_3$ |
| A-1797 | SO$_2$CH$_3$ | Cl | CH$_2$CH$_3$ | CH$_3$ |
| A-1798 | SO$_2$CH$_3$ | Cl | CH$_2$CH$_3$ | CH$_2$CH$_3$ |
| A-1799 | SO$_2$CH$_3$ | Cl | CH$_2$CH$_3$ | CH$_2$CH$_2$CH$_3$ |
| A-1800 | SO$_2$CH$_3$ | Cl | CH$_2$CH$_3$ | CH$_2$CH$_2$OCH$_3$ |
| A-1801 | SO$_2$CH$_3$ | Cl | CH$_2$OCH$_3$ | CH$_3$ |
| A-1802 | SO$_2$CH$_3$ | Cl | CH$_2$OCH$_3$ | CH$_2$CH$_3$ |
| A-1803 | SO$_2$CH$_3$ | Cl | CH$_2$OCH$_3$ | CH$_2$CH$_2$CH$_3$ |
| A-1804 | SO$_2$CH$_3$ | Cl | CH$_2$OCH$_3$ | CH$_2$CH$_2$OCH$_3$ |
| A-1805 | SO$_2$CH$_3$ | Cl | CH$_2$OCH$_2$CH$_3$ | CH$_3$ |
| A-1806 | SO$_2$CH$_3$ | Cl | CH$_2$OCH$_2$CH$_3$ | CH$_2$CH$_3$ |
| A-1807 | SO$_2$CH$_3$ | Cl | CH$_2$OCH$_2$CH$_3$ | CH$_2$CH$_2$CH$_3$ |
| A-1808 | SO$_2$CH$_3$ | Cl | CH$_2$OCH$_2$CH$_3$ | CH$_2$CH$_2$OCH$_3$ |
| A-1809 | SO$_2$CH$_3$ | Cl | CH$_2$(CO)OCH$_3$ | CH$_3$ |
| A-1810 | SO$_2$CH$_3$ | Cl | CH$_2$(CO)OCH$_3$ | CH$_2$CH$_3$ |
| A-1811 | SO$_2$CH$_3$ | Cl | CH$_2$(CO)OCH$_3$ | CH$_2$CH$_2$CH$_3$ |
| A-1812 | SO$_2$CH$_3$ | Cl | CH$_2$(CO)OCH$_3$ | CH$_2$CH$_2$OCH$_3$ |
| A-1813 | SO$_2$CH$_3$ | Cl | CH$_2$CHCH$_2$ | CH$_3$ |
| A-1814 | SO$_2$CH$_3$ | Cl | CH$_2$CHCH$_2$ | CH$_2$CH$_3$ |
| A-1815 | SO$_2$CH$_3$ | Cl | CH$_2$CHCH$_2$ | CH$_2$CH$_2$CH$_3$ |
| A-1816 | SO$_2$CH$_3$ | Cl | CH$_2$CHCH$_2$ | CH$_2$CH$_2$OCH$_3$ |
| A-1817 | SO$_2$CH$_3$ | Cl | CH$_2$CCH | CH$_3$ |
| A-1818 | SO$_2$CH$_3$ | Cl | CH$_2$CCH | CH$_2$CH$_3$ |
| A-1819 | SO$_2$CH$_3$ | Cl | CH$_2$CCH | CH$_2$CH$_2$CH$_3$ |
| A-1820 | SO$_2$CH$_3$ | Cl | CH$_2$CCH | CH$_2$CH$_2$OCH$_3$ |
| A-1821 | SO$_2$CH$_3$ | Cl | CH$_2$C$_6$H$_5$ | CH$_3$ |
| A-1822 | SO$_2$CH$_3$ | Cl | CH$_2$C$_6$H$_5$ | CH$_2$CH$_3$ |
| A-1823 | SO$_2$CH$_3$ | Cl | CH$_2$C$_6$H$_5$ | CH$_2$CH$_2$CH$_3$ |

TABLE A-continued

|  | R¹ | R³ | R⁶ | R⁷ |
|---|---|---|---|---|
| A-1824 | SO₂CH₃ | Cl | CH₂C₆H₅ | CH₂CH₂OCH₃ |
| A-1825 | SO₂CH₃ | Br | CH₃ | CH₃ |
| A-1826 | SO₂CH₃ | Br | CH₃ | CH₂CH₃ |
| A-1827 | SO₂CH₃ | Br | CH₃ | CH₂CH₂CH₃ |
| A-1828 | SO₂CH₃ | Br | CH₃ | CH₂CH₂OCH₃ |
| A-1829 | SO₂CH₃ | Br | CH₂CH₃ | CH₃ |
| A-1830 | SO₂CH₃ | Br | CH₂CH₃ | CH₂CH₃ |
| A-1831 | SO₂CH₃ | Br | CH₂CH₃ | CH₂CH₂CH₃ |
| A-1832 | SO₂CH₃ | Br | CH₂CH₃ | CH₂CH₂OCH₃ |
| A-1833 | SO₂CH₃ | Br | CH₂OCH₃ | CH₃ |
| A-1834 | SO₂CH₃ | Br | CH₂OCH₃ | CH₂CH₃ |
| A-1835 | SO₂CH₃ | Br | CH₂OCH₃ | CH₂CH₂CH₃ |
| A-1836 | SO₂CH₃ | Br | CH₂OCH₃ | CH₂CH₂OCH₃ |
| A-1837 | SO₂CH₃ | Br | CH₂OCH₂CH₃ | CH₃ |
| A-1838 | SO₂CH₃ | Br | CH₂OCH₂CH₃ | CH₂CH₃ |
| A-1839 | SO₂CH₃ | Br | CH₂OCH₂CH₃ | CH₂CH₂CH₃ |
| A-1840 | SO₂CH₃ | Br | CH₂OCH₂CH₃ | CH₂CH₂OCH₃ |
| A-1841 | SO₂CH₃ | Br | CH₂(CO)OCH₃ | CH₃ |
| A-1842 | SO₂CH₃ | Br | CH₂(CO)OCH₃ | CH₂CH₃ |
| A-1843 | SO₂CH₃ | Br | CH₂(CO)OCH₃ | CH₂CH₂CH₃ |
| A-1844 | SO₂CH₃ | Br | CH₂(CO)OCH₃ | CH₂CH₂OCH₃ |
| A-1845 | SO₂CH₃ | Br | CH₂CHCH₂ | CH₃ |
| A-1846 | SO₂CH₃ | Br | CH₂CHCH₂ | CH₂CH₃ |
| A-1847 | SO₂CH₃ | Br | CH₂CHCH₂ | CH₂CH₂CH₃ |
| A-1848 | SO₂CH₃ | Br | CH₂CHCH₂ | CH₂CH₂OCH₃ |
| A-1849 | SO₂CH₃ | Br | CH₂CCH | CH₃ |
| A-1850 | SO₂CH₃ | Br | CH₂CCH | CH₂CH₃ |
| A-1851 | SO₂CH₃ | Br | CH₂CCH | CH₂CH₂CH₃ |
| A-1852 | SO₂CH₃ | Br | CH₂CCH | CH₂CH₂OCH₃ |
| A-1853 | SO₂CH₃ | Br | CH₂C₆H₅ | CH₃ |
| A-1854 | SO₂CH₃ | Br | CH₂C₆H₅ | CH₂CH₃ |
| A-1855 | SO₂CH₃ | Br | CH₂C₆H₅ | CH₂CH₂CH₃ |
| A-1856 | SO₂CH₃ | Br | CH₂C₆H₅ | CH₂CH₂OCH₃ |
| A-1857 | SO₂CH₃ | CN | CH₃ | CH₃ |
| A-1858 | SO₂CH₃ | CN | CH₃ | CH₂CH₃ |
| A-1859 | SO₂CH₃ | CN | CH₃ | CH₂CH₂CH₃ |
| A-1860 | SO₂CH₃ | CN | CH₃ | CH₂CH₂OCH₃ |
| A-1861 | SO₂CH₃ | CN | CH₂CH₃ | CH₃ |
| A-1862 | SO₂CH₃ | CN | CH₂CH₃ | CH₂CH₃ |
| A-1863 | SO₂CH₃ | CN | CH₂CH₃ | CH₂CH₂CH₃ |
| A-1864 | SO₂CH₃ | CN | CH₂CH₃ | CH₂CH₂OCH₃ |
| A-1865 | SO₂CH₃ | CN | CH₂OCH₃ | CH₃ |
| A-1866 | SO₂CH₃ | CN | CH₂OCH₃ | CH₂CH₃ |
| A-1867 | SO₂CH₃ | CN | CH₂OCH₃ | CH₂CH₂CH₃ |
| A-1868 | SO₂CH₃ | CN | CH₂OCH₃ | CH₂CH₂OCH₃ |
| A-1869 | SO₂CH₃ | CN | CH₂OCH₂CH₃ | CH₃ |
| A-1870 | SO₂CH₃ | CN | CH₂OCH₂CH₃ | CH₂CH₃ |
| A-1871 | SO₂CH₃ | CN | CH₂OCH₂CH₃ | CH₂CH₂CH₃ |
| A-1872 | SO₂CH₃ | CN | CH₂OCH₂CH₃ | CH₂CH₂OCH₃ |
| A-1873 | SO₂CH₃ | CN | CH₂(CO)OCH₃ | CH₃ |
| A-1874 | SO₂CH₃ | CN | CH₂(CO)OCH₃ | CH₂CH₃ |
| A-1875 | SO₂CH₃ | CN | CH₂(CO)OCH₃ | CH₂CH₂CH₃ |
| A-1876 | SO₂CH₃ | CN | CH₂(CO)OCH₃ | CH₂CH₂OCH₃ |
| A-1877 | SO₂CH₃ | CN | CH₂CHCH₂ | CH₃ |
| A-1878 | SO₂CH₃ | CN | CH₂CHCH₂ | CH₂CH₃ |
| A-1879 | SO₂CH₃ | CN | CH₂CHCH₂ | CH₂CH₂CH₃ |
| A-1880 | SO₂CH₃ | CN | CH₂CHCH₂ | CH₂CH₂OCH₃ |
| A-1881 | SO₂CH₃ | CN | CH₂CCH | CH₃ |
| A-1882 | SO₂CH₃ | CN | CH₂CCH | CH₂CH₃ |
| A-1883 | SO₂CH₃ | CN | CH₂CCH | CH₂CH₂CH₃ |
| A-1884 | SO₂CH₃ | CN | CH₂CCH | CH₂CH₂OCH₃ |
| A-1885 | SO₂CH₃ | CN | CH₂C₆H₅ | CH₃ |
| A-1886 | SO₂CH₃ | CN | CH₂C₆H₅ | CH₂CH₃ |
| A-1887 | SO₂CH₃ | CN | CH₂C₆H₅ | CH₂CH₂CH₃ |
| A-1888 | SO₂CH₃ | CN | CH₂C₆H₅ | CH₂CH₂OCH₃ |
| A-1889 | SO₂CH₃ | CH₃ | CH₃ | CH₃ |
| A-1890 | SO₂CH₃ | CH₃ | CH₃ | CH₂CH₃ |
| A-1891 | SO₂CH₃ | CH₃ | CH₃ | CH₂CH₂CH₃ |
| A-1892 | SO₂CH₃ | CH₃ | CH₃ | CH₂CH₂OCH₃ |
| A-1893 | SO₂CH₃ | CH₃ | CH₂CH₃ | CH₃ |
| A-1894 | SO₂CH₃ | CH₃ | CH₂CH₃ | CH₂CH₃ |
| A-1895 | SO₂CH₃ | CH₃ | CH₂CH₃ | CH₂CH₂CH₃ |
| A-1896 | SO₂CH₃ | CH₃ | CH₂CH₃ | CH₂CH₂OCH₃ |
| A-1897 | SO₂CH₃ | CH₃ | CH₂OCH₃ | CH₃ |
| A-1898 | SO₂CH₃ | CH₃ | CH₂OCH₃ | CH₂CH₃ |
| A-1899 | SO₂CH₃ | CH₃ | CH₂OCH₃ | CH₂CH₂CH₃ |
| A-1900 | SO₂CH₃ | CH₃ | CH₂OCH₃ | CH₂CH₂OCH₃ |
| A-1901 | SO₂CH₃ | CH₃ | CH₂OCH₂CH₃ | CH₃ |

TABLE A-continued

| | $R^1$ | $R^3$ | $R^6$ | $R^7$ |
|---|---|---|---|---|
| A-1902 | SO₂CH₃ | CH₃ | CH₂OCH₂CH₃ | CH₃ |
| A-1903 | SO₂CH₃ | CH₃ | CH₂OCH₂CH₃ | CH₂CH₃ |
| A-1904 | SO₂CH₃ | CH₃ | CH₂OCH₂CH₃ | CH₂CH₂OCH₃ |
| A-1905 | SO₂CH₃ | CH₃ | CH₂(CO)OCH₃ | CH₃ |
| A-1906 | SO₂CH₃ | CH₃ | CH₂(CO)OCH₃ | CH₂CH₃ |
| A-1907 | SO₂CH₃ | CH₃ | CH₂(CO)OCH₃ | CH₂CH₂CH₃ |
| A-1908 | SO₂CH₃ | CH₃ | CH₂(CO)OCH₃ | CH₂CH₂OCH₃ |
| A-1909 | SO₂CH₃ | CH₃ | CH₂CHCH₂ | CH₃ |
| A-1910 | SO₂CH₃ | CH₃ | CH₂CHCH₂ | CH₂CH₃ |
| A-1911 | SO₂CH₃ | CH₃ | CH₂CHCH₂ | CH₂CH₂CH₃ |
| A-1912 | SO₂CH₃ | CH₃ | CH₂CHCH₂ | CH₂CH₂OCH₃ |
| A-1913 | SO₂CH₃ | CH₃ | CH₂CCH | CH₃ |
| A-1914 | SO₂CH₃ | CH₃ | CH₂CCH | CH₂CH₃ |
| A-1915 | SO₂CH₃ | CH₃ | CH₂CCH | CH₂CH₂CH₃ |
| A-1916 | SO₂CH₃ | CH₃ | CH₂CCH | CH₂CH₂OCH₃ |
| A-1917 | SO₂CH₃ | CH₃ | CH₂C₆H₅ | CH₃ |
| A-1918 | SO₂CH₃ | CH₃ | CH₂C₆H₅ | CH₂CH₃ |
| A-1919 | SO₂CH₃ | CH₃ | CH₂C₆H₅ | CH₂CH₂CH₃ |
| A-1920 | SO₂CH₃ | CH₃ | CH₂C₆H₅ | CH₂CH₂OCH₃ |
| A-1921 | SO₂CH₃ | CF₃ | CH₃ | CH₃ |
| A-1922 | SO₂CH₃ | CF₃ | CH₃ | CH₂CH₃ |
| A-1923 | SO₂CH₃ | CF₃ | CH₃ | CH₂CH₂CH₃ |
| A-1924 | SO₂CH₃ | CF₃ | CH₃ | CH₂CH₂OCH₃ |
| A-1925 | SO₂CH₃ | CF₃ | CH₂CH₃ | CH₃ |
| A-1926 | SO₂CH₃ | CF₃ | CH₂CH₃ | CH₂CH₃ |
| A-1927 | SO₂CH₃ | CF₃ | CH₂CH₃ | CH₂CH₂CH₃ |
| A-1928 | SO₂CH₃ | CF₃ | CH₂CH₃ | CH₂CH₂OCH₃ |
| A-1929 | SO₂CH₃ | CF₃ | CH₂OCH₃ | CH₃ |
| A-1930 | SO₂CH₃ | CF₃ | CH₂OCH₃ | CH₂CH₃ |
| A-1931 | SO₂CH₃ | CF₃ | CH₂OCH₃ | CH₂CH₂CH₃ |
| A-1932 | SO₂CH₃ | CF₃ | CH₂OCH₃ | CH₂CH₂OCH₃ |
| A-1933 | SO₂CH₃ | CF₃ | CH₂OCH₂CH₃ | CH₃ |
| A-1934 | SO₂CH₃ | CF₃ | CH₂OCH₂CH₃ | CH₂CH₃ |
| A-1935 | SO₂CH₃ | CF₃ | CH₂OCH₂CH₃ | CH₂CH₂CH₃ |
| A-1936 | SO₂CH₃ | CF₃ | CH₂OCH₂CH₃ | CH₂CH₂OCH₃ |
| A-1937 | SO₂CH₃ | CF₃ | CH₂(CO)OCH₃ | CH₃ |
| A-1938 | SO₂CH₃ | CF₃ | CH₂(CO)OCH₃ | CH₂CH₃ |
| A-1939 | SO₂CH₃ | CF₃ | CH₂(CO)OCH₃ | CH₂CH₂CH₃ |
| A-1940 | SO₂CH₃ | CF₃ | CH₂(CO)OCH₃ | CH₂CH₂OCH₃ |
| A-1941 | SO₂CH₃ | CF₃ | CH₂CHCH₂ | CH₃ |
| A-1942 | SO₂CH₃ | CF₃ | CH₂CHCH₂ | CH₂CH₃ |
| A-1943 | SO₂CH₃ | CF₃ | CH₂CHCH₂ | CH₂CH₂CH₃ |
| A-1944 | SO₂CH₃ | CF₃ | CH₂CHCH₂ | CH₂CH₂OCH₃ |
| A-1945 | SO₂CH₃ | CF₃ | CH₂CCH | CH₃ |
| A-1946 | SO₂CH₃ | CF₃ | CH₂CCH | CH₂CH₃ |
| A-1947 | SO₂CH₃ | CF₃ | CH₂CCH | CH₂CH₂CH₃ |
| A-1948 | SO₂CH₃ | CF₃ | CH₂CCH | CH₂CH₂OCH₃ |
| A-1949 | SO₂CH₃ | CF₃ | CH₂C₆H₅ | CH₃ |
| A-1950 | SO₂CH₃ | CF₃ | CH₂C₆H₅ | CH₂CH₃ |
| A-1951 | SO₂CH₃ | CF₃ | CH₂C₆H₅ | CH₂CH₂CH₃ |
| A-1952 | SO₂CH₃ | CF₃ | CH₂C₆H₅ | CH₂CH₂OCH₃ |
| A-1953 | SO₂CH₃ | SO₂CH₃ | CH₃ | CH₃ |
| A-1954 | SO₂CH₃ | SO₂CH₃ | CH₃ | CH₂CH₃ |
| A-1955 | SO₂CH₃ | SO₂CH₃ | CH₃ | CH₂CH₂CH₃ |
| A-1956 | SO₂CH₃ | SO₂CH₃ | CH₃ | CH₂CH₂OCH₃ |
| A-1957 | SO₂CH₃ | SO₂CH₃ | CH₂CH₃ | CH₃ |
| A-1958 | SO₂CH₃ | SO₂CH₃ | CH₂CH₃ | CH₂CH₃ |
| A-1959 | SO₂CH₃ | SO₂CH₃ | CH₂CH₃ | CH₂CH₂CH₃ |
| A-1960 | SO₂CH₃ | SO₂CH₃ | CH₂CH₃ | CH₂CH₂OCH₃ |
| A-1961 | SO₂CH₃ | SO₂CH₃ | CH₂OCH₃ | CH₃ |
| A-1962 | SO₂CH₃ | SO₂CH₃ | CH₂OCH₃ | CH₂CH₃ |
| A-1963 | SO₂CH₃ | SO₂CH₃ | CH₂OCH₃ | CH₂CH₂CH₃ |
| A-1964 | SO₂CH₃ | SO₂CH₃ | CH₂OCH₃ | CH₂CH₂OCH₃ |
| A-1965 | SO₂CH₃ | SO₂CH₃ | CH₂OCH₂CH₃ | CH₃ |
| A-1966 | SO₂CH₃ | SO₂CH₃ | CH₂OCH₂CH₃ | CH₂CH₃ |
| A-1967 | SO₂CH₃ | SO₂CH₃ | CH₂OCH₂CH₃ | CH₂CH₂CH₃ |
| A-1968 | SO₂CH₃ | SO₂CH₃ | CH₂OCH₂CH₃ | CH₂CH₂OCH₃ |
| A-1969 | SO₂CH₃ | SO₂CH₃ | CH₂(CO)OCH₃ | CH₃ |
| A-1970 | SO₂CH₃ | SO₂CH₃ | CH₂(CO)OCH₃ | CH₂CH₃ |
| A-1971 | SO₂CH₃ | SO₂CH₃ | CH₂(CO)OCH₃ | CH₂CH₂CH₃ |
| A-1972 | SO₂CH₃ | SO₂CH₃ | CH₂(CO)OCH₃ | CH₂CH₂OCH₃ |
| A-1973 | SO₂CH₃ | SO₂CH₃ | CH₂CHCH₂ | CH₃ |
| A-1974 | SO₂CH₃ | SO₂CH₃ | CH₂CHCH₂ | CH₂CH₃ |
| A-1975 | SO₂CH₃ | SO₂CH₃ | CH₂CHCH₂ | CH₂CH₂CH₃ |
| A-1976 | SO₂CH₃ | SO₂CH₃ | CH₂CHCH₂ | CH₂CH₂OCH₃ |
| A-1977 | SO₂CH₃ | SO₂CH₃ | CH₂CCH | CH₃ |
| A-1978 | SO₂CH₃ | SO₂CH₃ | CH₂CCH | CH₂CH₃ |
| A-1979 | SO₂CH₃ | SO₂CH₃ | CH₂CCH | CH₂CH₂CH₃ |

TABLE A-continued

|  | R¹ | R³ | R⁶ | R⁷ |
|---|---|---|---|---|
| A-1980 | $SO_2CH_3$ | $SO_2CH_3$ | $CH_2CCH$ | $CH_2CH_2OCH_3$ |
| A-1981 | $SO_2CH_3$ | $SO_2CH_3$ | $CH_2C_6H_5$ | $CH_3$ |
| A-1982 | $SO_2CH_3$ | $SO_2CH_3$ | $CH_2C_6H_5$ | $CH_2CH_3$ |
| A-1983 | $SO_2CH_3$ | $SO_2CH_3$ | $CH_2C_6H_5$ | $CH_2CH_2CH_3$ |
| A-1984 | $SO_2CH_3$ | $SO_2CH_3$ | $CH_2C_6H_5$ | $CH_2CH_2OCH_3$ |
| A-1985 | $SO_2CH_3$ | $NO_2$ | $CH_3$ | $CH_3$ |
| A-1986 | $SO_2CH_3$ | $NO_2$ | $CH_3$ | $CH_2CH_3$ |
| A-1987 | $SO_2CH_3$ | $NO_2$ | $CH_3$ | $CH_2CH_2CH_3$ |
| A-1988 | $SO_2CH_3$ | $NO_2$ | $CH_3$ | $CH_2CH_2OCH_3$ |
| A-1989 | $SO_2CH_3$ | $NO_2$ | $CH_2CH_3$ | $CH_3$ |
| A-1990 | $SO_2CH_3$ | $NO_2$ | $CH_2CH_3$ | $CH_2CH_3$ |
| A-1991 | $SO_2CH_3$ | $NO_2$ | $CH_2CH_3$ | $CH_2CH_2CH_3$ |
| A-1992 | $SO_2CH_3$ | $NO_2$ | $CH_2CH_3$ | $CH_2CH_2OCH_3$ |
| A-1993 | $SO_2CH_3$ | $NO_2$ | $CH_2OCH_3$ | $CH_3$ |
| A-1994 | $SO_2CH_3$ | $NO_2$ | $CH_2OCH_3$ | $CH_2CH_3$ |
| A-1995 | $SO_2CH_3$ | $NO_2$ | $CH_2OCH_3$ | $CH_2CH_2CH_3$ |
| A-1996 | $SO_2CH_3$ | $NO_2$ | $CH_2OCH_3$ | $CH_2CH_2OCH_3$ |
| A-1997 | $SO_2CH_3$ | $NO_2$ | $CH_2OCH_2CH_3$ | $CH_3$ |
| A-1998 | $SO_2CH_3$ | $NO_2$ | $CH_2OCH_2CH_3$ | $CH_2CH_3$ |
| A-1999 | $SO_2CH_3$ | $NO_2$ | $CH_2OCH_2CH_3$ | $CH_2CH_2CH_3$ |
| A-2000 | $SO_2CH_3$ | $NO_2$ | $CH_2OCH_2CH_3$ | $CH_2CH_2OCH_3$ |
| A-2001 | $SO_2CH_3$ | $NO_2$ | $CH_2(CO)OCH_3$ | $CH_3$ |
| A-2002 | $SO_2CH_3$ | $NO_2$ | $CH_2(CO)OCH_3$ | $CH_2CH_3$ |
| A-2003 | $SO_2CH_3$ | $NO_2$ | $CH_2(CO)OCH_3$ | $CH_2CH_2CH_3$ |
| A-2004 | $SO_2CH_3$ | $NO_2$ | $CH_2(CO)OCH_3$ | $CH_2CH_2OCH_3$ |
| A-2005 | $SO_2CH_3$ | $NO_2$ | $CH_2CHCH_2$ | $CH_3$ |
| A-2006 | $SO_2CH_3$ | $NO_2$ | $CH_2CHCH_2$ | $CH_2CH_3$ |
| A-2007 | $SO_2CH_3$ | $NO_2$ | $CH_2CHCH_2$ | $CH_2CH_2CH_3$ |
| A-2008 | $SO_2CH_3$ | $NO_2$ | $CH_2CHCH_2$ | $CH_2CH_2OCH_3$ |
| A-2009 | $SO_2CH_3$ | $NO_2$ | $CH_2CCH$ | $CH_3$ |
| A-2010 | $SO_2CH_3$ | $NO_2$ | $CH_2CCH$ | $CH_2CH_3$ |
| A-2011 | $SO_2CH_3$ | $NO_2$ | $CH_2CCH$ | $CH_2CH_2CH_3$ |
| A-2012 | $SO_2CH_3$ | $NO_2$ | $CH_2CCH$ | $CH_2CH_2OCH_3$ |
| A-2013 | $SO_2CH_3$ | $NO_2$ | $CH_2C_6H_5$ | $CH_3$ |
| A-2014 | $SO_2CH_3$ | $NO_2$ | $CH_2C_6H_5$ | $CH_2CH_3$ |
| A-2015 | $SO_2CH_3$ | $NO_2$ | $CH_2C_6H_5$ | $CH_2CH_2CH_3$ |
| A-2016 | $SO_2CH_3$ | $NO_2$ | $CH_2C_6H_5$ | $CH_2CH_2OCH_3$ |
| A-2017 | $CF_3$ | H | $CH_3$ | $CH_3$ |
| A-2018 | $CF_3$ | H | $CH_3$ | $CH_2CH_3$ |
| A-2019 | $CF_3$ | H | $CH_3$ | $CH_2CH_2CH_3$ |
| A-2020 | $CF_3$ | H | $CH_3$ | $CH_2CH_2OCH_3$ |
| A-2021 | $CF_3$ | H | $CH_2CH_3$ | $CH_3$ |
| A-2022 | $CF_3$ | H | $CH_2CH_3$ | $CH_2CH_3$ |
| A-2023 | $CF_3$ | H | $CH_2CH_3$ | $CH_2CH_2CH_3$ |
| A-2024 | $CF_3$ | H | $CH_2CH_3$ | $CH_2CH_2OCH_3$ |
| A-2025 | $CF_3$ | H | $CH_2OCH_3$ | $CH_3$ |
| A-2026 | $CF_3$ | H | $CH_2OCH_3$ | $CH_2CH_3$ |
| A-2027 | $CF_3$ | H | $CH_2OCH_3$ | $CH_2CH_2CH_3$ |
| A-2028 | $CF_3$ | H | $CH_2OCH_3$ | $CH_2CH_2OCH_3$ |
| A-2029 | $CF_3$ | H | $CH_2OCH_2CH_3$ | $CH_3$ |
| A-2030 | $CF_3$ | H | $CH_2OCH_2CH_3$ | $CH_2CH_3$ |
| A-2031 | $CF_3$ | H | $CH_2OCH_2CH_3$ | $CH_2CH_2CH_3$ |
| A-2032 | $CF_3$ | H | $CH_2OCH_2CH_3$ | $CH_2CH_2OCH_3$ |
| A-2033 | $CF_3$ | H | $CH_2(CO)OCH_3$ | $CH_3$ |
| A-2034 | $CF_3$ | H | $CH_2(CO)OCH_3$ | $CH_2CH_3$ |
| A-2035 | $CF_3$ | H | $CH_2(CO)OCH_3$ | $CH_2CH_2CH_3$ |
| A-2036 | $CF_3$ | H | $CH_2(CO)OCH_3$ | $CH_2CH_2OCH_3$ |
| A-2037 | $CF_3$ | H | $CH_2CHCH_2$ | $CH_3$ |
| A-2038 | $CF_3$ | H | $CH_2CHCH_2$ | $CH_2CH_3$ |
| A-2039 | $CF_3$ | H | $CH_2CHCH_2$ | $CH_2CH_2CH_3$ |
| A-2040 | $CF_3$ | H | $CH_2CHCH_2$ | $CH_2CH_2OCH_3$ |
| A-2041 | $CF_3$ | H | $CH_2CCH$ | $CH_3$ |
| A-2042 | $CF_3$ | H | $CH_2CCH$ | $CH_2CH_3$ |
| A-2043 | $CF_3$ | H | $CH_2CCH$ | $CH_2CH_2CH_3$ |
| A-2044 | $CF_3$ | H | $CH_2CCH$ | $CH_2CH_2OCH_3$ |
| A-2045 | $CF_3$ | H | $CH_2C_6H_5$ | $CH_3$ |
| A-2046 | $CF_3$ | H | $CH_2C_6H_5$ | $CH_2CH_3$ |
| A-2047 | $CF_3$ | H | $CH_2C_6H_5$ | $CH_2CH_2CH_3$ |
| A-2048 | $CF_3$ | H | $CH_2C_6H_5$ | $CH_2CH_2OCH_3$ |
| A-2049 | $CF_3$ | F | $CH_3$ | $CH_3$ |
| A-2050 | $CF_3$ | F | $CH_3$ | $CH_2CH_3$ |
| A-2051 | $CF_3$ | F | $CH_3$ | $CH_2CH_2CH_3$ |
| A-2052 | $CF_3$ | F | $CH_3$ | $CH_2CH_2OCH_3$ |
| A-2053 | $CF_3$ | F | $CH_2CH_3$ | $CH_3$ |
| A-2054 | $CF_3$ | F | $CH_2CH_3$ | $CH_2CH_3$ |
| A-2055 | $CF_3$ | F | $CH_2CH_3$ | $CH_2CH_2CH_3$ |
| A-2056 | $CF_3$ | F | $CH_2CH_3$ | $CH_2CH_2OCH_3$ |
| A-2057 | $CF_3$ | F | $CH_2OCH_3$ | $CH_3$ |

TABLE A-continued

|   | R¹ | R³ | R⁶ | R⁷ |
|---|---|---|---|---|
| A-2058 | CF₃ | F | CH₂OCH₃ | CH₂CH₃ |
| A-2059 | CF₃ | F | CH₂OCH₃ | CH₂CH₂CH₃ |
| A-2060 | CF₃ | F | CH₂OCH₃ | CH₂CH₂OCH₃ |
| A-2061 | CF₃ | F | CH₂OCH₂CH₃ | CH₃ |
| A-2062 | CF₃ | F | CH₂OCH₂CH₃ | CH₂CH₃ |
| A-2063 | CF₃ | F | CH₂OCH₂CH₃ | CH₂CH₂CH₃ |
| A-2064 | CF₃ | F | CH₂OCH₂CH₃ | CH₂CH₂OCH₃ |
| A-2065 | CF₃ | F | CH₂(CO)OCH₃ | CH₃ |
| A-2066 | CF₃ | F | CH₂(CO)OCH₃ | CH₂CH₃ |
| A-2067 | CF₃ | F | CH₂(CO)OCH₃ | CH₂CH₂CH₃ |
| A-2068 | CF₃ | F | CH₂(CO)OCH₃ | CH₂CH₂OCH₃ |
| A-2069 | CF₃ | F | CH₂CHCH₂ | CH₃ |
| A-2070 | CF₃ | F | CH₂CHCH₂ | CH₂CH₃ |
| A-2071 | CF₃ | F | CH₂CHCH₂ | CH₂CH₂CH₃ |
| A-2072 | CF₃ | F | CH₂CHCH₂ | CH₂CH₂OCH₃ |
| A-2073 | CF₃ | F | CH₂CCH | CH₃ |
| A-2074 | CF₃ | F | CH₂CCH | CH₂CH₃ |
| A-2075 | CF₃ | F | CH₂CCH | CH₂CH₂CH₃ |
| A-2076 | CF₃ | F | CH₂CCH | CH₂CH₂OCH₃ |
| A-2077 | CF₃ | F | CH₂C₆H₅ | CH₃ |
| A-2078 | CF₃ | F | CH₂C₆H₅ | CH₂CH₃ |
| A-2079 | CF₃ | F | CH₂C₆H₅ | CH₂CH₂CH₃ |
| A-2080 | CF₃ | F | CH₂C₆H₅ | CH₂CH₂OCH₃ |
| A-2081 | CF₃ | Cl | CH₃ | CH₃ |
| A-2082 | CF₃ | Cl | CH₃ | CH₂CH₃ |
| A-2083 | CF₃ | Cl | CH₃ | CH₂CH₂CH₃ |
| A-2084 | CF₃ | Cl | CH₃ | CH₂CH₂OCH₃ |
| A-2085 | CF₃ | Cl | CH₂CH₃ | CH₃ |
| A-2086 | CF₃ | Cl | CH₂CH₃ | CH₂CH₃ |
| A-2087 | CF₃ | Cl | CH₂CH₃ | CH₂CH₂CH₃ |
| A-2088 | CF₃ | Cl | CH₂CH₃ | CH₂CH₂OCH₃ |
| A-2089 | CF₃ | Cl | CH₂OCH₃ | CH₃ |
| A-2090 | CF₃ | Cl | CH₂OCH₃ | CH₂CH₃ |
| A-2091 | CF₃ | Cl | CH₂OCH₃ | CH₂CH₂CH₃ |
| A-2092 | CF₃ | Cl | CH₂OCH₃ | CH₂CH₂OCH₃ |
| A-2093 | CF₃ | Cl | CH₂OCH₂CH₃ | CH₃ |
| A-2094 | CF₃ | Cl | CH₂OCH₂CH₃ | CH₂CH₃ |
| A-2095 | CF₃ | Cl | CH₂OCH₂CH₃ | CH₂CH₂CH₃ |
| A-2096 | CF₃ | Cl | CH₂OCH₂CH₃ | CH₂CH₂OCH₃ |
| A-2097 | CF₃ | Cl | CH₂(CO)OCH₃ | CH₃ |
| A-2098 | CF₃ | Cl | CH₂(CO)OCH₃ | CH₂CH₃ |
| A-2099 | CF₃ | Cl | CH₂(CO)OCH₃ | CH₂CH₂CH₃ |
| A-2100 | CF₃ | Cl | CH₂(CO)OCH₃ | CH₂CH₂OCH₃ |
| A-2101 | CF₃ | Cl | CH₂CHCH₂ | CH₃ |
| A-2102 | CF₃ | Cl | CH₂CHCH₂ | CH₂CH₃ |
| A-2103 | CF₃ | Cl | CH₂CHCH₂ | CH₂CH₂CH₃ |
| A-2104 | CF₃ | Cl | CH₂CHCH₂ | CH₂CH₂OCH₃ |
| A-2105 | CF₃ | Cl | CH₂CCH | CH₃ |
| A-2106 | CF₃ | Cl | CH₂CCH | CH₂CH₃ |
| A-2107 | CF₃ | Cl | CH₂CCH | CH₂CH₂CH₃ |
| A-2108 | CF₃ | Cl | CH₂CCH | CH₂CH₂OCH₃ |
| A-2109 | CF₃ | Cl | CH₂C₆H₅ | CH₃ |
| A-2110 | CF₃ | Cl | CH₂C₆H₅ | CH₂CH₃ |
| A-2111 | CF₃ | Cl | CH₂C₆H₅ | CH₂CH₂CH₃ |
| A-2112 | CF₃ | Cl | CH₂C₆H₅ | CH₂CH₂OCH₃ |
| A-2113 | CF₃ | Br | CH₃ | CH₃ |
| A-2114 | CF₃ | Br | CH₃ | CH₂CH₃ |
| A-2115 | CF₃ | Br | CH₃ | CH₂CH₂CH₃ |
| A-2116 | CF₃ | Br | CH₃ | CH₂CH₂OCH₃ |
| A-2117 | CF₃ | Br | CH₂CH₃ | CH₃ |
| A-2118 | CF₃ | Br | CH₂CH₃ | CH₂CH₃ |
| A-2119 | CF₃ | Br | CH₂CH₃ | CH₂CH₂CH₃ |
| A-2120 | CF₃ | Br | CH₂CH₃ | CH₂CH₂OCH₃ |
| A-2121 | CF₃ | Br | CH₂OCH₃ | CH₃ |
| A-2122 | CF₃ | Br | CH₂OCH₃ | CH₂CH₃ |
| A-2123 | CF₃ | Br | CH₂OCH₃ | CH₂CH₂CH₃ |
| A-2124 | CF₃ | Br | CH₂OCH₃ | CH₂CH₂OCH₃ |
| A-2125 | CF₃ | Br | CH₂OCH₂CH₃ | CH₃ |
| A-2126 | CF₃ | Br | CH₂OCH₂CH₃ | CH₂CH₃ |
| A-2127 | CF₃ | Br | CH₂OCH₂CH₃ | CH₂CH₂CH₃ |
| A-2128 | CF₃ | Br | CH₂OCH₂CH₃ | CH₂CH₂OCH₃ |
| A-2129 | CF₃ | Br | CH₂(CO)OCH₃ | CH₃ |
| A-2130 | CF₃ | Br | CH₂(CO)OCH₃ | CH₂CH₃ |
| A-2131 | CF₃ | Br | CH₂(CO)OCH₃ | CH₂CH₂CH₃ |
| A-2132 | CF₃ | Br | CH₂(CO)OCH₃ | CH₂CH₂OCH₃ |
| A-2133 | CF₃ | Br | CH₂CHCH₂ | CH₃ |
| A-2134 | CF₃ | Br | CH₂CHCH₂ | CH₂CH₃ |
| A-2135 | CF₃ | Br | CH₂CHCH₂ | CH₂CH₂CH₃ |

TABLE A-continued

| | R¹ | R³ | R⁶ | R⁷ |
|---|---|---|---|---|
| A-2136 | CF₃ | Br | CH₂CHCH₂ | CH₂CH₂OCH₃ |
| A-2137 | CF₃ | Br | CH₂CCH | CH₃ |
| A-2138 | CF₃ | Br | CH₂CCH | CH₂CH₃ |
| A-2139 | CF₃ | Br | CH₂CCH | CH₂CH₂CH₃ |
| A-2140 | CF₃ | Br | CH₂CCH | CH₂CH₂OCH₃ |
| A-2141 | CF₃ | Br | CH₂C₆H₅ | CH₃ |
| A-2142 | CF₃ | Br | CH₂C₆H₅ | CH₂CH₃ |
| A-2143 | CF₃ | Br | CH₂C₆H₅ | CH₂CH₂CH₃ |
| A-2144 | CF₃ | Br | CH₂C₆H₅ | CH₂CH₂OCH₃ |
| A-2145 | CF₃ | CN | CH₃ | CH₃ |
| A-2146 | CF₃ | CN | CH₃ | CH₂CH₃ |
| A-2147 | CF₃ | CN | CH₃ | CH₂CH₂CH₃ |
| A-2148 | CF₃ | CN | CH₃ | CH₂CH₂OCH₃ |
| A-2149 | CF₃ | CN | CH₂CH₃ | CH₃ |
| A-2150 | CF₃ | CN | CH₂CH₃ | CH₂CH₃ |
| A-2151 | CF₃ | CN | CH₂CH₃ | CH₂CH₂CH₃ |
| A-2152 | CF₃ | CN | CH₂CH₃ | CH₂CH₂OCH₃ |
| A-2153 | CF₃ | CN | CH₂OCH₃ | CH₃ |
| A-2154 | CF₃ | CN | CH₂OCH₃ | CH₂CH₃ |
| A-2155 | CF₃ | CN | CH₂OCH₃ | CH₂CH₂CH₃ |
| A-2156 | CF₃ | CN | CH₂OCH₃ | CH₂CH₂OCH₃ |
| A-2157 | CF₃ | CN | CH₂OCH₂CH₃ | CH₃ |
| A-2158 | CF₃ | CN | CH₂OCH₂CH₃ | CH₂CH₃ |
| A-2159 | CF₃ | CN | CH₂OCH₂CH₃ | CH₂CH₂CH₃ |
| A-2160 | CF₃ | CN | CH₂OCH₂CH₃ | CH₂CH₂OCH₃ |
| A-2161 | CF₃ | CN | CH₂(CO)OCH₃ | CH₃ |
| A-2162 | CF₃ | CN | CH₂(CO)OCH₃ | CH₂CH₃ |
| A-2163 | CF₃ | CN | CH₂(CO)OCH₃ | CH₂CH₂CH₃ |
| A-2164 | CF₃ | CN | CH₂(CO)OCH₃ | CH₂CH₂OCH₃ |
| A-2165 | CF₃ | CN | CH₂CHCH₂ | CH₃ |
| A-2166 | CF₃ | CN | CH₂CHCH₂ | CH₂CH₃ |
| A-2167 | CF₃ | CN | CH₂CHCH₂ | CH₂CH₂CH₃ |
| A-2168 | CF₃ | CN | CH₂CHCH₂ | CH₂CH₂OCH₃ |
| A-2169 | CF₃ | CN | CH₂CCH | CH₃ |
| A-2170 | CF₃ | CN | CH₂CCH | CH₂CH₃ |
| A-2171 | CF₃ | CN | CH₂CCH | CH₂CH₂CH₃ |
| A-2172 | CF₃ | CN | CH₂CCH | CH₂CH₂OCH₃ |
| A-2173 | CF₃ | CN | CH₂C₆H₅ | CH₃ |
| A-2174 | CF₃ | CN | CH₂C₆H₅ | CH₂CH₃ |
| A-2175 | CF₃ | CN | CH₂C₆H₅ | CH₂CH₂CH₃ |
| A-2176 | CF₃ | CN | CH₂C₆H₅ | CH₂CH₂OCH₃ |
| A-2177 | CF₃ | CH₃ | CH₃ | CH₃ |
| A-2178 | CF₃ | CH₃ | CH₃ | CH₂CH₃ |
| A-2179 | CF₃ | CH₃ | CH₃ | CH₂CH₂CH₃ |
| A-2180 | CF₃ | CH₃ | CH₃ | CH₂CH₂OCH₃ |
| A-2181 | CF₃ | CH₃ | CH₂CH₃ | CH₃ |
| A-2182 | CF₃ | CH₃ | CH₂CH₃ | CH₂CH₃ |
| A-2183 | CF₃ | CH₃ | CH₂CH₃ | CH₂CH₂CH₃ |
| A-2184 | CF₃ | CH₃ | CH₂CH₃ | CH₂CH₂OCH₃ |
| A-2185 | CF₃ | CH₃ | CH₂OCH₃ | CH₃ |
| A-2186 | CF₃ | CH₃ | CH₂OCH₃ | CH₂CH₃ |
| A-2187 | CF₃ | CH₃ | CH₂OCH₃ | CH₂CH₂CH₃ |
| A-2188 | CF₃ | CH₃ | CH₂OCH₃ | CH₂CH₂OCH₃ |
| A-2189 | CF₃ | CH₃ | CH₂OCH₂CH₃ | CH₃ |
| A-2190 | CF₃ | CH₃ | CH₂OCH₂CH₃ | CH₂CH₃ |
| A-2191 | CF₃ | CH₃ | CH₂OCH₂CH₃ | CH₂CH₂CH₃ |
| A-2192 | CF₃ | CH₃ | CH₂OCH₂CH₃ | CH₂CH₂OCH₃ |
| A-2193 | CF₃ | CH₃ | CH₂(CO)OCH₃ | CH₃ |
| A-2194 | CF₃ | CH₃ | CH₂(CO)OCH₃ | CH₂CH₃ |
| A-2195 | CF₃ | CH₃ | CH₂(CO)OCH₃ | CH₂CH₂CH₃ |
| A-2196 | CF₃ | CH₃ | CH₂(CO)OCH₃ | CH₂CH₂OCH₃ |
| A-2197 | CF₃ | CH₃ | CH₂CHCH₂ | CH₃ |
| A-2198 | CF₃ | CH₃ | CH₂CHCH₂ | CH₂CH₃ |
| A-2199 | CF₃ | CH₃ | CH₂CHCH₂ | CH₂CH₂CH₃ |
| A-2200 | CF₃ | CH₃ | CH₂CHCH₂ | CH₂CH₂OCH₃ |
| A-2201 | CF₃ | CH₃ | CH₂CCH | CH₃ |
| A-2202 | CF₃ | CH₃ | CH₂CCH | CH₂CH₃ |
| A-2203 | CF₃ | CH₃ | CH₂CCH | CH₂CH₂CH₃ |
| A-2204 | CF₃ | CH₃ | CH₂CCH | CH₂CH₂OCH₃ |
| A-2205 | CF₃ | CH₃ | CH₂C₆H₅ | CH₃ |
| A-2206 | CF₃ | CH₃ | CH₂C₆H₅ | CH₂CH₃ |
| A-2207 | CF₃ | CH₃ | CH₂C₆H₅ | CH₂CH₂CH₃ |
| A-2208 | CF₃ | CH₃ | CH₂C₆H₅ | CH₂CH₂OCH₃ |
| A-2209 | CF₃ | CF₃ | CH₃ | CH₃ |
| A-2210 | CF₃ | CF₃ | CH₃ | CH₂CH₃ |
| A-2211 | CF₃ | CF₃ | CH₃ | CH₂CH₂CH₃ |
| A-2212 | CF₃ | CF₃ | CH₃ | CH₂CH₂OCH₃ |
| A-2213 | CF₃ | CF₃ | CH₂CH₃ | CH₃ |

TABLE A-continued

| | R¹ | R³ | R⁶ | R⁷ |
|---|---|---|---|---|
| A-2214 | CF₃ | CF₃ | CH₂CH₃ | CH₂CH₃ |
| A-2215 | CF₃ | CF₃ | CH₂CH₃ | CH₂CH₂CH₃ |
| A-2216 | CF₃ | CF₃ | CH₂CH₃ | CH₂CH₂OCH₃ |
| A-2217 | CF₃ | CF₃ | CH₂OCH₃ | CH₃ |
| A-2218 | CF₃ | CF₃ | CH₂OCH₃ | CH₂CH₃ |
| A-2219 | CF₃ | CF₃ | CH₂OCH₃ | CH₂CH₂CH₃ |
| A-2220 | CF₃ | CF₃ | CH₂OCH₃ | CH₂CH₂OCH₃ |
| A-2221 | CF₃ | CF₃ | CH₂OCH₂CH₃ | CH₃ |
| A-2222 | CF₃ | CF₃ | CH₂OCH₂CH₃ | CH₂CH₃ |
| A-2223 | CF₃ | CF₃ | CH₂OCH₂CH₃ | CH₂CH₂CH₃ |
| A-2224 | CF₃ | CF₃ | CH₂OCH₂CH₃ | CH₂CH₂OCH₃ |
| A-2225 | CF₃ | CF₃ | CH₂(CO)OCH₃ | CH₃ |
| A-2226 | CF₃ | CF₃ | CH₂(CO)OCH₃ | CH₂CH₃ |
| A-2227 | CF₃ | CF₃ | CH₂(CO)OCH₃ | CH₂CH₂CH₃ |
| A-2228 | CF₃ | CF₃ | CH₂(CO)OCH₃ | CH₂CH₂OCH₃ |
| A-2229 | CF₃ | CF₃ | CH₂CHCH₂ | CH₃ |
| A-2230 | CF₃ | CF₃ | CH₂CHCH₂ | CH₂CH₃ |
| A-2231 | CF₃ | CF₃ | CH₂CHCH₂ | CH₂CH₂CH₃ |
| A-2232 | CF₃ | CF₃ | CH₂CHCH₂ | CH₂CH₂OCH₃ |
| A-2233 | CF₃ | CF₃ | CH₂CCH | CH₃ |
| A-2234 | CF₃ | CF₃ | CH₂CCH | CH₂CH₃ |
| A-2235 | CF₃ | CF₃ | CH₂CCH | CH₂CH₂CH₃ |
| A-2236 | CF₃ | CF₃ | CH₂CCH | CH₂CH₂OCH₃ |
| A-2237 | CF₃ | CF₃ | CH₂C₆H₅ | CH₃ |
| A-2238 | CF₃ | CF₃ | CH₂C₆H₅ | CH₂CH₃ |
| A-2239 | CF₃ | CF₃ | CH₂C₆H₅ | CH₂CH₂CH₃ |
| A-2240 | CF₃ | CF₃ | CH₂C₆H₅ | CH₂CH₂OCH₃ |
| A-2241 | CF₃ | SO₂CH₃ | CH₃ | CH₃ |
| A-2242 | CF₃ | SO₂CH₃ | CH₃ | CH₂CH₃ |
| A-2243 | CF₃ | SO₂CH₃ | CH₃ | CH₂CH₂CH₃ |
| A-2244 | CF₃ | SO₂CH₃ | CH₃ | CH₂CH₂OCH₃ |
| A-2245 | CF₃ | SO₂CH₃ | CH₂CH₃ | CH₃ |
| A-2246 | CF₃ | SO₂CH₃ | CH₂CH₃ | CH₂CH₃ |
| A-2247 | CF₃ | SO₂CH₃ | CH₂CH₃ | CH₂CH₂CH₃ |
| A-2248 | CF₃ | SO₂CH₃ | CH₂CH₃ | CH₂CH₂OCH₃ |
| A-2249 | CF₃ | SO₂CH₃ | CH₂OCH₃ | CH₃ |
| A-2250 | CF₃ | SO₂CH₃ | CH₂OCH₃ | CH₂CH₃ |
| A-2251 | CF₃ | SO₂CH₃ | CH₂OCH₃ | CH₂CH₂CH₃ |
| A-2252 | CF₃ | SO₂CH₃ | CH₂OCH₃ | CH₂CH₂OCH₃ |
| A-2253 | CF₃ | SO₂CH₃ | CH₂OCH₂CH₃ | CH₃ |
| A-2254 | CF₃ | SO₂CH₃ | CH₂OCH₂CH₃ | CH₂CH₃ |
| A-2255 | CF₃ | SO₂CH₃ | CH₂OCH₂CH₃ | CH₂CH₂CH₃ |
| A-2256 | CF₃ | SO₂CH₃ | CH₂OCH₂CH₃ | CH₂CH₂OCH₃ |
| A-2257 | CF₃ | SO₂CH₃ | CH₂(CO)OCH₃ | CH₃ |
| A-2258 | CF₃ | SO₂CH₃ | CH₂(CO)OCH₃ | CH₂CH₃ |
| A-2259 | CF₃ | SO₂CH₃ | CH₂(CO)OCH₃ | CH₂CH₂CH₃ |
| A-2260 | CF₃ | SO₂CH₃ | CH₂(CO)OCH₃ | CH₂CH₂OCH₃ |
| A-2261 | CF₃ | SO₂CH₃ | CH₂CHCH₂ | CH₃ |
| A-2262 | CF₃ | SO₂CH₃ | CH₂CHCH₂ | CH₂CH₃ |
| A-2263 | CF₃ | SO₂CH₃ | CH₂CHCH₂ | CH₂CH₂CH₃ |
| A-2264 | CF₃ | SO₂CH₃ | CH₂CHCH₂ | CH₂CH₂OCH₃ |
| A-2265 | CF₃ | SO₂CH₃ | CH₂CCH | CH₃ |
| A-2266 | CF₃ | SO₂CH₃ | CH₂CCH | CH₂CH₃ |
| A-2267 | CF₃ | SO₂CH₃ | CH₂CCH | CH₂CH₂CH₃ |
| A-2268 | CF₃ | SO₂CH₃ | CH₂CCH | CH₂CH₂OCH₃ |
| A-2269 | CF₃ | SO₂CH₃ | CH₂C₆H₅ | CH₃ |
| A-2270 | CF₃ | SO₂CH₃ | CH₂C₆H₅ | CH₂CH₃ |
| A-2271 | CF₃ | SO₂CH₃ | CH₂C₆H₅ | CH₂CH₂CH₃ |
| A-2272 | CF₃ | SO₂CH₃ | CH₂C₆H₅ | CH₂CH₂OCH₃ |
| A-2273 | CF₃ | NO₂ | CH₃ | CH₃ |
| A-2274 | CF₃ | NO₂ | CH₃ | CH₂CH₃ |
| A-2275 | CF₃ | NO₂ | CH₃ | CH₂CH₂CH₃ |
| A-2276 | CF₃ | NO₂ | CH₃ | CH₂CH₂OCH₃ |
| A-2277 | CF₃ | NO₂ | CH₂CH₃ | CH₃ |
| A-2278 | CF₃ | NO₂ | CH₂CH₃ | CH₂CH₃ |
| A-2279 | CF₃ | NO₂ | CH₂CH₃ | CH₂CH₂CH₃ |
| A-2280 | CF₃ | NO₂ | CH₂CH₃ | CH₂CH₂OCH₃ |
| A-2281 | CF₃ | NO₂ | CH₂OCH₃ | CH₃ |
| A-2282 | CF₃ | NO₂ | CH₂OCH₃ | CH₂CH₃ |
| A-2283 | CF₃ | NO₂ | CH₂OCH₃ | CH₂CH₂CH₃ |
| A-2284 | CF₃ | NO₂ | CH₂OCH₃ | CH₂CH₂OCH₃ |
| A-2285 | CF₃ | NO₂ | CH₂OCH₂CH₃ | CH₃ |
| A-2286 | CF₃ | NO₂ | CH₂OCH₂CH₃ | CH₂CH₃ |
| A-2287 | CF₃ | NO₂ | CH₂OCH₂CH₃ | CH₂CH₂CH₃ |
| A-2288 | CF₃ | NO₂ | CH₂OCH₂CH₃ | CH₂CH₂OCH₃ |
| A-2289 | CF₃ | NO₂ | CH₂(CO)OCH₃ | CH₃ |
| A-2290 | CF₃ | NO₂ | CH₂(CO)OCH₃ | CH₂CH₃ |
| A-2291 | CF₃ | NO₂ | CH₂(CO)OCH₃ | CH₂CH₂CH₃ |

TABLE A-continued

| | R¹ | R³ | R⁶ | R⁷ |
|---|---|---|---|---|
| A-2292 | $CF_3$ | $NO_2$ | $CH_2(CO)OCH_3$ | $CH_2CH_2OCH_3$ |
| A-2293 | $CF_3$ | $NO_2$ | $CH_2CHCH_2$ | $CH_3$ |
| A-2294 | $CF_3$ | $NO_2$ | $CH_2CHCH_2$ | $CH_2CH_3$ |
| A-2295 | $CF_3$ | $NO_2$ | $CH_2CHCH_2$ | $CH_2CH_2CH_3$ |
| A-2296 | $CF_3$ | $NO_2$ | $CH_2CHCH_2$ | $CH_2CH_2OCH_3$ |
| A-2297 | $CF_3$ | $NO_2$ | $CH_2CCH$ | $CH_3$ |
| A-2298 | $CF_3$ | $NO_2$ | $CH_2CCH$ | $CH_2CH_3$ |
| A-2299 | $CF_3$ | $NO_2$ | $CH_2CCH$ | $CH_2CH_2CH_3$ |
| A-2300 | $CF_3$ | $NO_2$ | $CH_2CCH$ | $CH_2CH_2OCH_3$ |
| A-2301 | $CF_3$ | $NO_2$ | $CH_2C_6H_5$ | $CH_3$ |
| A-2302 | $CF_3$ | $NO_2$ | $CH_2C_6H_5$ | $CH_2CH_3$ |
| A-2303 | $CF_3$ | $NO_2$ | $CH_2C_6H_5$ | $CH_2CH_2CH_3$ |
| A-2304 | $CF_3$ | $NO_2$ | $CH_2C_6H_5$ | $CH_2CH_2OCH_3$ |

Examples of preferred compounds I.B, where X is $CR^2$, are the individual compounds compiled in Tables 21 to 480 below. Moreover, the meanings mentioned below for the individual variables in the Tables are per se, independently of the combination in which they are mentioned, a particularly preferred embodiment of the substituents in question.

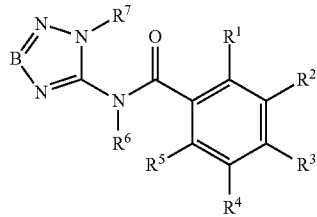

I.B

Table 21 Compounds of formula I.B1 (I.B1-1.1-I.B1-1.2304) in which B is CH, $R^2$ is $SCH_3$, $R^4$ is H and $R^5$ is F and the combination of $R^1$, $R^3$, $R^6$ and $R^7$ for a compound corresponds in each case to one row of Table A;

Table 22 Compounds of formula I.B1 (I.B1-2.1-I.B1-2.2304) in which B is CH, $R^2$ is $SCH_3$, $R^4$ is H and $R^5$ is Cl and the combination of $R^1$, $R^3$, $R^6$ and $R^7$ for a compound corresponds in each case to one row of Table A;

Table 23 Compounds of formula I.B1 (I.B1-3.1-I.B1-3.2304) in which B is CH, $R^2$ is $SCH_3$, $R^4$ is F and $R^5$ is F and the combination of $R^1$, $R^3$, $R^6$ and $R^7$ for a compound corresponds in each case to one row of Table A;

Table 24 Compounds of formula I.B1 (I.B1-4.1-I.B1-4.2304) in which B is CH, $R^2$ is $SCH_3$, $R^4$ is F and $R^5$ is Cl and the combination of $R^1$, $R^3$, $R^6$ and $R^7$ for a compound corresponds in each case to one row of Table A;

Table 25 Compounds of formula I.B1 (I.B1-5.1-I.B1-5.2304) in which B is CH, $R^2$ is $SCH_3$, $R^4$ is Cl and $R^5$ is F and the combination of $R^1$, $R^3$, $R^6$ and $R^7$ for a compound corresponds in each case to one row of Table A;

Table 26 Compounds of formula I.B1 (I.B1-6.1-I.B1-6.2304) in which B is CH, $R^2$ is $SCH_3$, $R^4$ is Cl and $R^5$ is Cl and the combination of $R^1$, $R^3$, $R^6$ and $R^7$ for a compound corresponds in each case to one row of Table A;

Table 27 Compounds of formula I.B1 (I.B1-7.1-I.B1-7.2304) in which B is CH, $R^2$ is $SCH_3$, $R^4$ is CN and $R^5$ is F and the combination of $R^1$, $R^3$, $R^6$ and $R^7$ for a compound corresponds in each case to one row of Table A;

Table 28 Compounds of formula I.B1 (I.B1-8.1-I.B1-8.2304) in which B is CH, $R^2$ is $SCH_3$, $R^4$ is CN and $R^5$ is Cl and the combination of $R^1$, $R^3$, $R^6$ and $R^7$ for a compound corresponds in each case to one row of Table A;

Table 29 Compounds of formula I.B1 (I.B1-9.1-I.B1-9.2304) in which B is CH, $R^2$ is $SCH_3$, $R^4$ is $CH_3$ and $R^5$ is F and the combination of $R^1$, $R^3$, $R^6$ and $R^7$ for a compound corresponds in each case to one row of Table A;

Table 30 Compounds of formula I.B1 (I.B1-10.1-I.B1-10.2304) in which B is CH, $R^2$ is $SCH_3$, $R^4$ is $CH_3$ and $R^5$ is Cl and the combination of $R^1$, $R^3$, $R^6$ and $R^7$ for a compound corresponds in each case to one row of Table A;

Table 31 Compounds of formula I.B2 (I.B2-1.1-I.B2-1.2304) in which B is CH, $R^2$ is $SCH_2CH_3$, $R^4$ is H and $R^5$ is F and the combination of $R^1$, $R^3$, $R^6$ and $R^7$ for a compound corresponds in each case to one row of Table A;

Table 32 Compounds of formula I.B2 (I.B2-2.1-I.B2-2.2304) in which B is CH, $R^2$ is $SCH_2CH_3$, $R^4$ is H and $R^5$ is Cl and the combination of $R^1$, $R^3$, $R^6$ and $R^7$ for a compound corresponds in each case to one row of Table A;

Table 33 Compounds of formula I.B2 (I.B2-3.1-I.B2-3.2304) in which B is CH, $R^2$ is $SCH_2CH_3$, $R^4$ is F and $R^5$ is F and the combination of $R^1$, $R^3$, $R^6$ and $R^7$ for a compound corresponds in each case to one row of Table A;

Table 34 Compounds of formula I.B2 (I.B2-4.1-I.B2-4.2304) in which B is CH, $R^2$ is $SCH_2CH_3$, $R^4$ is F and $R^5$ is Cl and the combination of $R^1$, $R^3$, $R^6$ and $R^7$ for a compound corresponds in each case to one row of Table A;

Table 35 Compounds of formula I.B2 (I.B2-5.1-I.B2-5.2304) in which B is CH, $R^2$ is $SCH_2CH_3$, $R^4$ is Cl and $R^5$ is F and the combination of $R^1$, $R^3$, $R^6$ and $R^7$ for a compound corresponds in each case to one row of Table A;

Table 36 Compounds of formula I.B2 (I.B2-6.1-I.B2-6.2304) in which B is CH, $R^2$ is $SCH_2CH_3$, $R^4$ is Cl and $R^5$ is Cl and the combination of $R^1$, $R^3$, $R^6$ and $R^7$ for a compound corresponds in each case to one row of Table A;

Table 37 Compounds of formula I.B2 (I.B2-7.1-I.B2-7.2304) in which B is CH, $R^2$ is $SCH_2CH_3$, $R^4$ is CN and $R^5$ is F and the combination of $R^1$, $R^3$, $R^6$ and $R^7$ for a compound corresponds in each case to one row of Table A;

Table 38 Compounds of formula I.B2 (I.B2-8.1-I.B2-8.2304) in which B is CH, $R^2$ is $SCH_2CH_3$, $R^4$ is CN and $R^5$ is Cl and the combination of $R^1$, $R^3$, $R^6$ and $R^7$ for a compound corresponds in each case to one row of Table A;

Table 39 Compounds of formula I.B2 (I.B2-9.1-I.B2-9.2304) in which B is CH, $R^2$ is $SCH_2CH_3$, $R^4$ is $CH_3$ and $R^5$ is F and the combination of $R^1$, $R^3$, $R^6$ and $R^7$ for a compound corresponds in each case to one row of Table A;

Table 40 Compounds of formula I.B2 (I.B2-10.1-I.B2-10.2304) in which B is CH, $R^2$ is $SCH_2CH_3$, $R^4$ is $CH_3$ and $R^5$ is Cl and the combination of $R^1$, $R^3$, $R^6$ and $R^7$ for a compound corresponds in each case to one row of Table A;

Table 41 Compounds of formula I.B3 (I.B3-1.1-I.B3-1.2304) in which B is CH, $R^2$ is $SO_2CH_2CH_3$, $R^4$ is H and $R^5$ is F and the combination of $R^1$, $R^3$, $R^6$ and $R^7$ for a compound corresponds in each case to one row of Table A;

Table 42 Compounds of formula I.B3 (I.B3-2.1-I.B3-2.2304) in which B is CH, $R^2$ is $SO_2CH_2CH_3$, $R^4$ is H and $R^5$ is Cl and the combination of $R^1$, $R^3$, $R^6$ and $R^7$ for a compound corresponds in each case to one row of Table A;

Table 43 Compounds of formula I.B3 (I.B3-3.1-I.B3-3.2304) in which B is CH, $R^2$ is $SO_2CH_2CH_3$, $R^4$ is F and $R^5$ is F and the combination of $R^1$, $R^3$, $R^6$ and $R^7$ for a compound corresponds in each case to one row of Table A;

Table 44 Compounds of formula I.B3 (I.B3-4.1-I.B3-4.2304) in which B is CH, $R^2$ is $SO_2CH_2CH_3$, $R^4$ is F and $R^5$ is Cl and the combination of $R^1$, $R^3$, $R^6$ and $R^7$ for a compound corresponds in each case to one row of Table A;

Table 45 Compounds of formula I.B3 (I.B3-5.1-I.B3-5.2304) in which B is CH, $R^2$ is $SO_2CH_2CH_3$, $R^4$ is Cl and $R^5$ is F and the combination of $R^1$, $R^3$, $R^6$ and $R^7$ for a compound corresponds in each case to one row of Table A;

Table 46 Compounds of formula I.B3 (I.B3-6.1-I.B3-6.2304) in which B is CH, $R^2$ is $SO_2CH_2CH_3$, $R^4$ is Cl and $R^5$ is Cl and the combination of $R^1$, $R^3$, $R^6$ and $R^7$ for a compound corresponds in each case to one row of Table A;

Table 47 Compounds of formula I.B3 (I.B3-7.1-I.B3-7.2304) in which B is CH, $R^2$ is $SO_2CH_2CH_3$, $R^4$ is CN and $R^5$ is F and the combination of $R^1$, $R^3$, $R^6$ and $R^7$ for a compound corresponds in each case to one row of Table A;

Table 48 Compounds of formula I.B3 (I.B3-8.1-I.B3-8.2304) in which B is CH, $R^2$ is $SO_2CH_2CH_3$, $R^4$ is CN and $R^5$ is Cl and the combination of $R^1$, $R^3$, $R^6$ and $R^7$ for a compound corresponds in each case to one row of Table A;

Table 49 Compounds of formula I.B3 (I.B3-9.1-I.B3-9.2304) in which B is CH, $R^2$ is $SO_2CH_2CH_3$, $R^4$ is $CH_3$ and $R^5$ is F and the combination of $R^1$, $R^3$, $R^6$ and $R^7$ for a compound corresponds in each case to one row of Table A;

Table 50 Compounds of formula I.B3 (I.B3-10.1-I.B3-10.2304) in which B is CH, $R^2$ is $SO_2CH_2CH_3$, $R^4$ is $CH_3$ and $R^5$ is Cl and the combination of $R^1$, $R^3$, $R^6$ and $R^7$ for a compound corresponds in each case to one row of Table A;

Table 51 Compounds of formula I.B4 (I.B4-1.1-I.B4-1.2304) in which B is CH, $R^2$ is $SOCH_3$, $R^4$ is H and $R^5$ is F and the combination of $R^1$, $R^3$, $R^6$ and $R^7$ for a compound corresponds in each case to one row of Table A;

Table 52 Compounds of formula I.B4 (I.B4-2.1-I.B4-2.2304) in which B is CH, $R^2$ is $SOCH_3$, $R^4$ is H and $R^5$ is Cl and the combination of $R^1$, $R^3$, $R^6$ and $R^7$ for a compound corresponds in each case to one row of Table A;

Table 53 Compounds of formula I.B4 (I.B4-3.1-I.B4-3.2304) in which B is CH, $R^2$ is $SOCH_3$, $R^4$ is F and $R^5$ is F and the combination of $R^1$, $R^3$, $R^6$ and $R^7$ for a compound corresponds in each case to one row of Table A;

Table 54 Compounds of formula I.B4 (I.B4-4.1-I.B4-4.2304) in which B is CH, $R^2$ is $SOCH_3$, $R^4$ is F and $R^5$ is Cl and the combination of $R^1$, $R^3$, $R^6$ and $R^7$ for a compound corresponds in each case to one row of Table A;

Table 55 Compounds of formula I.B4 (I.B4-5.1-I.B4-5.2304) in which B is CH, $R^2$ is $SOCH_3$, $R^4$ is Cl and $R^5$ is F and the combination of $R^1$, $R^3$, $R^6$ and $R^7$ for a compound corresponds in each case to one row of Table A;

Table 56 Compounds of formula I.B4 (I.B4-6.1-I.B4-6.2304) in which B is CH, $R^2$ is $SOCH_3$, $R^4$ is Cl and $R^5$ is Cl and the combination of $R^1$, $R^3$, $R^6$ and $R^7$ for a compound corresponds in each case to one row of Table A;

Table 57 Compounds of formula I.B4 (I.B4-7.1-I.B4-7.2304) in which B is CH, $R^2$ is $SOCH_3$, $R^4$ is CN and $R^5$ is F and the combination of $R^1$, $R^3$, $R^6$ and $R^7$ for a compound corresponds in each case to one row of Table A;

Table 58 Compounds of formula I.B4 (I.B4-8.1-I.B4-8.2304) in which B is CH, $R^2$ is $SOCH_3$, $R^4$ is CN and $R^5$ is Cl and the combination of $R^1$, $R^3$, $R^6$ and $R^7$ for a compound corresponds in each case to one row of Table A;

Table 59 Compounds of formula I.B4 (I.B4-9.1-I.B4-9.2304) in which B is CH, $R^2$ is $SOCH_3$, $R^4$ is $CH_3$ and $R^5$ is F and the combination of $R^1$, $R^3$, $R^6$ and $R^7$ for a compound corresponds in each case to one row of Table A;

Table 60 Compounds of formula I.B4 (I.B4-10.1-I.B4-10.2304) in which B is CH, $R^2$ is $SOCH_3$, $R^4$ is $CH_3$ and $R^5$ is Cl and the combination of $R^1$, $R^3$, $R^6$ and $R^7$ for a compound corresponds in each case to one row of Table A;

Table 61 Compounds of formula I.B5 (I.B5-1.1-I.B5-1.2304) in which B is CH, $R^2$ is $SOCH_2CH_3$, $R^4$ is H and $R^5$ is F and the combination of $R^1$, $R^3$, $R^6$ and $R^7$ for a compound corresponds in each case to one row of Table A;

Table 62 Compounds of formula I.B5 (I.B5-2.1-I.B5-2.2304) in which B is CH, $R^2$ is $SOCH_2CH_3$, $R^4$ is H and $R^5$ is Cl and the combination of $R^1$, $R^3$, $R^6$ and $R^7$ for a compound corresponds in each case to one row of Table A;

Table 63 Compounds of formula I.B5 (I.B5-3.1-I.B5-3.2304) in which B is CH, $R^2$ is $SOCH_2CH_3$, $R^4$ is F and R⁵ is F and the combination of R¹, R³, R⁶ and R⁷ for a compound corresponds in each case to one row of Table A;

Table 64 Compounds of formula I.B5 (I.B5-4.1-I.B5-4.2304) in which B is CH, R² is SOCH₂CH₃, R⁴ is F and R⁵ is Cl and the combination of R¹, R³, R⁶ and R⁷ for a compound corresponds in each case to one row of Table A;

Table 65 Compounds of formula I.B5 (I.B5-5.1-I.B5-5.2304) in which B is CH, R² is SOCH₂CH₃, R⁴ is Cl and R⁵ is F and the combination of R¹, R³, R⁶ and R⁷ for a compound corresponds in each case to one row of Table A;

Table 66 Compounds of formula I.B5 (I.B5-6.1-I.B5-6.2304) in which B is CH, R² is SOCH₂CH₃, R⁴ is Cl and R⁵ is Cl and the combination of R¹, R³, R⁶ and R⁷ for a compound corresponds in each case to one row of Table A;

Table 67 Compounds of formula I.B5 (I.B5-7.1-I.B5-7.2304) in which B is CH, R² is SOCH₂CH₃, R⁴ is CN and R⁵ is F and the combination of R¹, R³, R⁶ and R⁷ for a compound corresponds in each case to one row of Table A;

Table 68 Compounds of formula I.B5 (I.B5-8.1-I.B5-8.2304) in which B is CH, R² is SOCH₂CH₃, R⁴ is CN and R⁵ is Cl and the combination of R¹, R³, R⁶ and R⁷ for a compound corresponds in each case to one row of Table A;

Table 69 Compounds of formula I.B5 (I.B5-9.1-I.B5-9.2304) in which B is CH, R² is SOCH₂CH₃, R⁴ is CH₃ and R⁵ is F and the combination of R¹, R³, R⁶ and R⁷ for a compound corresponds in each case to one row of Table A;

Table 70 Compounds of formula I.B5 (I.B5-10.1-I.B5-10.2304) in which B is CH, R² is SOCH₂CH₃, R⁴ is CH₃ and R⁵ is Cl and the combination of R¹, R³, R⁶ and R⁷ for a compound corresponds in each case to one row of Table A;

Table 71 Compounds of formula I.B6 (I.B6-1.1-I.B6-1.2304) in which B is CH, R² is OCH₃, R⁴ is H and R⁵ is F and the combination of R¹, R³, R⁶ and R⁷ for a compound corresponds in each case to one row of Table A;

Table 72 Compounds of formula I.B6 (I.B6-2.1-I.B6-2.2304) in which B is CH, R² is OCH₃, R⁴ is H and R⁵ is Cl and the combination of R¹, R³, R⁶ and R⁷ for a compound corresponds in each case to one row of Table A;

Table 73 Compounds of formula I.B6 (I.B6-3.1-I.B6-3.2304) in which B is CH, R² is OCH₃, R⁴ is F and R⁵ is F and the combination of R¹, R³, R⁶ and R⁷ for a compound corresponds in each case to one row of Table A;

Table 74 Compounds of formula I.B6 (I.B6-4.1-I.B6-4.2304) in which B is CH, R² is OCH₃, R⁴ is F and R⁵ is Cl and the combination of R¹, R³, R⁶ and R⁷ for a compound corresponds in each case to one row of Table A;

Table 75 Compounds of formula I.B6 (I.B6-5.1-I.B6-5.2304) in which B is CH, R² is OCH₃, R⁴ is Cl and R⁵ is F and the combination of R¹, R³, R⁶ and R⁷ for a compound corresponds in each case to one row of Table A;

Table 76 Compounds of formula I.B6 (I.B6-6.1-I.B6-6.2304) in which B is CH, R² is OCH₃, R⁴ is Cl and R⁵ is Cl and the combination of R¹, R³, R⁶ and R⁷ for a compound corresponds in each case to one row of Table A;

Table 77 Compounds of formula I.B6 (I.B6-7.1-I.B6-7.2304) in which B is CH, R² is OCH₃, R⁴ is CN and R⁵ is F and the combination of R¹, R³, R⁶ and R⁷ for a compound corresponds in each case to one row of Table A;

Table 78 Compounds of formula I.B6 (I.B6-8.1-I.B6-8.2304) in which B is CH, R² is OCH₃, R⁴ is CN and R⁵ is Cl and the combination of R¹, R³, R⁶ and R⁷ for a compound corresponds in each case to one row of Table A;

Table 79 Compounds of formula I.B6 (I.B6-9.1-I.B6-9.2304) in which B is CH, R² is OCH₃, R⁴ is CH₃ and R⁵ is F and the combination of R¹, R³, R⁶ and R⁷ for a compound corresponds in each case to one row of Table A;

Table 80 Compounds of formula I.B6 (I.B6-10.1-I.B6-10.2304) in which B is CH, R² is OCH₃, R⁴ is CH₃ and R⁵ is Cl and the combination of R¹, R³, R⁶ and R⁷ for a compound corresponds in each case to one row of Table A;

Table 81 Compounds of formula I.B7 (I.B7-1.1-I.B7-1.2304) in which B is CH, R² is OCH₂CH₃, R⁴ is H and R⁵ is F and the combination of R¹, R³, R⁶ and R⁷ for a compound corresponds in each case to one row of Table A;

Table 82 Compounds of formula I.B7 (I.B7-2.1-I.B7-2.2304) in which B is CH, R² is OCH₂CH₃, R⁴ is H and R⁵ is Cl and the combination of R¹, R³, R⁶ and R⁷ for a compound corresponds in each case to one row of Table A;

Table 83 Compounds of formula I.B7 (I.B7-3.1-I.B7-3.2304) in which B is CH, R² is OCH₂CH₃, R⁴ is F and R⁵ is F and the combination of R¹, R³, R⁶ and R⁷ for a compound corresponds in each case to one row of Table A;

Table 84 Compounds of formula I.B7 (I.B7-4.1-I.B7-4.2304) in which B is CH, R² is OCH₂CH₃, R⁴ is F and R⁵ is Cl and the combination of R¹, R³, R⁶ and R⁷ for a compound corresponds in each case to one row of Table A;

Table 85 Compounds of formula I.B7 (I.B7-5.1-I.B7-5.2304) in which B is CH, R² is OCH₂CH₃, R⁴ is Cl and R⁵ is F and the combination of R¹, R³, R⁶ and R⁷ for a compound corresponds in each case to one row of Table A;

Table 86 Compounds of formula I.B7 (I.B7-6.1-I.B7-6.2304) in which B is CH, R² is OCH₂CH₃, R⁴ is Cl and R⁵ is Cl and the combination of R¹, R³, R⁶ and R⁷ for a compound corresponds in each case to one row of Table A;

Table 87 Compounds of formula I.B7 (I.B7-7.1-I.B7-7.2304) in which B is CH, R² is OCH₂CH₃, R⁴ is CN and R⁵ is F and the combination of R¹, R³, R⁶ and R⁷ for a compound corresponds in each case to one row of Table A;

Table 88 Compounds of formula I.B7 (I.B7-8.1-I.B7-8.2304) in which B is CH, R² is OCH₂CH₃, R⁴ is CN and R⁵ is Cl and the combination of R¹, R³, R⁶ and R⁷ for a compound corresponds in each case to one row of Table A;

Table 89 Compounds of formula I.B7 (I.B7-9.1-I.B7-9.2304) in which B is CH, R² is OCH₂CH₃, R⁴ is CH₃ and $R^5$ is F and the combination of $R^1$, $R^3$, $R^6$ and $R^7$ for a compound corresponds in each case to one row of Table A;

Table 90 Compounds of formula I.B7 (I.B7-10.1-I.B7-10.2304) in which B is CH, $R^2$ is $OCH_2CH_3$, $R^4$ is $CH_3$ and $R^5$ is Cl and the combination of $R^1$, $R^3$, $R^6$ and $R^7$ for a compound corresponds in each case to one row of Table A;

Table 91 Compounds of formula I.B8 (I.B8-1.1-I.B8-1.2304) in which B is CH, $R^2$ is $OCHF_2$, $R^4$ is H and $R^5$ is F and the combination of $R^1$, $R^3$, $R^6$ and $R^7$ for a compound corresponds in each case to one row of Table A;

Table 92 Compounds of formula I.B8 (I.B8-2.1-I.B8-2.2304) in which B is CH, $R^2$ is $OCHF_2$, $R^4$ is H and $R^5$ is Cl and the combination of $R^1$, $R^3$, $R^6$ and $R^7$ for a compound corresponds in each case to one row of Table A;

Table 93 Compounds of formula I.B8 (I.B8-3.1-I.B8-3.2304) in which B is CH, $R^2$ is $OCHF_2$, $R^4$ is F and $R^5$ is F and the combination of $R^1$, $R^3$, $R^6$ and $R^7$ for a compound corresponds in each case to one row of Table A;

Table 94 Compounds of formula I.B8 (I.B8-4.1-I.B8-4.2304) in which B is CH, $R^2$ is $OCHF_2$, $R^4$ is F and $R^5$ is Cl and the combination of $R^1$, $R^3$, $R^6$ and $R^7$ for a compound corresponds in each case to one row of Table A;

Table 95 Compounds of formula I.B8 (I.B8-5.1-I.B8-5.2304) in which B is CH, $R^2$ is $OCHF_2$, $R^4$ is Cl and $R^5$ is F and the combination of $R^1$, $R^3$, $R^6$ and $R^7$ for a compound corresponds in each case to one row of Table A;

Table 96 Compounds of formula I.B8 (I.B8-6.1-I.B8-6.2304) in which B is CH, $R^2$ is $OCHF_2$, $R^4$ is Cl and $R^5$ is Cl and the combination of $R^1$, $R^3$, $R^6$ and $R^7$ for a compound corresponds in each case to one row of Table A;

Table 97 Compounds of formula I.B8 (I.B8-7.1-I.B8-7.2304) in which B is CH, $R^2$ is $OCHF_2$, $R^4$ is CN and $R^5$ is F and the combination of $R^1$, $R^3$, $R^6$ and $R^7$ for a compound corresponds in each case to one row of Table A;

Table 98 Compounds of formula I.B8 (I.B8-8.1-I.B8-8.2304) in which B is CH, $R^2$ is $OCHF_2$, $R^4$ is CN and $R^5$ is Cl and the combination of $R^1$, $R^3$, $R^6$ and $R^7$ for a compound corresponds in each case to one row of Table A;

Table 99 Compounds of formula I.B8 (I.B8-9.1-I.B8-9.2304) in which B is CH, $R^2$ is $OCHF_2$, $R^4$ is $CH_3$ and $R^5$ is F and the combination of $R^1$, $R^3$, $R^6$ and $R^7$ for a compound corresponds in each case to one row of Table A;

Table 100 Compounds of formula I.B8 (I.B8-10.1-I.B8-10.2304) in which B is CH, $R^2$ is $OCHF_2$, $R^4$ is $CH_3$ and $R^5$ is Cl and the combination of $R^1$, $R^3$, $R^6$ and $R^7$ for a compound corresponds in each case to one row of Table A;

Table 101 Compounds of formula I.B9 (I.B9-1.1-I.B9-1.2304) in which B is CH, $R^2$ is $OCH_2CF_3$, $R^4$ is H and $R^5$ is F and the combination of $R^1$, $R^3$, $R^6$ and $R^7$ for a compound corresponds in each case to one row of Table A;

Table 102 Compounds of formula I.B9 (I.B9-2.1-I.B9-2.2304) in which B is CH, $R^2$ is $OCH_2CF_3$, $R^4$ is H and $R^5$ is Cl and the combination of $R^1$, $R^3$, $R^6$ and $R^7$ for a compound corresponds in each case to one row of Table A;

Table 103 Compounds of formula I.B9 (I.B9-3.1-I.B9-3.2304) in which B is CH, $R^2$ is $OCH_2CF_3$, $R^4$ is F and $R^5$ is F and the combination of $R^1$, $R^3$, $R^6$ and $R^7$ for a compound corresponds in each case to one row of Table A;

Table 104 Compounds of formula I.B9 (I.B9-4.1-I.B9-4.2304) in which B is CH, $R^2$ is $OCH_2CF_3$, $R^4$ is F and $R^5$ is Cl and the combination of $R^1$, $R^3$, $R^6$ and $R^7$ for a compound corresponds in each case to one row of Table A;

Table 105 Compounds of formula I.B9 (I.B9-5.1-I.B9-5.2304) in which B is CH, $R^2$ is $OCH_2CF_3$, $R^4$ is Cl and $R^5$ is F and the combination of $R^1$, $R^3$, $R^6$ and $R^7$ for a compound corresponds in each case to one row of Table A;

Table 106 Compounds of formula I.B9 (I.B9-6.1-I.B9-6.2304) in which B is CH, $R^2$ is $OCH_2CF_3$, $R^4$ is Cl and $R^5$ is Cl and the combination of $R^1$, $R^3$, $R^6$ and $R^7$ for a compound corresponds in each case to one row of Table A;

Table 107 Compounds of formula I.B9 (I.B9-7.1-I.B9-7.2304) in which B is CH, $R^2$ is $OCH_2CF_3$, $R^4$ is CN and $R^5$ is F and the combination of $R^1$, $R^3$, $R^6$ and $R^7$ for a compound corresponds in each case to one row of Table A;

Table 108 Compounds of formula I.B9 (I.B9-8.1-I.B9-8.2304) in which B is CH, $R^2$ is $OCH_2CF_3$, $R^4$ is CN and $R^5$ is Cl and the combination of $R^1$, $R^3$, $R^6$ and $R^7$ for a compound corresponds in each case to one row of Table A;

Table 109 Compounds of formula I.B9 (I.B9-9.1-I.B9-9.2304) in which B is CH, $R^2$ is $OCH_2CF_3$, $R^4$ is $CH_3$ and $R^5$ is F and the combination of $R^1$, $R^3$, $R^6$ and $R^7$ for a compound corresponds in each case to one row of Table A;

Table 110 Compounds of formula I.B9 (I.B9-10.1-I.B9-10.2304) in which B is CH, $R^2$ is $OCH_2CF_3$, $R^4$ is $CH_3$ and $R^5$ is Cl and the combination of $R^1$, $R^3$, $R^6$ and $R^7$ for a compound corresponds in each case to one row of Table A;

Table 111 Compounds of formula I.B10 (I.B10-1.1-I.B10-1.2304) in which B is CH, $R^2$ is $OCH_2CH_2OCH_3$, $R^4$ is H and $R^5$ is F and the combination of $R^1$, $R^3$, $R^6$ and $R^7$ for a compound corresponds in each case to one row of Table A;

Table 112 Compounds of formula I.B10 (I.B10-2.1-I.B10-2.2304) in which B is CH, $R^2$ is $OCH_2CH_2OCH_3$, $R^4$ is H and $R^5$ is Cl and the combination of $R^1$, $R^3$, $R^6$ and $R^7$ for a compound corresponds in each case to one row of Table A;

Table 113 Compounds of formula I.B10 (I.B10-3.1-I.B10-3.2304) in which B is CH, $R^2$ is $OCH_2CH_2OCH_3$, $R^4$ is F and $R^5$ is F and the combination of $R^1$, $R^3$, $R^6$ and $R^7$ for a compound corresponds in each case to one row of Table A;

Table 114 Compounds of formula I.B10 (I.B10-4.1-I.B10-4.2304) in which B is CH, $R^2$ is $OCH_2CH_2OCH_3$, $R^4$ is F and $R^5$ is Cl and the combination of $R^1$, $R^3$, $R^6$ and $R^7$ for a compound corresponds in each case to one row of Table A;

Table 115 Compounds of formula I.B10 (I.B10-5.1-I.B10-5.2304) in which B is CH, $R^2$ is $OCH_2CH_2OCH_3$, $R^4$ is Cl and R⁵ is F and the combination of R¹, R³, R⁶ and R⁷ for a compound corresponds in each case to one row of Table A;

Table 116 Compounds of formula I.B10 (I.B10-6.1-I.B10-6.2304) in which B is CH, R² is OCH₂CH₂OCH₃, R⁴ is Cl and R⁵ is Cl and the combination of R¹, R³, R⁶ and R⁷ for a compound corresponds in each case to one row of Table A;

Table 117 Compounds of formula I.B10 (I.B10-7.1-I.B10-7.2304) in which B is CH, R² is OCH₂CH₂OCH₃, R⁴ is CN and R⁵ is F and the combination of R¹, R³, R⁶ and R⁷ for a compound corresponds in each case to one row of Table A;

Table 118 Compounds of formula I.B10 (I.B10-8.1-I.B10-8.2304) in which B is CH, R² is OCH₂CH₂OCH₃, R⁴ is CN and R⁵ is Cl and the combination of R¹, R³, R⁶ and R⁷ for a compound corresponds in each case to one row of Table A;

Table 119 Compounds of formula I.B10 (I.B10-9.1-I.B10-9.2304) in which B is CH, R² is OCH₂CH₂OCH₃, R⁴ is CH₃ and R⁵ is F and the combination of R¹, R³, R⁶ and R⁷ for a compound corresponds in each case to one row of Table A;

Table 120 Compounds of formula I.B10 (I.B10-10.1-I.B10-10.2304) in which B is CH, R² is OCH₂CH₂OCH₃, R⁴ is CH₃ and R⁵ is Cl and the combination of R¹, R³, R⁶ and R⁷ for a compound corresponds in each case to one row of Table A;

Table 121 Compounds of formula I.B11 (I.B11-1.1-I.B11-1.2304) in which B is CH, R² is H, R⁴ is H and R⁵ is F and the combination of R¹, R³, R⁶ and R⁷ for a compound corresponds in each case to one row of Table A;

Table 122 Compounds of formula I.B11 (I.B11-2.1-I.B11-2.2304) in which B is CH, R² is H, R⁴ is H and R⁵ is Cl and the combination of R¹, R³, R⁶ and R⁷ for a compound corresponds in each case to one row of Table A;

Table 123 Compounds of formula I.B11 (I.B11-3.1-I.B11-3.2304) in which B is CH, R² is H, R⁴ is F and R⁵ is F and the combination of R¹, R³, R⁶ and R⁷ for a compound corresponds in each case to one row of Table A;

Table 124 Compounds of formula I.B11 (I.B11-4.1-I.B11-4.2304) in which B is CH, R² is H, R⁴ is F and R⁵ is Cl and the combination of R¹, R³, R⁶ and R⁷ for a compound corresponds in each case to one row of Table A;

Table 125 Compounds of formula I.B11 (I.B11-5.1-I.B11-5.2304) in which B is CH, R² is H, R⁴ is Cl and R⁵ is F and the combination of R¹, R³, R⁶ and R⁷ for a compound corresponds in each case to one row of Table A;

Table 126 Compounds of formula I.B11 (I.B11-6.1-I.B11-6.2304) in which B is CH, R² is H, R⁴ is Cl and R⁵ is Cl and the combination of R¹, R³, R⁶ and R⁷ for a compound corresponds in each case to one row of Table A;

Table 127 Compounds of formula I.B11 (I.B11-7.1-I.B11-7.2304) in which B is CH, R² is H, R⁴ is CN and R⁵ is F and the combination of R¹, R³, R⁶ and R⁷ for a compound corresponds in each case to one row of Table A;

Table 128 Compounds of formula I.B11 (I.B11-8.1-I.B11-8.2304) in which B is CH, R² is H, R⁴ is CN and R⁵ is Cl and the combination of R¹, R³, R⁶ and R⁷ for a compound corresponds in each case to one row of Table A;

Table 129 Compounds of formula I.B11 (I.B11-9.1-I.B11-9.2304) in which B is CH, R² is H, R⁴ is CH₃ and R⁵ is F and the combination of R¹, R³, R⁶ and R⁷ for a compound corresponds in each case to one row of Table A;

Table 130 Compounds of formula I.B11 (I.B11-10.1-I.B11-10.2304) in which B is CH, R² is H, R⁴ is CH₃ and R⁵ is Cl and the combination of R¹, R³, R⁶ and R⁷ for a compound corresponds in each case to one row of Table A;

Table 131 Compounds of formula I.B12 (I.B12-1.1-I.B12-1.2304) in which B is CH, R² is SO₂CH₃, R⁴ is H and R⁵ is F and the combination of R¹, R³, R⁶ and R⁷ for a compound corresponds in each case to one row of Table A;

Table 132 Compounds of formula I.B12 (I.B12-2.1-I.B12-2.2304) in which B is CH, R² is SO₂CH₃, R⁴ is H and R⁵ is Cl and the combination of R¹, R³, R⁶ and R⁷ for a compound corresponds in each case to one row of Table A;

Table 133 Compounds of formula I.B12 (I.B12-3.1-I.B12-3.2304) in which B is CH, R² is SO₂CH₃, R⁴ is F and R⁵ is F and the combination of R¹, R³, R⁶ and R⁷ for a compound corresponds in each case to one row of Table A;

Table 134 Compounds of formula I.B12 (I.B12-4.1-I.B12-4.2304) in which B is CH, R² is SO₂CH₃, R⁴ is F and R⁵ is Cl and the combination of R¹, R³, R⁶ and R⁷ for a compound corresponds in each case to one row of Table A;

Table 135 Compounds of formula I.B12 (I.B12-5.1-I.B12-5.2304) in which B is CH, R² is SO₂CH₃, R⁴ is Cl and R⁵ is F and the combination of R¹, R³, R⁶ and R⁷ for a compound corresponds in each case to one row of Table A;

Table 136 Compounds of formula I.B12 (I.B12-6.1-I.B12-6.2304) in which B is CH, R² is SO₂CH₃, R⁴ is Cl and R⁵ is Cl and the combination of R¹, R³, R⁶ and R⁷ for a compound corresponds in each case to one row of Table A;

Table 137 Compounds of formula I.B12 (I.B12-7.1-I.B12-7.2304) in which B is CH, R² is SO₂CH₃, R⁴ is CN and R⁵ is F and the combination of R¹, R³, R⁶ and R⁷ for a compound corresponds in each case to one row of Table A;

Table 138 Compounds of formula I.B12 (I.B12-8.1-I.B12-8.2304) in which B is CH, R² is SO₂CH₃, R⁴ is CN and R⁵ is Cl and the combination of R¹, R³, R⁶ and R⁷ for a compound corresponds in each case to one row of Table A;

Table 139 Compounds of formula I.B12 (I.B12-9.1-I.B12-9.2304) in which B is CH, R² is SO₂CH₃, R⁴ is CH₃ and R⁵ is F and the combination of R¹, R³, R⁶ and R⁷ for a compound corresponds in each case to one row of Table A;

Table 140 Compounds of formula I.B12 (I.B12-10.1-I.B12-10.2304) in which B is CH, R² is SO₂CH₃, R⁴ is CH₃ and R⁵ is Cl and the combination of R¹, R³, R⁶ and R⁷ for a compound corresponds in each case to one row of Table A;

Table 141 Compounds of formula I.B13 (I.B13-1.1-I.B13-1.2304) in which B is CH, R² is CH₂OCH₂CF₃, R⁴ is H and R⁵ is F and the combination of R¹, R³, R⁶ and R⁷ for a compound corresponds in each case to one row of Table A;

Table 142 Compounds of formula I.B13 (I.B13-2.1-I.B13-2.2304) in which B is CH, R² is CH₂OCH₂CF₃, R⁴ is H and R⁵ is Cl and the combination of R¹, R³, R⁶ and R⁷ for a compound corresponds in each case to one row of Table A;

Table 143 Compounds of formula I.B13 (I.B13-3.1-I.B13-3.2304) in which B is CH, R² is CH₂OCH₂CF₃, R⁴ is F and $R^5$ is F and the combination of $R^1$, $R^3$, $R^6$ and $R^7$ for a compound corresponds in each case to one row of Table A;

Table 144 Compounds of formula I.B13 (I.B13-4.1-I.B13-4.2304) in which B is CH, $R^2$ is $CH_2OCH_2CF_3$, $R^4$ is F and $R^5$ is Cl and the combination of $R^1$, $R^3$, $R^6$ and $R^7$ for a compound corresponds in each case to one row of Table A;

Table 145 Compounds of formula I.B13 (I.B13-5.1-I.B13-5.2304) in which B is CH, $R^2$ is $CH_2OCH_2CF_3$, $R^4$ is Cl and $R^5$ is F and the combination of $R^1$, $R^3$, $R^6$ and $R^7$ for a compound corresponds in each case to one row of Table A;

Table 146 Compounds of formula I.B13 (I.B13-6.1-I.B13-6.2304) in which B is CH, $R^2$ is $CH_2OCH_2CF_3$, $R^4$ is Cl and $R^5$ is Cl and the combination of $R^1$, $R^3$, $R^6$ and $R^7$ for a compound corresponds in each case to one row of Table A;

Table 147 Compounds of formula I.B13 (I.B13-7.1-I.B13-7.2304) in which B is CH, $R^2$ is $CH_2OCH_2CF_3$, $R^4$ is CN and $R^5$ is F and the combination of $R^1$, $R^3$, $R^6$ and $R^7$ for a compound corresponds in each case to one row of Table A;

Table 148 Compounds of formula I.B13 (I.B13-8.1-I.B13-8.2304) in which B is CH, $R^2$ is $CH_2OCH_2CF_3$, $R^4$ is CN and $R^5$ is Cl and the combination of $R^1$, $R^3$, $R^6$ and $R^7$ for a compound corresponds in each case to one row of Table A;

Table 149 Compounds of formula I.B13 (I.B13-9.1-I.B13-9.2304) in which B is CH, $R^2$ is $CH_2OCH_2CF_3$, $R^4$ is $CH_3$ and $R^5$ is F and the combination of $R^1$, $R^3$, $R^6$ and $R^7$ for a compound corresponds in each case to one row of Table A;

Table 150 Compounds of formula I.B13 (I.B13-10.1-I.B13-10.2304) in which B is CH, $R^2$ is $CH_2OCH_2CF_3$, $R^4$ is $CH_3$ and $R^5$ is Cl and the combination of $R^1$, $R^3$, $R^6$ and $R^7$ for a compound corresponds in each case to one row of Table A;

Table 151 Compounds of formula I.B14 (I.B14-1.1-I.B14-1.2304) in which B is CH, $R^2$ is isoxazolin-3-yl, $R^4$ is H and $R^5$ is F and the combination of $R^1$, $R^3$, $R^6$ and $R^7$ for a compound corresponds in each case to one row of Table A;

Table 152 Compounds of formula I.B14 (I.B14-2.1-I.B14-2.2304) in which B is CH, $R^2$ is isoxazolin-3-yl, $R^4$ is H and $R^5$ is Cl and the combination of $R^1$, $R^3$, $R^6$ and $R^7$ for a compound corresponds in each case to one row of Table A;

Table 153 Compounds of formula I.B14 (I.B14-3.1-I.B14-3.2304) in which B is CH, $R^2$ is isoxazolin-3-yl, $R^4$ is F and $R^5$ is F and the combination of $R^1$, $R^3$, $R^6$ and $R^7$ for a compound corresponds in each case to one row of Table A;

Table 154 Compounds of formula I.B14 (I.B14-4.1-I.B14-4.2304) in which B is CH, $R^2$ is isoxazolin-3-yl, $R^4$ is F and $R^5$ is Cl and the combination of $R^1$, $R^3$, $R^6$ and $R^7$ for a compound corresponds in each case to one row of Table A;

Table 155 Compounds of formula I.B14 (I.B14-5.1-I.B14-5.2304) in which B is CH, $R^2$ is isoxazolin-3-yl, $R^4$ is Cl and $R^5$ is F and the combination of $R^1$, $R^3$, $R^6$ and $R^7$ for a compound corresponds in each case to one row of Table A;

Table 156 Compounds of formula I.B14 (I.B14-6.1-I.B14-6.2304) in which B is CH, $R^2$ is isoxazolin-3-yl, $R^4$ is Cl and $R^5$ is Cl and the combination of $R^1$, $R^3$, $R^6$ and $R^7$ for a compound corresponds in each case to one row of Table A;

Table 157 Compounds of formula I.B14 (I.B14-7.1-I.B14-7.2304) in which B is CH, $R^2$ is isoxazolin-3-yl, $R^4$ is CN and $R^5$ is F and the combination of $R^1$, $R^3$, $R^6$ and $R^7$ for a compound corresponds in each case to one row of Table A;

Table 158 Compounds of formula I.B14 (I.B14-8.1-I.B14-8.2304) in which B is CH, $R^2$ is isoxazolin-3-yl, $R^4$ is CN and $R^5$ is Cl and the combination of $R^1$, $R^3$, $R^6$ and $R^7$ for a compound corresponds in each case to one row of Table A;

Table 159 Compounds of formula I.B14 (I.B14-9.1-I.B14-9.2304) in which B is CH, $R^2$ is isoxazolin-3-yl, $R^4$ is $CH_3$ and $R^5$ is F and the combination of $R^1$, $R^3$, $R^6$ and $R^7$ for a compound corresponds in each case to one row of Table A;

Table 160 Compounds of formula I.B14 (I.B14-10.1-I.B14-10.2304) in which B is CH, $R^2$ is isoxazolin-3-yl, $R^4$ is $CH_3$ and $R^5$ is Cl and the combination of $R^1$, $R^3$, $R^6$ and $R^7$ for a compound corresponds in each case to one row of Table A;

Table 161 Compounds of formula I.B15 (I.B15-1.1-I.B15-1.2304) in which B is CH, $R^2$ is 5-methyl-isoxazolin-3-yl, $R^4$ is H and $R^5$ is F and the combination of $R^1$, $R^3$, $R^6$ and $R^7$ for a compound corresponds in each case to one row of Table A;

Table 162 Compounds of formula I.B15 (I.B15-2.1-I.B15-2.2304) in which B is CH, $R^2$ is 5-methyl-isoxazolin-3-yl, $R^4$ is H and $R^5$ is Cl and the combination of $R^1$, $R^3$, $R^6$ and $R^7$ for a compound corresponds in each case to one row of Table A;

Table 163 Compounds of formula I.B15 (I.B15-3.1-I.B15-3.2304) in which B is CH, $R^2$ is 5-methyl-isoxazolin-3-yl, $R^4$ is F and $R^5$ is F and the combination of $R^1$, $R^3$, $R^6$ and $R^7$ for a compound corresponds in each case to one row of Table A;

Table 164 Compounds of formula I.B15 (I.B15-4.1-I.B15-4.2304) in which B is CH, $R^2$ is 5-methyl-isoxazolin-3-yl, $R^4$ is F and $R^5$ is Cl and the combination of $R^1$, $R^3$, $R^6$ and $R^7$ for a compound corresponds in each case to one row of Table A;

Table 165 Compounds of formula I.B15 (I.B15-5.1-I.B15-5.2304) in which B is CH, $R^2$ is 5-methyl-isoxazolin-3-yl, $R^4$ is Cl and $R^5$ is F and the combination of $R^1$, $R^3$, $R^6$ and $R^7$ for a compound corresponds in each case to one row of Table A;

Table 166 Compounds of formula I.B15 (I.B15-6.1-I.B15-6.2304) in which B is CH, $R^2$ is 5-methyl-isoxazolin-3-yl, $R^4$ is Cl and $R^5$ is Cl and the combination of $R^1$, $R^3$, $R^6$ and $R^7$ for a compound corresponds in each case to one row of Table A;

Table 167 Compounds of formula I.B15 (I.B15-7.1-I.B15-7.2304) in which B is CH, $R^2$ is 5-methyl-isoxazolin-3-yl, $R^4$ is CN and $R^5$ is F and the combination of $R^1$, $R^3$, $R^6$ and $R^7$ for a compound corresponds in each case to one row of Table A;

Table 168 Compounds of formula I.B15 (I.B15-8.1-I.B15-8.2304) in which B is CH, $R^2$ is 5-methyl-isoxazolin-3-yl, $R^4$ is CN and $R^5$ is Cl and the combination of $R^1$, $R^3$, $R^6$ and $R^7$ for a compound corresponds in each case to one row of Table A;

Table 169 Compounds of formula I.B15 (I.B15-9.1-I.B15-9.2304) in which B is CH, $R^2$ is 5-methyl-isoxazolin-3-yl, R⁴ is CH₃ and R⁵ is F and the combination of R¹, R³, R⁶ and R⁷ for a compound corresponds in each case to one row of Table A;

Table 170 Compounds of formula I.B15 (I.B15-10.1-I.B15-10.2304) in which B is CH, R² is 5-methyl-isoxazolin-3-yl, R⁴ is CH₃ and R⁵ is Cl and the combination of R¹, R³, R⁶ and R⁷ for a compound corresponds in each case to one row of Table A;

Table 171 Compounds of formula I.B16 (I.B16-1.1-I.B16-1.2304) in which B is CH, R² is isoxazol-3-yl, R⁴ is H and R⁵ is F and the combination of R¹, R³, R⁶ and R⁷ for a compound corresponds in each case to one row of Table A;

Table 172 Compounds of formula I.B16 (I.B16-2.1-I.B16-2.2304) in which B is CH, R² is isoxazol-3-yl, R⁴ is H and R⁵ is Cl and the combination of R¹, R³, R⁶ and R⁷ for a compound corresponds in each case to one row of Table A;

Table 173 Compounds of formula I.B16 (I.B16-3.1-I.B16-3.2304) in which B is CH, R² is isoxazol-3-yl, R⁴ is F and R⁵ is F and the combination of R¹, R³, R⁶ and R⁷ for a compound corresponds in each case to one row of Table A;

Table 174 Compounds of formula I.B16 (I.B16-4.1-I.B16-4.2304) in which B is CH, R² is isoxazol-3-yl, R⁴ is F and R⁵ is Cl and the combination of R¹, R³, R⁶ and R⁷ for a compound corresponds in each case to one row of Table A;

Table 175 Compounds of formula I.B16 (I.B16-5.1-I.B16-5.2304) in which B is CH, R² is isoxazol-3-yl, R⁴ is Cl and R⁵ is F and the combination of R¹, R³, R⁶ and R⁷ for a compound corresponds in each case to one row of Table A;

Table 176 Compounds of formula I.B16 (I.B16-6.1-I.B16-6.2304) in which B is CH, R² is isoxazol-3-yl, R⁴ is Cl and R⁵ is Cl and the combination of R¹, R³, R⁶ and R⁷ for a compound corresponds in each case to one row of Table A;

Table 177 Compounds of formula I.B16 (I.B16-7.1-I.B16-7.2304) in which B is CH, R² is isoxazol-3-yl, R⁴ is CN and R⁵ is F and the combination of R¹, R³, R⁶ and R⁷ for a compound corresponds in each case to one row of Table A;

Table 178 Compounds of formula I.B16 (I.B16-8.1-I.B16-8.2304) in which B is CH, R² is isoxazol-3-yl, R⁴ is CN and R⁵ is Cl and the combination of R¹, R³, R⁶ and R⁷ for a compound corresponds in each case to one row of Table A;

Table 179 Compounds of formula I.B16 (I.B16-9.1-I.B16-9.2304) in which B is CH, R² is isoxazol-3-yl, R⁴ is CH₃ and R⁵ is F and the combination of R¹, R³, R⁶ and R⁷ for a compound corresponds in each case to one row of Table A;

Table 180 Compounds of formula I.B16 (I.B16-10.1-I.B16-10.2304) in which B is CH, R² is isoxazol-3-yl, R⁴ is CH₃ and R⁵ is Cl and the combination of R¹, R³, R⁶ and R⁷ for a compound corresponds in each case to one row of Table A;

Table 181 Compounds of formula I.B17 (I.B17-1.1-I.B17-1.2304) in which B is CH, R² is 5-methyl-isoxazol-3-yl, R⁴ is H and R⁵ is F and the combination of R¹, R³, R⁶ and R⁷ for a compound corresponds in each case to one row of Table A;

Table 182 Compounds of formula I.B17 (I.B17-2.1-I.B17-2.2304) in which B is CH, R² is 5-methyl-isoxazol-3-yl, R⁴ is H and R⁵ is Cl and the combination of R¹, R³, R⁶ and R⁷ for a compound corresponds in each case to one row of Table A;

Table 183 Compounds of formula I.B17 (I.B17-3.1-I.B17-3.2304) in which B is CH, R² is 5-methyl-isoxazol-3-yl, R⁴ is F and R⁵ is F and the combination of R¹, R³, R⁶ and R⁷ for a compound corresponds in each case to one row of Table A;

Table 184 Compounds of formula I.B17 (I.B17-4.1-I.B17-4.2304) in which B is CH, R² is 5-methyl-isoxazol-3-yl, R⁴ is F and R⁵ is Cl and the combination of R¹, R³, R⁶ and R⁷ for a compound corresponds in each case to one row of Table A;

Table 185 Compounds of formula I.B17 (I.B17-5.1-I.B17-5.2304) in which B is CH, R² is 5-methyl-isoxazol-3-yl, R⁴ is Cl and R⁵ is F and the combination of R¹, R³, R⁶ and R⁷ for a compound corresponds in each case to one row of Table A;

Table 186 Compounds of formula I.B17 (I.B17-6.1-I.B17-6.2304) in which B is CH, R² is 5-methyl-isoxazol-3-yl, R⁴ is Cl and R⁵ is Cl and the combination of R¹, R³, R⁶ and R⁷ for a compound corresponds in each case to one row of Table A;

Table 187 Compounds of formula I.B17 (I.B17-7.1-I.B17-7.2304) in which B is CH, R² is 5-methyl-isoxazol-3-yl, R⁴ is CN and R⁵ is F and the combination of R¹, R³, R⁶ and R⁷ for a compound corresponds in each case to one row of Table A;

Table 188 Compounds of formula I.B17 (I.B17-8.1-I.B17-8.2304) in which B is CH, R² is 5-methyl-isoxazol-3-yl, R⁴ is CN and R⁵ is Cl and the combination of R¹, R³, R⁶ and R⁷ for a compound corresponds in each case to one row of Table A;

Table 189 Compounds of formula I.B17 (I.B17-9.1-I.B17-9.2304) in which B is CH, R² is 5-methyl-isoxazol-3-yl, R⁴ is CH₃ and R⁵ is F and the combination of R¹, R³, R⁶ and R⁷ for a compound corresponds in each case to one row of Table A;

Table 190 Compounds of formula I.B17 (I.B17-10.1-I.B17-10.2304) in which B is CH, R² is 5-methyl-isoxazol-3-yl, R⁴ is CH₃ and R⁵ is Cl and the combination of R¹, R³, R⁶ and R⁷ for a compound corresponds in each case to one row of Table A;

Table 191 Compounds of formula I.B18 (I.B18-1.1-I.B18-1.2304) in which B is CH, R² is 3-methyl-isoxazolin-5-yl, R⁴ is H and R⁵ is F and the combination of R¹, R³, R⁶ and R⁷ for a compound corresponds in each case to one row of Table A;

Table 192 Compounds of formula I.B18 (I.B18-2.1-I.B18-2.2304) in which B is CH, R² is 3-methyl-isoxazolin-5-yl, R⁴ is H and R⁵ is Cl and the combination of R¹, R³, R⁶ and R⁷ for a compound corresponds in each case to one row of Table A;

Table 193 Compounds of formula I.B18 (I.B18-3.1-I.B18-3.2304) in which B is CH, R² is 3-methyl-isoxazolin-5-yl, R⁴ is F and R⁵ is F and the combination of R¹, R³, R⁶ and R⁷ for a compound corresponds in each case to one row of Table A;

Table 194 Compounds of formula I.B18 (I.B18-4.1-I.B18-4.2304) in which B is CH, R² is 3-methyl-isoxazolin-5-yl, R⁴ is F and R⁵ is Cl and the combination of R¹, R³, R⁶ and R⁷ for a compound corresponds in each case to one row of Table A;

Table 195 Compounds of formula I.B18 (I.B18-5.1-I.B18-5.2304) in which B is CH, R² is 3-methyl-isoxazolin-5-yl, R⁴ is Cl and R⁵ is F and the combination of R¹, R³, R⁶ and R⁷ for a compound corresponds in each case to one row of Table A;

Table 196 Compounds of formula I.B18 (I.B18-6.1-I.B18-6.2304) in which B is CH, R² is 3-methyl-isoxazolin-5-yl, R⁴ is Cl and R⁵ is Cl and the combination of R¹, R³, R⁶ and R⁷ for a compound corresponds in each case to one row of Table A;

Table 197 Compounds of formula I.B18 (I.B18-7.1-I.B18-7.2304) in which B is CH, R² is 3-methyl-isoxazolin-5-yl, R⁴ is CN and R⁵ is F and the combination of R¹, R³, R⁶ and R⁷ for a compound corresponds in each case to one row of Table A;

Table 198 Compounds of formula I.B18 (I.B18-8.1-I.B18-8.2304) in which B is CH, R² is 3-methyl-isoxazolin-5-yl, R⁴ is CN and R⁵ is Cl and the combination of R¹, R³, R⁶ and R⁷ for a compound corresponds in each case to one row of Table A;

Table 199 Compounds of formula I.B18 (I.B18-9.1-I.B18-9.2304) in which B is CH, R² is 3-methyl-isoxazolin-5-yl, R⁴ is CH₃ and R⁵ is F and the combination of R¹, R³, R⁶ and R⁷ for a compound corresponds in each case to one row of Table A;

Table 200 Compounds of formula I.B18 (I.B18-10.1-I.B18-10.2304) in which B is CH, R² is 3-methyl-isoxazolin-5-yl, R⁴ is CH₃ and R⁵ is Cl and the combination of R¹, R³, R⁶ and R⁷ for a compound corresponds in each case to one row of Table A;

Table 201 Compounds of formula I.B19 (I.B19-1.1-I.B19-1.2304) in which B is CH, R² is 3-methyl-isoxazol-5-yl, R⁴ is H and R⁵ is F and the combination of R¹, R³, R⁶ and R⁷ for a compound corresponds in each case to one row of Table A;

Table 202 Compounds of formula I.B19 (I.B19-2.1-I.B19-2.2304) in which B is CH, R² is 3-methyl-isoxazol-5-yl, R⁴ is H and R⁵ is Cl and the combination of R¹, R³, R⁶ and R⁷ for a compound corresponds in each case to one row of Table A;

Table 203 Compounds of formula I.B19 (I.B19-3.1-I.B19-3.2304) in which B is CH, R² is 3-methyl-isoxazol-5-yl, R⁴ is F and R⁵ is F and the combination of R¹, R³, R⁶ and R⁷ for a compound corresponds in each case to one row of Table A;

Table 204 Compounds of formula I.B19 (I.B19-4.1-I.B19-4.2304) in which B is CH, R² is 3-methyl-isoxazol-5-yl, R⁴ is F and R⁵ is Cl and the combination of R¹, R³, R⁶ and R⁷ for a compound corresponds in each case to one row of Table A;

Table 205 Compounds of formula I.B19 (I.B19-5.1-I.B19-5.2304) in which B is CH, R² is 3-methyl-isoxazol-5-yl, R⁴ is Cl and R⁵ is F and the combination of R¹, R³, R⁶ and R⁷ for a compound corresponds in each case to one row of Table A;

Table 206 Compounds of formula I.B19 (I.B19-6.1-I.B19-6.2304) in which B is CH, R² is 3-methyl-isoxazol-5-yl, R⁴ is Cl and R⁵ is Cl and the combination of R¹, R³, R⁶ and R⁷ for a compound corresponds in each case to one row of Table A;

Table 207 Compounds of formula I.B19 (I.B19-7.1-I.B19-7.2304) in which B is CH, R² is 3-methyl-isoxazol-5-yl, R⁴ is CN and R⁵ is F and the combination of R¹, R³, R⁶ and R⁷ for a compound corresponds in each case to one row of Table A;

Table 208 Compounds of formula I.B19 (I.B19-8.1-I.B19-8.2304) in which B is CH, R² is 3-methyl-isoxazol-5-yl, R⁴ is CN and R⁵ is Cl and the combination of R¹, R³, R⁶ and R⁷ for a compound corresponds in each case to one row of Table A;

Table 209 Compounds of formula I.B19 (I.B19-9.1-I.B19-9.2304) in which B is CH, R² is 3-methyl-isoxazol-5-yl, R⁴ is CH₃ and R⁵ is F and the combination of R¹, R³, R⁶ and R⁷ for a compound corresponds in each case to one row of Table A;

Table 210 Compounds of formula I.B19 (I.B19-10.1-I.B19-10.2304) in which B is CH, R² is 3-methyl-isoxazol-5-yl, R⁴ is CH₃ and R⁵ is Cl and the combination of R¹, R³, R⁶ and R⁷ for a compound corresponds in each case to one row of Table A;

Table 211 Compounds of formula I.B20 (I.B20-1.1-I.B20-1.2304) in which B is CH, R² is CH₃, R⁴ is H and R⁵ is F and the combination of R¹, R³, R⁶ and R⁷ for a compound corresponds in each case to one row of Table A;

Table 212 Compounds of formula I.B20 (I.B20-2.1-I.B20-2.2304) in which B is CH, R² is CH₃, R⁴ is H and R⁵ is Cl and the combination of R¹, R³, R⁶ and R⁷ for a compound corresponds in each case to one row of Table A;

Table 213 Compounds of formula I.B20 (I.B20-3.1-I.B20-3.2304) in which B is CH, R² is CH₃, R⁴ is F and R⁵ is F and the combination of R¹, R³, R⁶ and R⁷ for a compound corresponds in each case to one row of Table A;

Table 214 Compounds of formula I.B20 (I.B20-4.1-I.B20-4.2304) in which B is CH, R² is CH₃, R⁴ is F and R⁵ is Cl and the combination of R¹, R³, R⁶ and R⁷ for a compound corresponds in each case to one row of Table A;

Table 215 Compounds of formula I.B20 (I.B20-5.1-I.B20-5.2304) in which B is CH, R² is CH₃, R⁴ is Cl and R⁵ is F and the combination of R¹, R³, R⁶ and R⁷ for a compound corresponds in each case to one row of Table A;

Table 216 Compounds of formula I.B20 (I.B20-6.1-I.B20-6.2304) in which B is CH, R² is CH₃, R⁴ is Cl and R⁵ is Cl and the combination of R¹, R³, R⁶ and R⁷ for a compound corresponds in each case to one row of Table A;

Table 217 Compounds of formula I.B20 (I.B20-7.1-I.B20-7.2304) in which B is CH, R² is CH₃, R⁴ is CN and R⁵ is F and the combination of R¹, R³, R⁶ and R⁷ for a compound corresponds in each case to one row of Table A;

Table 218 Compounds of formula I.B20 (I.B20-8.1-I.B20-8.2304) in which B is CH, R² is CH₃, R⁴ is CN and R⁵ is Cl and the combination of R¹, R³, R⁶ and R⁷ for a compound corresponds in each case to one row of Table A;

Table 219 Compounds of formula I.B20 (I.B20-9.1-I.B20-9.2304) in which B is CH, R² is CH₃, R⁴ is CH₃ and R⁵ is F and the combination of R¹, R³, R⁶ and R⁷ for a compound corresponds in each case to one row of Table A;

Table 220 Compounds of formula I.B20 (I.B20-10.1-I.B20-10.2304) in which B is CH, R² is CH₃, R⁴ is CH₃ and R⁵ is Cl and the combination of R¹, R³, R⁶ and R⁷ for a compound corresponds in each case to one row of Table A;

Table 221 Compounds of formula I.B21 (I.B21-1.1-I.B21-1.2304) in which B is CH, R² is CH₂OCH₃, R⁴ is H and R⁵ is F and the combination of R¹, R³, R⁶ and R⁷ for a compound corresponds in each case to one row of Table A;

Table 222 Compounds of formula I.B21 (I.B21-2.1-I.B21-2.2304) in which B is CH, $R^2$ is $CH_2OCH_3$, $R^4$ is H and $R^5$ is Cl and the combination of $R^1$, $R^3$, $R^6$ and $R^7$ for a compound corresponds in each case to one row of Table A;

Table 223 Compounds of formula I.B21 (I.B21-3.1-I.B21-3.2304) in which B is CH, $R^2$ is $CH_2OCH_3$, $R^4$ is F and $R^5$ is F and the combination of $R^1$, $R^3$, $R^6$ and $R^7$ for a compound corresponds in each case to one row of Table A;

Table 224 Compounds of formula I.B21 (I.B21-4.1-I.B21-4.2304) in which B is CH, $R^2$ is $CH_2OCH_3$, $R^4$ is F and $R^5$ is Cl and the combination of $R^1$, $R^3$, $R^6$ and $R^7$ for a compound corresponds in each case to one row of Table A;

Table 225 Compounds of formula I.B21 (I.B21-5.1-I.B21-5.2304) in which B is CH, $R^2$ is $CH_2OCH_3$, $R^4$ is Cl and $R^5$ is F and the combination of $R^1$, $R^3$, $R^6$ and $R^7$ for a compound corresponds in each case to one row of Table A;

Table 226 Compounds of formula I.B21 (I.B21-6.1-I.B21-6.2304) in which B is CH, $R^2$ is $CH_2OCH_3$, $R^4$ is Cl and $R^5$ is Cl and the combination of $R^1$, $R^3$, $R^6$ and $R^7$ for a compound corresponds in each case to one row of Table A;

Table 227 Compounds of formula I.B21 (I.B21-7.1-I.B21-7.2304) in which B is CH, $R^2$ is $CH_2OCH_3$, $R^4$ is CN and $R^5$ is F and the combination of $R^1$, $R^3$, $R^6$ and $R^7$ for a compound corresponds in each case to one row of Table A;

Table 228 Compounds of formula I.B21 (I.B21-8.1-I.B21-8.2304) in which B is CH, $R^2$ is $CH_2OCH_3$, $R^4$ is CN and $R^5$ is Cl and the combination of $R^1$, $R^3$, $R^6$ and $R^7$ for a compound corresponds in each case to one row of Table A;

Table 229 Compounds of formula I.B21 (I.B21-9.1-I.B21-9.2304) in which B is CH, $R^2$ is $CH_2OCH_3$, $R^4$ is $CH_3$ and $R^5$ is F and the combination of $R^1$, $R^3$, $R^6$ and $R^7$ for a compound corresponds in each case to one row of Table A;

Table 230 Compounds of formula I.B21 (I.B21-10.1-I.B21-10.2304) in which B is CH, $R^2$ is $CH_2OCH_3$, $R^4$ is $CH_3$ and $R^5$ is Cl and the combination of $R^1$, $R^3$, $R^6$ and $R^7$ for a compound corresponds in each case to one row of Table A;

Table 231 Compounds of formula I.B22 (I.B22-1.1-I.B22-1.2304) in which B is CH, $R^2$ is $OCH_2CH(CH_2)_2$, $R^4$ is H and $R^5$ is F and the combination of $R^1$, $R^3$, $R^6$ and $R^7$ for a compound corresponds in each case to one row of Table A;

Table 232 Compounds of formula I.B22 (I.B22-2.1-I.B22-2.2304) in which B is CH, $R^2$ is $OCH_2CH(CH_2)_2$, $R^4$ is H and $R^5$ is Cl and the combination of $R^1$, $R^3$, $R^6$ and $R^7$ for a compound corresponds in each case to one row of Table A;

Table 233 Compounds of formula I.B22 (I.B22-3.1-I.B22-3.2304) in which B is CH, $R^2$ is $OCH_2CH(CH_2)_2$, $R^4$ is F and $R^5$ is F and the combination of $R^1$, $R^3$, $R^6$ and $R^7$ for a compound corresponds in each case to one row of Table A;

Table 234 Compounds of formula I.B22 (I.B22-4.1-I.B22-4.2304) in which B is CH, $R^2$ is $OCH_2CH(CH_2)_2$, $R^4$ is F and $R^5$ is Cl and the combination of $R^1$, $R^3$, $R^6$ and $R^7$ for a compound corresponds in each case to one row of Table A;

Table 235 Compounds of formula I.B22 (I.B22-5.1-I.B22-5.2304) in which B is CH, $R^2$ is $OCH_2CH(CH_2)_2$, $R^4$ is Cl and $R^5$ is F and the combination of $R^1$, $R^3$, $R^6$ and $R^7$ for a compound corresponds in each case to one row of Table A;

Table 236 Compounds of formula I.B22 (I.B22-6.1-I.B22-6.2304) in which B is CH, $R^2$ is $OCH_2CH(CH_2)_2$, $R^4$ is Cl and $R^5$ is Cl and the combination of $R^1$, $R^3$, $R^6$ and $R^7$ for a compound corresponds in each case to one row of Table A;

Table 237 Compounds of formula I.B22 (I.B22-7.1-I.B22-7.2304) in which B is CH, $R^2$ is $OCH_2CH(CH_2)_2$, $R^4$ is CN and $R^5$ is F and the combination of $R^1$, $R^3$, $R^6$ and $R^7$ for a compound corresponds in each case to one row of Table A;

Table 238 Compounds of formula I.B22 (I.B22-8.1-I.B22-8.2304) in which B is CH, $R^2$ is $OCH_2CH(CH_2)_2$, $R^4$ is CN and $R^5$ is Cl and the combination of $R^1$, $R^3$, $R^6$ and $R^7$ for a compound corresponds in each case to one row of Table A;

Table 239 Compounds of formula I.B22 (I.B22-9.1-I.B22-9.2304) in which B is CH, $R^2$ is $OCH_2CH(CH_2)_2$, $R^4$ is $CH_3$ and $R^5$ is F and the combination of $R^1$, $R^3$, $R^6$ and $R^7$ for a compound corresponds in each case to one row of Table A;

Table 240 Compounds of formula I.B22 (I.B22-10.1-I.B22-10.2304) in which B is CH, $R^2$ is $OCH_2CH(CH_2)_2$, $R^4$ is $CH_3$ and $R^5$ is Cl and the combination of $R^1$, $R^3$, $R^6$ and $R^7$ for a compound corresponds in each case to one row of Table A;

Table 241 Compounds of formula I.B23 (I.B23-1.1-I.B23-1.2304) in which B is CH, $R^2$ is $NCH_3SO_2CH_3$, $R^4$ is H and $R^5$ is F and the combination of $R^1$, $R^3$, $R^6$ and $R^7$ for a compound corresponds in each case to one row of Table A;

Table 242 Compounds of formula I.B23 (I.B23-2.1-I.B23-2.2304) in which B is CH, $R^2$ is $NCH_3SO_2CH_3$, $R^4$ is H and $R^5$ is Cl and the combination of $R^1$, $R^3$, $R^6$ and $R^7$ for a compound corresponds in each case to one row of Table A;

Table 243 Compounds of formula I.B23 (I.B23-3.1-I.B23-3.2304) in which B is CH, $R^2$ is $NCH_3SO_2CH_3$, $R^4$ is F and $R^5$ is F and the combination of $R^1$, $R^3$, $R^6$ and $R^7$ for a compound corresponds in each case to one row of Table A;

Table 244 Compounds of formula I.B23 (I.B23-4.1-I.B23-4.2304) in which B is CH, $R^2$ is $NCH_3SO_2CH_3$, $R^4$ is F and $R^5$ is Cl and the combination of $R^1$, $R^3$, $R^6$ and $R^7$ for a compound corresponds in each case to one row of Table A;

Table 245 Compounds of formula I.B23 (I.B23-5.1-I.B23-5.2304) in which B is CH, $R^2$ is $NCH_3SO_2CH_3$, $R^4$ is Cl and $R^5$ is F and the combination of $R^1$, $R^3$, $R^6$ and $R^7$ for a compound corresponds in each case to one row of Table A;

Table 246 Compounds of formula I.B23 (I.B23-6.1-I.B23-6.2304) in which B is CH, $R^2$ is $NCH_3SO_2CH_3$, $R^4$ is Cl and $R^5$ is Cl and the combination of $R^1$, $R^3$, $R^6$ and $R^7$ for a compound corresponds in each case to one row of Table A;

Table 247 Compounds of formula I.B23 (I.B23-7.1-I.B23-7.2304) in which B is CH, $R^2$ is $NCH_3SO_2CH_3$, $R^4$ is CN and $R^5$ is F and the combination of $R^1$, $R^3$, $R^6$ and $R^7$ for a compound corresponds in each case to one row of Table A;

Table 248 Compounds of formula I.B23 (I.B23-8.1-I.B23-8.2304) in which B is CH, $R^2$ is $NCH_3SO_2CH_3$, $R^4$ is CN and $R^5$ is Cl and the combination of $R^1$, $R^3$, $R^6$ and $R^7$ for a compound corresponds in each case to one row of Table A;

Table 249 Compounds of formula I.B23 (I.B23-9.1-I.B23-9.2304) in which B is CH, $R^2$ is $NCH_3SO_2CH_3$, $R^4$ is $CH_3$ and $R^5$ is F and the combination of $R^1$, $R^3$, $R^6$ and $R^7$ for a compound corresponds in each case to one row of Table A;

Table 250 Compounds of formula I.B23 (I.B23-10.1-I.B23-10.2304) in which B is CH, $R^2$ is $NCH_3SO_2CH_3$, $R^4$ is $CH_3$ and $R^5$ is Cl and the combination of $R^1$, $R^3$, $R^6$ and $R^7$ for a compound corresponds in each case to one row of Table A;

Table 251 Compounds of formula I.B1 (I.B1-11.1-I.B1-11.2304) in which B is N, $R^2$ is $SCH_3$, $R^4$ is H and $R^5$ is F and the combination of $R^1$, $R^3$, $R^6$ and $R^7$ for a compound corresponds in each case to one row of Table A;

Table 252 Compounds of formula I.B1 (I.B1-12.1-I.B1-12.2304) in which B is N, $R^2$ is $SCH_3$, $R^4$ is H and $R^5$ is Cl and the combination of $R^1$, $R^3$, $R^6$ and $R^7$ for a compound corresponds in each case to one row of Table A;

Table 253 Compounds of formula I.B1 (I.B1-13.1-I.B1-13.2304) in which B is N, $R^2$ is $SCH_3$, $R^4$ is F and $R^5$ is F and the combination of $R^1$, $R^3$, $R^6$ and $R^7$ for a compound corresponds in each case to one row of Table A;

Table 254 Compounds of formula I.B1 (I.B1-14.1-I.B1-14.2304) in which B is N, $R^2$ is $SCH_3$, $R^4$ is F and $R^5$ is Cl and the combination of $R^1$, $R^3$, $R^6$ and $R^7$ for a compound corresponds in each case to one row of Table A;

Table 255 Compounds of formula I.B1 (I.B1-15.1-I.B1-15.2304) in which B is N, $R^2$ is $SCH_3$, $R^4$ is Cl and $R^5$ is F and the combination of $R^1$, $R^3$, $R^6$ and $R^7$ for a compound corresponds in each case to one row of Table A;

Table 256 Compounds of formula I.B1 (I.B1-16.1-I.B1-16.2304) in which B is N, $R^2$ is $SCH_3$, $R^4$ is Cl and $R^5$ is Cl and the combination of $R^1$, $R^3$, $R^6$ and $R^7$ for a compound corresponds in each case to one row of Table A;

Table 257 Compounds of formula I.B1 (I.B1-17.1-I.B1-17.2304) in which B is N, $R^2$ is $SCH_3$, $R^4$ is CN and $R^5$ is F and the combination of $R^1$, $R^3$, $R^6$ and $R^7$ for a compound corresponds in each case to one row of Table A;

Table 258 Compounds of formula I.B1 (I.B1-18.1-I.B1-18.2304) in which B is N, $R^2$ is $SCH_3$, $R^4$ is CN and $R^5$ is Cl and the combination of $R^1$, $R^3$, $R^6$ and $R^7$ for a compound corresponds in each case to one row of Table A;

Table 259 Compounds of formula I.B1 (I.B1-19.1-I.B1-19.2304) in which B is N, $R^2$ is $SCH_3$, $R^4$ is $CH_3$ and $R^5$ is F and the combination of $R^1$, $R^3$, $R^6$ and $R^7$ for a compound corresponds in each case to one row of Table A;

Table 260 Compounds of formula I.B1 (I.B1-20.1-I.B1-20.2304) in which B is N, $R^2$ is $SCH_3$, $R^4$ is $CH_3$ and $R^5$ is Cl and the combination of $R^1$, $R^3$, $R^6$ and $R^7$ for a compound corresponds in each case to one row of Table A;

Table 261 Compounds of formula I.B2 (I.B2-11.1-I.B2-11.2304) in which B is N, $R^2$ is $SCH_2CH_3$, $R^4$ is H and $R^5$ is F and the combination of $R^1$, $R^3$, $R^6$ and $R^7$ for a compound corresponds in each case to one row of Table A;

Table 262 Compounds of formula I.B2 (I.B2-12.1-I.B2-12.2304) in which B is N, $R^2$ is $SCH_2CH_3$, $R^4$ is H and $R^5$ is Cl and the combination of $R^1$, $R^3$, $R^6$ and $R^7$ for a compound corresponds in each case to one row of Table A;

Table 263 Compounds of formula I.B2 (I.B2-13.1-I.B2-13.2304) in which B is N, $R^2$ is $SCH_2CH_3$, $R^4$ is F and $R^5$ is F and the combination of $R^1$, $R^3$, $R^6$ and $R^7$ for a compound corresponds in each case to one row of Table A;

Table 264 Compounds of formula I.B2 (I.B2-14.1-I.B2-14.2304) in which B is N, $R^2$ is $SCH_2CH_3$, $R^4$ is F and $R^5$ is Cl and the combination of $R^1$, $R^3$, $R^6$ and $R^7$ for a compound corresponds in each case to one row of Table A;

Table 265 Compounds of formula I.B2 (I.B2-15.1-I.B2-15.2304) in which B is N, $R^2$ is $SCH_2CH_3$, $R^4$ is Cl and $R^5$ is F and the combination of $R^1$, $R^3$, $R^6$ and $R^7$ for a compound corresponds in each case to one row of Table A;

Table 266 Compounds of formula I.B2 (I.B2-16.1-I.B2-16.2304) in which B is N, $R^2$ is $SCH_2CH_3$, $R^4$ is Cl and $R^5$ is Cl and the combination of $R^1$, $R^3$, $R^6$ and $R^7$ for a compound corresponds in each case to one row of Table A;

Table 267 Compounds of formula I.B2 (I.B2-17.1-I.B2-17.2304) in which B is N, $R^2$ is $SCH_2CH_3$, $R^4$ is CN and $R^5$ is F and the combination of $R^1$, $R^3$, $R^6$ and $R^7$ for a compound corresponds in each case to one row of Table A;

Table 268 Compounds of formula I.B2 (I.B2-18.1-I.B2-18.2304) in which B is N, $R^2$ is $SCH_2CH_3$, $R^4$ is CN and $R^5$ is Cl and the combination of $R^1$, $R^3$, $R^6$ and $R^7$ for a compound corresponds in each case to one row of Table A;

Table 269 Compounds of formula I.B2 (I.B2-19.1-I.B2-19.2304) in which B is N, $R^2$ is $SCH_2CH_3$, $R^4$ is $CH_3$ and $R^5$ is F and the combination of $R^1$, $R^3$, $R^6$ and $R^7$ for a compound corresponds in each case to one row of Table A;

Table 270 Compounds of formula I.B2 (I.B2-20.1-I.B2-20.2304) in which B is N, $R^2$ is $SCH_2CH_3$, $R^4$ is $CH_3$ and $R^5$ is Cl and the combination of $R^1$, $R^3$, $R^6$ and $R^7$ for a compound corresponds in each case to one row of Table A;

Table 271 Compounds of formula I.B3 (I.B3-11.1-I.B3-11.2304) in which B is N, $R^2$ is $SO_2CH_2CH_3$, $R^4$ is H and $R^5$ is F and the combination of $R^1$, $R^3$, $R^6$ and $R^7$ for a compound corresponds in each case to one row of Table A;

Table 272 Compounds of formula I.B3 (I.B3-12.1-I.B3-12.2304) in which B is N, $R^2$ is $SO_2CH_2CH_3$, $R^4$ is H and $R^5$ is Cl and the combination of $R^1$, $R^3$, $R^6$ and $R^7$ for a compound corresponds in each case to one row of Table A;

Table 273 Compounds of formula I.B3 (I.B3-13.1-I.B3-13.2304) in which B is N, $R^2$ is $SO_2CH_2CH_3$, $R^4$ is F and $R^5$ is F and the combination of $R^1$, $R^3$, $R^6$ and $R^7$ for a compound corresponds in each case to one row of Table A;

Table 274 Compounds of formula I.B3 (I.B3-14.1-I.B3-14.2304) in which B is N, $R^2$ is $SO_2CH_2CH_3$, $R^4$ is F and R⁵ is Cl and the combination of R¹, R³, R⁶ and R⁷ for a compound corresponds in each case to one row of Table A;

Table 275 Compounds of formula I.B3 (I.B3-15.1-I.B3-15.2304) in which B is N, R² is SO₂CH₂CH₃, R⁴ is Cl and R⁵ is F and the combination of R¹, R³, R⁶ and R⁷ for a compound corresponds in each case to one row of Table A;

Table 276 Compounds of formula I.B3 (I.B3-16.1-I.B3-16.2304) in which B is N, R² is SO₂CH₂CH₃, R⁴ is Cl and R⁵ is Cl and the combination of R¹, R³, R⁶ and R⁷ for a compound corresponds in each case to one row of Table A;

Table 277 Compounds of formula I.B3 (I.B3-17.1-I.B3-17.2304) in which B is N, R² is SO₂CH₂CH₃, R⁴ is CN and R⁵ is F and the combination of R¹, R³, R⁶ and R⁷ for a compound corresponds in each case to one row of Table A;

Table 278 Compounds of formula I.B3 (I.B3-18.1-I.B3-18.2304) in which B is N, R² is SO₂CH₂CH₃, R⁴ is CN and R⁵ is Cl and the combination of R¹, R³, R⁶ and R⁷ for a compound corresponds in each case to one row of Table A;

Table 279 Compounds of formula I.B3 (I.B3-19.1-I.B3-19.2304) in which B is N, R² is SO₂CH₂CH₃, R⁴ is CH₃ and R⁵ is F and the combination of R¹, R³, R⁶ and R⁷ for a compound corresponds in each case to one row of Table A;

Table 280 Compounds of formula I.B3 (I.B3-20.1-I.B3-20.2304) in which B is N, R² is SO₂CH₂CH₃, R⁴ is CH₃ and R⁵ is Cl and the combination of R¹, R³, R⁶ and R⁷ for a compound corresponds in each case to one row of Table A;

Table 281 Compounds of formula I.B4 (I.B4-11.1-I.B4-11.2304) in which B is N, R² is SOCH₃, R⁴ is H and R⁵ is F and the combination of R¹, R³, R⁶ and R⁷ for a compound corresponds in each case to one row of Table A;

Table 282 Compounds of formula I.B4 (I.B4-12.1-I.B4-12.2304) in which B is N, R² is SOCH₃, R⁴ is H and R⁵ is Cl and the combination of R¹, R³, R⁶ and R⁷ for a compound corresponds in each case to one row of Table A;

Table 283 Compounds of formula I.B4 (I.B4-13.1-I.B4-13.2304) in which B is N, R² is SOCH₃, R⁴ is F and R⁵ is F and the combination of R¹, R³, R⁶ and R⁷ for a compound corresponds in each case to one row of Table A;

Table 284 Compounds of formula I.B4 (I.B4-14.1-I.B4-14.2304) in which B is N, R² is SOCH₃, R⁴ is F and R⁵ is Cl and the combination of R¹, R³, R⁶ and R⁷ for a compound corresponds in each case to one row of Table A;

Table 285 Compounds of formula I.B4 (I.B4-15.1-I.B4-15.2304) in which B is N, R² is SOCH₃, R⁴ is Cl and R⁵ is F and the combination of R¹, R³, R⁶ and R⁷ for a compound corresponds in each case to one row of Table A;

Table 286 Compounds of formula I.B4 (I.B4-16.1-I.B4-16.2304) in which B is N, R² is SOCH₃, R⁴ is Cl and R⁵ is Cl and the combination of R¹, R³, R⁶ and R⁷ for a compound corresponds in each case to one row of Table A;

Table 287 Compounds of formula I.B4 (I.B4-17.1-I.B4-17.2304) in which B is N, R² is SOCH₃, R⁴ is CN and R⁵ is F and the combination of R¹, R³, R⁶ and R⁷ for a compound corresponds in each case to one row of Table A;

Table 288 Compounds of formula I.B4 (I.B4-18.1-I.B4-18.2304) in which B is N, R² is SOCH₃, R⁴ is CN and R⁵ is Cl and the combination of R¹, R³, R⁶ and R⁷ for a compound corresponds in each case to one row of Table A;

Table 289 Compounds of formula I.B4 (I.B4-19.1-I.B4-19.2304) in which B is N, R² is SOCH₃, R⁴ is CH₃ and R⁵ is F and the combination of R¹, R³, R⁶ and R⁷ for a compound corresponds in each case to one row of Table A;

Table 290 Compounds of formula I.B4 (I.B4-20.1-I.B4-20.2304) in which B is N, R² is SOCH₃, R⁴ is CH₃ and R⁵ is Cl and the combination of R¹, R³, R⁶ and R⁷ for a compound corresponds in each case to one row of Table A;

Table 291 Compounds of formula I.B5 (I.B5-11.1-I.B5-11.2304) in which B is N, R² is SOCH₂CH₃, R⁴ is H and R⁵ is F and the combination of R¹, R³, R⁶ and R⁷ for a compound corresponds in each case to one row of Table A;

Table 292 Compounds of formula I.B5 (I.B5-12.1-I.B5-12.2304) in which B is N, R² is SOCH₂CH₃, R⁴ is H and R⁵ is Cl and the combination of R¹, R³, R⁶ and R⁷ for a compound corresponds in each case to one row of Table A;

Table 293 Compounds of formula I.B5 (I.B5-13.1-I.B5-13.2304) in which B is N, R² is SOCH₂CH₃, R⁴ is F and R⁵ is F and the combination of R¹, R³, R⁶ and R⁷ for a compound corresponds in each case to one row of Table A;

Table 294 Compounds of formula I.B5 (I.B5-14.1-I.B5-14.2304) in which B is N, R² is SOCH₂CH₃, R⁴ is F and R⁵ is Cl and the combination of R¹, R³, R⁶ and R⁷ for a compound corresponds in each case to one row of Table A;

Table 295 Compounds of formula I.B5 (I.B5-15.1-I.B5-15.2304) in which B is N, R² is SOCH₂CH₃, R⁴ is Cl and R⁵ is F and the combination of R¹, R³, R⁶ and R⁷ for a compound corresponds in each case to one row of Table A;

Table 296 Compounds of formula I.B5 (I.B5-16.1-I.B5-16.2304) in which B is N, R² is SOCH₂CH₃, R⁴ is Cl and R⁵ is Cl and the combination of R¹, R³, R⁶ and R⁷ for a compound corresponds in each case to one row of Table A;

Table 297 Compounds of formula I.B5 (I.B5-17.1-I.B5-17.2304) in which B is N, R² is SOCH₂CH₃, R⁴ is CN and R⁵ is F and the combination of R¹, R³, R⁶ and R⁷ for a compound corresponds in each case to one row of Table A;

Table 298 Compounds of formula I.B5 (I.B5-18.1-I.B5-18.2304) in which B is N, R² is SOCH₂CH₃, R⁴ is CN and R⁵ is Cl and the combination of R¹, R³, R⁶ and R⁷ for a compound corresponds in each case to one row of Table A;

Table 299 Compounds of formula I.B5 (I.B5-19.1-I.B5-19.2304) in which B is N, R² is SOCH₂CH₃, R⁴ is CH₃ and R⁵ is F and the combination of R¹, R³, R⁶ and R⁷ for a compound corresponds in each case to one row of Table A;

Table 300 Compounds of formula I.B5 (I.B5-20.1-I.B5-20.2304) in which B is N, R² is SOCH₂CH₃, R⁴ is CH₃ and $R^5$ is Cl and the combination of $R^1$, $R^3$, $R^6$ and $R^7$ for a compound corresponds in each case to one row of Table A;

Table 301 Compounds of formula I.B6 (I.B6-11.1-I.B6-11.2304) in which B is N, $R^2$ is $OCH_3$, $R^4$ is H and $R^5$ is F and the combination of $R^1$, $R^3$, $R^6$ and $R^7$ for a compound corresponds in each case to one row of Table A;

Table 302 Compounds of formula I.B6 (I.B6-12.1-I.B6-12.2304) in which B is N, $R^2$ is $OCH_3$, $R^4$ is H and $R^5$ is Cl and the combination of $R^1$, $R^3$, $R^6$ and $R^7$ for a compound corresponds in each case to one row of Table A;

Table 303 Compounds of formula I.B6 (I.B6-13.1-I.B6-13.2304) in which B is N, $R^2$ is $OCH_3$, $R^4$ is F and $R^5$ is F and the combination of $R^1$, $R^3$, $R^6$ and $R^7$ for a compound corresponds in each case to one row of Table A;

Table 304 Compounds of formula I.B6 (I.B6-14.1-I.B6-14.2304) in which B is N, $R^2$ is $OCH_3$, $R^4$ is F and $R^5$ is Cl and the combination of $R^1$, $R^3$, $R^6$ and $R^7$ for a compound corresponds in each case to one row of Table A;

Table 305 Compounds of formula I.B6 (I.B6-15.1-I.B6-15.2304) in which B is N, $R^2$ is $OCH_3$, $R^4$ is Cl and $R^5$ is F and the combination of $R^1$, $R^3$, $R^6$ and $R^7$ for a compound corresponds in each case to one row of Table A;

Table 306 Compounds of formula I.B6 (I.B6-16.1-I.B6-16.2304) in which B is N, $R^2$ is $OCH_3$, $R^4$ is Cl and $R^5$ is Cl and the combination of $R^1$, $R^3$, $R^6$ and $R^7$ for a compound corresponds in each case to one row of Table A;

Table 307 Compounds of formula I.B6 (I.B6-17.1-I.B6-17.2304) in which B is N, $R^2$ is $OCH_3$, $R^4$ is CN and $R^5$ is F and the combination of $R^1$, $R^3$, $R^6$ and $R^7$ for a compound corresponds in each case to one row of Table A;

Table 308 Compounds of formula I.B6 (I.B6-18.1-I.B6-18.2304) in which B is N, $R^2$ is $OCH_3$, $R^4$ is CN and $R^5$ is Cl and the combination of $R^1$, $R^3$, $R^6$ and $R^7$ for a compound corresponds in each case to one row of Table A;

Table 309 Compounds of formula I.B6 (I.B6-19.1-I.B6-19.2304) in which B is N, $R^2$ is $OCH_3$, $R^4$ is $CH_3$ and $R^5$ is F and the combination of $R^1$, $R^3$, $R^6$ and $R^7$ for a compound corresponds in each case to one row of Table A;

Table 310 Compounds of formula I.B6 (I.B6-20.1-I.B6-20.2304) in which B is N, $R^2$ is $OCH_3$, $R^4$ is $CH_3$ and $R^5$ is Cl and the combination of $R^1$, $R^3$, $R^6$ and $R^7$ for a compound corresponds in each case to one row of Table A;

Table 311 Compounds of formula I.B7 (I.B7-11.1-I.B7-11.2304) in which B is N, $R^2$ is $OCH_2CH_3$, $R^4$ is H and $R^5$ is F and the combination of $R^1$, $R^3$, $R^6$ and $R^7$ for a compound corresponds in each case to one row of Table A;

Table 312 Compounds of formula I.B7 (I.B7-12.1-I.B7-12.2304) in which B is N, $R^2$ is $OCH_2CH_3$, $R^4$ is H and $R^5$ is Cl and the combination of $R^1$, $R^3$, $R^6$ and $R^7$ for a compound corresponds in each case to one row of Table A;

Table 313 Compounds of formula I.B7 (I.B7-13.1-I.B7-13.2304) in which B is N, $R^2$ is $OCH_2CH_3$, $R^4$ is F and $R^5$ is F and the combination of $R^1$, $R^3$, $R^6$ and $R^7$ for a compound corresponds in each case to one row of Table A;

Table 314 Compounds of formula I.B7 (I.B7-14.1-I.B7-14.2304) in which B is N, $R^2$ is $OCH_2CH_3$, $R^4$ is F and $R^5$ is Cl and the combination of $R^1$, $R^3$, $R^6$ and $R^7$ for a compound corresponds in each case to one row of Table A;

Table 315 Compounds of formula I.B7 (I.B7-15.1-I.B7-15.2304) in which B is N, $R^2$ is $OCH_2CH_3$, $R^4$ is Cl and $R^5$ is F and the combination of $R^1$, $R^3$, $R^6$ and $R^7$ for a compound corresponds in each case to one row of Table A;

Table 316 Compounds of formula I.B7 (I.B7-16.1-I.B7-16.2304) in which B is N, $R^2$ is $OCH_2CH_3$, $R^4$ is Cl and $R^5$ is Cl and the combination of $R^1$, $R^3$, $R^6$ and $R^7$ for a compound corresponds in each case to one row of Table A;

Table 317 Compounds of formula I.B7 (I.B7-17.1-I.B7-17.2304) in which B is N, $R^2$ is $OCH_2CH_3$, $R^4$ is CN and $R^5$ is F and the combination of $R^1$, $R^3$, $R^6$ and $R^7$ for a compound corresponds in each case to one row of Table A;

Table 318 Compounds of formula I.B7 (I.B7-18.1-I.B7-18.2304) in which B is N, $R^2$ is $OCH_2CH_3$, $R^4$ is CN and $R^5$ is Cl and the combination of $R^1$, $R^3$, $R^6$ and $R^7$ for a compound corresponds in each case to one row of Table A;

Table 319 Compounds of formula I.B7 (I.B7-19.1-I.B7-19.2304) in which B is N, $R^2$ is $OCH_2CH_3$, $R^4$ is $CH_3$ and $R^5$ is F and the combination of $R^1$, $R^3$, $R^6$ and $R^7$ for a compound corresponds in each case to one row of Table A;

Table 320 Compounds of formula I.B7 (I.B7-20.1-I.B7-20.2304) in which B is N, $R^2$ is $OCH_2CH_3$, $R^4$ is $CH_3$ and $R^5$ is Cl and the combination of $R^1$, $R^3$, $R^6$ and $R^7$ for a compound corresponds in each case to one row of Table A;

Table 321 Compounds of formula I.B8 (I.B8-11.1-I.B8-11.2304) in which B is N, $R^2$ is $OCHF_2$, $R^4$ is H and $R^5$ is F and the combination of $R^1$, $R^3$, $R^6$ and $R^7$ for a compound corresponds in each case to one row of Table A;

Table 322 Compounds of formula I.B8 (I.B8-12.1-I.B8-12.2304) in which B is N, $R^2$ is $OCHF_2$, $R^4$ is H and $R^5$ is Cl and the combination of $R^1$, $R^3$, $R^6$ and $R^7$ for a compound corresponds in each case to one row of Table A;

Table 323 Compounds of formula I.B8 (I.B8-13.1-I.B8-13.2304) in which B is N, $R^2$ is $OCHF_2$, $R^4$ is F and $R^5$ is F and the combination of $R^1$, $R^3$, $R^6$ and $R^7$ for a compound corresponds in each case to one row of Table A;

Table 324 Compounds of formula I.B8 (I.B8-14.1-I.B8-14.2304) in which B is N, $R^2$ is $OCHF_2$, $R^4$ is F and $R^5$ is Cl and the combination of $R^1$, $R^3$, $R^6$ and $R^7$ for a compound corresponds in each case to one row of Table A;

Table 325 Compounds of formula I.B8 (I.B8-15.1-I.B8-15.2304) in which B is N, $R^2$ is $OCHF_2$, $R^4$ is Cl and $R^5$ is F and the combination of $R^1$, $R^3$, $R^6$ and $R^7$ for a compound corresponds in each case to one row of Table A;

Table 326 Compounds of formula I.B8 (I.B8-16.1-I.B8-16.2304) in which B is N, $R^2$ is $OCHF_2$, $R^4$ is Cl and $R^5$ Table 327 Compounds of formula I.B8 (I.B8-17.1-I.B8-17.2304) in which B is N, $R^2$ is $OCHF_2$, $R^4$ is CN and $R^5$ is F and the combination of $R^1$, $R^3$, $R^6$ and $R^7$ for a compound corresponds in each case to one row of Table A;

Table 328 Compounds of formula I.B8 (I.B8-18.1-I.B8-18.2304) in which B is N, $R^2$ is $OCHF_2$, $R^4$ is CN and $R^5$ is Cl and the combination of $R^1$, $R^3$, $R^6$ and $R^7$ for a compound corresponds in each case to one row of Table A;

Table 329 Compounds of formula I.B8 (I.B8-19.1-I.B8-19.2304) in which B is N, $R^2$ is $OCHF_2$, $R^4$ is $CH_3$ and $R^5$ is F and the combination of $R^1$, $R^3$, $R^6$ and $R^7$ for a compound corresponds in each case to one row of Table A;

Table 330 Compounds of formula I.B8 (I.B8-20.1-I.B8-20.2304) in which B is N, $R^2$ is $OCHF_2$, $R^4$ is $CH_3$ and $R^5$ is Cl and the combination of $R^1$, $R^3$, $R^6$ and $R^7$ for a compound corresponds in each case to one row of Table A;

Table 331 Compounds of formula I.B9 (I.B9-11.1-I.B9-11.2304) in which B is N, $R^2$ is $OCH_2CF_3$, $R^4$ is H and $R^5$ is F and the combination of $R^1$, $R^3$, $R^6$ and $R^7$ for a compound corresponds in each case to one row of Table A;

Table 332 Compounds of formula I.B9 (I.B9-12.1-I.B9-12.2304) in which B is N, $R^2$ is $OCH_2CF_3$, $R^4$ is H and $R^5$ is Cl and the combination of $R^1$, $R^3$, $R^6$ and $R^7$ for a compound corresponds in each case to one row of Table A;

Table 333 Compounds of formula I.B9 (I.B9-13.1-I.B9-13.2304) in which B is N, $R^2$ is $OCH_2CF_3$, $R^4$ is F and $R^5$ is F and the combination of $R^1$, $R^3$, $R^6$ and $R^7$ for a compound corresponds in each case to one row of Table A;

Table 334 Compounds of formula I.B9 (I.B9-14.1-I.B9-14.2304) in which B is N, $R^2$ is $OCH_2CF_3$, $R^4$ is F and $R^5$ is Cl and the combination of $R^1$, $R^3$, $R^6$ and $R^7$ for a compound corresponds in each case to one row of Table A;

Table 335 Compounds of formula I.B9 (I.B9-15.1-I.B9-15.2304) in which B is N, $R^2$ is $OCH_2CF_3$, $R^4$ is Cl and $R^5$ is F and the combination of $R^1$, $R^3$, $R^6$ and $R^7$ for a compound corresponds in each case to one row of Table A;

Table 336 Compounds of formula I.B9 (I.B9-16.1-I.B9-16.2304) in which B is N, $R^2$ is $OCH_2CF_3$, $R^4$ is Cl and $R^5$ is Cl and the combination of $R^1$, $R^3$, $R^6$ and $R^7$ for a compound corresponds in each case to one row of Table A;

Table 337 Compounds of formula I.B9 (I.B9-17.1-I.B9-17.2304) in which B is N, $R^2$ is $OCH_2CF_3$, $R^4$ is CN and $R^5$ is F and the combination of $R^1$, $R^3$, $R^6$ and $R^7$ for a compound corresponds in each case to one row of Table A;

Table 338 Compounds of formula I.B9 (I.B9-18.1-I.B9-18.2304) in which B is N, $R^2$ is $OCH_2CF_3$, $R^4$ is CN and $R^5$ is Cl and the combination of $R^1$, $R^3$, $R^6$ and $R^7$ for a compound corresponds in each case to one row of Table A;

Table 339 Compounds of formula I.B9 (I.B9-19.1-I.B9-19.2304) in which B is N, $R^2$ is $OCH_2CF_3$, $R^4$ is $CH_3$ and $R^5$ is F and the combination of $R^1$, $R^3$, $R^6$ and $R^7$ for a compound corresponds in each case to one row of Table A;

Table 340 Compounds of formula I.B9 (I.B9-20.1-I.B9-20.2304) in which B is N, $R^2$ is $OCH_2CF_3$, $R^4$ is $CH_3$ and $R^5$ is Cl and the combination of $R^1$, $R^3$, $R^6$ and $R^7$ for a compound corresponds in each case to one row of Table A;

Table 341 Compounds of formula I.B10 (I.B10-11.1-I.B10-11.2304) in which B is N, $R^2$ is $OCH_2CH_2OCH_3$, $R^4$ is H and $R^5$ is F and the combination of $R^1$, $R^3$, $R^6$ and $R^7$ for a compound corresponds in each case to one row of Table A;

Table 342 Compounds of formula I.B10 (I.B10-12.1-I.B10-12.2304) in which B is N, $R^2$ is $OCH_2CH_2OCH_3$, $R^4$ is H and $R^5$ is Cl and the combination of $R^1$, $R^3$, $R^6$ and $R^7$ for a compound corresponds in each case to one row of Table A;

Table 343 Compounds of formula I.B10 (I.B10-13.1-I.B10-13.2304) in which B is N, $R^2$ is $OCH_2CH_2OCH_3$, $R^4$ is F and $R^5$ is F and the combination of $R^1$, $R^3$, $R^6$ and $R^7$ for a compound corresponds in each case to one row of Table A;

Table 344 Compounds of formula I.B10 (I.B10-14.1-I.B10-14.2304) in which B is N, $R^2$ is $OCH_2CH_2OCH_3$, $R^4$ is F and $R^5$ is Cl and the combination of $R^1$, $R^3$, $R^6$ and $R^7$ for a compound corresponds in each case to one row of Table A;

Table 345 Compounds of formula I.B10 (I.B10-15.1-I.B10-15.2304) in which B is N, $R^2$ is $OCH_2CH_2OCH_3$, $R^4$ is Cl and $R^5$ is F and the combination of $R^1$, $R^3$, $R^6$ and $R^7$ for a compound corresponds in each case to one row of Table A;

Table 346 Compounds of formula I.B10 (I.B10-16.1-I.B10-16.2304) in which B is N, $R^2$ is $OCH_2CH_2OCH_3$, $R^4$ is Cl and $R^5$ is Cl and the combination of $R^1$, $R^3$, $R^6$ and $R^7$ for a compound corresponds in each case to one row of Table A;

Table 347 Compounds of formula I.B10 (I.B10-17.1-I.B10-17.2304) in which B is N, $R^2$ is $OCH_2CH_2OCH_3$, $R^4$ is CN and $R^5$ is F and the combination of $R^1$, $R^3$, $R^6$ and $R^7$ for a compound corresponds in each case to one row of Table A;

Table 348 Compounds of formula I.B10 (I.B10-18.1-I.B10-18.2304) in which B is N, $R^2$ is $OCH_2CH_2OCH_3$, $R^4$ is CN and $R^5$ is Cl and the combination of $R^1$, $R^3$, $R^6$ and $R^7$ for a compound corresponds in each case to one row of Table A;

Table 349 Compounds of formula I.B10 (I.B10-19.1-I.B10-19.2304) in which B is N, $R^2$ is $OCH_2CH_2OCH_3$, $R^4$ is $CH_3$ and $R^5$ is F and the combination of $R^1$, $R^3$, $R^6$ and $R^7$ for a compound corresponds in each case to one row of Table A;

Table 350 Compounds of formula I.B10 (I.B10-20.1-I.B10-20.2304) in which B is N, $R^2$ is $OCH_2CH_2OCH_3$, $R^4$ is $CH_3$ and $R^5$ is Cl and the combination of $R^1$, $R^3$, $R^6$ and $R^7$ for a compound corresponds in each case to one row of Table A;

Table 351 Compounds of formula I.B11 (I.B11-11.1-I.B11-11.2304) in which B is N, $R^2$ is H, $R^4$ is H and $R^5$ is F and the combination of $R^1$, $R^3$, $R^6$ and $R^7$ for a compound corresponds in each case to one row of Table A;

Table 352 Compounds of formula I.B11 (I.B11-12.1-I.B11-12.2304) in which B is N, $R^2$ is H, $R^4$ is H and $R^5$ is Cl and the combination of $R^1$, $R^3$, $R^6$ and $R^7$ for a compound corresponds in each case to one row of Table A;

Table 353 Compounds of formula I.B11 (I.B11-13.1-I.B11-13.2304) in which B is N, $R^2$ is H, $R^4$ is F and $R^5$ is F and the combination of $R^1$, $R^3$, $R^6$ and $R^7$ for a compound corresponds in each case to one row of Table A;

Table 354 Compounds of formula I.B11 (I.B11-14.1-I.B11-14.2304) in which B is N, $R^2$ is H, $R^4$ is F and $R^5$ is Cl and the combination of $R^1$, $R^3$, $R^6$ and $R^7$ for a compound corresponds in each case to one row of Table A;

Table 355 Compounds of formula I.B11 (I.B11-15.1-I.B11-15.2304) in which B is N, $R^2$ is H, $R^4$ is Cl and $R^5$ is F and the combination of $R^1$, $R^3$, $R^6$ and $R^7$ for a compound corresponds in each case to one row of Table A;

Table 356 Compounds of formula I.B11 (I.B11-16.1-I.B11-16.2304) in which B is N, $R^2$ is H, $R^4$ is Cl and $R^5$ is Cl and the combination of $R^1$, $R^3$, $R^6$ and $R^7$ for a compound corresponds in each case to one row of Table A;

Table 357 Compounds of formula I.B11 (I.B11-17.1-I.B11-17.2304) in which B is N, $R^2$ is H, $R^4$ is CN and $R^5$ is F and the combination of $R^1$, $R^3$, $R^6$ and $R^7$ for a compound corresponds in each case to one row of Table A;

Table 358 Compounds of formula I.B11 (I.B11-18.1-I.B11-18.2304) in which B is N, $R^2$ is H, $R^4$ is CN and $R^5$ is Cl and the combination of $R^1$, $R^3$, $R^6$ and $R^7$ for a compound corresponds in each case to one row of Table A;

Table 359 Compounds of formula I.B11 (I.B11-19.1-I.B11-19.2304) in which B is N, $R^2$ is H, $R^4$ is $CH_3$ and $R^5$ is F and the combination of $R^1$, $R^3$, $R^6$ and $R^7$ for a compound corresponds in each case to one row of Table A;

Table 360 Compounds of formula I.B11 (I.B11-20.1-I.B11-20.2304) in which B is N, $R^2$ is H, $R^4$ is $CH_3$ and $R^5$ is Cl and the combination of $R^1$, $R^3$, $R^6$ and $R^7$ for a compound corresponds in each case to one row of Table A;

Table 361 Compounds of formula I.B12 (I.B12-11.1-I.B12-11.2304) in which B is N, $R^2$ is $SO_2CH_3$, $R^4$ is H and $R^5$ is F and the combination of $R^1$, $R^3$, $R^6$ and $R^7$ for a compound corresponds in each case to one row of Table A;

Table 362 Compounds of formula I.B12 (I.B12-12.1-I.B12-12.2304) in which B is N, $R^2$ is $SO_2CH_3$, $R^4$ is H and $R^5$ is Cl and the combination of $R^1$, $R^3$, $R^6$ and $R^7$ for a compound corresponds in each case to one row of Table A;

Table 363 Compounds of formula I.B12 (I.B12-13.1-I.B12-13.2304) in which B is N, $R^2$ is $SO_2CH_3$, $R^4$ is F and $R^5$ is F and the combination of $R^1$, $R^3$, $R^6$ and $R^7$ for a compound corresponds in each case to one row of Table A;

Table 364 Compounds of formula I.B12 (I.B12-14.1-I.B12-14.2304) in which B is N, $R^2$ is $SO_2CH_3$, $R^4$ is F and $R^5$ is Cl and the combination of $R^1$, $R^3$, $R^6$ and $R^7$ for a compound corresponds in each case to one row of Table A;

Table 365 Compounds of formula I.B12 (I.B12-15.1-I.B12-15.2304) in which B is N, $R^2$ is $SO_2CH_3$, $R^4$ is Cl and $R^5$ is F and the combination of $R^1$, $R^3$, $R^6$ and $R^7$ for a compound corresponds in each case to one row of Table A;

Table 366 Compounds of formula I.B12 (I.B12-16.1-I.B12-16.2304) in which B is N, $R^2$ is $SO_2CH_3$, $R^4$ is Cl and $R^5$ is Cl and the combination of $R^1$, $R^3$, $R^6$ and $R^7$ for a compound corresponds in each case to one row of Table A;

Table 367 Compounds of formula I.B12 (I.B12-17.1-I.B12-17.2304) in which B is N, $R^2$ is $SO_2CH_3$, $R^4$ is CN and $R^5$ is F and the combination of $R^1$, $R^3$, $R^6$ and $R^7$ for a compound corresponds in each case to one row of Table A;

Table 368 Compounds of formula I.B12 (I.B12-18.1-I.B12-18.2304) in which B is N, $R^2$ is $SO_2CH_3$, $R^4$ is CN and $R^5$ is Cl and the combination of $R^1$, $R^3$, $R^6$ and $R^7$ for a compound corresponds in each case to one row of Table A;

Table 369 Compounds of formula I.B12 (I.B12-19.1-I.B12-19.2304) in which B is N, $R^2$ is $SO_2CH_3$, $R^4$ is $CH_3$ and $R^5$ is F and the combination of $R^1$, $R^3$, $R^6$ and $R^7$ for a compound corresponds in each case to one row of Table A;

Table 370 Compounds of formula I.B12 (I.B12-20.1-I.B12-20.2304) in which B is N, $R^2$ is $SO_2CH_3$, $R^4$ is $CH_3$ and $R^5$ is Cl and the combination of $R^1$, $R^3$, $R^6$ and $R^7$ for a compound corresponds in each case to one row of Table A;

Table 371 Compounds of formula I.B13 (I.B13-11.1-I.B13-11.2304) in which B is N, $R^2$ is $CH_2OCH_2CF_3$, $R^4$ is H and $R^5$ is F and the combination of $R^1$, $R^3$, $R^6$ and $R^7$ for a compound corresponds in each case to one row of Table A;

Table 372 Compounds of formula I.B13 (I.B13-12.1-I.B13-12.2304) in which B is N, $R^2$ is $CH_2OCH_2CF_3$, $R^4$ is H and $R^5$ is Cl and the combination of $R^1$, $R^3$, $R^6$ and $R^7$ for a compound corresponds in each case to one row of Table A;

Table 373 Compounds of formula I.B13 (I.B13-13.1-I.B13-13.2304) in which B is N, $R^2$ is $CH_2OCH_2CF_3$, $R^4$ is F and $R^5$ is F and the combination of $R^1$, $R^3$, $R^6$ and $R^7$ for a compound corresponds in each case to one row of Table A;

Table 374 Compounds of formula I.B13 (I.B13-14.1-I.B13-14.2304) in which B is N, $R^2$ is $CH_2OCH_2CF_3$, $R^4$ is F and $R^5$ is Cl and the combination of $R^1$, $R^3$, $R^6$ and $R^7$ for a compound corresponds in each case to one row of Table A;

Table 375 Compounds of formula I.B13 (I.B13-15.1-I.B13-15.2304) in which B is N, $R^2$ is $CH_2OCH_2CF_3$, $R^4$ is Cl and $R^5$ is F and the combination of $R^1$, $R^3$, $R^6$ and $R^7$ for a compound corresponds in each case to one row of Table A;

Table 376 Compounds of formula I.B13 (I.B13-16.1-I.B13-16.2304) in which B is N, $R^2$ is $CH_2OCH_2CF_3$, $R^4$ is Cl and $R^5$ is Cl and the combination of $R^1$, $R^3$, $R^6$ and $R^7$ for a compound corresponds in each case to one row of Table A;

Table 377 Compounds of formula I.B13 (I.B13-17.1-I.B13-17.2304) in which B is N, $R^2$ is $CH_2OCH_2CF_3$, $R^4$ is CN and $R^5$ is F and the combination of $R^1$, $R^3$, $R^6$ and $R^7$ for a compound corresponds in each case to one row of Table A;

Table 378 Compounds of formula I.B13 (I.B13-18.1-I.B13-18.2304) in which B is N, $R^2$ is $CH_2OCH_2CF_3$, $R^4$ is CN and $R^5$ is Cl and the combination of $R^1$, $R^3$, $R^6$ and $R^7$ for a compound corresponds in each case to one row of Table A;

Table 379 Compounds of formula I.B13 (I.B13-19.1-I.B13-19.2304) in which B is N, $R^2$ is $CH_2OCH_2CF_3$, $R^4$ is $CH_3$ and $R^5$ is F and the combination of $R^1$, $R^3$, $R^6$ and $R^7$ for a compound corresponds in each case to one row of Table A;

Table 380 Compounds of formula I.B13 (I.B13-20.1-I.B13-20.2304) in which B is N, $R^2$ is $CH_2OCH_2CF_3$, $R^4$ is $CH_3$ and $R^5$ is Cl and the combination of $R^1$, $R^3$, $R^6$ and $R^7$ for a compound corresponds in each case to one row of Table A;

Table 381 Compounds of formula I.B14 (I.B14-11.1-I.B14-11.2304) in which B is N, $R^2$ is isoxazolin-3-yl, $R^4$ is H and R⁵ is F and the combination of R¹, R³, R⁶ and R⁷ for a compound corresponds in each case to one row of Table A;

Table 382 Compounds of formula I.B14 (I.B14-12.1-I.B14-12.2304) in which B is N, R² is isoxazolin-3-yl, R⁴ is H and R⁵ is Cl and the combination of R¹, R³, R⁶ and R⁷ for a compound corresponds in each case to one row of Table A;

Table 383 Compounds of formula I.B14 (I.B14-13.1-I.B14-13.2304) in which B is N, R² is isoxazolin-3-yl, R⁴ is F and R⁵ is F and the combination of R¹, R³, R⁶ and R⁷ for a compound corresponds in each case to one row of Table A;

Table 384 Compounds of formula I.B14 (I.B14-14.1-I.B14-14.2304) in which B is N, R² is isoxazolin-3-yl, R⁴ is F and R⁵ is Cl and the combination of R¹, R³, R⁶ and R⁷ for a compound corresponds in each case to one row of Table A;

Table 385 Compounds of formula I.B14 (I.B14-15.1-I.B14-15.2304) in which B is N, R² is isoxazolin-3-yl, R⁴ is Cl and R⁵ is F and the combination of R¹, R³, R⁶ and R⁷ for a compound corresponds in each case to one row of Table A;

Table 386 Compounds of formula I.B14 (I.B14-16.1-I.B14-16.2304) in which B is N, R² is isoxazolin-3-yl, R⁴ is Cl and R⁵ is Cl and the combination of R¹, R³, R⁶ and R⁷ for a compound corresponds in each case to one row of Table A;

Table 387 Compounds of formula I.B14 (I.B14-17.1-I.B14-17.2304) in which B is N, R² is isoxazolin-3-yl, R⁴ is CN and R⁵ is F and the combination of R¹, R³, R⁶ and R⁷ for a compound corresponds in each case to one row of Table A;

Table 388 Compounds of formula I.B14 (I.B14-18.1-I.B14-18.2304) in which B is N, R² is isoxazolin-3-yl, R⁴ is CN and R⁵ is Cl and the combination of R¹, R³, R⁶ and R⁷ for a compound corresponds in each case to one row of Table A;

Table 389 Compounds of formula I.B14 (I.B14-19.1-I.B14-19.2304) in which B is N, R² is isoxazolin-3-yl, R⁴ is CH₃ and R⁵ is F and the combination of R¹, R³, R⁶ and R⁷ for a compound corresponds in each case to one row of Table A;

Table 390 Compounds of formula I.B14 (I.B14-20.1-I.B14-20.2304) in which B is N, R² is isoxazolin-3-yl, R⁴ is CH₃ and R⁵ is Cl and the combination of R¹, R³, R⁶ and R⁷ for a compound corresponds in each case to one row of Table A;

Table 391 Compounds of formula I.B15 (I.B15-11.1-I.B15-11.2304) in which B is N, R² is 5-methyl-isoxazolin-3-yl, R⁴ is H and R⁵ is F and the combination of R¹, R³, R⁶ and R⁷ for a compound corresponds in each case to one row of Table A;

Table 392 Compounds of formula I.B15 (I.B15-12.1-I.B15-12.2304) in which B is N, R² is 5-methyl-isoxazolin-3-yl, R⁴ is H and R⁵ is Cl and the combination of R¹, R³, R⁶ and R⁷ for a compound corresponds in each case to one row of Table A;

Table 393 Compounds of formula I.B15 (I.B15-13.1-I.B15-13.2304) in which B is N, R² is 5-methyl-isoxazolin-3-yl, R⁴ is F and R⁵ is F and the combination of R¹, R³, R⁶ and R⁷ for a compound corresponds in each case to one row of Table A;

Table 394 Compounds of formula I.B15 (I.B15-14.1-I.B15-14.2304) in which B is N, R² is 5-methyl-isoxazolin-3-yl, R⁴ is F and R⁵ is Cl and the combination of R¹, R³, R⁶ and R⁷ for a compound corresponds in each case to one row of Table A;

Table 395 Compounds of formula I.B15 (I.B15-15.1-I.B15-15.2304) in which B is N, R² is 5-methyl-isoxazolin-3-yl, R⁴ is Cl and R⁵ is F and the combination of R¹, R³, R⁶ and R⁷ for a compound corresponds in each case to one row of Table A;

Table 396 Compounds of formula I.B15 (I.B15-16.1-I.B15-16.2304) in which B is N, R² is 5-methyl-isoxazolin-3-yl, R⁴ is Cl and R⁵ is Cl and the combination of R¹, R³, R⁶ and R⁷ for a compound corresponds in each case to one row of Table A;

Table 397 Compounds of formula I.B15 (I.B15-17.1-I.B15-17.2304) in which B is N, R² is 5-methyl-isoxazolin-3-yl, R⁴ is CN and R⁵ is F and the combination of R¹, R³, R⁶ and R⁷ for a compound corresponds in each case to one row of Table A;

Table 398 Compounds of formula I.B15 (I.B15-18.1-I.B15-18.2304) in which B is N, R² is 5-methyl-isoxazolin-3-yl, R⁴ is CN and R⁵ is Cl and the combination of R¹, R³, R⁶ and R⁷ for a compound corresponds in each case to one row of Table A;

Table 399 Compounds of formula I.B15 (I.B15-19.1-I.B15-19.2304) in which B is N, R² is 5-methyl-isoxazolin-3-yl, R⁴ is CH₃ and R⁵ is F and the combination of R¹, R³, R⁶ and R⁷ for a compound corresponds in each case to one row of Table A;

Table 400 Compounds of formula I.B15 (I.B15-20.1-I.B15-20.2304) in which B is N, R² is 5-methyl-isoxazolin-3-yl, R⁴ is CH₃ and R⁵ is Cl and the combination of R¹, R³, R⁶ and R⁷ for a compound corresponds in each case to one row of Table A;

Table 401 Compounds of formula I.B16 (I.B16-11.1-I.B16-11.2304) in which B is N, R² is isoxazol-3-yl, R⁴ is H and R⁵ is F and the combination of R¹, R³, R⁶ and R⁷ for a compound corresponds in each case to one row of Table A;

Table 402 Compounds of formula I.B16 (I.B16-12.1-I.B16-12.2304) in which B is N, R² is isoxazol-3-yl, R⁴ is H and R⁵ is Cl and the combination of R¹, R³, R⁶ and R⁷ for a compound corresponds in each case to one row of Table A;

Table 403 Compounds of formula I.B16 (I.B16-13.1-I.B16-13.2304) in which B is N, R² is isoxazol-3-yl, R⁴ is F and R⁵ is F and the combination of R¹, R³, R⁶ and R⁷ for a compound corresponds in each case to one row of Table A;

Table 404 Compounds of formula I.B16 (I.B16-14.1-I.B16-14.2304) in which B is N, R² is isoxazol-3-yl, R⁴ is F and R⁵ is Cl and the combination of R¹, R³, R⁶ and R⁷ for a compound corresponds in each case to one row of Table A;

Table 405 Compounds of formula I.B16 (I.B16-15.1-I.B16-15.2304) in which B is N, R² is isoxazol-3-yl, R⁴ is Cl and R⁵ is F and the combination of R¹, R³, R⁶ and R⁷ for a compound corresponds in each case to one row of Table A;

Table 406 Compounds of formula I.B16 (I.B16-16.1-I.B16-16.2304) in which B is N, R² is isoxazol-3-yl, R⁴ is Cl and R⁵ is Cl and the combination of R¹, R³, R⁶ and R⁷ for a compound corresponds in each case to one row of Table A;

Table 407 Compounds of formula I.B16 (I.B16-17.1-I.B16-17.2304) in which B is N, R² is isoxazol-3-yl, R⁴ is CN and R⁵ is F and the combination of R¹, R³, R⁶ and R⁷ for a compound corresponds in each case to one row of Table A;

Table 408 Compounds of formula I.B16 (I.B16-18.1-I.B16-18.2304) in which B is N, R² is isoxazol-3-yl, R⁴ is CN and R⁵ is Cl and the combination of R¹, R³, R⁶ and R⁷ for a compound corresponds in each case to one row of Table A;

Table 409 Compounds of formula I.B16 (I.B16-19.1-I.B16-19.2304) in which B is N, R² is isoxazol-3-yl, R⁴ is CH₃ and R⁵ is F and the combination of R¹, R³, R⁶ and R⁷ for a compound corresponds in each case to one row of Table A;

Table 410 Compounds of formula I.B16 (I.B16-20.1-I.B16-20.2304) in which B is N, R² is isoxazol-3-yl, R⁴ is CH₃ and R⁵ is Cl and the combination of R¹, R³, R⁶ and R⁷ for a compound corresponds in each case to one row of Table A;

Table 411 Compounds of formula I.B17 (I.B17-11.1-I.B17-11.2304) in which B is N, R² is 5-methyl-isoxazol-3-yl, R⁴ is H and R⁵ is F and the combination of R¹, R³, R⁶ and R⁷ for a compound corresponds in each case to one row of Table A;

Table 412 Compounds of formula I.B17 (I.B17-12.1-I.B17-12.2304) in which B is N, R² is 5-methyl-isoxazol-3-yl, R⁴ is H and R⁵ is Cl and the combination of R¹, R³, R⁶ and R⁷ for a compound corresponds in each case to one row of Table A;

Table 413 Compounds of formula I.B17 (I.B17-13.1-I.B17-13.2304) in which B is N, R² is 5-methyl-isoxazol-3-yl, R⁴ is F and R⁵ is F and the combination of R¹, R³, R⁶ and R⁷ for a compound corresponds in each case to one row of Table A;

Table 414 Compounds of formula I.B17 (I.B17-14.1-I.B17-14.2304) in which B is N, R² is 5-methyl-isoxazol-3-yl, R⁴ is F and R⁵ is Cl and the combination of R¹, R³, R⁶ and R⁷ for a compound corresponds in each case to one row of Table A;

Table 415 Compounds of formula I.B17 (I.B17-15.1-I.B17-15.2304) in which B is N, R² is 5-methyl-isoxazol-3-yl, R⁴ is Cl and R⁵ is F and the combination of R¹, R³, R⁶ and R⁷ for a compound corresponds in each case to one row of Table A;

Table 416 Compounds of formula I.B17 (I.B17-16.1-I.B17-16.2304) in which B is N, R² is 5-methyl-isoxazol-3-yl, R⁴ is Cl and R⁵ is Cl and the combination of R¹, R³, R⁶ and R⁷ for a compound corresponds in each case to one row of Table A;

Table 417 Compounds of formula I.B17 (I.B17-17.1-I.B17-17.2304) in which B is N, R² is 5-methyl-isoxazol-3-yl, R⁴ is CN and R⁵ is F and the combination of R¹, R³, R⁶ and R⁷ for a compound corresponds in each case to one row of Table A;

Table 418 Compounds of formula I.B17 (I.B17-18.1-I.B17-18.2304) in which B is N, R² is 5-methyl-isoxazol-3-yl, R⁴ is CN and R⁵ is Cl and the combination of R¹, R³, R⁶ and R⁷ for a compound corresponds in each case to one row of Table A;

Table 419 Compounds of formula I.B17 (I.B17-19.1-I.B17-19.2304) in which B is N, R² is 5-methyl-isoxazol-3-yl, R⁴ is CH₃ and R⁵ is F and the combination of R¹, R³, R⁶ and R⁷ for a compound corresponds in each case to one row of Table A;

Table 420 Compounds of formula I.B17 (I.B17-20.1-I.B17-20.2304) in which B is N, R² is 5-methyl-isoxazol-3-yl, R⁴ is CH₃ and R⁵ is Cl and the combination of R¹, R³, R⁶ and R⁷ for a compound corresponds in each case to one row of Table A;

Table 421 Compounds of formula I.B18 (I.B18-11.1-I.B18-11.2304) in which B is N, R² is 3-methyl-isoxazolin-5-yl, R⁴ is H and R⁵ is F and the combination of R¹, R³, R⁶ and R⁷ for a compound corresponds in each case to one row of Table A;

Table 422 Compounds of formula I.B18 (I.B18-12.1-I.B18-12.2304) in which B is N, R² is 3-methyl-isoxazolin-5-yl, R⁴ is H and R⁵ is Cl and the combination of R¹, R³, R⁶ and R⁷ for a compound corresponds in each case to one row of Table A;

Table 423 Compounds of formula I.B18 (I.B18-13.1-I.B18-13.2304) in which B is N, R² is 3-methyl-isoxazolin-5-yl, R⁴ is F and R⁵ is F and the combination of R¹, R³, R⁶ and R⁷ for a compound corresponds in each case to one row of Table A;

Table 424 Compounds of formula I.B18 (I.B18-14.1-I.B18-14.2304) in which B is N, R² is 3-methyl-isoxazolin-5-yl, R⁴ is F and R⁵ is Cl and the combination of R¹, R³, R⁶ and R⁷ for a compound corresponds in each case to one row of Table A;

Table 425 Compounds of formula I.B18 (I.B18-15.1-I.B18-15.2304) in which B is N, R² is 3-methyl-isoxazolin-5-yl, R⁴ is Cl and R⁵ is F and the combination of R¹, R³, R⁶ and R⁷ for a compound corresponds in each case to one row of Table A;

Table 426 Compounds of formula I.B18 (I.B18-16.1-I.B18-16.2304) in which B is N, R² is 3-methyl-isoxazolin-5-yl, R⁴ is Cl and R⁵ is Cl and the combination of R¹, R³, R⁶ and R⁷ for a compound corresponds in each case to one row of Table A;

Table 427 Compounds of formula I.B18 (I.B18-17.1-I.B18-17.2304) in which B is N, R² is 3-methyl-isoxazolin-5-yl, R⁴ is CN and R⁵ is F and the combination of R¹, R³, R⁶ and R⁷ for a compound corresponds in each case to one row of Table A;

Table 428 Compounds of formula I.B18 (I.B18-18.1-I.B18-18.2304) in which B is N, R² is 3-methyl-isoxazolin-5-yl, R⁴ is CN and R⁵ is Cl and the combination of R¹, R³, R⁶ and R⁷ for a compound corresponds in each case to one row of Table A;

Table 429 Compounds of formula I.B18 (I.B18-19.1-I.B18-19.2304) in which B is N, R² is 3-methyl-isoxazolin-5-yl, R⁴ is CH₃ and R⁵ is F and the combination of R¹, R³, R⁶ and R⁷ for a compound corresponds in each case to one row of Table A;

Table 430 Compounds of formula I.B18 (I.B18-20.1-I.B18-20.2304) in which B is N, R² is 3-methyl-isoxazolin-5-yl, R⁴ is CH₃ and R⁵ is Cl and the combination of R¹, R³, R⁶ and R⁷ for a compound corresponds in each case to one row of Table A;

Table 431 Compounds of formula I.B19 (I.B19-11.1-I.B19-11.2304) in which B is N, R² is 3-methyl-isoxazol-5-yl, R⁴ is H and R⁵ is F and the combination of R¹, R³, R⁶ and R⁷ for a compound corresponds in each case to one row of Table A;

Table 432 Compounds of formula I.B19 (I.B19-12.1-I.B19-12.2304) in which B is N, R² is 3-methyl-isoxazol-5-yl, R⁴ is H and R⁵ is Cl and the combination of R¹, R³, R⁶ and R⁷ for a compound corresponds in each case to one row of Table A;

Table 433 Compounds of formula I.B19 (I.B19-13.1-I.B19-13.2304) in which B is N, R² is 3-methyl-isoxazol-5-yl, $R^4$ is F and $R^5$ is F and the combination of $R^1$, $R^3$, $R^6$ and $R^7$ for a compound corresponds in each case to one row of Table A;

Table 434 Compounds of formula I.B19 (I.B19-14.1-I.B19-14.2304) in which B is N, $R^2$ is 3-methyl-isoxazol-5-yl, $R^4$ is F and $R^5$ is Cl and the combination of $R^1$, $R^3$, $R^6$ and $R^7$ for a compound corresponds in each case to one row of Table A;

Table 435 Compounds of formula I.B19 (I.B19-15.1-I.B19-15.2304) in which B is N, $R^2$ is 3-methyl-isoxazol-5-yl, $R^4$ is Cl and $R^5$ is F and the combination of $R^1$, $R^3$, $R^6$ and $R^7$ for a compound corresponds in each case to one row of Table A;

Table 436 Compounds of formula I.B19 (I.B19-16.1-I.B19-16.2304) in which B is N, $R^2$ is 3-methyl-isoxazol-5-yl, $R^4$ is Cl and $R^5$ is Cl and the combination of $R^1$, $R^3$, $R^6$ and $R^7$ for a compound corresponds in each case to one row of Table A;

Table 437 Compounds of formula I.B19 (I.B19-17.1-I.B19-17.2304) in which B is N, $R^2$ is 3-methyl-isoxazol-5-yl, $R^4$ is CN and $R^5$ is F and the combination of $R^1$, $R^3$, $R^6$ and $R^7$ for a compound corresponds in each case to one row of Table A;

Table 438 Compounds of formula I.B19 (I.B19-18.1-I.B19-18.2304) in which B is N, $R^2$ is 3-methyl-isoxazol-5-yl, $R^4$ is CN and $R^5$ is Cl and the combination of $R^1$, $R^3$, $R^6$ and $R^7$ for a compound corresponds in each case to one row of Table A;

Table 439 Compounds of formula I.B19 (I.B19-19.1-I.B19-19.2304) in which B is N, $R^2$ is 3-methyl-isoxazol-5-yl, $R^4$ is $CH_3$ and $R^5$ is F and the combination of $R^1$, $R^3$, $R^6$ and $R^7$ for a compound corresponds in each case to one row of Table A;

Table 440 Compounds of formula I.B19 (I.B19-20.1-I.B19-20.2304) in which B is N, $R^2$ is 3-methyl-isoxazol-5-yl, $R^4$ is $CH_3$ and $R^5$ is Cl and the combination of $R^1$, $R^3$, $R^6$ and $R^7$ for a compound corresponds in each case to one row of Table A;

Table 441 Compounds of formula I.B20 (I.B20-11.1-I.B20-11.2304) in which B is N, $R^2$ is $CH_3$, $R^4$ is H and $R^5$ is F and the combination of $R^1$, $R^3$, $R^6$ and $R^7$ for a compound corresponds in each case to one row of Table A;

Table 442 Compounds of formula I.B20 (I.B20-12.1-I.B20-12.2304) in which B is N, $R^2$ is $CH_3$, $R^4$ is H and $R^5$ is Cl and the combination of $R^1$, $R^3$, $R^6$ and $R^7$ for a compound corresponds in each case to one row of Table A;

Table 443 Compounds of formula I.B20 (I.B20-13.1-I.B20-13.2304) in which B is N, $R^2$ is $CH_3$, $R^4$ is F and $R^5$ is F and the combination of $R^1$, $R^3$, $R^6$ and $R^7$ for a compound corresponds in each case to one row of Table A;

Table 444 Compounds of formula I.B20 (I.B20-14.1-I.B20-14.2304) in which B is N, $R^2$ is $CH_3$, $R^4$ is F and $R^5$ is Cl and the combination of $R^1$, $R^3$, $R^6$ and $R^7$ for a compound corresponds in each case to one row of Table A;

Table 445 Compounds of formula I.B20 (I.B20-15.1-I.B20-15.2304) in which B is N, $R^2$ is $CH_3$, $R^4$ is Cl and $R^5$ is F and the combination of $R^1$, $R^3$, $R^6$ and $R^7$ for a compound corresponds in each case to one row of Table A;

Table 446 Compounds of formula I.B20 (I.B20-16.1-I.B20-16.2304) in which B is N, $R^2$ is $CH_3$, $R^4$ is Cl and $R^5$ is Cl and the combination of $R^1$, $R^3$, $R^6$ and $R^7$ for a compound corresponds in each case to one row of Table A;

Table 447 Compounds of formula I.B20 (I.B20-17.1-I.B20-17.2304) in which B is N, $R^2$ is $CH_3$, $R^4$ is CN and $R^5$ is F and the combination of $R^1$, $R^3$, $R^6$ and $R^7$ for a compound corresponds in each case to one row of Table A;

Table 448 Compounds of formula I.B20 (I.B20-18.1-I.B20-18.2304) in which B is N, $R^2$ is $CH_3$, $R^4$ is CN and $R^5$ is Cl and the combination of $R^1$, $R^3$, $R^6$ and $R^7$ for a compound corresponds in each case to one row of Table A;

Table 449 Compounds of formula I.B20 (I.B20-19.1-I.B20-19.2304) in which B is N, $R^2$ is $CH_3$, $R^4$ is $CH_3$ and $R^5$ is F and the combination of $R^1$, $R^3$, $R^6$ and $R^7$ for a compound corresponds in each case to one row of Table A;

Table 450 Compounds of formula I.B20 (I.B20-20.1-I.B20-20.2304) in which B is N, $R^2$ is $CH_3$, $R^4$ is $CH_3$ and $R^5$ is Cl and the combination of $R^1$, $R^3$, $R^6$ and $R^7$ for a compound corresponds in each case to one row of Table A;

Table 451 Compounds of formula I.B21 (I.B21-11.1-I.B21-11.2304) in which B is N, $R^2$ is $CH_2OCH_3$, $R^4$ is H and $R^5$ is F and the combination of $R^1$, $R^3$, $R^6$ and $R^7$ for a compound corresponds in each case to one row of Table A;

Table 452 Compounds of formula I.B21 (I.B21-12.1-I.B21-12.2304) in which B is N, $R^2$ is $CH_2OCH_3$, $R^4$ is H and $R^5$ is Cl and the combination of $R^1$, $R^3$, $R^6$ and $R^7$ for a compound corresponds in each case to one row of Table A;

Table 453 Compounds of formula I.B21 (I.B21-13.1-I.B21-13.2304) in which B is N, $R^2$ is $CH_2OCH_3$, $R^4$ is F and $R^5$ is F and the combination of $R^1$, $R^3$, $R^6$ and $R^7$ for a compound corresponds in each case to one row of Table A;

Table 454 Compounds of formula I.B21 (I.B21-14.1-I.B21-14.2304) in which B is N, $R^2$ is $CH_2OCH_3$, $R^4$ is F and $R^5$ is Cl and the combination of $R^1$, $R^3$, $R^6$ and $R^7$ for a compound corresponds in each case to one row of Table A;

Table 455 Compounds of formula I.B21 (I.B21-15.1-I.B21-15.2304) in which B is N, $R^2$ is $CH_2OCH_3$, $R^4$ is Cl and $R^5$ is F and the combination of $R^1$, $R^3$, $R^6$ and $R^7$ for a compound corresponds in each case to one row of Table A;

Table 456 Compounds of formula I.B21 (I.B21-16.1-I.B21-16.2304) in which B is N, $R^2$ is $CH_2OCH_3$, $R^4$ is Cl and $R^5$ is Cl and the combination of $R^1$, $R^3$, $R^6$ and $R^7$ for a compound corresponds in each case to one row of Table A;

Table 457 Compounds of formula I.B21 (I.B21-17.1-I.B21-17.2304) in which B is N, $R^2$ is $CH_2OCH_3$, $R^4$ is CN and $R^5$ is F and the combination of $R^1$, $R^3$, $R^6$ and $R^7$ for a compound corresponds in each case to one row of Table A;

Table 458 Compounds of formula I.B21 (I.B21-18.1-I.B21-18.2304) in which B is N, $R^2$ is $CH_2OCH_3$, $R^4$ is CN and $R^5$ is Cl and the combination of $R^1$, $R^3$, $R^6$ and $R^7$ for a compound corresponds in each case to one row of Table A;

Table 459 Compounds of formula I.B21 (I.B21-19.1-I.B21-19.2304) in which B is N, $R^2$ is $CH_2OCH_3$, $R^4$ is $CH_3$ and $R^5$ is F and the combination of $R^1$, $R^3$, $R^6$ and $R^7$ for a compound corresponds in each case to one row of Table A;

Table 460 Compounds of formula I.B21 (I.B21-20.1-I.B21-20.2304) in which B is N, $R^2$ is $CH_2OCH_3$, $R^4$ is $CH_3$ and $R^5$ is Cl and the combination of $R^1$, $R^3$, $R^6$ and $R^7$ for a compound corresponds in each case to one row of Table A;

Table 461 Compounds of formula I.B22 (I.B22-11.1-I.B22-11.2304) in which B is N, $R^2$ is $OCH_2CH(CH_2)_2$, $R^4$ is H and $R^5$ is F and the combination of $R^1$, $R^3$, $R^6$ and $R^7$ for a compound corresponds in each case to one row of Table A;

Table 462 Compounds of formula I.B22 (I.B22-12.1-I.B22-12.2304) in which B is N, $R^2$ is $OCH_2CH(CH_2)_2$, $R^4$ is H and $R^5$ is Cl and the combination of $R^1$, $R^3$, $R^6$ and $R^7$ for a compound corresponds in each case to one row of Table A;

Table 463 Compounds of formula I.B22 (I.B22-13.1-I.B22-13.2304) in which B is N, $R^2$ is $OCH_2CH(CH_2)_2$, $R^4$ is F and $R^5$ is F and the combination of $R^1$, $R^3$, $R^6$ and $R^7$ for a compound corresponds in each case to one row of Table A;

Table 464 Compounds of formula I.B22 (I.B22-14.1-I.B22-14.2304) in which B is N, $R^2$ is $OCH_2CH(CH_2)_2$, $R^4$ is F and $R^5$ is Cl and the combination of $R^1$, $R^3$, $R^6$ and $R^7$ for a compound corresponds in each case to one row of Table A;

Table 465 Compounds of formula I.B22 (I.B22-15.1-I.B22-15.2304) in which B is N, $R^2$ is $OCH_2CH(CH_2)_2$, $R^4$ is Cl and $R^5$ is F and the combination of $R^1$, $R^3$, $R^6$ and $R^7$ for a compound corresponds in each case to one row of Table A;

Table 466 Compounds of formula I.B22 (I.B22-16.1-I.B22-16.2304) in which B is N, $R^2$ is $OCH_2CH(CH_2)_2$, $R^4$ is Cl and $R^5$ is Cl and the combination of $R^1$, $R^3$, $R^6$ and $R^7$ for a compound corresponds in each case to one row of Table A;

Table 467 Compounds of formula I.B22 (I.B22-17.1-I.B22-17.2304) in which B is N, $R^2$ is $OCH_2CH(CH_2)_2$, $R^4$ is CN and $R^5$ is F and the combination of $R^1$, $R^3$, $R^6$ and $R^7$ for a compound corresponds in each case to one row of Table A;

Table 468 Compounds of formula I.B22 (I.B22-18.1-I.B22-18.2304) in which B is N, $R^2$ is $OCH_2CH(CH_2)_2$, $R^4$ is CN and $R^5$ is Cl and the combination of $R^1$, $R^3$, $R^6$ and $R^7$ for a compound corresponds in each case to one row of Table A;

Table 469 Compounds of formula I.B22 (I.B22-19.1-I.B22-19.2304) in which B is N, $R^2$ is $OCH_2CH(CH_2)_2$, $R^4$ is $CH_3$ and $R^5$ is F and the combination of $R^1$, $R^3$, $R^6$ and $R^7$ for a compound corresponds in each case to one row of Table A;

Table 470 Compounds of formula I.B22 (I.B22-20.1-I.B22-20.2304) in which B is N, $R^2$ is $OCH_2CH(CH_2)_2$, $R^4$ is $CH_3$ and $R^5$ is Cl and the combination of $R^1$, $R^3$, $R^6$ and $R^7$ for a compound corresponds in each case to one row of Table A;

Table 471 Compounds of formula I.B23 (I.B23-11.1-I.B23-11.2304) in which B is N, $R^2$ is $NCH_3SO_2CH_3$, $R^4$ is H and $R^5$ is F and the combination of $R^1$, $R^3$, $R^6$ and $R^7$ for a compound corresponds in each case to one row of Table A;

Table 472 Compounds of formula I.B23 (I.B23-12.1-I.B23-12.2304) in which B is N, $R^2$ is $NCH_3SO_2CH_3$, $R^4$ is H and $R^5$ is Cl and the combination of $R^1$, $R^3$, $R^6$ and $R^7$ for a compound corresponds in each case to one row of Table A;

Table 473 Compounds of formula I.B23 (I.B23-13.1-I.B23-13.2304) in which B is N, $R^2$ is $NCH_3SO_2CH_3$, $R^4$ is F and $R^5$ is F and the combination of $R^1$, $R^3$, $R^6$ and $R^7$ for a compound corresponds in each case to one row of Table A;

Table 474 Compounds of formula I.B23 (I.B23-14.1-I.B23-14.2304) in which B is N, $R^2$ is $NCH_3SO_2CH_3$, $R^4$ is F and $R^5$ is Cl and the combination of $R^1$, $R^3$, $R^6$ and $R^7$ for a compound corresponds in each case to one row of Table A;

Table 475 Compounds of formula I.B23 (I.B23-15.1-I.B23-15.2304) in which B is N, $R^2$ is $NCH_3SO_2CH_3$, $R^4$ is Cl and $R^5$ is F and the combination of $R^1$, $R^3$, $R^6$ and $R^7$ for a compound corresponds in each case to one row of Table A;

Table 476 Compounds of formula I.B23 (I.B23-16.1-I.B23-16.2304) in which B is N, $R^2$ is $NCH_3SO_2CH_3$, $R^4$ is Cl and $R^5$ is Cl and the combination of $R^1$, $R^3$, $R^6$ and $R^7$ for a compound corresponds in each case to one row of Table A;

Table 477 Compounds of formula I.B23 (I.B23-17.1-I.B23-17.2304) in which B is N, $R^2$ is $NCH_3SO_2CH_3$, $R^4$ is CN and $R^5$ is F and the combination of $R^1$, $R^3$, $R^6$ and $R^7$ for a compound corresponds in each case to one row of Table A;

Table 478 Compounds of formula I.B23 (I.B23-18.1-I.B23-18.2304) in which B is N, $R^2$ is $NCH_3SO_2CH_3$, $R^4$ is CN and $R^5$ is Cl and the combination of $R^1$, $R^3$, $R^6$ and $R^7$ for a compound corresponds in each case to one row of Table A;

Table 479 Compounds of formula I.B23 (I.B23-19.1-I.B23-19.2304) in which B is N, $R^2$ is $NCH_3SO_2CH_3$, $R^4$ is $CH_3$ and $R^5$ is F and the combination of $R^1$, $R^3$, $R^6$ and $R^7$ for a compound corresponds in each case to one row of Table A;

Table 480 Compounds of formula I.B23 (I.B23-20.1-I.B23-20.2304) in which B is N, $R^2$ is $NCH_3SO_2CH_3$, $R^4$ is $CH_3$ and $R^5$ is Cl and the combination of $R^1$, $R^3$, $R^6$ and $R^7$ for a compound corresponds in each case to one row of Table A;

The compounds of formula I can be prepared by standard methods of organic chemistry, e.g. by the methods described hereinafter in schemes 1 to 8. The substituents, variables and indices in schemes 1 to 8 are as defined above for formula I, if not otherwise specified.

The compounds of formula I can be prepared analogous to Scheme 1 below.

Scheme 1:

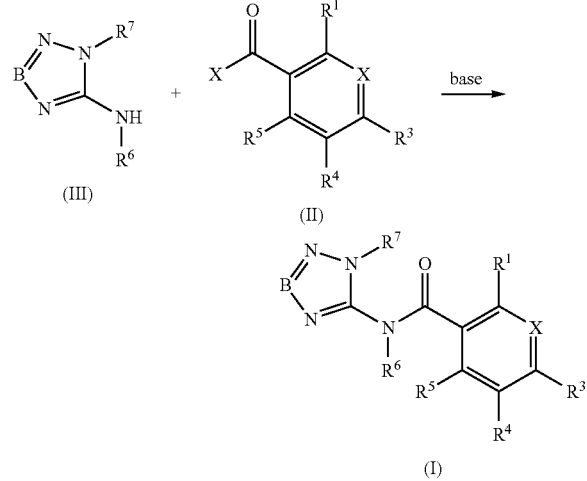

5-Amino-1-R-1,2,4-triazole or 5-amino-1-R-tetrazole compounds of formula III can be re-acted with benzoyl derivatives of formula II to afford compounds of formula I. X is a leaving group, such as halogen, in particular Cl, an anhydride residue or an active ester residue. Especially in case of X being halogen the reaction is suitably carried out in the presence of a base. Suitable bases are for example carbonates, such as lithium, sodium or potassium carbonates, amines, such as trimethylamine or triethylamine, and basic N-heterocycles, such as pyridine, 2,6-dimethylpyridine or 2,4,6-trimethylpyridine. Suitable solvents are in particular aprotic solvents such as pentane, hexane, heptane, octane, cyclohexane, dichloromethane, chloroform, 1,2-dichlorethane, benzene, chlorobenzene, toluene, the xylenes, dichlorobenzene, trimethylbenzene, pyridine, 2,6-dimethylpyridine, 2,4,6-trimethylpyridine, acetonitrile, diethyl ether, tetrahydrofuran, 2-methyl tetrahydrofuran, methyl tert-butylether, 1,4-dioxane, N,N-dimethyl formamide, N-methyl pyrrolidinone or mixtures thereof. The starting materials are generally re-acted with one another in equimolar or nearly equimolar amounts at a reaction temperature usually in the range of −20° C. to 100° C. and preferably in the range of −5° C. to 50° C.

Alternatively, compounds of formula I can also be prepared as shown in Scheme 2. Reaction of 5-amino-1-R-1,2,4-triazole or 5-amino-1-R-tetrazole of formula III with a benzoic acid derivative of formula IV yields compound I. The reaction is preferably carried out in the presence of a suitable activating agent, which converts the acid group of compound IV into an activated ester or amide. For this purpose activating agents known in the art, such as 1,1',carbonyldiimidazole (CDI), dicyclohexyl carbodiimide (DCC), 1-ethyl-3-(3-dimethylaminopropyl)carbodiimide (EDC) or 2,4,6-tripropyl-1,3,5,2,4,6-trioxatriphosphorinane-2,4,6-trioxide (T3P) can be employed. The activated ester or amide can be formed, depending in particular on the specific activating agent used, either in situ by contacting compound IV with the activating agent in the presence of compound III, or in a separate step prior to the reaction with compound III. It may be advantageous, especially in cases where DCC or EDC are used as activating agent, to include further additives in the activating reaction, such as hydroxybenzotriazole (HOBt), nitrophenol, pentafluorophenol, 2,4,5-trichlorophenol or N-hydroxysuccinimide. It may further be advantageous to prepare the activated ester or amide in the presence of a base, for example a tertiary amine. The activated ester or amide is either in situ or subsequently re-acted with the amine of formula III to afford the amide of formula I. The reaction normally takes place in anhydrous inert solvents, such as chlorinated hydrocarbons, e.g. dichloromethane or dichloroethane, ethers, e.g. tetrahydrofuran or 1,4-dioxane or carboxamides, e.g. N,N-dimethylformamide, N,N-dimethylacetamide or N-methylpyrrolidone. The reaction is ordinarily carried out at temperatures in the range from −20° C. to +25° C.

Scheme 2:

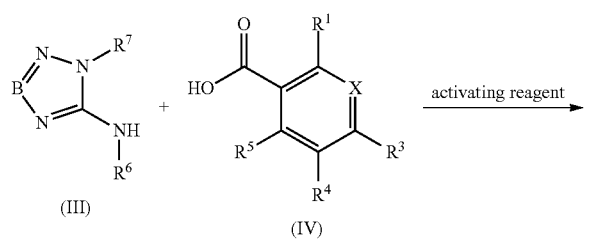

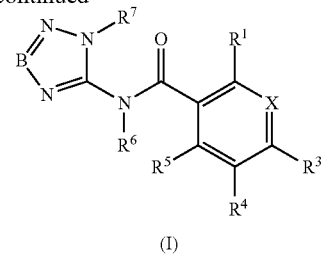

The compounds of formula II and their respective benzoic acid precursors of formula IV can be purchased or can be prepared by processes known in the art or disclosed in the literature, e.g. in WO 9746530, WO 9831676, WO 9831681, WO 2002/018352, WO 2000/003988, US 2007/0191335, U.S. Pat. No. 6,277,847.

Furthermore, compounds of formula I, can be obtained by treating N-(1H-1,2,4-triazol-5-yl)benzamides or N-(1H-tetrazol-5-yl)benzamides of formula V with, for example, alkylating agents such as alkyl halides according to Scheme 3.

Scheme 3.

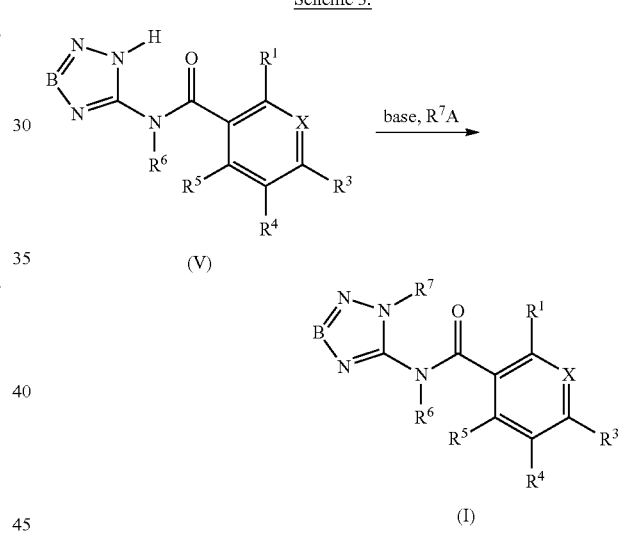

The 5-amino-1-R-tetrazoles of formula III, where R is for example alkyl, are either commercially available or are obtainable according to methods known from the literature. For example, 5-amino-1-R-tetrazole can be prepared from 5-aminotetrazole according to the method described in the Journal of the American Chemical Society, 1954, 76, 923-924 (Scheme 4).

Scheme 4.

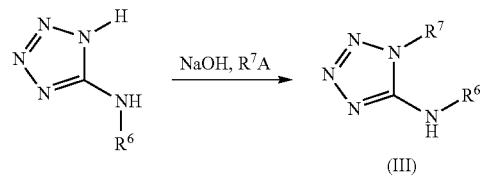

Alternatively, 5-amino-1-R-tetrazole compounds of formula III can be prepared according to the method described in the Journal of the American Chemical Society, 1954, 76, 88-89 (Scheme 5).

Scheme 5:

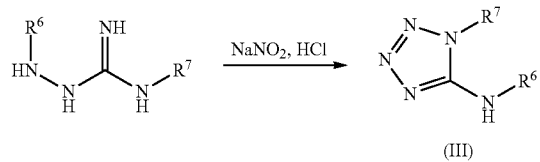

As shown in Scheme 6, 5-amino-1-R-triazoles of formula III, where R is for example alkyl, are either commercially available or are obtainable according to methods described in the literature. For example, 5-amino-1-R-triazole can be prepared from 5-aminotriazole according to the method described in Zeitschrift fuir Chemie, 1990, 30, 12, 436-437.

Scheme 6:

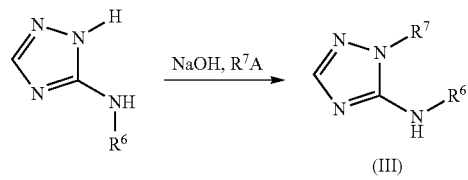

5-Amino-1-R-triazole compounds of formula III, can also be prepared analogous to the synthesis described in Chemische Berichte, 1964, 97, 2, 396-404, as shown in Scheme 7.

Scheme 7:

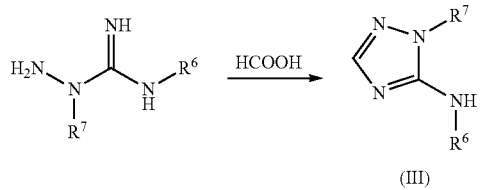

As a rule, the compounds of formula I including their stereoisomers, salts, tautomers and N-oxides, and their precursors in the synthesis process, can be prepared by the methods described above. If individual compounds can not be prepared via the above-described routes, they can be prepared by derivatization of other compounds I or the respective precursor or by customary modifications of the synthesis routes described. For example, in individual cases, certain compounds of formula I can advantageously be prepared from other compounds of formula I by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

The compounds of formula I and their agriculturally suitable salts are useful as herbicides. They are useful as such or as an appropriately formulated composition. The herbicidal compositions comprising the compound I, in particular the preferred aspects thereof, control vegetation on non-crop areas very efficiently, especially at high rates of application. They act against broad-leaved weeds and weed grasses in crops such as wheat, rice, corn, soybeans and cotton without causing any significant damage to the crop plants. This effect is mainly observed at low rates of application.

Depending on the application method in question, the compounds of formula I, in particular the preferred aspects thereof, or compositions comprising them can additionally be employed in a further number of crop plants for eliminating unwanted plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (s. *vulgare*), *Theobroma cacao, Trifolium pratense, Triticum aestivum, Triticale, Triticum durum, Vicia faba, Vitis vinifera, Zea mays.*

The term "crop plants" also includes plants which have been modified by breeding, muta-genesis or genetic engineering. Genetically modified plants are plants whose genetic material has been modified in a manner which does not occur under natural conditions by crossing, mutations or natural recombination (i.e. reassembly of the genetic information). Here, in general, one or more genes are integrated into the genetic material of the plant to improve the properties of the plant.

Accordingly, the term "crop plants" also includes plants which, by breeding and genetic engineering, have acquired tolerance to certain classes of herbicides, such as hydroxyphenylpyruvate dioxygenase (HPPD) inhibitors, acetolactate synthase (ALS) inhibitors, such as, for example, sulfonylureas (EP-A-0257993, U.S. Pat. No. 5,013,659) or imidazolinones (see, for example, U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073), enolpyruvylshikimate 3-phosphate synthase (EPSPS) inhibitors, such as, for example, glyphosate (see, for example, WO 92/00377), glutamine synthetase (GS) inhibitors, such as, for example, glufosinate (see, for example, EP-A-0242236, EP-A-242246), or oxynil herbicides (see, for example, U.S. Pat. No. 5,559,024).

Numerous crop plants, for example Clearfield® oilseed rape, tolerant to imidazolinones, for example imazamox, have been generated with the aid of classic breeding methods (muta-genesis). Crop plants such as soybeans, cotton, corn, beet and oilseed rape, resistant to glyphosate or glufosinate, which are available under the tradenames RoundupReady® (glyphosate) and Liberty Link® (glufosinate) have been generated with the aid of genetic engineering methods.

Accordingly, the term "crop plants" also includes plants which, with the aid of genetic engineering, produce one or more toxins, for example those of the bacterial strain *Bacillus* ssp. Toxins which are produced by such genetically modified plants include, for example, insecticidal proteins of *Bacillus* spp., in particular *B. thuringiensis*, such as the endotoxins Cry1Ab, Cry1Ac, Cry1F, Cry1Fa2, Cry2Ab, Cry3A, Cry3Bb1, Cry9c, Cry34Ab1 or Cry35Ab1; or vegetative insecticidal proteins (VIPs), for example VIP1, VIP2, VIP3, or VIP3A; insecticidal proteins of nema-tode-colonizing bacteria, for example *Photorhabdus* spp. or *Xenorhabdus* spp.; toxins of animal organisms, for example wasp, spider or scorpion toxins; fungal toxins, for example from Streptomycetes; plant lectins, for example from peas or barley; agglutinins; proteinase inhibitors, for example trypsin inhibitors, serine protease inhibitors, patatin, cystatin or papain inhibitors, ribo-some-inactivating proteins (RIPs), for example ricin, corn-RIP, abrin, luffin, saporin or bryodin; steroid-metabolizing enzymes, for example 3-hydroxysteroid oxidase, ecdysteroid-IDP glycosyl transferase, cholesterol oxidase, ecdysone inhibitors, or HMG-CoA reductase; ion channel blockers, for example inhibitors of sodium channels or calcium channels; juvenile hormone es-terase; receptors of the diuretic hormone (helicokinin receptors); stilbene synthase, bibenzyl synthase, chitinases and glucanases. In the plants, these toxins may also be produced as pre-toxins, hybrid proteins or truncated or otherwise modified proteins. Hybrid proteins are charac-terized by a novel combination of different protein domains (see, for example, WO 2002/015701). Further examples of such toxins or genetically modified plants which produce these toxins are disclosed in EP-A 374 753, WO 93/007278, WO 95/34656, EP-A 427 529, EP-A 451 878, WO 03/018810 and WO 03/052073. The methods for producing these genetically modified plants are known to the person skilled in the art and disclosed, for example, in the publications mentioned above. Numerous of the toxins mentioned above bestow, upon the plants by which they are produced, tolerance to pests from all taxonomic classes of arthropods, in particular to beetles (Coeleropta), dipterans (Diptera) and butterflies (Lepidoptera) and to nema-todes (Nematoda).

Genetically modified plants which produce one or more genes coding for insecticidal toxins are described, for example, in the publications mentioned above, and some of them are commercially available, such as, for example, YieldGard® (corn varieties producing the toxin Cry1Ab), YieldGard® Plus (corn varieties which produce the toxins Cry1Ab and Cry3Bb1), Star-link® (corn varieties which produce the toxin Cry9c), Herculex® RW (corn varieties which produce the toxins Cry34Ab1, Cry35Ab1 and the enzyme phosphinothricin-N-acetyltransferase [PAT]); NuCOTN® 33B (cotton varieties which produce the toxin Cry1Ac), Bollgard® I (cotton varieties which produce the toxin Cry1Ac), Bollgard® II (cotton varieties which produce the toxins Cry1Ac and Cry2Ab2); VIPCOT® (cotton varieties which produce a VIP toxin); NewLeaf® (potato varieties which produce the toxin Cry3A); Bt-Xtra®, NatureGard®, KnockOut®, BiteGard®, Protecta®, Btl 1 (for example Agrisure® CB) and Bt176 from Syngenta Seeds SAS, France (corn varieties which produce the toxin Cry1Ab and the PAT enyzme), MIR604 from Syngenta Seeds SAS, France (corn varieties which produce a modified version of the toxin Cry3A, see WO 03/018810), MON 863 from Monsanto Europe S.A., Belgium (corn varieties which produce the toxin Cry3Bb1), IPC 531 from Monsanto Europe S.A., Belgium (cotton varieties which produce a modified version of the toxin Cry1Ac) and 1507 from Pioneer Overseas Corporation, Belgium (corn varieties which produce the toxin Cry1F and the PAT enzyme).

Accordingly, the term "crop plants" also includes plants which, with the aid of genetic engineering, produce one or more proteins which are more robust or have increased resistance to bacterial, viral or fungal pathogens, such as, for example, pathogenesis-related proteins (PR proteins, see EP-A 0 392 225), resistance proteins (for example potato varieties producing two resistance genes against *Phytophthora infestans* from the wild Mexican potato *Solanum bulbocastanum*) or T4 lysozyme (for example potato cultivars which, by producing this protein, are resistant to bacteria such as *Erwinia amylvora*).

Accordingly, the term "crop plants" also includes plants whose productivity has been improved with the aid of genetic engineering methods, for example by enhancing the potential yield (for example biomass, grain yield, starch, oil or protein content), tolerance to drought, salt or other limiting environmental factors or resistance to pests and fungal, bacterial and viral pathogens.

The term "crop plants" also includes plants whose ingredients have been modified with the aid of genetic engineering methods in particular for improving human or animal diet, for example by oil plants producing health-promoting long-chain omega 3 fatty acids or monounsaturated omega 9 fatty acids (for example Nexera® oilseed rape).

The term "crop plants" also includes plants which have been modified with the aid of genetic engineering methods for improving the production of raw materials, for example by increasing the amylopectin content of potatoes (Amflora® potato).

Furthermore, it has been found that the compounds of formula I are also suitable for the defoliation and/or desiccation of plant parts, for which crop plants such as cotton, potato, oilseed rape, sunflower, soybean or field beans, in particular cotton, are suitable. In this regard, there have been found compositions for the desiccation and/or defoliation of plants, processes for preparing these compositions and methods for desiccating and/or defoliating plants using the compounds of formula I.

As desiccants, the compounds of formula I are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pomaceous fruit, stone fruit and nuts. The same mechanism, i.e. the promotion of the development of abscission tissue between fruit part or leaf part and shoot part of the plants is also essential for the readily controllable defoliation of useful plants, in particular cotton.

Moreover, a shortening of the time interval in which the individual cotton plants mature leads to an increased fiber quality after harvesting.

The compounds of formula I, or the herbicidal compositions comprising the compounds of formula I, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in each case, they should ensure the finest possible distribution of the active ingredients according to the invention.

The herbicidal compositions comprise a herbicidally effective amount of at least one compound of the formula I or an agriculturally useful salt of I, and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, if appropriate colorants and, for seed formulations, adhesives.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulation. Examples of bactericides are bactericides based on diclorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF SE), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g. methylcellulose), hydrophobically modified starches, polyvinyl alcohol (Mowiol types Clariant), polycarboxylates (BASF SE, Sokalan types), polyalkoxylates, polyvinylamine (BASF SE, Lupamine types), polyethyleneimine (BASF SE, Lupasol types), polyvinylpyrrolidone and copolymers thereof.

Powders, materials for broadcasting and dusts can be prepared by mixing or grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water. To prepare emulsions, pastes or oil dispersions, the compounds of formula I or Ia, either as such or dissolved in an oil or solvent, can be homogenized in water by means of a wetting agent, tackifier, dispersant or emulsifier. Alternatively, it is also possible to prepare concentrates comprising active substance, wetting agent, tackifier, dispersant or emulsifier and, if desired, solvent or oil, which are suitable for dilution with water.

The concentrations of the compounds of formula I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to NMR spectrum).

The formulations or ready-to-use preparations may also comprise acids, bases or buffer systems, suitable examples being phosphoric acid or sulfuric acid, or urea or ammonia.

The compounds of formula I of the invention can for example be formulated as follows:

1. Products for Dilution with Water

A. Water-Soluble Concentrates 10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight.

B. Dispersible Concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C. Emulsifiable Concentrates 15 parts by weight of active compound are dissolved in 75 parts by weight of an organic solvent (e.g. alkylaromatics) with addition of calcium dodecylbenzenesulfonate and castor oil ethoxylate (in each case 5 parts by weight). Dilution with water gives an emulsion. The formulation has an active compound content of 15% by weight.

D. Emulsions 25 parts by weight of active compound are dissolved in 35 parts by weight of an organic solvent (e.g. alkylaromatics) with addition of calcium dodecylbenzenesulfonate and castor oil ethoxylate (in each case 5 parts by weight). This mixture is introduced into 30 parts by weight of water by means of an emulsifier (e.g. Ultraturrax) and made into a homogeneous emulsion. Dilution with water gives an emulsion. The formulation has an active compound content of 25% by weight.

E. Suspensions

In an agitated ball mill, 20 parts by weight of active compound are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F. Water-Dispersible Granules and Water-Soluble Granules 50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G. Water-Dispersible Powders and Water-Soluble Powders 75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.

H. Gel Formulations

In a ball mill, 20 parts by weight of active compound, 10 parts by weight of dispersant, 1 part by weight of gelling agent and 70 parts by weight of water or of an organic solvent are ground to give a fine suspension. Dilution with water gives a stable suspension with active compound content of 20% by weight.

2. Products to be Applied Undiluted

I. Dusts 5 parts by weight of active compound are ground finely and mixed intimately with 95 parts by weight of finely divided kaolin. This gives a dusting powder with an active compound content of 5% by weight.

J. Granules (GR, FG, GG, MG)

0.5 parts by weight of active compound are ground finely and associated with 99.5 parts by weight of carriers. Current methods here are extrusion, spray-drying or the fluidized bed.

This gives granules to be applied undiluted with an active compound content of 0.5% by weight.

K. ULV Solutions (UL)

10 parts by weight of active compound are dissolved in 90 parts by weight of an organic solvent, for example xylene. This gives a product to be applied undiluted with an active compound content of 10% by weight.

The compounds of formula I or the herbicidal compositions comprising them can be applied pre- or post-emergence, or together with the seed of a crop plant. It is also possible to apply the herbicidal compositions or active compounds by applying seed, pretreated with the herbicidal compositions or active compounds, of a crop plant. If the active compounds are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

In a further embodiment, the compounds of formula I or the herbicidal compositions can be applied by treating seed.

The treatment of seed comprises essentially all procedures familiar to the person skilled in the art (seed dressing, seed coating, seed dusting, seed soaking, seed film coating, seed multi-layer coating, seed encrusting, seed dripping and seed pelleting) based on the compounds of formula I according to the invention or the compositions prepared therefrom. Here, the herbicidal compositions can be applied diluted or undiluted.

The term seed comprises seed of all types, such as, for example, corns, seeds, fruits, tubers, cuttings and similar forms. Here, preferably, the term seed describes corns and seeds.

The seed used can be seed of the useful plants mentioned above, but also the seed of transgenic plants or plants obtained by customary breeding methods.

The rates of application of active compound are from 0.001 to 3.0, preferably 0.01 to 1.0, kg/ha of active substance (a.s.), depending on the control target, the season, the target plants and the growth stage. To treat the seed, the compounds of formula I are generally employed in amounts of from 0.001 to 10 kg per 100 kg of seed.

It may also be advantageous to use the compounds of formula I in combination with safeners. Safeners are chemical compounds which prevent or reduce damage to useful plants without substantially affecting the herbicidal action of the compounds of formula I on unwanted plants. They can be used both before sowing (for example in the treatment of seed, or on cuttings or seedlings) and before or after the emergence of the useful plant. The safeners and the compounds of formula I can be used simultaneously or in succession.

Suitable safeners are, for example, (quinolin-8-oxy)acetic acids, 1-phenyl-5-haloalkyl-1H-1,2,4-triazole-3-carboxylic acids, 1-phenyl-4,5-dihydro-5-alkyl-1H-pyrazole-3,5-dicarboxylic acids, 4,5-dihydro-5,5-diaryl-3-isoxazolecarboxylic acids, dichloroacetamides, alpha-oximinophenylacetonitriles, acetophenone oximes, 4,6-dihalo-2-phenylpyrimidines, N-[[4-(aminocarbonyl)phenyl]sulfonyl]-2-benzamides, 1,8-naphthalic anhydride, 2-halo-4-(haloalkyl)-5-thiazolecarboxylic acids, phosphorothiolates and O-phenyl N-alkylcarbamates and their agriculturally useful salts and, provided that they have an acid function, their agriculturally useful derivatives, such as amides, esters and thioesters.

To broaden the activity spectrum and to obtain synergistic effects, the compounds of the formula I can be mixed and jointly applied with numerous representatives of other herbicidal or growth-regulating groups of active compounds or with safeners. Suitable mixing partners are, for example, 1,2,4-thiadiazoles, 1,3,4-thiadiazoles, amides, aminophosphoric acid and its derivatives, aminotriazoles, anilides, aryloxy/heteroaryloxyalkanoic acids and their derivatives, benzoic acid and its derivatives, benzothiadiazinones, 2-(hetaroyl/aroyl)-1,3-cyclohexanediones, heteroaryl aryl ketones, benzylisoxazolidinones, meta-CF$_3$-phenyl derivatives, carbamates, quinoline carboxylic acid and its derivatives, chloroacetanilides, cyclohexenone oxime ether derivates, diazines, dichloropropionic acid and its derivatives, dihydrobenzofurans, dihydrofu-ran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypro-pionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils and also phenylpyrazolines and isoxazolines and their derivatives.

Moreover, it may be useful to apply the compounds of formula I alone or in combination with other herbicides or else also mixed with further crop protection agents, jointly, for example with compositions for controlling pests or phytopathogenic fungi or bacteria. Also of interest is the miscibility with mineral salt solutions which are employed for alleviating nutritional and trace element deficiencies. Other additives such as nonphytotoxic oils and oil concentrates may also be added.

Examples of herbicides which can be used in combination with the Compounds of formula I according to the present invention are:

b1) from the group of the lipid biosynthesis inhibitors:
alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
amidosulfuron, azimsulfuron, bensulfuron, bensulfuron-methyl, bispyribac, bispyribac-sodium, chlorimuron, chlorimuron-ethyl, chlorsulfuron, cinosulfuron, cloransulam, cloransulam-methyl, cyclosulfamuron, diclosulam, ethametsulfuron, ethametsulfuron-methyl, ethoxysulfuron, flazasulfuron, florasulam, flucarbazone, flucarbazone-sodium, flucetosulfuron, flumetsulam, flupyrsulfuron, flupyrsulfuron-methyl-sodium, foramsulfuron, halosulfuron, halosulfuron-methyl, imazamethabenz, imazamethabenz-methyl, imazamox, imazapic, imazapyr, imazaquin, imazethapyr, imazosulfuron, iodosulfuron, iodosulfuron-methyl-sodium, mesosulfuron, metosulam, metsulfuron, metsulfuron-methyl, nicosulfuron, orthosulfamuron, oxasulfuron, penoxsulam, primisulfuron, primisulfuron-methyl, propoxycarbazone, propoxycarbazone-sodium, prosulfuron, pyrazosulfuron, pyrazosulfuron-ethyl, pyribenzoxim, pyrimisulfan, pyriftalid, pyriminobac, pyriminobac-methyl, pyrithiobac, pyrithiobac-sodium, pyroxsulam, rimsulfuron, sulfometuron, sulfometuron-methyl, sulfosulfuron, thiencarbazone, thiencarbazone-methyl, thifensulfuron, thifensulfuron-methyl, triasulfuron, tribenuron, tribenuron-methyl, trifloxysulfuron, triflusulfuron, triflusulfuron-methyl and tritosulfuron;

b3) from the group of the photosynthesis inhibitors:
ametryn, amicarbazone, atrazine, bentazon, bentazone-sodium, bromacil, bromofenoxim, bromoxynil and its salts and esters, chlorobromuron, chloridazone, chlorotoluron, chloroxuron, cyanazine, desmedipham, desmetryn, dimefuron, dimethametryn, diquat, diquat-dibromide, diuron, fluometuron, hexazinone, ioxynil and its salts and esters, isoproturon, isouron, karbutilate, lenacil, linuron, metamitron, methabenzthiazuron, metobenzuron, metoxuron, metribuzin, monolinuron, neburon, paraquat, paraquat-dichloride, paraquat-dimetilsulfate, pentanochlor, phenmedipham, phenmedipham-ethyl, prometon, prometryn, propanil, propazine, pyridafol, pyridate, siduron, simazine, simetryn, tebuthiuron, terbacil, terbumeton, terbuthylazine, terbutryn, thidiazuron and trietazine;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, 2-chloro-5-[3,6-dihydro-3-methyl-2,6-dioxo-4-(trifluoromethyl)-1(2H)-pyrimidinyl]-4-fluoro-N-[(isopropyl)methylsulfamoyl]benzamide (H-1; CAS 372137-35-4), ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (H-2; CAS 353292-31-6), N-ethyl-3-(2,6-dichloro-4-trifluoromethylphenoxy)-5-methyl-1H-pyrazole-1-carboxamide (H-3; CAS 452098-92-9), N-tetrahydrofurfuryl-3-(2,6-dichloro-4-trifluoromethylphenoxy)-5-methyl-1H-pyrazole-1-carboxamide (H-4; CAS 915396-43-9), N-ethyl-3-(2-chloro-6-fluoro-4-trifluoromethylphenoxy)-5-methyl-1H-pyrazole-1-carboxamide (H-5; CAS 452099-05-7), N-tetrahydrofurfuryl-3-(2-chloro-6-fluoro-4-trifluoromethylphenoxy)-5-methyl-1H-pyrazole-1-carboxamide (H-6; CAS 45100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;

b5) from the group of the bleacher herbicides:
aclonifen, amitrol, beflubutamid, benzobicyclon, benzofenap, clomazone, diflufenican, fluridone, flurochloridone, flurtamone, isoxaflutole, mesotrione, norflurazon, picolinafen, pyrasulfutole, pyrazolynate, pyrazoxyfen, sulcotrione, tefuryltrione, tembotrione, topramezone, 4-hydroxy-3-[[2-[(2-methoxyethoxy)methyl]-6-(trifluoromethyl)-3-pyridyl]

carbonyl]bicyclo[3.2.1]oct-3-en-2-one (H-7; CAS 352010-68-5) and 4-(3-trifluoromethylphenoxy)-2-(4-trifluoromethylphenyl)pyrimidine (H-8; CAS 180608-33-7);

b6) from the group of the EPSP synthase inhibitors:
glyphosate, glyphosate-isopropylammonium and glyphosate-trimesium (sulfosate);

b7) from the group of the glutamine synthase inhibitors:
bilanaphos (bialaphos), bilanaphos-sodium, glufosinate and glufosinate-ammonium;

b8) from the group of the DHP synthase inhibitors:
asulam;

b9) from the group of the mitose inhibitors:
amiprophos, amiprophos-methyl, benfluralin, butamiphos, butralin, carbetamide, chlorpropham, chlorthal, chlorthal-dimethyl, dinitramine, dithiopyr, ethalfluralin, fluchloralin, oryzalin, pendimethalin, prodiamine, propham, propyzamide, tebutam, thiazopyr and trifluralin;

b10) from the group of the VLCFA inhibitors:
acetochlor, alachlor, anilofos, butachlor, cafenstrole, dimethachlor, dimethanamid, dimethenamid-P, diphenamid, fentrazamide, flufenacet, mefenacet, metazachlor, metolachlor, metolachlor-S, naproanilide, napropamide, pethoxamid, piperophos, pretilachlor, propachlor, propisochlor, pyroxasulfone (KIH-485) and thenylchlor;

Compounds of the Formula 2:

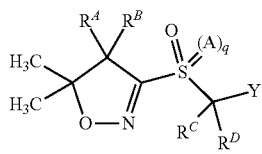

in which the variables have the following meanings:
Y is phenyl or 5- or 6-membered heteroaryl as defined at the outset, which radicals may be substituted by one to three groups $R^{aa}$; $R^A$, $R^B$, $R^C$, $R^D$ are H, halogen or $C_1$-$C_4$-alkyl; A is O or NH; q is 0 or 1.

Compounds of the formula 2 have in particular the following meanings:
Y is

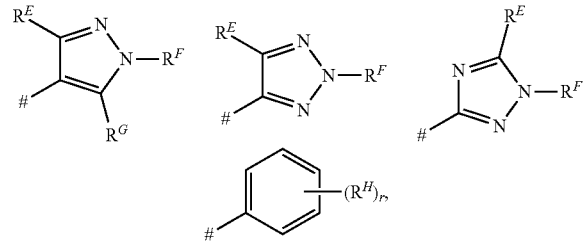

where # denotes the bond to the skeleton of the molecule; and $R^A$, $R^B$, $R^C$, $R^D$ are H, Cl, F or $CH_3$; $R^E$ is halogen, $C_1$-$C_4$-alkyl or $C_1$-$C_4$-haloalkyl; $R^F$ is $C_1$-$C_4$-alkyl; $R^G$ is halogen, $C_1$-$C_4$-alkoxy or $C_1$-$C_4$-haloalkoxy; $R^H$ is H, halogen, $C_1$-$C_4$-alkyl, $C_1$-$C_4$-haloalkyl or $C_1$-$C_4$-haloalkoxy; r is 0, 1, 2 or 3; A is oxygen; q is 0 or 1.

Preferred compounds of the formula 2 have the following meanings:

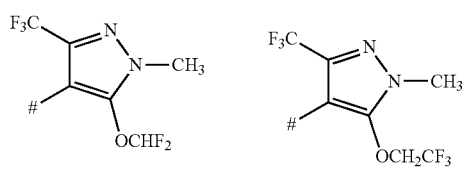

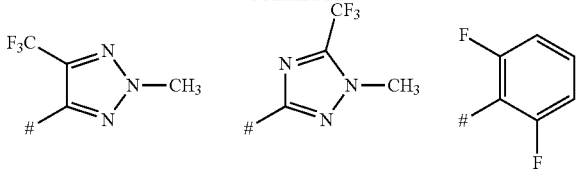

$R^A$ is H; $R^B$, $R^C$ are F; $R^{24}$ is H or F; A is oxygen; q is 0 or 1.

Particularly preferred compounds of the formula 2 are:
3-[5-(2,2-difluoroethoxy)-1-methyl-3-trifluoromethyl-1H-pyrazol-4-ylmethane-sulfonyl]-4-fluoro-5,5-dimethyl-4,5-dihydroisoxazole (2-1); 3-{[5-(2,2-difluoroethoxy)-1-methyl-3-trifluoromethyl-1H-pyrazol-4-yl]fluoromethanesulfonyl}-5,5-dimethyl-4,5-dihydroisoxazole (2-2); 4-(4-fluoro-5,5-dimethyl-4,5-dihydroisoxazole-3-sulfonylmethyl)-2-methyl-5-trifluoromethyl-2H-[1,2,3]triazole (2-3); 4-[(5,5-dimethyl-4,5-dihydroisoxazole-3-sulfonyl)fluoromethyl]-2-methyl-5-trifluoromethyl-2H-[1,2,3]triazole (2-4); 4-(5,5-dimethyl-4,5-dihydroisoxazole-3-sulfonylmethyl)-2-methyl-5-trifluoromethyl-2H-[1,2,3]triazole (2-5); 3-{[5-(2,2-difluoroethoxy)-1-methyl-3-trifluoromethyl-1H-pyrazol-4-yl]difluoromethanesulfonyl}-5,5-dimethyl-4,5-dihydroisoxazole (2-6); 4-[(5,5-dimethyl-4,5-dihydroisoxazole-3-sulfonyl)difluoromethyl]-2-methyl-5-trifluoromethyl-2H-[1,2,3]triazole (2-7); 3-{[5-(2,2-difluoroethoxy)-1-methyl-3-trifluoromethyl-1H-pyrazol-4-yl]difluoromethanesulfonyl}-4-fluoro-5,5-dimethyl-4,5-dihydroisoxazole (2-8); 4-[difluoro-(4-fluoro-5,5-dimethyl-4,5-dihydroisoxazole-3-sulfonyl)methyl]-2-methyl-5-trifluoromethyl-2H-[1,2,3]triazole (2-9);

b11) from the group of the cellulose biosynthesis inhibitors:
chlorthiamid, dichlobenil, flupoxam and isoxaben;

b12) from the group of the decoupler herbicides:
dinoseb, dinoterb and DNOC and its salts;

b13) from the group of the auxin herbicides:
2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, and 5,6-dichloro-2-cyclopropyl-4-pyrimidinecarboxylic acid (H-9; CAS 858956-08-8) and its salts and esters;

b14) from the group of the auxin transport inhibitors:
diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (H-10; CAS 499223-49-3) and its salts and esters.

Examples of preferred safeners C are benoxacor, cloquintocet, cyometrinil, cyprosulfamide, dichlormid, dicyclonone, dietholate, fenchlorazole, fenclorim, flurazole, fluxofenim, furi-lazole, isoxadifen, mefenpyr, mephenate, naphthalic anhydride, oxabetrinil, 4-(dichloroacetyl)-1-oxa-4-azaspiro[4.5]decane (H-11; MON4660, CAS 71526-07-3) and 2,2,5-trimethyl-3-(dichloroacetyl)-1,3-oxazolidine (H-12; R-29148, CAS 52836-31-4).

The active compounds of groups b1) to b15) and the safeners C are known herbicides and safeners, see, for example, The Compendium of Pesticide Common Names (http://www.alanwood.net/pesticides/); B. Hock, C. Fedtke, R. R. Schmidt, Herbizide [Herbicides], Georg Thieme Verlag, Stuttgart, 1995. Further herbicidally active compounds are known from WO 96/26202, WO 97/41116, WO 97/41117, WO 97/41118, WO 01/83459 and WO 2008/074991 and from W. Kramer et al. (ed.) "Modern Crop Protection Compounds", Vol. 1, Wiley VCH, 2007 and the literature quoted therein.

The invention also relates to compositions in the form of a crop protection composition formulated as a 1-component composition comprising an active compound combination comprising at least one compound of the formula I and at least one further active compound, preferably selected from the active compounds of groups b1 to b15, and at least one solid or liquid carrier and/or one or more surfactants and, if desired, one or more further auxiliaries customary for crop protection compositions.

The invention also relates to compositions in the form of a crop protection composition formulated as a 2-component composition comprising a first component comprising at least one compound of the formula I, a solid or liquid carrier and/or one or more surfactants and a second component comprising at least one further active compound selected from the active compounds of groups b1 to b15, a solid or liquid carrier and/or one or more surfactants, where additionally both components may also comprise further auxiliaries customary for crop protection compositions.

In binary compositions comprising at least one compound of the formula I as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of the formula I as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one compound of the formula I as component A, at least one herbicide B and at least one safener C, the relative parts by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1; the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1; and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. Preferably, the weight ratio of the components A+B to the component C is in the range of from 1:500 to 500:1, in particular in the range of from 1:250 to 250:1 and particularly preferably in the range of from 1:75 to 75:1.

Examples of particularly preferred compositions according to the invention comprising in each case one individualized compound of the formula I and one mixing partner or a mixing partner combination are given in Table B below.

A further aspect of the invention relates to the compositions B-1 to B-1236 listed in Table B below, where in each case one row of Table B corresponds to a herbicidal composition comprising one of the compounds of formula I individualized in the above description (component 1) and the further active compound from groups b1) to b15) and/or safener C stated in each case in the row in question (component 2). The active compounds in the compositions described are in each case preferably present in synergistically effective amounts.

TABLE B

| | Herbicide(s) B | Safener C |
|---|---|---|
| B-1 | clodinafop-propargyl | — |
| B-2 | cycloxydim | — |
| B-3 | cyhalofop-butyl | — |
| B-4 | fenoxaprop-P-ethyl | — |
| B-5 | pinoxaden | — |
| B-6 | profoxydim | — |
| B-7 | tepraloxydim | — |
| B-8 | tralkoxydim | — |
| B-9 | esprocarb | — |
| B-10 | prosulfocarb | — |
| B-11 | thiobencarb | — |
| B-12 | triallate | — |
| B-13 | bensulfuron-methyl | — |
| B-14 | bispyribac-sodium | — |
| B-15 | cyclosulfamuron | — |
| B-16 | flumetsulam | — |
| B-17 | flupyrsulfuron-methyl-sodium | — |
| B-18 | foramsulfuron | — |
| B-19 | imazamox | — |
| B-20 | imazapic | — |
| B-21 | imazapyr | — |
| B-22 | imazaquin | — |
| B-23 | imazethapyr | — |
| B-24 | imazosulfuron | — |
| B-25 | iodosulfuron-methyl-sodium | — |
| B-26 | mesosulfuron | — |
| B-27 | nicosulfuron | — |
| B-28 | penoxsulam | — |
| B-29 | propoxycarbazone-sodium | — |
| B-30 | pyrazosulfuron-ethyl | — |
| B-31 | pyroxsulam | — |
| B-32 | rimsulfuron | — |
| B-33 | sulfosulfuron | — |
| B-34 | thiencarbazone-methyl | — |
| B-35 | tritosulfuron | — |
| B-36 | 2,4-D and its salts and esters | — |
| B-37 | aminopyralid and its salts and esters | — |
| B-38 | clopyralid and its salts and esters | — |
| B-39 | dicamba and its salts and esters | — |
| B-40 | fluroxypyr-meptyl | — |
| B-41 | quinclorac | — |
| B-42 | quinmerac | — |
| B-43 | H-9 | — |
| B-44 | diflufenzopyr | — |
| B-45 | diflufenzopyr-sodium | — |
| B-46 | clomazone | — |
| B-47 | diflufenican | — |
| B-48 | fluorochloridone | — |
| B-49 | isoxaflutol | — |

TABLE B-continued

| | Herbicide(s) B | Safener C |
|---|---|---|
| B-50 | mesotrione | — |
| B-51 | picolinafen | — |
| B-52 | sulcotrione | — |
| B-53 | tefuryltrione | — |
| B-54 | tembotrione | — |
| B-55 | topramezone | — |
| B-56 | H-7 | — |
| B-57 | atrazine | — |
| B-58 | diuron | — |
| B-59 | fluometuron | — |
| B-60 | hexazinone | — |
| B-61 | isoproturon | — |
| B-62 | metribuzin | — |
| B-63 | propanil | — |
| B-64 | terbuthylazine | — |
| B-65 | paraquat dichloride | — |
| B-66 | flumioxazin | — |
| B-67 | oxyfluorfen | — |
| B-68 | saflufenacil | — |
| B-69 | sulfentrazone | — |
| B-70 | H-1 | — |
| B-71 | H-2 | — |
| B-72 | glyphosate | — |
| B-73 | glyphosate-isopropylammonium | — |
| B-74 | glyphosate-trimesium (sulfosate) | — |
| B-75 | glufosinate | — |
| B-76 | glufosinate-ammonium | — |
| B-77 | pendimethalin | — |
| B-78 | trifluralin | — |
| B-79 | acetochlor | — |
| B-80 | cafenstrole | — |
| B-81 | dimethenamid-P | — |
| B-82 | fentrazamide | — |
| B-83 | flufenacet | — |
| B-84 | mefenacet | — |
| B-85 | metazachlor | — |
| B-86 | metolachlor-S | — |
| B-87 | pyroxasulfone | — |
| B-88 | isoxaben | — |
| B-89 | dymron | — |
| B-90 | indanofan | — |
| B-91 | oxaziclomefone | — |
| B-92 | triaziflam | — |
| B-93 | chlorotoluron | — |
| B-94 | atrazine + H-1 | — |
| B-95 | atrazine + glyphosate | — |
| B-96 | atrazine + mesotrione | — |
| B-97 | atrazine + nicosulfuron | — |
| B-98 | atrazine + tembotrione | — |
| B-99 | atrazine + topramezone | — |
| B-100 | clomazone + glyphosate | — |
| B-101 | diflufenican + clodinafop-propargyl | — |
| B-102 | diflufenican + fenoxaprop-P-ethyl | — |
| B-103 | diflufenican + flupyrsulfuron-methyl-sodium | — |
| B-104 | diflufenican + glyphosate | — |
| B-105 | diflufenican + mesosulfuron-methyl | — |
| B-106 | diflufenican + pinoxaden | — |
| B-107 | diflufenican + pyroxsulam | — |
| B-108 | flumetsulam + glyphosate | — |
| B-109 | flumioxazin + glyphosate | — |
| B-110 | imazapic + glyphosate | — |
| B-111 | imazethapyr + glyphosate | — |
| B-112 | isoxaflutol + H-1 | — |
| B-113 | isoxaflutol + glyphosate | — |
| B-114 | metazachlor + H-1 | — |
| B-115 | metazachlor + glyphosate | — |
| B-116 | metazachlor + mesotrione | — |
| B-117 | metazachlor + nicosulfuron | — |
| B-118 | metazachlor + terbuthylazine | — |
| B-119 | metazachlor + topramezone | — |
| B-120 | metribuzin + glyphosate | — |
| B-121 | pendimethalin + H-1 | — |
| B-122 | pendimethalin + clodinafop-propargyl | — |
| B-123 | pendimethalin + fenoxaprop-P-ethyl | — |
| B-124 | pendimethalin + flupyrsulfuron-methyl-sodium | — |
| B-125 | pendimethalin + glyphosate | — |
| B-126 | pendimethalin + mesosulfuron-methyl | — |
| B-127 | pendimethalin + mesotrione | — |
| B-128 | pendimethalin + nicosulfuron | — |
| B-129 | pendimethalin + pinoxaden | — |
| B-130 | pendimethalin + pyroxsulam | — |
| B-131 | pendimethalin + tembotrione | — |
| B-132 | pendimethalin + topramezone | — |
| B-133 | pyroxasulfone + tembotrione | — |
| B-134 | pyroxasulfone + topramezone | — |
| B-135 | sulfentrazone + glyphosate | — |
| B-136 | terbuthylazine + H-1 | — |
| B-137 | terbuthylazine + foramsulfuron | — |
| B-138 | terbuthylazine + glyphosate | — |
| B-139 | terbuthylazine + mesotrione | — |
| B-140 | terbuthylazine + nicosulfuron | — |
| B-141 | terbuthylazine + tembotrione | — |
| B-142 | terbuthylazine + topramezone | — |
| B-143 | trifluralin + glyphosate | — |
| B-144 | — | benoxacor |
| B-145 | — | cloquintocet |
| B-146 | — | cyprosulfamide |
| B-147 | — | dichlormid |
| B-148 | — | fenchlorazole |
| B-149 | — | isoxadifen |
| B-150 | — | mefenpyr |
| B-151 | — | H-11 |
| B-152 | — | H-12 |
| B-153 | clodinafop-propargyl | benoxacor |
| B-154 | cycloxydim | benoxacor |
| B-155 | cyhalofop-butyl | benoxacor |
| B-156 | fenoxaprop-P-ethyl | benoxacor |
| B-157 | pinoxaden | benoxacor |
| B-158 | profoxydim | benoxacor |
| B-159 | tepraloxydim | benoxacor |
| B-160 | tralkoxydim | benoxacor |
| B-161 | esprocarb | benoxacor |
| B-162 | prosulfocarb | benoxacor |
| B-163 | thiobencarb | benoxacor |
| B-164 | triallate | benoxacor |
| B-165 | bensulfuron-methyl | benoxacor |
| B-166 | bispyribac-sodium | benoxacor |
| B-167 | cyclosulfamuron | benoxacor |
| B-168 | flumetsulam | benoxacor |
| B-169 | flupyrsulfuron-methyl-sodium | benoxacor |
| B-170 | foramsulfuron | benoxacor |
| B-171 | imazamox | benoxacor |
| B-172 | imazapic | benoxacor |
| B-173 | imazapyr | benoxacor |
| B-174 | imazaquin | benoxacor |
| B-175 | imazethapyr | benoxacor |
| B-176 | imazosulfuron | benoxacor |
| B-177 | iodosulfuron-methyl-sodium | benoxacor |
| B-178 | mesosulfuron | benoxacor |
| B-179 | nicosulfuron | benoxacor |
| B-180 | penoxsulam | benoxacor |
| B-181 | propoxycarbazone-sodium | benoxacor |
| B-182 | pyrazosulfuron-ethyl | benoxacor |
| B-183 | pyroxsulam | benoxacor |
| B-184 | rimsulfuron | benoxacor |
| B-185 | sulfosulfuron | benoxacor |
| B-186 | thiencarbazone-methyl | benoxacor |
| B-187 | tritosulfuron | benoxacor |
| B-188 | 2,4-D and its salts and esters | benoxacor |
| B-189 | aminopyralid and its salts and esters | benoxacor |
| B-190 | clopyralid and its salts and esters | benoxacor |
| B-191 | dicamba and its salts and esters | benoxacor |
| B-192 | fluroxypyr-meptyl | benoxacor |
| B-193 | quinclorac | benoxacor |
| B-194 | quinmerac | benoxacor |
| B-195 | H-9 | benoxacor |
| B-196 | diflufenzopyr | benoxacor |
| B-197 | diflufenzopyr-sodium | benoxacor |
| B-198 | clomazone | benoxacor |
| B-199 | diflufenican | benoxacor |
| B-200 | fluorochloridone | benoxacor |
| B-201 | isoxaflutol | benoxacor |
| B-202 | mesotrione | benoxacor |
| B-203 | picolinafen | benoxacor |
| B-204 | sulcotrione | benoxacor |
| B-205 | tefuryltrione | benoxacor |

TABLE B-continued

| | Herbicide(s) B | Safener C |
|---|---|---|
| B-206 | tembotrione | benoxacor |
| B-207 | topramezone | benoxacor |
| B-208 | H-7 | benoxacor |
| B-209 | atrazine | benoxacor |
| B-210 | diuron | benoxacor |
| B-211 | fluometuron | benoxacor |
| B-212 | hexazinone | benoxacor |
| B-213 | isoproturon | benoxacor |
| B-214 | metribuzin | benoxacor |
| B-215 | propanil | benoxacor |
| B-216 | terbuthylazine | benoxacor |
| B-217 | paraquat dichloride | benoxacor |
| B-218 | flumioxazin | benoxacor |
| B-219 | oxyfluorfen | benoxacor |
| B-220 | saflufenacil | benoxacor |
| B-221 | sulfentrazone | benoxacor |
| B-222 | H-1 | benoxacor |
| B-223 | H-2 | benoxacor |
| B-224 | glyphosate | benoxacor |
| B-225 | glyphosate-isopropylammonium | benoxacor |
| B-226 | glyphosate-trimesium (sulfosate) | benoxacor |
| B-227 | glufosinate | benoxacor |
| B-228 | glufosinate-ammonium | benoxacor |
| B-229 | pendimethalin | benoxacor |
| B-230 | trifluralin | benoxacor |
| B-231 | acetochlor | benoxacor |
| B-232 | cafenstrole | benoxacor |
| B-233 | dimethenamid-P | benoxacor |
| B-234 | fentrazamide | benoxacor |
| B-235 | flufenacet | benoxacor |
| B-236 | mefenacet | benoxacor |
| B-237 | metazachlor | benoxacor |
| B-238 | metolachlor-S | benoxacor |
| B-239 | pyroxasulfone | benoxacor |
| B-240 | isoxaben | benoxacor |
| B-241 | dymron | benoxacor |
| B-242 | indanofan | benoxacor |
| B-243 | oxaziclomefone | benoxacor |
| B-244 | triaziflam | benoxacor |
| B-245 | atrazine + H-1 | benoxacor |
| B-246 | atrazine + glyphosate | benoxacor |
| B-247 | atrazine + mesotrione | benoxacor |
| B-248 | atrazine + nicosulfuron | benoxacor |
| B-249 | atrazine + tembotrione | benoxacor |
| B-250 | atrazine + topramezone | benoxacor |
| B-251 | clomazone + glyphosate | benoxacor |
| B-252 | diflufenican + clodinafop-propargyl | benoxacor |
| B-253 | diflufenican + fenoxaprop-P-ethyl | benoxacor |
| B-254 | diflufenican + flupyrsulfuron-methyl-sodium | benoxacor |
| B-255 | diflufenican + glyphosate | benoxacor |
| B-256 | diflufenican + mesosulfuron-methyl | benoxacor |
| B-257 | diflufenican + pinoxaden | benoxacor |
| B-258 | diflufenican + pyroxsulam | benoxacor |
| B-259 | flumetsulam + glyphosate | benoxacor |
| B-260 | flumioxazin + glyphosate | benoxacor |
| B-261 | imazapic + glyphosate | benoxacor |
| B-262 | imazethapyr + glyphosate | benoxacor |
| B-263 | isoxaflutol + H-1 | benoxacor |
| B-264 | isoxaflutol + glyphosate | benoxacor |
| B-265 | metazachlor + H-1 | benoxacor |
| B-266 | metazachlor + glyphosate | benoxacor |
| B-267 | metazachlor + mesotrione | benoxacor |
| B-268 | metazachlor + nicosulfuron | benoxacor |
| B-269 | metazachlor + terbuthylazine | benoxacor |
| B-270 | metazachlor + topramezone | benoxacor |
| B-271 | metribuzin + glyphosate | benoxacor |
| B-272 | pendimethalin + H-1 | benoxacor |
| B-273 | pendimethalin + clodinafop-propargyl | benoxacor |
| B-274 | pendimethalin + fenoxaprop-P-ethyl | benoxacor |
| B-275 | pendimethalin + flupyrsulfuron-methyl-sodium | benoxacor |
| B-276 | pendimethalin + glyphosate | benoxacor |
| B-277 | pendimethalin + mesosulfuron-methyl | benoxacor |
| B-278 | pendimethalin + mesotrione | benoxacor |
| B-279 | pendimethalin + nicosulfuron | benoxacor |
| B-280 | pendimethalin + pinoxaden | benoxacor |
| B-281 | pendimethalin + pyroxsulam | benoxacor |
| B-282 | pendimethalin + tembotrione | benoxacor |
| B-283 | pendimethalin + topramezone | benoxacor |
| B-284 | pyroxasulfone + tembotrione | benoxacor |
| B-285 | pyroxasulfone + topramezone | benoxacor |
| B-286 | sulfentrazone + glyphosate | benoxacor |
| B-287 | terbuthylazine + H-1 | benoxacor |
| B-288 | terbuthylazine + foramsulfuron | benoxacor |
| B-289 | terbuthylazine + glyphosate | benoxacor |
| B-290 | terbuthylazine + mesotrione | benoxacor |
| B-291 | terbuthylazine + nicosulfuron | benoxacor |
| B-292 | terbuthylazine + tembotrione | benoxacor |
| B-293 | terbuthylazine + topramezone | benoxacor |
| B-294 | trifluralin + glyphosate | benoxacor |
| B-295 | clodinafop-propargyl | cloquintocet |
| B-296 | cycloxydim | cloquintocet |
| B-297 | cyhalofop-butyl | cloquintocet |
| B-298 | fenoxaprop-P-ethyl | cloquintocet |
| B-299 | pinoxaden | cloquintocet |
| B-300 | profoxydim | cloquintocet |
| B-301 | tepraloxydim | cloquintocet |
| B-302 | tralkoxydim | cloquintocet |
| B-303 | esprocarb | cloquintocet |
| B-304 | prosulfocarb | cloquintocet |
| B-305 | thiobencarb | cloquintocet |
| B-306 | triallate | cloquintocet |
| B-307 | bensulfuron-methyl | cloquintocet |
| B-308 | bispyribac-sodium | cloquintocet |
| B-309 | cyclosulfamuron | cloquintocet |
| B-310 | flumetsulam | cloquintocet |
| B-311 | flupyrsulfuron-methyl-sodium | cloquintocet |
| B-312 | foramsulfuron | cloquintocet |
| B-313 | imazamox | cloquintocet |
| B-314 | imazapic | cloquintocet |
| B-315 | imazapyr | cloquintocet |
| B-316 | imazaquin | cloquintocet |
| B-317 | imazethapyr | cloquintocet |
| B-318 | imazosulfuron | cloquintocet |
| B-319 | iodosulfuron-methyl-sodium | cloquintocet |
| B-320 | mesosulfuron | cloquintocet |
| B-321 | nicosulfuron | cloquintocet |
| B-322 | penoxsulam | cloquintocet |
| B-323 | propoxycarbazone-sodium | cloquintocet |
| B-324 | pyrazosulfuron-ethyl | cloquintocet |
| B-325 | pyroxsulam | cloquintocet |
| B-326 | rimsulfuron | cloquintocet |
| B-327 | sulfosulfuron | cloquintocet |
| B-328 | thiencarbazone-methyl | cloquintocet |
| B-329 | tritosulfuron | cloquintocet |
| B-330 | 2,4-D and its salts and esters | cloquintocet |
| B-331 | aminopyralid and its salts and esters | cloquintocet |
| B-332 | clopyralid and its salts and esters | cloquintocet |
| B-333 | dicamba and its salts and esters | cloquintocet |
| B-334 | fluroxypyr-meptyl | cloquintocet |
| B-335 | quinclorac | cloquintocet |
| B-336 | quinmerac | cloquintocet |
| B-337 | H-9 | cloquintocet |
| B-338 | diflufenzopyr | cloquintocet |
| B-339 | diflufenzopyr-sodium | cloquintocet |
| B-340 | clomazone | cloquintocet |
| B-341 | diflufenican | cloquintocet |
| B-342 | fluorochloridone | cloquintocet |
| B-343 | isoxaflutol | cloquintocet |
| B-344 | mesotrione | cloquintocet |
| B-345 | picolinafen | cloquintocet |
| B-346 | sulcotrione | cloquintocet |
| B-347 | tefuryltrione | cloquintocet |
| B-348 | tembotrione | cloquintocet |
| B-349 | topramezone | cloquintocet |
| B-350 | H-7 | cloquintocet |
| B-351 | atrazine | cloquintocet |
| B-352 | diuron | cloquintocet |
| B-353 | fluometuron | cloquintocet |
| B-354 | hexazinone | cloquintocet |
| B-355 | isoproturon | cloquintocet |
| B-356 | metribuzin | cloquintocet |
| B-357 | propanil | cloquintocet |
| B-358 | terbuthylazine | cloquintocet |
| B-359 | paraquat dichloride | cloquintocet |
| B-360 | flumioxazin | cloquintocet |
| B-361 | oxyfluorfen | cloquintocet |

TABLE B-continued

| | Herbicide(s) B | Safener C |
|---|---|---|
| B-362 | saflufenacil | cloquintocet |
| B-363 | sulfentrazone | cloquintocet |
| B-364 | H-1 | cloquintocet |
| B-365 | H-2 | cloquintocet |
| B-366 | glyphosate | cloquintocet |
| B-367 | glyphosate-isopropylammonium | cloquintocet |
| B-368 | glyphosate-trimesium (sulfosate) | cloquintocet |
| B-369 | glufosinate | cloquintocet |
| B-370 | glufosinate-ammonium | cloquintocet |
| B-371 | pendimethalin | cloquintocet |
| B-372 | trifluralin | cloquintocet |
| B-373 | acetochlor | cloquintocet |
| B-374 | cafenstrole | cloquintocet |
| B-375 | dimethenamid-P | cloquintocet |
| B-376 | fentrazamide | cloquintocet |
| B-377 | flufenacet | cloquintocet |
| B-378 | mefenacet | cloquintocet |
| B-379 | metazachlor | cloquintocet |
| B-380 | metolachlor-S | cloquintocet |
| B-381 | pyroxasulfone | cloquintocet |
| B-382 | isoxaben | cloquintocet |
| B-383 | dymron | cloquintocet |
| B-384 | indanofan | cloquintocet |
| B-385 | oxaziclomefone | cloquintocet |
| B-386 | triaziflam | cloquintocet |
| B-387 | atrazine + H-1 | cloquintocet |
| B-388 | atrazine + glyphosate | cloquintocet |
| B-389 | atrazine + mesotrione | cloquintocet |
| B-390 | atrazine + nicosulfuron | cloquintocet |
| B-391 | atrazine + tembotrione | cloquintocet |
| B-392 | atrazine + topramezone | cloquintocet |
| B-393 | clomazone + glyphosate | cloquintocet |
| B-394 | diflufenican + clodinafop-propargyl | cloquintocet |
| B-395 | diflufenican + fenoxaprop-p-ethyl | cloquintocet |
| B-396 | diflufenican + flupyrsulfuron-methyl-sodium | cloquintocet |
| B-397 | diflufenican + glyphosate | cloquintocet |
| B-398 | diflufenican + mesosulfuron-methyl | cloquintocet |
| B-399 | diflufenican + pinoxaden | cloquintocet |
| B-400 | diflufenican + pyroxsulam | cloquintocet |
| B-401 | flumetsulam + glyphosate | cloquintocet |
| B-402 | flumioxazin + glyphosate | cloquintocet |
| B-403 | imazapic + glyphosate | cloquintocet |
| B-404 | imazethapyr + glyphosate | cloquintocet |
| B-405 | isoxaflutol + H-1 | cloquintocet |
| B-406 | isoxaflutol + glyphosate | cloquintocet |
| B-407 | metazachlor + H-1 | cloquintocet |
| B-408 | metazachlor + glyphosate | cloquintocet |
| B-409 | metazachlor + mesotrione | cloquintocet |
| B-410 | metazachlor + nicosulfuron | cloquintocet |
| B-411 | metazachlor + terbuthylazine | cloquintocet |
| B-412 | metazachlor + topramezone | cloquintocet |
| B-413 | metribuzin + glyphosate | cloquintocet |
| B-414 | pendimethalin + H-1 | cloquintocet |
| B-415 | pendimethalin + clodinafop-propargyl | cloquintocet |
| B-416 | pendimethalin + fenoxaprop-P-ethyl | cloquintocet |
| B-417 | pendimethalin + flupyrsulfuron-methyl-sodium | cloquintocet |
| B-418 | pendimethalin + glyphosate | cloquintocet |
| B-419 | pendimethalin + mesosulfuron-methyl | cloquintocet |
| B-420 | pendimethalin + mesotrione | cloquintocet |
| B-421 | pendimethalin + nicosulfuron | cloquintocet |
| B-422 | pendimethalin + pinoxaden | cloquintocet |
| B-423 | pendimethalin + pyroxsulam | cloquintocet |
| B-424 | pendimethalin + tembotrione | cloquintocet |
| B-425 | pendimethalin + topramezone | cloquintocet |
| B-426 | pyroxasulfone + tembotrione | cloquintocet |
| B-427 | pyroxasulfone + topramezone | cloquintocet |
| B-428 | sulfentrazone + glyphosate | cloquintocet |
| B-429 | terbuthylazine + H-1 | cloquintocet |
| B-430 | terbuthylazine + foramsulfuron | cloquintocet |
| B-431 | terbuthylazine + glyphosate | cloquintocet |
| B-432 | terbuthylazine + mesotrione | cloquintocet |
| B-433 | terbuthylazine + nicosulfuron | cloquintocet |
| B-434 | terbuthylazine + tembotrione | cloquintocet |
| B-435 | terbuthylazine + topramezone | cloquintocet |
| B-436 | trifluralin + glyphosate | cloquintocet |
| B-437 | clodinafop-propargyl | dichlormid |
| B-438 | cycloxydim | dichlormid |
| B-439 | cyhalofop-butyl | dichlormid |
| B-440 | fenoxaprop-P-ethyl | dichlormid |
| B-441 | pinoxaden | dichlormid |
| B-442 | profoxydim | dichlormid |
| B-443 | tepraloxydim | dichlormid |
| B-444 | tralkoxydim | dichlormid |
| B-445 | esprocarb | dichlormid |
| B-446 | prosulfocarb | dichlormid |
| B-447 | thiobencarb | dichlormid |
| B-448 | triallate | dichlormid |
| B-449 | bensulfuron-methyl | dichlormid |
| B-450 | bispyribac-sodium | dichlormid |
| B-451 | cyclosulfamuron | dichlormid |
| B-452 | flumetsulam | dichlormid |
| B-453 | flupyrsulfuron-methyl-sodium | dichlormid |
| B-454 | foramsulfuron | dichlormid |
| B-455 | imazamox | dichlormid |
| B-456 | imazapic | dichlormid |
| B-457 | imazapyr | dichlormid |
| B-458 | imazaquin | dichlormid |
| B-459 | imazethapyr | dichlormid |
| B-460 | imazosulfuron | dichlormid |
| B-461 | iodosulfuron-methyl-sodium | dichlormid |
| B-462 | mesosulfuron | dichlormid |
| B-463 | nicosulfuron | dichlormid |
| B-464 | penoxsulam | dichlormid |
| B-465 | propoxycarbazone-sodium | dichlormid |
| B-466 | pyrazosulfuron-ethyl | dichlormid |
| B-467 | pyroxsulam | dichlormid |
| B-468 | rimsulfuron | dichlormid |
| B-469 | sulfosulfuron | dichlormid |
| B-470 | thiencarbazone-methyl | dichlormid |
| B-471 | tritosulfuron | dichlormid |
| B-472 | 2,4-D and its salts and esters | dichlormid |
| B-473 | aminopyralid and its salts and esters | dichlormid |
| B-474 | clopyralid and its salts and esters | dichlormid |
| B-475 | dicamba and its salts and esters | dichlormid |
| B-476 | fluroxypyr-meptyl | dichlormid |
| B-477 | quinclorac | dichlormid |
| B-478 | quinmerac | dichlormid |
| B-479 | H-9 | dichlormid |
| B-480 | diflufenzopyr | dichlormid |
| B-481 | diflufenzopyr-sodium | dichlormid |
| B-482 | clomazone | dichlormid |
| B-483 | diflufenican | dichlormid |
| B-484 | fluorochloridone | dichlormid |
| B-485 | isoxaflutol | dichlormid |
| B-486 | mesotrione | dichlormid |
| B-487 | picolinafen | dichlormid |
| B-488 | sulcotrione | dichlormid |
| B-489 | tefuryltrione | dichlormid |
| B-490 | tembotrione | dichlormid |
| B-491 | topramezone | dichlormid |
| B-492 | H-7 | dichlormid |
| B-493 | atrazine | dichlormid |
| B-494 | diuron | dichlormid |
| B-495 | fluometuron | dichlormid |
| B-496 | hexazinone | dichlormid |
| B-497 | isoproturon | dichlormid |
| B-498 | metribuzin | dichlormid |
| B-499 | propanil | dichlormid |
| B-500 | terbuthylazine | dichlormid |
| B-501 | paraquat dichloride | dichlormid |
| B-502 | flumioxazin | dichlormid |
| B-503 | oxyfluorfen | dichlormid |
| B-504 | saflufenacil | dichlormid |
| B-505 | sulfentrazone | dichlormid |
| B-506 | H-1 | dichlormid |
| B-507 | H-2 | dichlormid |
| B-508 | glyphosate | dichlormid |
| B-509 | glyphosate-isopropylammonium | dichlormid |
| B-510 | glyphosate-trimesium (sulfosate) | dichlormid |
| B-511 | glufosinate | dichlormid |
| B-512 | glufosinate-ammonium | dichlormid |
| B-513 | pendimethalin | dichlormid |
| B-514 | trifluralin | dichlormid |
| B-515 | acetochlor | dichlormid |
| B-516 | cafenstrole | dichlormid |
| B-517 | dimethenamid-P | dichlormid |

TABLE B-continued

| | Herbicide(s) B | Safener C |
|---|---|---|
| B-518 | fentrazamide | dichlormid |
| B-519 | flufenacet | dichlormid |
| B-520 | mefenacet | dichlormid |
| B-521 | metazachlor | dichlormid |
| B-522 | metolachlor-S | dichlormid |
| B-523 | pyroxasulfone | dichlormid |
| B-524 | isoxaben | dichlormid |
| B-525 | dymron | dichlormid |
| B-526 | indanofan | dichlormid |
| B-527 | oxaziclomefone | dichlormid |
| B-528 | triaziflam | dichlormid |
| B-529 | atrazine + H-1 | dichlormid |
| B-530 | atrazine + glyphosate | dichlormid |
| B-531 | atrazine + mesotrione | dichlormid |
| B-532 | atrazine + nicosulfuron | dichlormid |
| B-533 | atrazine + tembotrione | dichlormid |
| B-534 | atrazine + topramezone | dichlormid |
| B-535 | clomazone + glyphosate | dichlormid |
| B-536 | diflufenican + clodinafop-propargyl | dichlormid |
| B-537 | diflufenican + fenoxaprop-p-ethyl | dichlormid |
| B-538 | diflufenican + flupyrsulfuron-methyl-sodium | dichlormid |
| B-539 | diflufenican + glyphosate | dichlormid |
| B-540 | diflufenican + mesosulfuron-methyl | dichlormid |
| B-541 | diflufenican + pinoxaden | dichlormid |
| B-542 | diflufenican + pyroxsulam | dichlormid |
| B-543 | flumetsulam + glyphosate | dichlormid |
| B-544 | flumioxazin + glyphosate | dichlormid |
| B-545 | imazapic + glyphosate | dichlormid |
| B-546 | imazethapyr + glyphosate | dichlormid |
| B-547 | isoxaflutol + H-1 | dichlormid |
| B-548 | isoxaflutol + glyphosate | dichlormid |
| B-549 | metazachlor + H-1 | dichlormid |
| B-550 | metazachlor + glyphosate | dichlormid |
| B-551 | metazachlor + mesotrione | dichlormid |
| B-552 | metazachlor + nicosulfuron | dichlormid |
| B-553 | metazachlor + terbuthylazine | dichlormid |
| B-554 | metazachlor + topramezone | dichlormid |
| B-555 | metribuzin + glyphosate | dichlormid |
| B-556 | pendimethalin + H-1 | dichlormid |
| B-557 | pendimethalin + clodinafop-propargyl | dichlormid |
| B-558 | pendimethalin + fenoxaprop-P-ethyl | dichlormid |
| B-559 | pendimethalin + flupyrsulfuron-methyl-sodium | dichlormid |
| B-560 | pendimethalin + glyphosate | dichlormid |
| B-561 | pendimethalin + mesosulfuron-methyl | dichlormid |
| B-562 | pendimethalin + mesotrione | dichlormid |
| B-563 | pendimethalin + nicosulfuron | dichlormid |
| B-564 | pendimethalin + pinoxaden | dichlormid |
| B-565 | pendimethalin + pyroxsulam | dichlormid |
| B-566 | pendimethalin + tembotrione | dichlormid |
| B-567 | pendimethalin + topramezone | dichlormid |
| B-568 | pyroxasulfone + tembotrione | dichlormid |
| B-569 | pyroxasulfone + topramezone | dichlormid |
| B-570 | sulfentrazone + glyphosate | dichlormid |
| B-571 | terbuthylazine + H-1 | dichlormid |
| B-572 | terbuthylazine + foramsulfuron | dichlormid |
| B-573 | terbuthylazine + glyphosate | dichlormid |
| B-574 | terbuthylazine + mesotrione | dichlormid |
| B-575 | terbuthylazine + nicosulfuron | dichlormid |
| B-576 | terbuthylazine + tembotrione | dichlormid |
| B-577 | terbuthylazine + topramezone | dichlormid |
| B-578 | trifluralin + glyphosate | dichlormid |
| B-579 | clodinafop-propargyl | fenchlorazole |
| B-580 | cycloxydim | fenchlorazole |
| B-581 | cyhalofop-butyl | fenchlorazole |
| B-582 | fenoxaprop-P-ethyl | fenchlorazole |
| B-583 | pinoxaden | fenchlorazole |
| B-584 | profoxydim | fenchlorazole |
| B-585 | tepraloxydim | fenchlorazole |
| B-586 | tralkoxydim | fenchlorazole |
| B-587 | esprocarb | fenchlorazole |
| B-588 | prosulfocarb | fenchlorazole |
| B-589 | thiobencarb | fenchlorazole |
| B-590 | triallate | fenchlorazole |
| B-591 | bensulfuron-methyl | fenchlorazole |
| B-592 | bispyribac-sodium | fenchlorazole |
| B-593 | cyclosulfamuron | fenchlorazole |
| B-594 | flumetsulam | fenchlorazole |
| B-595 | flupyrsulfuron-methyl-sodium | fenchlorazole |
| B-596 | foramsulfuron | fenchlorazole |
| B-597 | imazamox | fenchlorazole |
| B-598 | imazapic | fenchlorazole |
| B-599 | imazapyr | fenchlorazole |
| B-600 | imazaquin | fenchlorazole |
| B-601 | imazethapyr | fenchlorazole |
| B-602 | imazosulfuron | fenchlorazole |
| B-603 | iodosulfuron-methyl-sodium | fenchlorazole |
| B-604 | mesosulfuron | fenchlorazole |
| B-605 | nicosulfuron | fenchlorazole |
| B-606 | penoxsulam | fenchlorazole |
| B-607 | propoxycarbazone-sodium | fenchlorazole |
| B-608 | pyrazosulfuron-ethyl | fenchlorazole |
| B-609 | pyroxsulam | fenchlorazole |
| B-610 | rimsulfuron | fenchlorazole |
| B-611 | sulfosulfuron | fenchlorazole |
| B-612 | thiencarbazone-methyl | fenchlorazole |
| B-613 | tritosulfuron | fenchlorazole |
| B-614 | 2,4-D and its salts and esters | fenchlorazole |
| B-615 | aminopyralid and its salts and esters | fenchlorazole |
| B-616 | clopyralid and its salts and esters | fenchlorazole |
| B-617 | dicamba and its salts and esters | fenchlorazole |
| B-618 | fluroxypyr-meptyl | fenchlorazole |
| B-619 | quinclorac | fenchlorazole |
| B-620 | quinmerac | fenchlorazole |
| B-621 | H-9 | fenchlorazole |
| B-622 | diflufenzopyr | fenchlorazole |
| B-623 | diflufenzopyr-sodium | fenchlorazole |
| B-624 | clomazone | fenchlorazole |
| B-625 | diflufenican | fenchlorazole |
| B-626 | fluorochloridone | fenchlorazole |
| B-627 | isoxaflutol | fenchlorazole |
| B-628 | mesotrione | fenchlorazole |
| B-629 | picolinafen | fenchlorazole |
| B-630 | sulcotrione | fenchlorazole |
| B-631 | tefuryltrione | fenchlorazole |
| B-632 | tembotrione | fenchlorazole |
| B-633 | topramezone | fenchlorazole |
| B-634 | H-7 | fenchlorazole |
| B-635 | atrazine | fenchlorazole |
| B-636 | diuron | fenchlorazole |
| B-637 | fluometuron | fenchlorazole |
| B-638 | hexazinone | fenchlorazole |
| B-639 | isoproturon | fenchlorazole |
| B-640 | metribuzin | fenchlorazole |
| B-641 | propanil | fenchlorazole |
| B-642 | terbuthylazine | fenchlorazole |
| B-643 | paraquat dichloride | fenchlorazole |
| B-644 | flumioxazin | fenchlorazole |
| B-645 | oxyfluorfen | fenchlorazole |
| B-646 | saflufenacil | fenchlorazole |
| B-647 | sulfentrazone | fenchlorazole |
| B-648 | H-1 | fenchlorazole |
| B-649 | H-2 | fenchlorazole |
| B-650 | glyphosate | fenchlorazole |
| B-651 | glyphosate-isopropylammonium | fenchlorazole |
| B-652 | glyphosate-trimesium (sulfosate) | fenchlorazole |
| B-653 | glufosinate | fenchlorazole |
| B-654 | glufosinate-ammonium | fenchlorazole |
| B-655 | pendimethalin | fenchlorazole |
| B-656 | trifluralin | fenchlorazole |
| B-657 | acetochlor | fenchlorazole |
| B-658 | cafenstrole | fenchlorazole |
| B-659 | dimethenamid-P | fenchlorazole |
| B-660 | fentrazamide | fenchlorazole |
| B-661 | flufenacet | fenchlorazole |
| B-662 | mefenacet | fenchlorazole |
| B-663 | metazachlor | fenchlorazole |
| B-664 | metolachlor-S | fenchlorazole |
| B-665 | pyroxasulfone | fenchlorazole |
| B-666 | isoxaben | fenchlorazole |
| B-667 | dymron | fenchlorazole |
| B-668 | indanofan | fenchlorazole |
| B-669 | oxaziclomefone | fenchlorazole |
| B-670 | triaziflam | fenchlorazole |
| B-671 | atrazine + H-1 | fenchlorazole |
| B-672 | atrazine + glyphosate | fenchlorazole |
| B-673 | atrazine + mesotrione | fenchlorazole |

TABLE B-continued

| | Herbicide(s) B | Safener C |
|---|---|---|
| B-674 | atrazine + nicosulfuron | fenchlorazole |
| B-675 | atrazine + tembotrione | fenchlorazole |
| B-676 | atrazine + topramezone | fenchlorazole |
| B-677 | clomazone + glyphosate | fenchlorazole |
| B-678 | diflufenican + clodinafop-propargyl | fenchlorazole |
| B-679 | diflufenican + fenoxaprop-P-ethyl | fenchlorazole |
| B-680 | diflufenican + flupyrsulfuron-methyl-sodium | fenchlorazole |
| B-681 | diflufenican + glyphosate | fenchlorazole |
| B-682 | diflufenican + mesosulfuron-methyl | fenchlorazole |
| B-683 | diflufenican + pinoxaden | fenchlorazole |
| B-684 | diflufenican + pyroxsulam | fenchlorazole |
| B-685 | flumetsulam + glyphosate | fenchlorazole |
| B-686 | flumioxazin + glyphosate | fenchlorazole |
| B-687 | imazapic + glyphosate | fenchlorazole |
| B-688 | imazethapyr + glyphosate | fenchlorazole |
| B-689 | isoxaflutol + H-1 | fenchlorazole |
| B-690 | isoxaflutol + glyphosate | fenchlorazole |
| B-691 | metazachlor + H-1 | fenchlorazole |
| B-692 | metazachlor + glyphosate | fenchlorazole |
| B-693 | metazachlor + mesotrione | fenchlorazole |
| B-694 | metazachlor + nicosulfuron | fenchlorazole |
| B-695 | metazachlor + terbuthylazine | fenchlorazole |
| B-696 | metazachlor + topramezone | fenchlorazole |
| B-697 | metribuzin + glyphosate | fenchlorazole |
| B-698 | pendimethalin + H-1 | fenchlorazole |
| B-699 | pendimethalin + clodinafop-propargyl | fenchlorazole |
| B-700 | pendimethalin + fenoxaprop-P-ethyl | fenchlorazole |
| B-701 | pendimethalin + flupyrsulfuron-methyl-sodium | fenchlorazole |
| B-702 | pendimethalin + glyphosate | fenchlorazole |
| B-703 | pendimethalin + mesosulfuron-methyl | fenchlorazole |
| B-704 | pendimethalin + mesotrione | fenchlorazole |
| B-705 | pendimethalin + nicosulfuron | fenchlorazole |
| B-706 | pendimethalin + pinoxaden | fenchlorazole |
| B-707 | pendimethalin + pyroxsulam | fenchlorazole |
| B-708 | pendimethalin + tembotrione | fenchlorazole |
| B-709 | pendimethalin + topramezone | fenchlorazole |
| B-710 | pyroxasulfone + tembotrione | fenchlorazole |
| B-711 | pyroxasulfone + topramezone | fenchlorazole |
| B-712 | sulfentrazone + glyphosate | fenchlorazole |
| B-713 | terbuthylazine + H-1 | fenchlorazole |
| B-714 | terbuthylazine + foramsulfuron | fenchlorazole |
| B-715 | terbuthylazine + glyphosate | fenchlorazole |
| B-716 | terbuthylazine + mesotrione | fenchlorazole |
| B-717 | terbuthylazine + nicosulfuron | fenchlorazole |
| B-718 | terbuthylazine + tembotrione | fenchlorazole |
| B-719 | terbuthylazine + topramezone | fenchlorazole |
| B-720 | trifluralin + glyphosate | fenchlorazole |
| B-721 | clodinafop-propargyl | isoxadifen |
| B-722 | cycloxydim | isoxadifen |
| B-723 | cyhalofop-butyl | isoxadifen |
| B-724 | fenoxaprop-P-ethyl | isoxadifen |
| B-725 | pinoxaden | isoxadifen |
| B-726 | profoxydim | isoxadifen |
| B-727 | tepraloxydim | isoxadifen |
| B-728 | tralkoxydim | isoxadifen |
| B-729 | esprocarb | isoxadifen |
| B-730 | prosulfocarb | isoxadifen |
| B-731 | thiobencarb | isoxadifen |
| B-732 | triallate | isoxadifen |
| B-733 | bensulfuron-methyl | isoxadifen |
| B-734 | bispyribac-sodium | isoxadifen |
| B-735 | cyclosulfamuron | isoxadifen |
| B-736 | flumetsulam | isoxadifen |
| B-737 | flupyrsulfuron-methyl-sodium | isoxadifen |
| B-738 | foramsulfuron | isoxadifen |
| B-739 | imazamox | isoxadifen |
| B-740 | imazapic | isoxadifen |
| B-741 | imazapyr | isoxadifen |
| B-742 | imazaquin | isoxadifen |
| B-743 | imazethapyr | isoxadifen |
| B-744 | imazosulfuron | isoxadifen |
| B-745 | iodosulfuron-methyl-sodium | isoxadifen |
| B-746 | mesosulfuron | isoxadifen |
| B-747 | nicosulfuron | isoxadifen |
| B-748 | penoxsulam | isoxadifen |
| B-749 | propoxycarbazone-sodium | isoxadifen |
| B-750 | pyrazosulfuron-ethyl | isoxadifen |
| B-751 | pyroxsulam | isoxadifen |
| B-752 | rimsulfuron | isoxadifen |
| B-753 | sulfosulfuron | isoxadifen |
| B-754 | thiencarbazone-methyl | isoxadifen |
| B-755 | tritosulfuron | isoxadifen |
| B-756 | 2,4-D and its salts and esters | isoxadifen |
| B-757 | aminopyralid and its salts and esters | isoxadifen |
| B-758 | clopyralid and its salts and esters | isoxadifen |
| B-759 | dicamba and its salts and esters | isoxadifen |
| B-760 | fluroxypyr-meptyl | isoxadifen |
| B-761 | quinclorac | isoxadifen |
| B-762 | quinmerac | isoxadifen |
| B-763 | H-9 | isoxadifen |
| B-764 | diflufenzopyr | isoxadifen |
| B-765 | diflufenzopyr-sodium | isoxadifen |
| B-766 | clomazone | isoxadifen |
| B-767 | diflufenican | isoxadifen |
| B-768 | fluorochloridone | isoxadifen |
| B-769 | isoxaflutol | isoxadifen |
| B-770 | mesotrione | isoxadifen |
| B-771 | picolinafen | isoxadifen |
| B-772 | sulcotrione | isoxadifen |
| B-773 | tefuryltrione | isoxadifen |
| B-774 | tembotrione | isoxadifen |
| B-775 | topramezone | isoxadifen |
| B-776 | H-7 | isoxadifen |
| B-777 | atrazine | isoxadifen |
| B-778 | diuron | isoxadifen |
| B-779 | fluometuron | isoxadifen |
| B-780 | hexazinone | isoxadifen |
| B-781 | isoproturon | isoxadifen |
| B-782 | metribuzin | isoxadifen |
| B-783 | propanil | isoxadifen |
| B-784 | terbuthylazine | isoxadifen |
| B-785 | paraquat dichloride | isoxadifen |
| B-786 | flumioxazin | isoxadifen |
| B-787 | oxyfluorfen | isoxadifen |
| B-788 | saflufenacil | isoxadifen |
| B-789 | sulfentrazone | isoxadifen |
| B-790 | H-1 | isoxadifen |
| B-791 | H-2 | isoxadifen |
| B-792 | glyphosate | isoxadifen |
| B-793 | glyphosate-isopropylammonium | isoxadifen |
| B-794 | glyphosate-trimesium (sulfosate) | isoxadifen |
| B-795 | glufosinate | isoxadifen |
| B-796 | glufosinate-ammonium | isoxadifen |
| B-797 | pendimethalin | isoxadifen |
| B-798 | trifluralin | isoxadifen |
| B-799 | acetochlor | isoxadifen |
| B-800 | cafenstrole | isoxadifen |
| B-801 | dimethenamid-P | isoxadifen |
| B-802 | fentrazamide | isoxadifen |
| B-803 | flufenacet | isoxadifen |
| B-804 | mefenacet | isoxadifen |
| B-805 | metazachlor | isoxadifen |
| B-806 | metolachlor-S | isoxadifen |
| B-807 | pyroxasulfone | isoxadifen |
| B-808 | isoxaben | isoxadifen |
| B-809 | dymron | isoxadifen |
| B-810 | indanofan | isoxadifen |
| B-811 | oxaziclomefone | isoxadifen |
| B-812 | triaziflam | isoxadifen |
| B-813 | atrazine + H-1 | isoxadifen |
| B-814 | atrazine + glyphosate | isoxadifen |
| B-815 | atrazine + mesotrione | isoxadifen |
| B-816 | atrazine + nicosulfuron | isoxadifen |
| B-817 | atrazine + tembotrione | isoxadifen |
| B-818 | atrazine + topramezone | isoxadifen |
| B-819 | clomazone + glyphosate | isoxadifen |
| B-820 | diflufenican + clodinafop-propargyl | isoxadifen |
| B-821 | diflufenican + fenoxaprop-P-ethyl | isoxadifen |
| B-822 | diflufenican + flupyrsulfuron-methyl-sodium | isoxadifen |
| B-823 | diflufenican + glyphosate | isoxadifen |
| B-824 | diflufenican + mesosulfuron-methyl | isoxadifen |
| B-825 | diflufenican + pinoxaden | isoxadifen |
| B-826 | diflufenican + pyroxsulam | isoxadifen |
| B-827 | flumetsulam + glyphosate | isoxadifen |
| B-828 | flumioxazin + glyphosate | isoxadifen |
| B-829 | imazapic + glyphosate | isoxadifen |

TABLE B-continued

| | Herbicide(s) B | Safener C |
|---|---|---|
| B-830 | imazethapyr + glyphosate | isoxadifen |
| B-831 | isoxaflutol + H-1 | isoxadifen |
| B-832 | isoxaflutol + glyphosate | isoxadifen |
| B-833 | metazachlor + H-1 | isoxadifen |
| B-834 | metazachlor + glyphosate | isoxadifen |
| B-835 | metazachlor + mesotrione | isoxadifen |
| B-836 | metazachlor + nicosulfuron | isoxadifen |
| B-837 | metazachlor + terbuthylazine | isoxadifen |
| B-838 | metazachlor + topramezone | isoxadifen |
| B-839 | metribuzin + glyphosate | isoxadifen |
| B-840 | pendimethalin + H-1 | isoxadifen |
| B-841 | pendimethalin + clodinafop-propargyl | isoxadifen |
| B-842 | pendimethalin + fenoxaprop-P-ethyl | isoxadifen |
| B-843 | pendimethalin + flupyrsulfuron-methyl-sodium | isoxadifen |
| B-844 | pendimethalin + glyphosate | isoxadifen |
| B-845 | pendimethalin + mesosulfuron-methyl | isoxadifen |
| B-846 | pendimethalin + mesotrione | isoxadifen |
| B-847 | pendimethalin + nicosulfuron | isoxadifen |
| B-848 | pendimethalin + pinoxaden | isoxadifen |
| B-849 | pendimethalin + pyroxsulam | isoxadifen |
| B-850 | pendimethalin + tembotrione | isoxadifen |
| B-851 | pendimethalin + topramezone | isoxadifen |
| B-852 | pyroxasulfone + tembotrione | isoxadifen |
| B-853 | pyroxasulfone + topramezone | isoxadifen |
| B-854 | sulfentrazone + glyphosate | isoxadifen |
| B-855 | terbuthylazine + H-1 | isoxadifen |
| B-856 | terbuthylazine + foramsulfuron | isoxadifen |
| B-857 | terbuthylazine + glyphosate | isoxadifen |
| B-858 | terbuthylazine + mesotrione | isoxadifen |
| B-859 | terbuthylazine + nicosulfuron | isoxadifen |
| B-860 | terbuthylazine + tembotrione | isoxadifen |
| B-861 | terbuthylazine + topramezone | isoxadifen |
| B-862 | trifluralin + glyphosate | isoxadifen |
| B-863 | clodinafop-propargyl | mefenpyr |
| B-864 | cycloxydim | mefenpyr |
| B-865 | cyhalofop-butyl | mefenpyr |
| B-866 | fenoxaprop-P-ethyl | mefenpyr |
| B-867 | pinoxaden | mefenpyr |
| B-868 | profoxydim | mefenpyr |
| B-869 | tepraloxydim | mefenpyr |
| B-870 | tralkoxydim | mefenpyr |
| B-871 | esprocarb | mefenpyr |
| B-872 | prosulfocarb | mefenpyr |
| B-873 | thiobencarb | mefenpyr |
| B-874 | triallate | mefenpyr |
| B-875 | bensulfuron-methyl | mefenpyr |
| B-876 | bispyribac-sodium | mefenpyr |
| B-877 | cyclosulfamuron | mefenpyr |
| B-878 | flumetsulam | mefenpyr |
| B-879 | flupyrsulfuron-methyl-sodium | mefenpyr |
| B-880 | foramsulfuron | mefenpyr |
| B-881 | imazamox | mefenpyr |
| B-882 | imazapic | mefenpyr |
| B-883 | imazapyr | mefenpyr |
| B-884 | imazaquin | mefenpyr |
| B-885 | imazethapyr | mefenpyr |
| B-886 | imazosulfuron | mefenpyr |
| B-887 | iodosulfuron-methyl-sodium | mefenpyr |
| B-888 | mesosulfuron | mefenpyr |
| B-889 | nicosulfuron | mefenpyr |
| B-890 | penoxsulam | mefenpyr |
| B-891 | propoxycarbazone-sodium | mefenpyr |
| B-892 | pyrazosulfuron-ethyl | mefenpyr |
| B-893 | pyroxsulam | mefenpyr |
| B-894 | rimsulfuron | mefenpyr |
| B-895 | sulfosulfuron | mefenpyr |
| B-896 | thiencarbazone-methyl | mefenpyr |
| B-897 | tritosulfuron | mefenpyr |
| B-898 | 2,4-D and its salts and esters | mefenpyr |
| B-899 | aminopyralid and its salts and esters | mefenpyr |
| B-900 | clopyralid and its salts and esters | mefenpyr |
| B-901 | dicamba and its salts and esters | mefenpyr |
| B-902 | fluroxypyr-meptyl | mefenpyr |
| B-903 | quinclorac | mefenpyr |
| B-904 | quinmerac | mefenpyr |
| B-905 | H-9 | mefenpyr |
| B-906 | diflufenzopyr | mefenpyr |
| B-907 | diflufenzopyr-sodium | mefenpyr |
| B-908 | clomazone | mefenpyr |
| B-909 | diflufenican | mefenpyr |
| B-910 | fluorochloridone | mefenpyr |
| B-911 | isoxaflutol | mefenpyr |
| B-912 | mesotrione | mefenpyr |
| B-913 | picolinafen | mefenpyr |
| B-914 | sulcotrione | mefenpyr |
| B-915 | tefuryltrione | mefenpyr |
| B-916 | tembotrione | mefenpyr |
| B-917 | topramezone | mefenpyr |
| B-918 | H-7 | mefenpyr |
| B-919 | atrazine | mefenpyr |
| B-920 | diuron | mefenpyr |
| B-921 | fluometuron | mefenpyr |
| B-922 | hexazinone | mefenpyr |
| B-923 | isoproturon | mefenpyr |
| B-924 | metribuzin | mefenpyr |
| B-925 | propanil | mefenpyr |
| B-926 | terbuthylazine | mefenpyr |
| B-927 | paraquat dichloride | mefenpyr |
| B-928 | flumioxazin | mefenpyr |
| B-929 | oxyfluorfen | mefenpyr |
| B-930 | saflufenacil | mefenpyr |
| B-931 | sulfentrazone | mefenpyr |
| B-932 | H-1 | mefenpyr |
| B-933 | H-2 | mefenpyr |
| B-934 | glyphosate | mefenpyr |
| B-935 | glyphosate-isopropylammonium | mefenpyr |
| B-936 | glyphosate-trimesium (sulfosate) | mefenpyr |
| B-937 | glufosinate | mefenpyr |
| B-938 | glufosinate-ammonium | mefenpyr |
| B-939 | pendimethalin | mefenpyr |
| B-940 | trifluralin | mefenpyr |
| B-941 | acetochlor | mefenpyr |
| B-942 | cafenstrole | mefenpyr |
| B-943 | dimethenamid-P | mefenpyr |
| B-944 | fentrazamide | mefenpyr |
| B-945 | flufenacet | mefenpyr |
| B-946 | mefenacet | mefenpyr |
| B-947 | metazachlor | mefenpyr |
| B-948 | metolachlor-S | mefenpyr |
| B-949 | pyroxasulfone | mefenpyr |
| B-950 | isoxaben | mefenpyr |
| B-951 | dymron | mefenpyr |
| B-952 | indanofan | mefenpyr |
| B-953 | oxaziclomefone | mefenpyr |
| B-954 | triaziflam | mefenpyr |
| B-955 | atrazine + H-1 | mefenpyr |
| B-956 | atrazine + glyphosate | mefenpyr |
| B-957 | atrazine + mesotrione | mefenpyr |
| B-958 | atrazine + nicosulfuron | mefenpyr |
| B-959 | atrazine + tembotrione | mefenpyr |
| B-960 | atrazine + topramezone | mefenpyr |
| B-961 | clomazone + glyphosate | mefenpyr |
| B-962 | diflufenican + clodinafop-propargyl | mefenpyr |
| B-963 | diflufenican + fenoxaprop-P-ethyl | mefenpyr |
| B-964 | diflufenican + flupyrsulfuron-methyl-sodium | mefenpyr |
| B-965 | diflufenican + glyphosate | mefenpyr |
| B-966 | diflufenican + mesosulfuron-methyl | mefenpyr |
| B-967 | diflufenican + pinoxaden | mefenpyr |
| B-968 | diflufenican + pyroxsulam | mefenpyr |
| B-969 | flumetsulam + glyphosate | mefenpyr |
| B-970 | flumioxazin + glyphosate | mefenpyr |
| B-971 | imazapic + glyphosate | mefenpyr |
| B-972 | imazethapyr + glyphosate | mefenpyr |
| B-973 | isoxaflutol + H-1 | mefenpyr |
| B-974 | isoxaflutol + glyphosate | mefenpyr |
| B-975 | metazachlor + H-1 | mefenpyr |
| B-976 | metazachlor + glyphosate | mefenpyr |
| B-977 | metazachlor + mesotrione | mefenpyr |
| B-978 | metazachlor + nicosulfuron | mefenpyr |
| B-979 | metazachlor + terbuthylazine | mefenpyr |
| B-980 | metazachlor + topramezone | mefenpyr |
| B-981 | metribuzin + glyphosate | mefenpyr |
| B-982 | pendimethalin + H-1 | mefenpyr |
| B-983 | pendimethalin + clodinafop-propargyl | mefenpyr |
| B-984 | pendimethalin + fenoxaprop-P-ethyl | mefenpyr |
| B-985 | pendimethalin + flupyrsulfuron-methyl-sodium | mefenpyr |

TABLE B-continued

| | Herbicide(s) B | Safener C |
|---|---|---|
| B-986 | pendimethalin + glyphosate | mefenpyr |
| B-987 | pendimethalin + mesosulfuron-methyl | mefenpyr |
| B-988 | pendimethalin + mesotrione | mefenpyr |
| B-989 | pendimethalin + nicosulfuron | mefenpyr |
| B-990 | pendimethalin + pinoxaden | mefenpyr |
| B-991 | pendimethalin + pyroxsulam | mefenpyr |
| B-992 | pendimethalin + tembotrione | mefenpyr |
| B-993 | pendimethalin + topramezone | mefenpyr |
| B-994 | pyroxasulfone + tembotrione | mefenpyr |
| B-995 | pyroxasulfone + topramezone | mefenpyr |
| B-996 | sulfentrazone + glyphosate | mefenpyr |
| B-997 | terbuthylazine + H-1 | mefenpyr |
| B-998 | terbuthylazine + foramsulfuron | mefenpyr |
| B-999 | terbuthylazine + glyphosate | mefenpyr |
| B-1000 | terbuthylazine + mesotrione | mefenpyr |
| B-1001 | terbuthylazine + nicosulfuron | mefenpyr |
| B-1002 | terbuthylazine + tembotrione | mefenpyr |
| B-1003 | terbuthylazine + topramezone | mefenpyr |
| B-1004 | trifluralin + glyphosate | mefenpyr |
| B-1005 | clodinafop-propargyl | H-12 |
| B-1006 | cycloxydim | H-12 |
| B-1007 | cyhalofop-butyl | H-12 |
| B-1008 | fenoxaprop-P-ethyl | H-12 |
| B-1009 | pinoxaden | H-12 |
| B-1010 | profoxydim | H-12 |
| B-1011 | tepraloxydim | H-12 |
| B-1012 | tralkoxydim | H-12 |
| B-1013 | esprocarb | H-12 |
| B-1014 | prosulfocarb | H-12 |
| B-1015 | thiobencarb | H-12 |
| B-1016 | triallate | H-12 |
| B-1017 | bensulfuron-methyl | H-12 |
| B-1018 | bispyribac-sodium | H-12 |
| B-1019 | cyclosulfamuron | H-12 |
| B-1020 | flumetsulam | H-12 |
| B-1021 | flupyrsulfuron-methyl-sodium | H-12 |
| B-1022 | foramsulfuron | H-12 |
| B-1023 | imazamox | H-12 |
| B-1024 | imazapic | H-12 |
| B-1025 | imazapyr | H-12 |
| B-1026 | imazaquin | H-12 |
| B-1027 | imazethapyr | H-12 |
| B-1028 | imazosulfuron | H-12 |
| B-1029 | iodosulfuron-methyl-sodium | H-12 |
| B-1030 | mesosulfuron | H-12 |
| B-1031 | nicosulfuron | H-12 |
| B-1032 | penoxsulam | H-12 |
| B-1033 | propoxycarbazone-sodium | H-12 |
| B-1034 | pyrazosulfuron-ethyl | H-12 |
| B-1035 | pyroxsulam | H-12 |
| B-1036 | rimsulfuron | H-12 |
| B-1037 | sulfosulfuron | H-12 |
| B-1038 | thiencarbazone-methyl | H-12 |
| B-1039 | tritosulfuron | H-12 |
| B-1040 | 2,4-D and its salts and esters | H-12 |
| B-1041 | aminopyralid and its salts and esters | H-12 |
| B-1042 | clopyralid and its salts and esters | H-12 |
| B-1043 | dicamba and its salts and esters | H-12 |
| B-1044 | fluroxypyr-meptyl | H-12 |
| B-1045 | quinclorac | H-12 |
| B-1046 | quinmerac | H-12 |
| B-1047 | B-9 | H-12 |
| B-1048 | diflufenzopyr | H-12 |
| B-1049 | diflufenzopyr-sodium | H-12 |
| B-1050 | clomazone | H-12 |
| B-1051 | diflufenican | H-12 |
| B-1052 | fluorochloridone | H-12 |
| B-1053 | isoxaflutol | H-12 |
| B-1054 | mesotrione | H-12 |
| B-1055 | picolinafen | H-12 |
| B-1056 | sulcotrione | H-12 |
| B-1057 | tefuryltrione | H-12 |
| B-1058 | tembotrione | H-12 |
| B-1059 | topramezone | H-12 |
| B-1060 | H-7 | H-12 |
| B-1061 | atrazine | H-12 |
| B-1062 | diuron | H-12 |
| B-1063 | fluometuron | H-12 |
| B-1064 | hexazinone | H-12 |
| B-1065 | isoproturon | H-12 |
| B-1066 | metribuzin | H-12 |
| B-1067 | propanil | H-12 |
| B-1068 | terbuthylazine | H-12 |
| B-1069 | paraquat dichloride | H-12 |
| B-1070 | flumioxazin | H-12 |
| B-1071 | oxyfluorfen | H-12 |
| B-1072 | saflufenacil | H-12 |
| B-1073 | sulfentrazone | H-12 |
| B-1074 | H-1 | H-12 |
| B-1075 | H-2 | H-12 |
| B-1076 | glyphosate | H-12 |
| B-1077 | glyphosate-isopropylammonium | H-12 |
| B-1078 | glyphosate-trimesium (sulfosate) | H-12 |
| B-1079 | glufosinate | H-12 |
| B-1080 | glufosinate-ammonium | H-12 |
| B-1081 | pendimethalin | H-12 |
| B-1082 | trifluralin | H-12 |
| B-1083 | acetochlor | H-12 |
| B-1084 | cafenstrole | H-12 |
| B-1085 | dimethenamid-P | H-12 |
| B-1086 | fentrazamide | H-12 |
| B-1087 | flufenacet | H-12 |
| B-1088 | mefenacet | H-12 |
| B-1089 | metazachlor | H-12 |
| B-1090 | metolachlor-S | H-12 |
| B-1091 | pyroxasulfone | H-12 |
| B-1092 | isoxaben | H-12 |
| B-1093 | dymron | H-12 |
| B-1094 | indanofan | H-12 |
| B-1095 | oxaziclomefone | H-12 |
| B-1096 | triaziflam | H-12 |
| B-1097 | atrazine + H-1 | H-12 |
| B-1098 | atrazine + glyphosate | H-12 |
| B-1099 | atrazine + mesotrione | H-12 |
| B-1100 | atrazine + nicosulfuron | H-12 |
| B-1101 | atrazine + tembotrione | H-12 |
| B-1102 | atrazine + topramezone | H-12 |
| B-1103 | clomazone + glyphosate | H-12 |
| B-1104 | diflufenican + clodinafop-propargyl | H-12 |
| B-1105 | diflufenican + fenoxaprop-P-ethyl | H-12 |
| B-1106 | diflufenican + flupyrsulfuron-methyl-sodium | H-12 |
| B-1107 | diflufenican + glyphosate | H-12 |
| B-1108 | diflufenican + mesosulfuron-methyl | H-12 |
| B-1109 | diflufenican + pinoxaden | H-12 |
| B-1110 | diflufenican + pyroxsulam | H-12 |
| B-1111 | flumetsulam + glyphosate | H-12 |
| B-1112 | flumioxazin + glyphosate | H-12 |
| B-1113 | imazapic + glyphosate | H-12 |
| B-1114 | imazethapyr + glyphosate | H-12 |
| B-1115 | isoxaflutol + H-1 | H-12 |
| B-1116 | isoxaflutol + glyphosate | H-12 |
| B-1117 | metazachlor + H-1 | H-12 |
| B-1118 | metazachlor + glyphosate | H-12 |
| B-1119 | metazachlor + mesotrione | H-12 |
| B-1120 | metazachlor + nicosulfuron | H-12 |
| B-1121 | metazachlor + terbuthylazine | H-12 |
| B-1122 | metazachlor + topramezone | H-12 |
| B-1123 | metribuzin + glyphosate | H-12 |
| B-1124 | pendimethalin + H-1 | H-12 |
| B-1125 | pendimethalin + clodinafop-propargyl | H-12 |
| B-1126 | pendimethalin + fenoxaprop-P-ethyl | H-12 |
| B-1127 | pendimethalin + flupyrsulfuron-methyl-sodium | H-12 |
| B-1128 | pendimethalin + glyphosate | H-12 |
| B-1129 | pendimethalin + mesosulfuron-methyl | H-12 |
| B-1130 | pendimethalin + mesotrione | H-12 |
| B-1131 | pendimethalin + nicosulfuron | H-12 |
| B-1132 | pendimethalin + pinoxaden | H-12 |
| B-1133 | pendimethalin + pyroxsulam | H-12 |
| B-1134 | pendimethalin + tembotrione | H-12 |
| B-1135 | pendimethalin + topramezone | H-12 |
| B-1136 | pyroxasulfone + tembotrione | H-12 |
| B-1137 | pyroxasulfone + topramezone | H-12 |
| B-1138 | sulfentrazone + glyphosate | H-12 |
| B-1139 | terbuthylazine + H-1 | H-12 |
| B-1140 | terbuthylazine + foramsulfuron | H-12 |
| B-1141 | terbuthylazine + glyphosate | H-12 |

TABLE B-continued

| Herbicide(s) B | | Safener C |
|---|---|---|
| B-1142 | terbuthylazine + mesotrione | H-12 |
| B-1143 | terbuthylazine + nicosulfuron | H-12 |
| B-1144 | terbuthylazine + tembotrione | H-12 |
| B-1145 | terbuthylazine + topramezone | H-12 |
| B-1146 | trifluralin + glyphosate | H-12 |
| B-1147 | 2-1 | — |
| B-1148 | 2-2 | — |
| B-1149 | 2-3 | — |
| B-1150 | 2-4 | — |
| B-1151 | 2-5 | — |
| B-1152 | 2-6 | — |
| B-1153 | 2-7 | — |
| B-1154 | 2-8 | — |
| B-1155 | 2-9 | — |
| B-1156 | 2-1 | benoxacor |
| B-1157 | 2-2 | benoxacor |
| B-1158 | 2-3 | benoxacor |
| B-1159 | 2-4 | benoxacor |
| B-1160 | 2-5 | benoxacor |
| B-1161 | 2-6 | benoxacor |
| B-1162 | 2-7 | benoxacor |
| B-1163 | 2-8 | benoxacor |
| B-1164 | 2-9 | benoxacor |
| B-1165 | 2-1 | cloquintocet |
| B-1166 | 2-2 | cloquintocet |
| B-1167 | 2-3 | cloquintocet |
| B-1168 | 2-4 | cloquintocet |
| B-1169 | 2-5 | cloquintocet |
| B-1170 | 2-6 | cloquintocet |
| B-1171 | 2-7 | cloquintocet |
| B-1172 | 2-8 | cloquintocet |
| B-1173 | 2-9 | cloquintocet |
| B-1174 | 2-1 | cyprosulfamide |
| B-1175 | 2-2 | cyprosulfamide |
| B-1176 | 2-3 | cyprosulfamide |
| B-1177 | 2-4 | cyprosulfamide |
| B-1178 | 2-5 | cyprosulfamide |
| B-1179 | 2-6 | cyprosulfamide |
| B-1180 | 2-7 | cyprosulfamide |
| B-1181 | 2-8 | cyprosulfamide |
| B-1182 | 2-9 | cyprosulfamide |
| B-1183 | 2-1 | dichlormid |
| B-1184 | 2-2 | dichlormid |
| B-1185 | 2-3 | dichlormid |
| B-1186 | 2-4 | dichlormid |
| B-1187 | 2-5 | dichlormid |
| B-1188 | 2-6 | dichlormid |
| B-1189 | 2-7 | dichlormid |
| B-1190 | 2-8 | dichlormid |
| B-1191 | 2-9 | dichlormid |
| B-1192 | 2-1 | fenchlorazole |
| B-1193 | 2-2 | fenchlorazole |
| B-1194 | 2-3 | fenchlorazole |
| B-1195 | 2-4 | fenchlorazole |
| B-1196 | 2-5 | fenchlorazole |
| B-1197 | 2-6 | fenchlorazole |
| B-1198 | 2-7 | fenchlorazole |
| B-1199 | 2-8 | fenchlorazole |
| B-1200 | 2-9 | fenchlorazole |
| B-1201 | 2-1 | isoxadifen |
| B-1202 | 2-2 | isoxadifen |
| B-1203 | 2-3 | isoxadifen |
| B-1204 | 2-4 | isoxadifen |
| B-1205 | 2-5 | isoxadifen |
| B-1206 | 2-6 | isoxadifen |
| B-1207 | 2-7 | isoxadifen |
| B-1208 | 2-8 | isoxadifen |
| B-1209 | 2-9 | isoxadifen |
| B-1210 | 2-1 | mefenpyr |
| B-1211 | 2-2 | mefenpyr |
| B-1212 | 2-3 | mefenpyr |
| B-1213 | 2-4 | mefenpyr |
| B-1214 | 2-5 | mefenpyr |
| B-1215 | 2-6 | mefenpyr |
| B-1216 | 2-7 | mefenpyr |
| B-1217 | 2-8 | mefenpyr |
| B-1218 | 2-9 | mefenpyr |
| B-1219 | 2-1 | H-11 |
| B-1220 | 2-2 | H-11 |
| B-1221 | 2-3 | H-11 |
| B-1222 | 2-4 | H-11 |
| B-1223 | 2-5 | H-11 |
| B-1224 | 2-6 | H-11 |
| B-1225 | 2-7 | H-11 |
| B-1226 | 2-8 | H-11 |
| B-1227 | 2-9 | H-11 |
| B-1228 | 2-1 | H-12 |
| B-1229 | 2-2 | H-12 |
| B-1230 | 2-3 | H-12 |
| B-1231 | 2-4 | H-12 |
| B-1232 | 2-5 | H-12 |
| B-1233 | 2-6 | H-12 |
| B-1234 | 2-7 | H-12 |
| B-1235 | 2-8 | H-12 |
| B-1236 | 2-9 | H-12 |

The compounds of formula I and the compositions according to the invention may also have a plant-strengthening action. Accordingly, they are suitable for mobilizing the defense system of the plants against attack by unwanted microorganisms, such as harmful fungi, but also viruses and bacteria. Plant-strengthening (resistance-inducing) substances are to be understood as meaning, in the present context, those substances which are capable of stimulating the defense system of treated plants in such a way that, when subsequently inoculated by unwanted microorganisms, the treated plants display a substantial degree of resistance to these microorganisms.

The compounds of formula I can be employed for protecting plants against attack by unwanted microorganisms within a certain period of time after the treatment. The period of time within which their protection is effected generally extends from 1 to 28 days, preferably from 1 to 14 days, after the treatment of the plants with the compounds of formula I, or, after treatment of the seed, for up to 9 months after sowing.

The compounds of formula I and the compositions according to the invention are also suitable for increasing the harvest yield.

Moreover, they have reduced toxicity and are tolerated well by the plants.

The invention claimed is:

1. A compound of formula I,

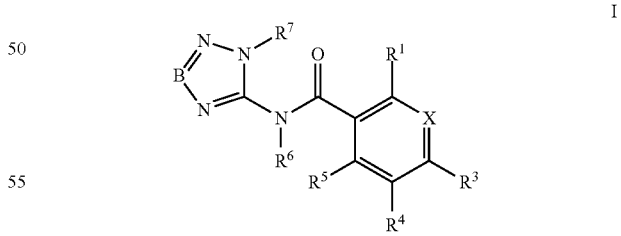

an N-oxide or an agriculturally suitable salt thereof, wherein $R^1$ is selected from the group consisting of halogen, $C_1$-$C_8$-alkyl, $C_1$-$C_8$-haloalkyl, nitro, $C_1$-$C_4$-alkoxy-$C_1$-$C_4$-alkyl, cyano-$Z^1$, $C_2$-$C_8$-alkenyl, $C_2$-$C_8$-alkynyl, $C_3$-$C_{10}$-cycloalkyl-$Z^1$, $C_2$-$C_8$-haloalkenyl, $C_3$-$C_8$-haloalkynyl, $C_1$-$C_8$-alkoxy, $C_1$-$C_4$-alkoxy-$C_1$-$C_4$-alkoxy-$Z^1$, $C_1$-$C_4$-alkylthio-$C_1$-$C_4$-alkyl, $C_1$-$C_4$-alkylthio-$C_1$-$C_4$-alkylthio-$Z^1$, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkyl, $C_1$-$C_4$-haloalkoxy-$C_1$-$C_4$-alkoxy-$Z^1$, $R^{1b}$—S(O)$_k$—$Z^1$, phenoxy-$Z^1$ and heterocyclyloxy-$Z^1$, where heterocyclyloxy is an oxygen bound 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenoxy and heterocyclyloxy are unsubstituted or substituted by 1, 2, 3 or 4 groups $R^{11}$, which are identical or different;

X is N;

$R^2$ is selected from the group consisting of hydrogen, halogen, hydroxy-$Z^2$, nitro, $C_1$-$C_4$-nitroalkyl, cyano, $C_1$-$C_4$-cyanoalkyl, $C_1$-$C_6$-alkyl, $C_2$-$C_8$-alkenyl, $C_2$-$C_8$-alkynyl, $C_3$-$C_{10}$-cycloalkyl-$Z^2$, $C_3$-$C_{10}$-cycloalkoxy-$Z^2$, where the $C_3$-$C_{10}$-cycloalkyl groups in the two aforementioned radicals are unsubstituted or partially or completely halogenated, $C_1$-$C_8$-haloalkyl, $C_2$-$C_8$-haloalkenyl, $C_3$-$C_8$-haloalkynyl, $C_1$-$C_8$-alkoxy-$Z^2$, $C_1$-$C_8$-haloalkoxy-$Z^2$, $C_3$-$C_{10}$-cycloalkyl-$C_1$-$C_2$-alkoxy, $C_1$-$C_4$-alkoxy-$C_1$-$C_4$-alkoxy-$Z^2$, $C_1$-$C_4$-alkylthio-$C_1$-$C_4$-alkylthio-$Z^2$, $C_2$-$C_8$-alkenyloxy-$Z^2$, $C_2$-$C_8$-alkynyloxy-$Z^2$, $C_2$-$C_8$-haloalkenyloxy-$Z^2$, $C_3$-$C_8$-haloalkynyloxy-$Z^2$, $C_1$-$C_4$-haloalkoxy-$C_1$-$C_4$-alkoxy-$Z^2$, (tri-$C_1$-$C_4$-alkyl)silyl-$Z^2$, $R^{2b}$—S(O)$_k$—$Z^2$, $R^{2c}$—C(=O)—$Z^2$, $R^{2d}$O—C(=O)—$Z^2$, $R^{2d}$O—N=CH—$Z^2$, $R^{2d}$O—N=CC$_1$-$C_4$-alkyl-$Z^2$, $R^{2d}$O—N=CC$_1$-$C_4$-haloalkyl-$Z^2$, $R^{2c}R^{2d}$C=N—O—$C_1$-$C_4$-alkyl, $R^{2e}R^{2f}$N—C(=O)—$Z^2$, $R^{2g}R^{2h}$N—$Z^2$, phenyl-$Z^{2a}$, heterocyclyl-$Z^{2a}$, where heterocyclyl is a 3-, 4-, 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenyl-$Z^{2a}$ and heterocyclyl-$Z^{2a}$ are unsubstituted or substituted by 1, 2, 3 or 4 groups $R^{21}$, which are identical or different, rhodano, $C_3$-$C_6$-cycloalkenyl, OC(O)R$^{22}$, OC(O)N(R$^{22}$)$_2$, ONC(R$^{23}$)$_2$, OSO$_2$R$^{25}$, SO$_2$OR$^{22}$, SO$_2$N(R$^{22}$)$_2$, N(R$^{22}$)C(O) OR$^{22}$, N(R$^{22}$)C(O)N(R$^{22}$)$_2$, C(O)N(R$^{22}$)OR$^{22}$, P(O)(O—$C_1$-$C_4$-alkyl)$_2$, $C_1$-$C_6$-alkyl-OC(O)R$^{22}$, $C_1$-$C_6$-alkyl-OSO$_2$R$^{25}$, $C_1$-$C_6$-alkyl-SO$_2$OR$^{22}$, $C_1$-$C_6$-alkyl-SO$_2$N(R$^{22}$)$_2$, $C_1$-$C_6$-alkyl-P(O)(O—$C_1$-$C_4$-alkyl)$_2$,

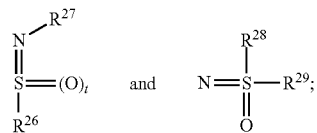

$R^3$ is selected from the group consisting of hydrogen, halogen, hydroxy-$Z^2$, nitro, $C_1$-$C_4$-nitroalkyl, cyano, $C_1$-$C_4$-cyanoalkyl, $C_1$-$C_6$-alkyl, $C_2$-$C_8$-alkenyl, $C_2$-$C_8$-alkynyl, $C_3$-$C_{10}$-cycloalkyl-$Z^2$, $C_3$-$C_{10}$-cycloalkoxy-$Z^2$, where the $C_3$-$C_{10}$-cycloalkyl groups in the two aforementioned radicals are unsubstituted or partially or completely halogenated, $C_1$-$C_8$-haloalkyl, $C_2$-$C_8$-haloalkenyl, $C_3$-$C_8$-haloalkynyl , $C_1$-$C_8$-alkoxy-$Z^2$, $C_1$-$C_8$-haloalkoxy-$Z^2$, $C_3$-$C_{10}$-cycloalkyl-$C_1$-$C_2$-alkoxy, $C_1$-$C_4$-alkoxy-$C_1$-$C_4$-alkoxy-$Z^2$, $C_1$-$C_4$-alkylthio-$C_1$-$C_4$-alkylthio-$Z^2$, $C_2$-$C_8$-alkenyloxy-$Z^2$, $C_2$-$C_8$-alkynyloxy-$Z^2$, $C_2$-$C_8$-haloalkenyloxy-$Z^2$, $C_3$-$C_8$-haloalkynyloxy-$Z^2$, $C_1$-$C_4$-haloalkoxy-$C_1$-$C_4$-alkoxy-$Z^2$, (tri-$C_1$-$C_4$-alkyl)silyl-$Z^2$, $R^{2b}$—S(O)$_k$—$Z^2$, $R^{2c}$—C(=O)—$Z^2$, $R^{2d}$O—C(=O)—$Z^2$, $R^{2d}$O—N=CH—$Z^2$, $R^{2c}R^{2d}$C=N—O—$C_1$-$C_4$-alkyl, $R^{2e}R^{2f}$N—C(=O)—$Z^2$, $R^{2g}R^{2h}$N—$Z^2$, phenyl-$Z^{2a}$, heterocyclyl-$Z^{2a}$, where heterocyclyl is a 3-, 4-, 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenyl-$Z^{2a}$ and heterocyclyl-$Z^{2a}$ are unsubstituted or substituted by 1, 2, 3 or 4 groups $R^{21}$, which are identical or different, rhodano, $C_3$-$C_6$-cycloalkenyl, $C_3$-$C_6$-halocycloalkenyl, $C_3$-$C_6$-cycloalkenyl-$C_1$-$C_6$-alkyl, $C_3$-$C_6$-halocycloalkenyl-$C_1$-$C_6$-alkyl, OC(O)R$^{22}$, OC(O)OR$^{25}$, OC(O)N(R$^{22}$)$_2$, OSO$_2$R$^{25}$, SO$_2$OR$^{22}$, SO$_2$N(R$^{22}$)$_2$, SO$_2$N(R$^{22}$)C(O)R$^{22}$, SO$_2$N(R$^{22}$)C(O)OR$^{25}$, SO$_2$N(R$^{22}$)C(O)N(R$^{22}$)$_2$, N(R$^{22}$)C(O)OR$^{25}$, N(R$^{22}$)C(O)N(R$^{22}$)$_2$, N(R$^{22}$)S(O)$_2$OR$^{22}$, N(R$^{22}$)S(O)$_2$N(R$^{22}$)$_2$, C(O)N(R$^{22}$)OR$^{22}$, C(O)N(R$^{22}$)N(R$^{22}$)$_2$, C(O)N(R$^{22}$)C(O)R$^{22}$, C(O)N(R$^{22}$)C(O)OR$^{25}$, C(O)N(R$^{22}$)C(O)N(R$^{22}$)$_2$, C(O)N(R$^{22}$)SO$_2$R$^{25}$, C(O)N(R$^{22}$)SO$_2$OR$^{22}$, C(O)N(R$^{22}$)SO$_2$N(R$^{22}$)$_2$, P(O)(OH)$_2$, P(O)(O—$C_1$-$C_4$-alkyl)$_2$, $C_1$-$C_6$-alkyl-OC(O)R$^{22}$, $C_1$-$C_6$-alkyl-OC(O)OR$^{25}$, $C_1$-$C_6$-alkyl-OC(O)N(R$^{22}$)$_2$, $C_1$-$C_6$-alkyl-OSO$_2$R$^{25}$, $C_1$-$C_6$-alkyl-SO$_2$OR$^{22}$, $C_1$-$C_6$-alkyl-SO$_2$N(R$^{22}$)$_2$, $C_1$-$C_6$-alkyl-SO$_2$N(R$^{22}$)C(O)R$^{22}$, $C_1$-$C_6$-alkyl-SO$_2$N(R$^{22}$)C(O)OR$^{25}$, $C_1$-$C_6$-alkyl -SO$_2$N(R$^{22}$)C(O)N(R$^{22}$)$_2$, $C_1$-$C_6$-alkyl-N(R$^{22}$)C(O)OR$^{25}$, $C_1$-$C_6$-alkyl-N(R$^{22}$)C(O)N(R$^{22}$)$_2$, $C_1$-$C_6$-alkyl-N(R$^{22}$)S(O)$_2$OR$^{22}$, $C_1$-$C_6$-alkyl-N(R$^{22}$)S(O)$_2$N(R$^{22}$)$_2$, $C_1$-$C_6$-alkyl-C(O)N(R$^{22}$)OR$^{22}$, $C_1$-$C_6$-alkyl-C(O)N(R$^{22}$)N(R$^{22}$)$_2$, $C_1$-$C_6$-alkyl-C(O)N(R$^{22}$)C(O)R$^{22}$, $C_1$-$C_6$-alkyl-C(O)N(R$^{22}$)C(O)OR$^{25}$, $C_1$-$C_6$-alkyl-C(O)N(R$^{22}$)C(O)N(R$^{22}$)$_2$, $C_1$-$C_6$-alkyl-C(O)N(R$^{22}$)SO$_2$R$^{25}$, $C_1$-$C_6$-alkyl-C(O)N(R$^{22}$)SO$_2$OR$^{22}$, $C_1$-$C_6$-alkyl-C(O)N(R$^{22}$)SO$_2$N(R$^{22}$)$_2$, $C_1$-$C_6$-alkyl-P(O)(OH)$_2$ and $C_1$-$C_6$-alkyl-P(O)(O—$C_1$-$C_4$-alkyl)$_2$;

$R^4$ is selected from the group consisting of hydrogen, halogen, $C_1$-$C_8$-alkyl, cyano-$Z^1$, nitro, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_2$-$C_8$-alkenyl, $C_2$-$C_8$-alkynyl, $C_1$-$C_8$-haloalkyl, $C_1$-$C_3$-alkylamino, $C_1$-$C_3$-dialkylamino, $C_1$-$C_3$-alkylamino-S(O)$_k$, $C_1$-$C_3$-alkylcarbonyl, $C_1$-$C_8$-alkoxy, $C_1$-$C_4$-alkoxy-$C_1$-$C_4$-alkyl, $C_1$-$C_4$-alkoxy-$C_1$-$C_4$-alkoxy-$Z^1$, $C_1$-$C_4$-alkylthio-$C_1$-$C_4$-alkyl, $C_1$-$C_4$-alkylthio-$C_1$-$C_4$-alkylthio-$Z^1$, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkyl, $C_1$-$C_4$-haloalkoxy-$C_1$-$C_4$-alkoxy-$Z^1$, $R^{1b}$—S(O)$_k$—$Z^1$, phenoxy-$Z^1$ and heterocyclyloxy-$Z^1$, where heterocyclyloxy is an oxygen bound 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenoxy and heterocyclyloxy are and wherein $R^5$ is not methyl; or substituted by 1, 2, 3 or 4 groups $R^{11}$, which are identical or different; and wherein $R^5$ is not methyl;

$R^5$ is selected from the group consisting of halogen, cyano-$Z^1$, nitro, $C_1$-$C_8$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_2$-$C_8$-alkenyl, $C_2$-$C_8$-alkynyl, $C_1$-$C_8$-haloalkyl, $C_1$-$C_3$-alkylamino, $C_1$-$C_3$-dialkylamino, $C_1$-$C_3$-alkylamino-S(O)$_k$, $C_1$-$C_3$-alkylcarbonyl, $C_1$-$C_8$-alkoxy, $C_1$-$C_4$-alkoxy-$C_1$-$C_4$-alkyl, $C_1$-$C_4$-alkoxy-$C_1$-$C_4$-alkoxy-$Z^1$, $C_1$-$C_4$-alylthio-$C_1$-$C_4$-alkyl, $C_1$-$C_4$-alkylthio-$C_1$-$C_4$-alkylthio-$Z^1$, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkyl, $C_1$-$C_4$-haloalkoxy-$C_1$-$C_4$-alkoxy-$Z^1$, $R^{1b}$—S(O)$_k$-$Z^1$, phenoxy-$Z^1$ and heterocyclyloxy-$Z^1$, where heterocyclyloxy is an oxygen bound 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenoxy and heterocyclyloxy are unsubstituted or substituted by 1, 2, 3 or 4 groups $R^{11}$, which are identical or different;

$R^6$ is selected from the group consisting of cyano, nitro, hydroxy, amino, $C_1$-$C_6$-alkyl, $C_1$-$C_6$-cyano-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_1$-$C_6$-alkoxy, $C_1$-$C_6$-alkylcarbonyl, $C_1$-$C_6$-alkyaminocarbonyl, $C_1$-$C_6$-dialkyl-aminocarbonyl, $C_1$-$C_6$-alkyamino, $C_1$-$C_6$-dialkyl-amino, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-haloalkoxy-$C_1$-$C_4$-alkyl, $R^b R^b N$—S(O)$_n$—Z, $R^b O$—S(O)$_n$—Z, $R^b$—S(O)$_n$—Z, $R^c R^c N$—$C_1$-$C_3$-alkyl-S(O)$_n$—$C_1$-$C_3$-alkyl, $R^c$—C(=O)—$C_1$-$C_3$-alkyl, $R^d$—C(=O)O—$C_1$-$C_3$-alkyl, $R^d$—O—C(=O)O—$C_1$-$C_3$-alkyl, $R^d O$—C(=O)—$C_1$-$C_3$-alkyl, $R^e R^f N$—C(=O)—$C_1$-$C_3$-alkyl, $R^c$—C(=O)$R^e N$—$C_1$-$C_3$-alkyl, $R^b$—S(O)$_n$—$R^e N$—$C_1$-$C_3$-alkyl, $R^c R^c N$—$C_1$-$C_3$-allkyl, phenyl-Z and heterocyclyl-Z, where heterocyclyl is a 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups R', which are identical or different;

$R^7$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-haloalkoxy-$C_1$-$C_4$-alkyl, $R^b$—S(O)n-$C_1$-$C_3$-alkyl, $R^c$—C(=O)—$C_1$-$C_3$-alkyl, $R^d O$—(=O)—C1-C3-alkyl, ReRfN—C(=O)—$C_1$-$C_3$-alkyl, $R^g R^h N$—$C_1$-$C_3$-alkyl, phenyl-Z and heterocyclyl-Z, where heterocyclyl is a 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups R', which are identical or different;

B is N;

R', $R^{11}$, $R^{21}$ independently of each other are selected from the group consisting of halogen, $NO_2$, CN, $C_1$-$C_6$-alkyl, $C_3 C_7$-cycloalkyl, $C_3$-$C_7$-halocycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_4$-alkoxy-$C_1$-$C_4$-alkyl, $C_1$-$C_4$-alkylthio-$C_1$-$C_4$-alkyl, $C_1$-$C_4$-haloalkoxy-$C_1$-$C_4$-alkyl, $C_1$-$C_4$-alkoxy-$C_1$-$C_4$-alkoxy, $C_3$-$C_7$-cycloalkoxy and $C_1$-$C_6$-haloalkyloxy, or two vicinal radicals R', $R^{11}$ or $R^{21}$ together may form a group =O;

Z, $Z^1$, $Z^2$ independently of each other are selected from the group consisting of a covalent bond and $C_1$-$C_4$-alkanediyl;

$Z^{2a}$ is s $Z^{2a}$ selected from the group consisting of a covalent bond, $C_1$-$C_4$-alkanediyl, O—$C_4$-alkanediyl, $C_1$-$C_4$-alkanediyl-O and $C_1$-$C_4$-alkanediyl-O—$C_1$-$C_4$-alkanediyl;

$R^b$, $R^{1b}$, $R^{2b}$ independently of each other are selected from the group consisting of $C_1$-$C_6$-alkyl, $C_3$-$C_7$-cycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, phenyl and heterocyclyl, where heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^c$, $R^{2c}$ independently of each other are selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl, benzyl and heterocyclyl, where heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl, benzyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^d$, $R^{2d}$ independently of each other are selected from the group consisting of $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^e R^f$ independently of each other are selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy -$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^e$, $R^f$ together with the nitrogen atom, to which they are bound may form a 5-, 6 or 7-membered, saturated or unsaturated N-bound heterocyclic radical, which may carry as a ring member a further heteroatom selected from the group consisting of O, S and N and which is unsubstituted or may carry 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^{2e}$, $R^{2f}$ independently of each other have the meanings given for $R^e$, $R^f$;

$R^g$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-alkylsulfonyl, $C_1$-$C_4$-alkylcarbonyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^h$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-alkylsulfonyl, $C_1$-$C_4$-alkylcarbonyl, a radical C(=O)—$R^k$, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^g$, $R^h$ together with the nitrogen atom, to which they are bound may form a 5-, 6 or 7-membered, saturated or unsaturated N-bound heterocyclic radical, which may carry as a ring member a further heteroatom selected from the group consisting of O, S and N and which is unsubstituted or may carry 1, 2, 3 or 4 groups, which are identical or different and selected from the group consisting of =O, halogen, $C_1$-$C_4$-alkyl, $C_1$-$C_4$-haloalkyl, $C_1$-$C_4$-alkoxy and $C_1$-$C_4$-haloalkoxy;

$R^{2g}$, $R^{2h}$ independently of each other have the meanings given for $R^g$, $R^h$;

$R^k$ has the meanings given for $R^c$;

$R^{22}$ is selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, $C_3$-$C_6$-cycloalkenyl, $C_3$-$C_6$-halocycloalkyl, $C_3$-$C_6$-cycloalkyl-$C_1$-$C_6$-alkyl, $C_1$-$C_6$-alkoxy-$C_1$-$C_6$-alkyl, $C_3$-$C_6$-cycloalkyl-$C_1$-$C_6$-alkoxy-$C_1$-$C_6$-alkyl,
phenyl, phenyl-$C_1$-$C_6$-alkyl, heteroaryl, heteroaryl-$C_1$-$C_6$-alkyl, heterocyclyl, heterocyclyl-$C_1$-$C_6$-alkyl, phenyl-O—$C_1$-$C_6$-alkyl, heteroaryl-O—$C_1$-$C_6$-alkyl, heterocyclyl-O—$C_1$-$C_6$-alkyl, phenyl-N($R^{23}$)—$C_1$-$C_6$-alkyl, heteroaryl-N($R^{23}$)—$C_1$-$C_6$-alkyl, heterocyclyl-N($R^{23}$)—$C_1$-$C_6$-alkyl, phenyl-S(O)$_n$—$C_1$-$C_6$-alkyl, heteroaryl-S(O)$_n$—$C_1$-$C_6$-alkyl, heterocyclyl-S(O)$_n$—$C_1$-$C_6$-alkyl, where the 15 aforementioned radicals are substituted by s residues selected from the group consisting of nitro, halogen, cyano, rhodano, $C_1$-$C_6$-alkyl, $C_1$-$C_6$-haloalkyl, $C_3$-$C_6$-cycloalkyl, C(O)O$R^{23}$, C(O)N($R^{23}$)$_2$, O$R^{23}$, N($R^{23}$)$_2$, S(O)$_n$$R^{24}$, S(O)$_2$O$R^{23}$, S(O)$_2$N($R^{23}$)$_2$ and $R^{23}$O—$C_1$-$C_6$-alkyl, and where heterocyclyl bears 0, 1 or 2 oxo groups;

$R^{23}$ is selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl and phenyl;

$R^{24}$ is selected from the group consisting of $C_1$-$C_6$-alkyl, $C_1$-$C_6$-haloalkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl and phenyl;

$R^{25}$ is selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, $C_3$-$C_6$-cycloalkenyl, $C_3$-$C_6$-halocycloalkyl, $C_3$-$C_6$-cycloalkyl-$C_1$-$C_6$-alkyl, $C_1$-$C_6$-alkoxy-$C_1$-$C_6$-alkyl, $C_3$-$C_6$-cycloalkyl-$C_1$-$C_6$-alkoxy-$C_1$-$C_6$-alkyl, phenyl, phenyl-$C_1$-$C_6$-alkyl, heteroaryl, heteroaryl-$C_1$-$C_6$-alkyl, heterocyclyl, heterocyclyl-$C_1$-$C_6$-alkyl, phenyl-O—$C_1$-$C_6$-alkyl, heteroaryl-O—$C_1$-$C_6$-alkyl, heterocyclyl-O—$C_1$-$C_6$-alkyl, phenyl-N($R^{23}$)—$C_1$-$C_6$-alkyl, heteroaryl-N($R^{23}$)—$C_1$-$C_6$-alkyl, heterocyclyl-N($R^{23}$)—$C_1$-$C_6$-alkyl, phenyl-S(O)$_n$—$C_1$-$C_6$-alkyl, heteroaryl-S(O)$_n$—$C_1$-$C_6$-alkyl, heterocyclyl-S(O)$_n$—$C_1$-$C_6$-alkyl, where the 15 aforementioned radicals are substituted by s residues selected from the group consisting of nitro, halogen, cyano, rhodano, $C_1$-$C_6$-alkyl, $C_1$-$C_6$-haloalkyl, $C_3$-$C_6$-cycloalkyl, C(O)O$R^{23}$, C(O)N($R^{23}$)$_2$, O$R^{23}$, N($R^{23}$)$_2$, S(O)$_2$O$R^{24}$, S(O)$_2$O$R^{23}$, S(O)$_2$N($R^{23}$)$_2$ and $R^{23}$O—$C_1$-$C_6$-alkyl, and where heterocyclyl bears 0, 1 or 2 oxo groups;

$R^{26}$ is $C_1$-$C_6$-alkyl or $C_1$-$C_4$-alkoxy-$C_1$-$C_4$-alkyl;

$R^{27}$ is selected from the group consisting of hydrogen, cyano and $C_1$-$C_4$-haloalkylcarbonyl;

$R^{28}$, $R^{29}$ independently of each other are $C_1$-$C_6$-alkyl, or $R^{28}$, $R^{29}$ together with the sulfur atom, to which they are bound may form a 5- or 6-membered saturated ring, which may carry as a ring member 1 oxygen atom;

k is 0, 1 or 2;
n is 0, 1 or 2;
s is 0, 1, 2 or 3;
t is 0 or 1.

2. The compound of claim 1, an N-oxide or an agriculturally suitable salt thereof, wherein B is N.

3. The compound of claim 1, an N-oxide or an agriculturally suitable salt thereof, wherein $R^1$ is selected from the group consisting of cyano, halogen, nitro, $C_1$-$C_6$-alkyl, $C_3$-$C_6$-cycloalkyl, $C_2$-$C_6$-alkenyl, $C_2$-$C_6$-alkynyl, $C_1$-$C_6$-haloalkyl, $C_1$-$C_6$-alkoxy, $C_1$-$C_4$-alkyl, $C_1$-$C_4$-haloalkoxy-$C_1$-$C_4$-alkyl, $C_1$-$C_4$-alkoxy-$C_1$-$C_4$-alkoxy-$Z^1$, $C_1$-$C_4$-alkylthio-$C_1$-$C_4$-alkyl, $C_1$-$C_4$-alkylthio-$C_1$-$C_4$alkylthio-$Z^1$, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy and R1$^b$—S(O)$_k$, wherein $Z^1$ is as defined in claim 2, wherein k is 0, 1 or 2 and wherein $R^{1b}$ is selected from the group consisting of $C_1$-$C_4$-alkyl and $C_1$-$C_4$-haloalkyl.

4. The compound of claim 1, an N-oxide or an agriculturally suitable salt thereof, wherein $R^1$ is selected from the group consisting of halogen, CN, nitro, $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkyl, $C_1$-$C_4$-alkylthio-$C_1$-$C_4$-alkylthio-$C_1$-$C_4$-alkyl, $C_1$-$C_4$-alkoxy, $C_1$-$C_4$-haloalkoxy, $C_3$-$C_4$-alkenyloxy, $C_3$-$C_4$-alkynyloxy, $C_1$-$C_4$-alkoxy-$C_1$-$C_4$-alkoxy, $C_1$-$C_4$-haloalkoxy-$C_1$-$C_4$-alkoxy, $C_1$-$C_4$-alkyl-$S(O)_k$ and $C_1$-$C_4$-haloalkyl-$S(O)_k$, wherein K is 0 or 2.

5. The compound of claim 1, an N-oxide or an agriculturally suitable salt thereof, wherein $R^1$ is selected from the group consisting of halogen, nitro, $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl, $C_1$-$C_4$-alkoxy $C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio and $C_1$-$C_4$-alkylsulfonyl.

6. The compound of claim 1, an N-oxide or an agriculturally suitable salt thereof, wherein X is N.

7. The compound of claim 1, an N-oxide or an agriculturally suitable salt thereof, wherein X is $CR^2$ and $R^2$ is not hydrogen.

8. The compound of claim 1, an N-oxide or an agriculturally suitable salt thereof, wherein X is $CR^2$ and $R^2$ is hydrogen.

9. The compound of claim 1, an N-oxide or an agriculturally suitable salt thereof, wherein $R^2$ is 5- or 6-membered heterocyclyl, wherein heterocyclyl is a saturated, partially unsaturated or aromatic heterocyclic radical, which contains as a ring member 1 heteroatom selected from the group consisting of O, N and S and 0, 1, 2 or 3 further nitrogen atoms, wherein heterocyclyl is unsubstituted or carries 1, 2 or 3 radicals $R^{21}$ which are identical or different.

10. The compound of claim 1, an N-oxide or an agriculturally suitable salt thereof, wherein $R^2$ is 5- or 6-membered heterocyclyl selected from the group consisting of isoxazolinyl, 1,2-dihydrotetrazolonyl, 1,4-dihydrotetrazolonyl, tetrahydrofuryl, dioxolanyl, piperidinyl, morpholinyl, piperazinyl, isoxazolyl, pyrazolyl, thiazolyl, oxazolyl, furyl, pyridinyl, pyrimidinyl and pyrazinyl, wherein heterocyclyl is unsubstituted or carries 1, 2 or 3 radicals $R^{21}$ which are identical or different and selected from the group consisting of $C_1$-$C_4$-alkyl, $C_1$-$C_4$-haloalkyl, $C_1$-$C_4$-alkoxy, $C_1$-$C_4$-alkoxy-$C_1$-$C_4$-alkyl and $C_1$-$C_4$-alkylthio-$C_1$-$C_4$-alkyl.

11. The compound of claim 1, an N-oxide or an agriculturally suitable salt thereof, wherein $R^2$ is selected from the group consisting of hydrogen, halogen, $C_1$-$C_6$-alkyl, $C_3$-$C_6$-cycloalkyl-$C_1$-$C_4$-alkoxy, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxy-$C_1$-$C_4$-alkoxy, $C_1$-$C_4$-alkoxycarbonyl, $C_1$-$C_4$-alkyl-$S(O)_k$ and $C_1$-$C_4$-haloalkyl-$S(O)_k$, wherein k is 0, 1 or 2, $N(C_1$-$C_4$-alkyl$)SO_2(C_1$-$C_4$-alkyl), isoxazolyl and isoxazolinyl, wherein the last two mentioned radicals may be unsubstituted or carry 1 or 2 radicals selected from the group consisting of halogen and $C_1$-$C_4$-alkyl.

12. The compound of claim 1, an N-oxide or an agriculturally suitable salt thereof, wherein $R^2$ is

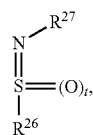

wherein
$R^{26}$ is selected from the group consisting of methyl, ethyl and methoxyethyl, $R^{27}$ is selected from the group consisting of hydrogen, cyano and trifluoroacetyl,
t is 0 or 1;
or

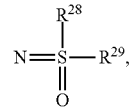

wherein
$R^{28}$ is ethyl and $R^{29}$ is ethyl, or
$R^{28}$ and $R^{29}$ together are —$(CH_2)_5$— or —$(CH_2)_2$—O—$(CH_2)_2$—.

13. The compound of claim 1, an N-oxide or an agriculturally suitable salt thereof, wherein $R^3$ is selected from the group consisting of hydrogen, halogen, cyano, nitro, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_3$-$C_4$-alkenyloxy, $C_3$-$C_4$-alkynyloxy or $R^{2b}$—$S(O)_k$, where k is 0, 1 or 2 and wherein $R^{2b}$ is selected from the group consisting of $C_1$-$C_4$-alkyl and $C_1$-$C_4$-haloalkyl.

14. The compound of claim 1, an N-oxide or an agriculturally suitable salt thereof, wherein $R^3$ is selected from the group consisting of hydrogen, halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkyl-$S(O)_2$ and $C_1$-$C_4$-haloalkyl-$S(O)_2$.

15. The compound of claim 1, an N-oxide or an agriculturally suitable salt thereof, wherein $R^4$ is selected from the group consisting of hydrogen, $CHF_2$, $CF_3$, CN, $NO_2$, $CH_3$ and halogen.

16. The compound of claim 1, an N-oxide or an agriculturally suitable salt thereof, wherein $R^5$ is selected from the group consisting of $CHF_2$, $CF_3$ and halogen.

17. The compound of claim 1, an N-oxide or an agriculturally suitable salt thereof, wherein $R^6$ is selected from the group consisting of cyano, $C_1$-$C_6$-alkyl, $C_1$-$C_6$-cyano-alkyl, $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-haloalkoxy-$C_1$-$C_4$-alkyl, $R^bR^bN$—$S(O)_n$—Z, $R^bO$—$S(O)_n$—Z, $R^b$—$S(O)_n$—Z, $R^d$—$C(=O)O$—$C_1$-$C_3$-alkyl, $R^d$—O—$C(=O)O$—$C_1$-$C_3$-alkyl, $R^dO$—$C(=O)$—$C_1$-$C_3$-alkyl, $R^eR^fN$—$C(=O)$—$C_1$-$C_3$-alkyl, phenyl-Z and wherein phenyl is unsubstituted or substituted by 1, 2, 3 or 4 groups R', which are identical or different.

18. The compound of claim 1, an N-oxide or an agriculturally suitable salt thereof, wherein $R^6$ is selected from the group consisting of $C_1$-$C_6$-alkyl, $C_2$-$C_6$-alkenyl, $C_2$-$C_6$-alkynyl, $C_1$-$C_4$-alkoxy-$C_1$-$C_4$-alkyl, $R^dO$—$C(=O)$—$C_1$-$C_3$-alkyl, phenyl-Z and wherein phenyl is unsubstituted or substituted by 1, 2, 3 or 4 groups R', which are identical or different.

19. The compound of claim 1, an N-oxide or an agriculturally suitable salt thereof, wherein $R^7$ is selected from the group consisting of $C_1$-$C_4$-alkyl, $C_3$-$C_7$-cycloalkyl, $C_1$-$C_4$-haloalkyl, $C_2$-$C_6$-alkenyl, $C_2$-$C_6$-alkynyl, and $C_1$-$C_4$-alkoxy-$C_1$-$C_4$-alkyl.

20. The compound of claim 1, an N-oxide or an agriculturally suitable salt thereof, wherein
$R^1$ is selected from the group consisting of halogen, nitro, $C_1$-$C_4$-alkyl, $C_3$-$C_6$-cycloalkyl, $C_1$-$C_4$-halolalkyl, $C_1$-$C_4$alkoxy-$C_1$-$C_4$-alkyl, $C_1$-$C_4$-alkoxy-$C_1$-$C_4$- alkoxy-$C_1$-$C_4$-alkyl, $C_1$-$C_4$alkoxy, $C_1$-$C_4$-haloalkoxy, $C_1$-$C_4$-alkylthio, $C_1$-$C_4$-haloalkylthio and $C_1$-$C_4$-alkylsulfonyl; and $R^3$ is selected from the group consisting of hydrogen, halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio and $C_1$-$C_4$-alkylsulfonyl.

21. The compound of claim 1, an N-oxide or an agriculturally suitable salt thereof, wherein X is $CR^2$ and the variables $R^1$, $R^2$, $R^3$, $R^4$, $R^5$, $R^6$ and $R^7$ have the following meanings:

$R^1$ is selected from the group consisting of halogen, nitro, cyclopropyl, $C_1$-$C_4$-alkyl, $C_1$-$C_4$-haloalkyl, $C_1$-$C_4$-alkoxy-$C_1$-$C_4$-alkyl, -$C_1$-$C_4$-alkoxyl-$C_1$-$C_4$-alkyl and $C_1$-$C_4$-alkyl-S(O)$_2$;

$R^2$ is selected from the group consisting of hydrogen, halogen, $C_1$-$C_4$-alkyl, $C_1$-$C_4$-alkoxy, $C_1$-$C_4$-haloalkoxy, $C_3$-$C_6$-cycloalkyl-$C_1$-$C_2$-alkoxy, $C_1$-$C_2$-alkoxy-$C_1$-$C_2$-alkyl, $C_1$-$C_2$-haloalkoxy-$C_1$-$C_2$-alkyl, $C_1$-$C_2$-alkoxy-$C_1$-$C_2$-alkoxy, $C_1$-$C_4$-alkyl-S(O)$_k$, where k is 0, 1 or 2, N($C_1$-$C_4$-alkyl)SO$_2$($C_1$-$C_4$-alkyl), isoxazolyl and isoxazolinyl, where the last two mentioned radicals may be unsubstituted or carry 1 or 2 radicals selected from halogen and $C_1$-$C_4$-alkyl;

$R^3$ is selected from the group consisting of hydrogen, halogen, cyano, nitro, $C_1$-$C_4$-alkyl, $C_1$-$C_4$-haloalkyl and $C_1$-$C_4$-alkyl-S(O)$_2$;

$R^4$ is selected from the group consisting of hydrogen, cyano, methyl and halogen;

$R^5$ is selected from the group consisting of halogen, CHF$_2$ and CF$_3$;

$R^6$ is selected from the group consisting of $C_1$-$C_4$-alkyl, $C_1$-$C_2$-alkoxy-$C_1$-$C_2$-alkyl, $C_2$-$C_4$-alkenyl, $C_2$-$C_4$-alkynyl, $C_1$-$C_4$-alkoxycarbonyl-$C_1$-$C_4$-alkyl and phenyl-$C_1$-$C_2$-alkyl;

$R^7$ is selected from the group consisting of $C_1$-$C_4$-alkyl and $C_1$-$C_2$-alkoxy-$C_1$-$C_2$-alkyl.

22. The compound of claim 1, an N-oxide or an agriculturally suitable salt thereof, wherein X is $CR^2$ and the variables $R^1$, $R^2$, $R^3$, $R^4$, $R^5$, $R^6$ and $R^7$ have the following meanings:

$R^1$ is selected from the group consisting of chlorine, nitro, methyl, cyclopropyl, trifluoromethyl, methoxymethyl, CH$_2$OCH$_2$CH$_2$OCH$_3$ and methyl sulfonyl;

$R^2$ is selected from the group consisting of hydrogen, chlorine, fluorine, methyl, methoxy, ethoxy, OCH$_2$(cyclo-$C_3$H$_5$), OCHF$_2$, OCH$_2$CF$_3$, OCH$_2$CH$_2$OCH$_3$, methoxymethyl, CH$_2$OCH$_2$CF$_3$, methyl sulfonyl, ethyl sulfonyl, methylsulfinyl, ethylsulfinyl, methylsulfanyl, ethylsulfanyl, NCH$_3$SO$_2$CH$_3$, 3-isoxazolinyl, 5-methyl-3-isoxazolinyl, 5-isoxazolinyl, 3-methyl-5-isoxazolinyl, 3-isoxazolyl, 5-methyl-3-isoxazolyl, 5-isoxazolyl and 3-methyl-5-isoxazolyl;

$R^3$ is selected from the group consisting of hydrogen, fluorine, chlorine, bromine, cyano, nitro, methyl, trifluoromethyl and methylsulfonyl;

$R^4$ is selected from the group consisting of hydrogen, cyano, methyl, chlorine and fluorine;

$R^5$ is selected from the group consisting of chlorine and fluorine;

$R^6$ is selected from the group consisting of methyl, ethyl, methoxymethyl, ethoxymethyl, prop-2-enyl, prop-2-ynyl, methoxycarbonylmethyl and benzyl;

$R^7$ is selected from the group consisting of methyl, ethyl, propyl, methoxymethyl, methoxyethyl and ethoxymethyl.

23. The compound of claim 1, an N-oxide or an agriculturally suitable salt thereof, wherein X is N and the variables $R^1$, $R^3$, $R^4$, $R^5$, $R^6$ and $R^7$ have the following meanings:

$R^1$ is selected from the group consisting of halogen, nitro, cyclopropyl, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl and $C_1$-$C_4$-alkyl-S(O)$_2$;

$R^3$ is selected from the group consisting of hydrogen, halogen, cyano, nitro, $C_1$-$C_4$-alkyl, $C_1$-$C_4$-haloalkyl and $C_1$-$C_4$-alkyl-S(O)$_2$;

$R^4$ is selected from the group consisting of hydrogen, cyano, methyl and halogen;

$R^5$ is selected from the group consisting of halogen, CHF$_2$ and CF$_3$;

$R^6$ is selected from the group consisting of $C_1$-$C_4$-alkyl, $C_1$-$C_2$-alkoxy-$C_1$-$C_2$-alkyl, $C_2$-$C_4$-alkenyl, $C_2$-$C_4$-alkynyl, $C_1$-$C_4$-alkoxycarbonyl-$C_1$-$C_4$-alkyl and phenyl-$C_1$-$C_2$-alkyl;

$R^7$ is selected from the group consisting of $C_1$-$C_4$-alkyl and $C_1$-$C_2$-alkoxy-$C_1$-$C_2$-alkyl.

24. The compound of claim 1, an N-oxide or an agriculturally suitable salt thereof, wherein X is N and the variables $R^1$, $R^3$, $R^4$, $R^5$, $R^6$ and $R^7$ have the following meanings:

$R^1$ is selected from the group consisting of chlorine, nitro, methyl, cyclopropyl, trifluoromethyl, methoxymethyl, CH$_2$OCH$_2$CH$_2$OCH$_3$ and methyl sulfonyl;

$R^3$ is selected from the group consisting of hydrogen, fluorine, chlorine, bromine, cyano, nitro, methyl, trifluoromethyl and methylsulfonyl;

$R^4$ is selected from the group consisting of hydrogen, cyano, methyl, chlorine and fluorine;

$R^5$ is selected from the group consisting of chlorine and fluorine;

$R^6$ is selected from the group consisting of methyl, ethyl, methoxymethyl, ethoxymethyl, prop-2-enyl, prop-2-ynyl, methoxycarbonylmethyl and benzyl;

$R^7$ is selected from the group consisting of methyl, ethyl, propyl, methoxymethyl, methoxyethyl and ethoxymethyl.

25. The compound of claim 1, an N-oxide or an agriculturally suitable salt thereof, wherein X is $CR^2$ and the variables $R^1$, $R^2$, $R^3$, $R^4$, $R^5$, $R^6$ and $R^7$ have the following meanings:

$R^1$ is selected from the group consisting of chlorine, nitro, methyl, cyclopropyl, trifluoromethyl, methoxymethyl, CH$_2$OCH$_2$CH$_2$OCH$_3$ and methyl sulfonyl;

$R^2$ is selected from the group consisting of hydrogen, chlorine, fluorine, methyl, CH$_2$OCH$_2$CF$_3$, methylsulfonyl, ethylsulfonyl, methylsulfanyl, ethylsulfanyl, 3-isoxazolinyl, 5-methyl-3-isoxazolinyl, 5-isoxazolinyl, 3-methyl-5-isoxazolinyl, 3-isoxazolyl, 5-methyl-3-isoxazolyl, 5-isoxazolyl and 3-methyl-5-isoxazolyl;

$R^3$ is selected from the group consisting of hydrogen, fluorine, chlorine, cyano, nitro, methyl, trifluoromethyl and methylsulfonyl;

$R^4$ is selected from the group consisting of hydrogen, cyano, methyl, chlorine and fluorine;

$R^5$ is selected from the group consisting of chlorine and flourine;

$R^6$ is selected from the group consisting of methyl, ethyl, methoxymethyl, ethoxymethyl, prop-2-ynyl and methoxycarbonylmethyl;

$R^7$ is selected from the group consisting of methyl, ethyl and methoxyethyl.

26. The compound of claim 1, an N-oxide or an agriculturally suitable salt thereof, wherein X is $CR^2$ and the variable $R^3$ is not hydrogen.

27. The compound of claim 1, an N-oxide or an agriculturally suitable salt thereof, wherein X is $CR^2$ and the variables $R^2$ and $R^3$ are not hydrogen.

28. A composition comprising at least one compound of claim 1, an N-oxide or an agriculturally suitable salt thereof, and at least one auxiliary, which is customary for formulating crop protection compounds.

29. A method for controlling unwanted vegetation, comprising applying a herbicidally effective amount of at least one compound of claim 1, an N-oxide or an agriculturally suitable salt thereof, on plants, their seed, or their habitat.

30. A method for controlling unwanted vegetation, comprising applying a herbicidally effective amount the composition of claim 28 on plants, their seed, or their habitat.

* * * * *

UNITED STATES PATENT AND TRADEMARK OFFICE
CERTIFICATE OF CORRECTION

PATENT NO. : 9,902,704 B2
APPLICATION NO. : 15/027891
DATED : February 27, 2018
INVENTOR(S) : Frederick Calo et al.

Page 1 of 1

It is certified that error appears in the above-identified patent and that said Letters Patent is hereby corrected as shown below:

In the Claims

Column 159, Line 12, please delete "X is N" and insert in place thereof --X is $CR^2$--

Signed and Sealed this
Twenty-sixth Day of June, 2018

Andrei Iancu
*Director of the United States Patent and Trademark Office*